(12) United States Patent
Shelton, IV

(10) Patent No.: US 11,141,156 B2
(45) Date of Patent: *Oct. 12, 2021

(54) SURGICAL STAPLING ASSEMBLY COMPRISING FLEXIBLE OUTPUT SHAFT

(71) Applicant: Cilag GmbH International, Zug (CH)

(72) Inventor: Frederick E. Shelton, IV, Hillsboro, OH (US)

(73) Assignee: Cilag GmbH International, Zug (CH)

(\*) Notice: Subject to any disclaimer, the term of this patent is extended or adjusted under 35 U.S.C. 154(b) by 62 days.

This patent is subject to a terminal disclaimer.

(21) Appl. No.: 16/367,932

(22) Filed: Mar. 28, 2019

(65) Prior Publication Data

US 2019/0290274 A1 Sep. 26, 2019

Related U.S. Application Data

(63) Continuation of application No. 15/079,526, filed on Mar. 24, 2016, now Pat. No. 10,485,541, which is a (Continued)

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/072* (2013.01); (Continued)

(58) Field of Classification Search
CPC ...... A61B 17/07207; A61B 2017/2905; A61B 2017/2927; A61B 2017/00309; A61B 2017/00314
See application file for complete search history.

(56) References Cited

U.S. PATENT DOCUMENTS

| 66,052 A | 6/1867 | Smith |
| 662,587 A | 11/1900 | Blake |

(Continued)

FOREIGN PATENT DOCUMENTS

| AU | 2012200594 A1 | 2/2012 |
| AU | 2012203035 A1 | 6/2012 |

(Continued)

OTHER PUBLICATIONS

ASTM procedure D2240-00, "Standard Test Method for Rubber Property-Durometer Hardness," (Published Aug. 2000).
(Continued)

*Primary Examiner* — Joshua G Kotis

(57) ABSTRACT

A surgical tool for use with a robotic system that includes a tool drive assembly that is operatively coupled to a control unit of the robotic system that is operable by inputs from an operator and is configured to robotically-generate output motions. A drive system is configured to interface with a corresponding portion of the tool drive assembly for receiving the robotically-generated output motions and applying the output motions to a drive shaft assembly which is configured to apply control motions to a surgical end effector operably coupled thereto. A manually-actuatable control system operably interfaces with the drive shaft assembly to facilitate the selective application of manually-generated control motions to the drive shaft assembly.

15 Claims, 126 Drawing Sheets

Related U.S. Application Data continuation of application No. 13/536,323, filed on Jun. 28, 2012, now Pat. No. 9,408,606.

(51) Int. Cl.

| | | |
|---|---|---|
| A61B 34/30 | (2016.01) | |
| A61B 17/00 | (2006.01) | |
| A61B 17/29 | (2006.01) | |
| A61M 39/00 | (2006.01) | |
| A61M 39/10 | (2006.01) | |
| A61B 34/00 | (2016.01) | |
| A61B 90/00 | (2016.01) | |
| A61B 17/32 | (2006.01) | |
| A61B 34/37 | (2016.01) | |
| A61B 17/295 | (2006.01) | |

(52) U.S. Cl.
CPC ..... *A61B 17/295* (2013.01); *A61B 17/320016* (2013.01); *A61B 34/30* (2016.02); *A61B 34/37* (2016.02); *A61B 34/70* (2016.02); *A61B 34/71* (2016.02); *A61B 34/74* (2016.02); *A61B 2017/003* (2013.01); *A61B 2017/0046* (2013.01); *A61B 2017/00199* (2013.01); *A61B 2017/00309* (2013.01); *A61B 2017/00314* (2013.01); *A61B 2017/00327* (2013.01); *A61B 2017/00398* (2013.01); *A61B 2017/00464* (2013.01); *A61B 2017/00473* (2013.01); *A61B 2017/00477* (2013.01); *A61B 2017/00685* (2013.01); *A61B 2017/00734* (2013.01); *A61B 2017/00876* (2013.01); *A61B 2017/07257* (2013.01); *A61B 2017/07271* (2013.01); *A61B 2017/07278* (2013.01); *A61B 2017/07285* (2013.01); *A61B 2017/2903* (2013.01); *A61B 2017/2905* (2013.01); *A61B 2017/2908* (2013.01); *A61B 2017/2923* (2013.01); *A61B 2017/2927* (2013.01); *A61B 2017/2929* (2013.01); *A61B 2017/2931* (2013.01); *A61B 2017/2939* (2013.01); *A61B 2017/2943* (2013.01); *A61B 2017/2946* (2013.01); *A61B 2034/306* (2016.02); *A61B 2090/0811* (2016.02); *A61B 2090/0812* (2016.02); *A61B 2090/0814* (2016.02); *A61M 39/00* (2013.01); *A61M 39/1055* (2013.01); *A61M 2039/1061* (2013.01); *Y10T 29/49826* (2015.01); *Y10T 74/18056* (2015.01); *Y10T 74/20329* (2015.01)

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,075,556 A | 10/1913 | Fenoughty |
| 1,188,721 A | 6/1916 | Bittner |
| 1,306,107 A | 6/1919 | Elliott |
| 1,314,601 A * | 9/1919 | McCaskey ............... F16D 3/04 464/147 |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,028,635 A | 1/1936 | Wappler |
| 2,037,727 A | 4/1936 | La Chapelle |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Royal |
| 2,441,096 A | 5/1948 | Happe |
| 2,448,741 A | 9/1948 | Scott et al. |
| 2,450,527 A | 10/1948 | Smith |
| 2,491,872 A | 12/1949 | Neuman |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,724,289 A | 11/1955 | Wight |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,026,744 A | 3/1962 | Rouse |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,339 A | 5/1972 | Shimizu |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,724,237 A | 4/1973 | Wood |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |

(56) References Cited

U.S. PATENT DOCUMENTS

| | | |
|---|---|---|
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,863,940 A | 2/1975 | Cummings |
| 3,883,624 A | 5/1975 | McKenzie et al. |
| 3,885,491 A | 5/1975 | Curtis |
| 3,887,393 A | 6/1975 | La Rue, Jr. |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,973,179 A | 8/1976 | Weber et al. |
| 3,981,051 A | 9/1976 | Brumlik |
| 3,999,110 A | 12/1976 | Ramstrom et al. |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,154,122 A | 5/1979 | Severin |
| 4,160,857 A | 7/1979 | Nardella et al. |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,203,444 A | 5/1980 | Bonnell et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,282,573 A | 8/1981 | Imai et al. |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,389,963 A | 6/1983 | Pearson |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,421,264 A | 12/1983 | Arter et al. |
| 4,423,456 A | 12/1983 | Zaidenweber |
| 4,425,915 A | 1/1984 | Ivanov |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,459,519 A | 7/1984 | Erdman |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,476,864 A | 10/1984 | Tezel |
| 4,478,220 A | 10/1984 | Di Giovanni et al. |
| 4,480,641 A | 11/1984 | Failla et al. |
| 4,481,458 A | 11/1984 | Lane |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |

(56) References Cited

U.S. PATENT DOCUMENTS

| | | |
|---|---|---|
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,980 A | 9/1986 | Aihara |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,619,262 A | 10/1986 | Taylor |
| 4,619,391 A | 10/1986 | Sharkany et al. |
| 4,624,401 A | 11/1986 | Gassner et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,642,738 A | 2/1987 | Meller |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,651,734 A | 3/1987 | Doss et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,755,070 A | 7/1988 | Cerutti |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,552 A | 5/1989 | Bojar et al. |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,096 A | 5/1989 | Oh et al. |
| 4,834,720 A | 5/1989 | Blinkhorn |
| 4,838,859 A | 6/1989 | Strassmann |

(56) References Cited

U.S. PATENT DOCUMENTS

| | | |
|---|---|---|
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,681 A | 10/1990 | Yang |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,976,173 A | 12/1990 | Yang |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,033,552 A | 7/1991 | Hu |
| 5,035,040 A | 7/1991 | Kerrigan et al. |
| 5,037,018 A | 8/1991 | Matsuda et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,056,953 A | 10/1991 | Marot et al. |
| 5,060,658 A | 10/1991 | Dejter, Jr. et al. |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,151,102 A | 9/1992 | Kamiyama et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,181,514 A | 1/1993 | Solomon et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |

(56) References Cited

U.S. PATENT DOCUMENTS

| | | | |
|---|---|---|---|
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A * | 12/1993 | Grant .......... A61B 17/115 227/179.1 |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,281,400 A | 1/1994 | Berry, Jr. |
| 5,282,806 A | 2/1994 | Haber et al. |
| 5,282,826 A | 2/1994 | Quadri |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,291,133 A | 3/1994 | Gokhale et al. |
| 5,292,053 A | 3/1994 | Bilotti et al. |
| 5,293,024 A | 3/1994 | Sugahara et al. |
| 5,297,714 A | 3/1994 | Kramer |
| 5,303,606 A | 4/1994 | Kokinda |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,486 A | 7/1994 | Wilk |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,338,317 A | 8/1994 | Hasson et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,104 A | 9/1994 | Main et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,353,798 A | 10/1994 | Sieben |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |

(56) References Cited

U.S. PATENT DOCUMENTS

| | | |
|---|---|---|
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,874 A | 1/1995 | Jackson et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,355 A | 6/1995 | Kulick |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |
| 5,433,721 A * | 7/1995 | Hooven ............... A61B 17/068 227/175.1 |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,441,499 A | 8/1995 | Fritzsch |
| 5,443,197 A | 8/1995 | Malis et al. |
| 5,443,198 A | 8/1995 | Viola et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,474,738 A | 12/1995 | Nichols et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |

(56) References Cited

U.S. PATENT DOCUMENTS

| | | |
|---|---|---|
| 5,485,952 A * | 1/1996 | Fontayne ......... A61B 17/07207 227/111 |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,164 A | 3/1996 | Ward et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,507,773 A | 4/1996 | Huitema et al. |
| 5,509,596 A | 4/1996 | Green et al. |
| 5,509,916 A | 4/1996 | Taylor |
| 5,509,918 A | 4/1996 | Romano |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,945 A | 8/1996 | Fritzsch |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,436 A | 3/1997 | Pratt et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |

(56) References Cited

U.S. PATENT DOCUMENTS

| | | |
|---|---|---|
| 5,624,452 A | 4/1997 | Yates |
| 5,626,587 A | 5/1997 | Bishop et al. |
| 5,626,595 A | 5/1997 | Sklar et al. |
| 5,626,979 A | 5/1997 | Mitsui et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,631,973 A | 5/1997 | Green |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,184 A | 10/1997 | Hassler, Jr. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,711,960 A | 1/1998 | Shikinami |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,836 A | 2/1998 | Kliegis et al. |
| 5,715,987 A | 2/1998 | Kelley et al. |
| 5,715,988 A | 2/1998 | Palmer |
| 5,716,352 A | 2/1998 | Viola et al. |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,736,271 A | 4/1998 | Cisar et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,755,726 A | 5/1998 | Pratt et al. |

(56) References Cited

U.S. PATENT DOCUMENTS

| | | |
|---|---|---|
| 5,758,814 A | 6/1998 | Gallagher et al. |
| 5,762,255 A | 6/1998 | Chrisman et al. |
| 5,762,256 A | 6/1998 | Mastri et al. |
| 5,762,458 A | 6/1998 | Wang et al. |
| 5,765,565 A | 6/1998 | Adair |
| 5,766,188 A | 6/1998 | Igaki |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,099 A | 6/1998 | Gravener |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,241 A * | 9/1998 | Heimberger ......... A61B 1/0055 600/139 |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A * | 5/1999 | Ouchi ................... A61B 10/06 600/104 |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,907,664 A | 5/1999 | Wang et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |

(56) References Cited

U.S. PATENT DOCUMENTS

| | | |
|---|---|---|
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,013,991 A | 1/2000 | Philipp |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,019,780 A | 2/2000 | Lombardo et al. |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,126 A | 3/2000 | Hsieh |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,072,299 A | 6/2000 | Kurle et al. |
| 6,074,386 A | 6/2000 | Goble et al. |
| 6,074,401 A | 6/2000 | Gardiner et al. |
| 6,075,441 A | 6/2000 | Maloney |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,090,123 A | 7/2000 | Culp et al. |
| 6,093,186 A | 7/2000 | Goble |
| D429,252 S | 8/2000 | Haitani et al. |
| 6,099,537 A | 8/2000 | Sugai et al. |
| 6,099,551 A | 8/2000 | Gabbay |
| 6,102,271 A | 8/2000 | Longo et al. |
| 6,102,926 A | 8/2000 | Tartaglia et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |

(56) References Cited

U.S. PATENT DOCUMENTS

| | | |
|---|---|---|
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,186,957 B1 | 2/2001 | Milam |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,311 B1 | 3/2001 | Danek et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,211,626 B1 | 4/2001 | Lys et al. |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,246 B1 | 7/2001 | Pantages et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,269,997 B1 | 8/2001 | Balazs et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,317,616 B1 | 11/2001 | Glossop |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| 6,349,868 B1 | 2/2002 | Mattingly et al. |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,364,828 B1 | 4/2002 | Yeung et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |

(56) References Cited

U.S. PATENT DOCUMENTS

| | | |
|---|---|---|
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,457,338 B1 | 10/2002 | Frenken |
| 6,457,625 B1 | 10/2002 | Tormala et al. |
| 6,458,077 B1 | 10/2002 | Boebel et al. |
| 6,458,142 B1 | 10/2002 | Faller et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,189 B1 * | 12/2002 | Lang ............... A61B 17/1611 606/170 |
| 6,500,194 B2 | 12/2002 | Benderev et al. |
| D468,749 S | 1/2003 | Friedman |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| D471,206 S | 3/2003 | Buzzard et al. |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,572 B1 | 7/2003 | Suzuta |
| 6,592,597 B2 | 7/2003 | Grant et al. |
| 6,594,552 B1 | 7/2003 | Nowlin et al. |
| 6,595,914 B2 | 7/2003 | Kato |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |

(56) References Cited

U.S. PATENT DOCUMENTS

| | | |
|---|---|---|
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,215 B1 | 4/2004 | David et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,106 B1 | 4/2004 | Charles et al. |
| 6,723,109 B2 | 4/2004 | Solingen |
| 6,726,651 B1 | 4/2004 | Robinson et al. |
| 6,726,697 B2 | 4/2004 | Nicholas et al. |
| 6,726,705 B2 | 4/2004 | Peterson et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,810 B2 | 5/2004 | Hoey et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,763,307 B2 | 7/2004 | Berg et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B2 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,778,846 B1 | 8/2004 | Martinez et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,784,775 B2 | 8/2004 | Mandell et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,806,867 B1 | 10/2004 | Arruda et al. |
| 6,808,525 B2 | 10/2004 | Latterell et al. |
| 6,810,359 B2 | 10/2004 | Sakaguchi |

(56) References Cited

U.S. PATENT DOCUMENTS

| | | |
|---|---|---|
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,876,850 B2 | 4/2005 | Maeshima et al. |
| 6,877,647 B2 | 4/2005 | Green et al. |
| 6,878,106 B1 | 4/2005 | Herrmann |
| 6,882,127 B2 | 4/2005 | Konigbauer |
| 6,883,199 B1 | 4/2005 | Lundell et al. |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,244 B1 | 5/2005 | Walker et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,705 B2 | 5/2005 | Niemeyer |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,949,196 B2 | 9/2005 | Schmitz et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| D511,525 S | 11/2005 | Hernandez et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,991,146 B2 | 1/2006 | Sinisi et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |

(56) References Cited

U.S. PATENT DOCUMENTS

| | | |
|---|---|---|
| 6,998,816 B2 | 2/2006 | Wieck et al. |
| 6,999,821 B2 | 2/2006 | Jenney et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,213 B2 | 3/2006 | Clark et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,399 B2 | 4/2006 | Driessen |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,033,378 B2 | 4/2006 | Smith et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,038,421 B2 | 5/2006 | Trifilo |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,716 B1 | 5/2006 | Kucharczyk et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,123 B2 | 6/2006 | Gregorio et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,081,318 B2 | 7/2006 | Lee et al. |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 * | 8/2006 | Danitz ................ A61B 1/0055 600/141 |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| D530,339 S | 10/2006 | Hernandez et al. |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |

(56) References Cited

U.S. PATENT DOCUMENTS

| | | |
|---|---|---|
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,117 B2 | 1/2007 | Hellenkamp |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,226,467 B2 | 6/2007 | Lucatero et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,254,320 B2 | 8/2007 | Kang |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |

(56) References Cited

U.S. PATENT DOCUMENTS

| | | |
|---|---|---|
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,367,973 B2 | 5/2008 | Manzo et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| D570,868 S | 6/2008 | Hosokawa et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| D575,793 S | 8/2008 | Ording |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 * | 8/2008 | Corcoran ............ A61B 17/0057 604/523 |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,450,991 B2 | 11/2008 | Smith et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,455,687 B2 | 11/2008 | Saunders et al. |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,147 B2 | 1/2009 | Honeycutt et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,492,261 B2 | 2/2009 | Cambre et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,497,137 B2 | 3/2009 | Tellenbach et al. |
| 7,500,979 B2 | 3/2009 | Hueil et al. |
| 7,501,198 B2 | 3/2009 | Barley et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |

(56) References Cited

U.S. PATENT DOCUMENTS

| | | | |
|---|---|---|---|
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 * | 6/2009 | Marczyk .......... A61B 17/07207 227/175.1 |
| 7,544,197 B2 | 6/2009 | Kelsch et al. |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,572,285 B2 | 8/2009 | Frey et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 * | 9/2009 | Racenet ................ A61B 17/105 227/181.1 |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| D605,201 S | 12/2009 | Lorenz et al. |
| D606,992 S | 12/2009 | Liu et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,625,388 B2 | 12/2009 | Boukhny et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,003 B2 | 2/2010 | Lorang et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,678,121 B1 | 3/2010 | Knodel |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,690,547 B2 | 4/2010 | Racenet et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,706,853 B2 | 4/2010 | Hacker et al. |
| 7,708,180 B2 | 5/2010 | Murray et al. |

(56) References Cited

U.S. PATENT DOCUMENTS

| | | |
|---|---|---|
| 7,708,181 B2 | 5/2010 | Cole et al. |
| 7,708,182 B2 | 5/2010 | Viola |
| 7,708,758 B2 | 5/2010 | Lee et al. |
| 7,708,768 B2 | 5/2010 | Danek et al. |
| 7,709,136 B2 | 5/2010 | Touchton et al. |
| 7,712,182 B2 | 5/2010 | Zeiler et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,758,613 B2 | 7/2010 | Whitman |
| 7,762,462 B2 | 7/2010 | Gelbman |
| 7,762,998 B2 | 7/2010 | Birk et al. |
| D622,286 S | 8/2010 | Umezawa |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,651 B2 | 8/2010 | Madhani et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,819,894 B2 | 10/2010 | Mitsuishi et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,829,416 B2 | 11/2010 | Kudou et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,840,253 B2 | 11/2010 | Tremblay et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |

(56) References Cited

U.S. PATENT DOCUMENTS

| | | |
|---|---|---|
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,845,538 B2 | 12/2010 | Whitman |
| 7,846,085 B2 | 12/2010 | Silverman et al. |
| 7,846,149 B2 | 12/2010 | Jankowski |
| 7,846,161 B2 | 12/2010 | Dumbauld et al. |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,883,540 B2 | 2/2011 | Niwa et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,671 B2 | 3/2011 | Kim et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,954,688 B2 | 6/2011 | Argentine et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,508 B2 | 7/2011 | Hoag |
| 7,976,563 B2 | 7/2011 | Summerer |
| 7,979,137 B2 | 7/2011 | Tracey et al. |
| 7,980,443 B2 | 7/2011 | Scheib et al. |
| 7,981,102 B2 | 7/2011 | Patel et al. |

(56) References Cited

U.S. PATENT DOCUMENTS

| | | |
|---|---|---|
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |

(56) References Cited

U.S. PATENT DOCUMENTS

| | | |
|---|---|---|
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,190,238 B2 | 5/2012 | Moll et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,207,863 B2 | 6/2012 | Neubauer et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,266,232 B2 | 9/2012 | Piper et al. |
| 8,267,300 B2 | 9/2012 | Boudreaux |
| 8,267,849 B2 | 9/2012 | Wazer et al. |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |

(56) References Cited

U.S. PATENT DOCUMENTS

| | | |
|---|---|---|
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,290,883 B2 | 10/2012 | Takeuchi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| D672,784 S | 12/2012 | Clanton et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,271 B2 | 12/2012 | Humayun et al. |
| 8,323,789 B2 | 12/2012 | Rozhin et al. |
| 8,324,585 B2 | 12/2012 | McBroom et al. |
| 8,327,514 B2 | 12/2012 | Kim |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,065 B2 | 12/2012 | Shah |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,719 B2 | 2/2013 | Markey et al. |
| 8,366,787 B2 | 2/2013 | Brown et al. |
| 8,368,327 B2 | 2/2013 | Benning et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,374,723 B2 | 2/2013 | Zhao et al. |
| 8,376,865 B2 * | 2/2013 | Forster ............... A61M 25/0113 464/78 |
| 8,377,029 B2 | 2/2013 | Nagao et al. |
| 8,377,044 B2 | 2/2013 | Coe et al. |
| 8,377,059 B2 | 2/2013 | Deville et al. |
| 8,381,828 B2 | 2/2013 | Whitman et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,972 B2 | 3/2013 | Kostrzewski |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,108 B2 | 3/2013 | Powell et al. |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |
| 8,403,198 B2 | 3/2013 | Sorrentino et al. |
| 8,403,832 B2 | 3/2013 | Cunningham et al. |
| 8,403,926 B2 | 3/2013 | Nobis et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| D680,646 S | 4/2013 | Hunt et al. |
| 8,408,439 B2 | 4/2013 | Huang et al. |
| 8,408,442 B2 | 4/2013 | Racenet et al. |

(56) References Cited

U.S. PATENT DOCUMENTS

| | | |
|---|---|---|
| 8,409,079 B2 | 4/2013 | Okamoto et al. |
| 8,409,174 B2 | 4/2013 | Omori |
| 8,409,175 B2 | 4/2013 | Lee et al. |
| 8,409,211 B2 | 4/2013 | Baroud |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,469 B2 | 4/2013 | Diolaiti |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,419,755 B2 | 4/2013 | Deem et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| D686,244 S | 7/2013 | Moriya et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,852 B2 | 7/2013 | Viola |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,673 B2 | 8/2013 | Keller |
| 8,499,966 B2 | 8/2013 | Palmer et al. |
| 8,499,992 B2 | 8/2013 | Whitman et al. |
| 8,499,993 B2 | 8/2013 | Shelton, IV et al. |
| 8,499,994 B2 | 8/2013 | D'Arcangelo |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,938 B2 | 8/2013 | Eisenhardt et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,787 B2 | 9/2013 | Ludwin et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,599 B2 | 9/2013 | Holsten |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,646 B2 | 9/2013 | Mendez-Coll |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |

(56) References Cited

U.S. PATENT DOCUMENTS

| | | |
|---|---|---|
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,620,473 B2 | 12/2013 | Diolaiti et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,467 B2 | 1/2014 | Whitman et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,656,929 B2 | 2/2014 | Miller et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,706,316 B1 | 4/2014 | Hoevenaar |
| 8,708,210 B2 | 4/2014 | Zemlok et al. |
| 8,708,211 B2 | 4/2014 | Zemlok et al. |
| 8,708,212 B2 | 4/2014 | Williams |
| 8,708,213 B2 | 4/2014 | Shelton, IV et al. |
| 8,709,012 B2 | 4/2014 | Muller |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,611 B2 | 5/2014 | Milliman |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |

(56) References Cited

U.S. PATENT DOCUMENTS

| | | |
|---|---|---|
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,765,942 B2 | 7/2014 | Feraud et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,159 B2 | 8/2014 | Moriyama |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,828,046 B2 | 9/2014 | Stefanchik et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,851,215 B2 | 10/2014 | Goto |
| 8,851,354 B2 | 10/2014 | Swensgard et al. |
| 8,851,355 B2 | 10/2014 | Aranyi et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,547 B2 | 10/2014 | Brogna |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,869,912 B2 | 10/2014 | Roßkamp et al. |
| 8,869,913 B2 | 10/2014 | Matthias et al. |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,910,847 B2 | 12/2014 | Nalagatla et al. |
| 8,911,426 B2 | 12/2014 | Coppeta et al. |

(56) References Cited

U.S. PATENT DOCUMENTS

| | | |
|---|---|---|
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,920,368 B2 | 12/2014 | Sandhu et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,939,898 B2 | 1/2015 | Omoto |
| 8,944,069 B2 | 2/2015 | Miller et al. |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,984,711 B2 | 3/2015 | Ota et al. |
| 8,985,240 B2 | 3/2015 | Winnard |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,014,856 B2 | 4/2015 | Manzo et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,017,849 B2 | 4/2015 | Stulen et al. |
| 9,017,851 B2 | 4/2015 | Felder et al. |
| D729,274 S | 5/2015 | Clement et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,030,166 B2 | 5/2015 | Kano |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,238 B2 | 6/2015 | Orszulak |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,089 B2 | 6/2015 | Orszulak |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |

(56) References Cited

U.S. PATENT DOCUMENTS

| | | |
|---|---|---|
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,338 B2 | 7/2015 | Smith et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,098,153 B2 | 8/2015 | Shen et al. |
| 9,099,863 B2 | 8/2015 | Smith et al. |
| 9,099,877 B2 | 8/2015 | Banos et al. |
| 9,099,922 B2 | 8/2015 | Toosky et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,101,621 B2 | 8/2015 | Zeldis |
| 9,107,663 B2 | 8/2015 | Swensgard |
| 9,107,667 B2 | 8/2015 | Hodgkinson |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,651 B2 | 9/2015 | Mandakolathur Vasudevan et al. |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D740,414 S | 10/2015 | Katsura |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,161,855 B2 | 10/2015 | Rousseau et al. |
| 9,164,271 B2 | 10/2015 | Ebata et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,171,244 B2 | 10/2015 | Endou et al. |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,376 B2 | 11/2015 | Almodovar |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 * | 12/2015 | Shelton, IV ............ A61B 34/35 |
| 9,204,880 B2 | 12/2015 | Baxter, III et al. |
| 9,204,881 B2 | 12/2015 | Penna |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,504 B2 | 12/2015 | Viola et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,760 B2 | 1/2016 | Shelton, IV |
| 9,226,761 B2 | 1/2016 | Burbank |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,241,758 B2 | 1/2016 | Franer et al. |
| 9,244,524 B2 | 1/2016 | Inoue et al. |
| D748,668 S | 2/2016 | Kim et al. |
| D749,128 S | 2/2016 | Perez et al. |
| D749,623 S | 2/2016 | Gray et al. |
| D750,122 S | 2/2016 | Shardlow et al. |

(56) References Cited

U.S. PATENT DOCUMENTS

| | | |
|---|---|---|
| D750,129 S | 2/2016 | Kwon |
| 9,254,131 B2 | 2/2016 | Soltz et al. |
| 9,254,170 B2 | 2/2016 | Parihar et al. |
| 9,259,265 B2 | 2/2016 | Harris et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,811 B2 | 4/2016 | Goldberg et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,291 B2 | 4/2016 | Schall et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,326,824 B2 | 5/2016 | Inoue et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,352,071 B2 | 5/2016 | Landgrebe et al. |
| D758,433 S | 6/2016 | Lee et al. |
| D759,063 S | 6/2016 | Chen |
| 9,358,003 B2 | 6/2016 | Hall et al. |
| 9,358,004 B2 | 6/2016 | Sniffin et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,358,065 B2 | 6/2016 | Ladtkow et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,362 B2 | 6/2016 | Petty et al. |
| 9,370,364 B2 | 6/2016 | Smith et al. |
| 9,370,400 B2 | 6/2016 | Parihar |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,392,885 B2 | 7/2016 | Vogler et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,393,354 B2 | 7/2016 | Freedman et al. |
| 9,396,669 B2 | 7/2016 | Karkanias et al. |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |

(56) References Cited

U.S. PATENT DOCUMENTS

| | | |
|---|---|---|
| 9,402,629 B2 | 8/2016 | Ehrenfels et al. |
| 9,402,679 B2 | 8/2016 | Ginnebaugh et al. |
| 9,402,688 B2 | 8/2016 | Min et al. |
| 9,408,604 B2 | 8/2016 | Shelton, IV et al. |
| 9,408,605 B1 | 8/2016 | Knodel et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,421,682 B2 | 8/2016 | McClaskey et al. |
| 9,427,223 B2 | 8/2016 | Park et al. |
| 9,427,231 B2 | 8/2016 | Racenet et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Overes et al. |
| 9,451,958 B2 | 9/2016 | Shelton, IV et al. |
| D768,152 S | 10/2016 | Gutierrez et al. |
| D768,156 S | 10/2016 | Frincke |
| D768,167 S | 10/2016 | Jones et al. |
| D769,315 S | 10/2016 | Scotti |
| D769,930 S | 10/2016 | Agrawal |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 * | 11/2016 | Altman ............... A61B 17/068 |
| 9,486,214 B2 | 11/2016 | Shelton, IV |
| 9,486,215 B2 | 11/2016 | Olson et al. |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,172 B2 | 11/2016 | Weisshaupt et al. |
| 9,492,189 B2 | 11/2016 | Williams et al. |
| 9,492,192 B2 | 11/2016 | To et al. |
| 9,492,237 B2 | 11/2016 | Kang et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,520 B2 | 11/2016 | Worrell et al. |
| 9,504,521 B2 | 11/2016 | Deutmeyer et al. |
| 9,504,528 B2 | 11/2016 | Ivinson et al. |
| 9,507,399 B2 | 11/2016 | Chien |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,065 B2 | 12/2016 | Simms et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,014 B2 | 12/2016 | Nishizawa et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| 9,526,921 B2 | 12/2016 | Kimball et al. |
| D776,683 S | 1/2017 | Gobinski et al. |
| D777,773 S | 1/2017 | Shi |
| 9,532,783 B2 | 1/2017 | Swayze et al. |
| 9,539,060 B2 | 1/2017 | Lightcap et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,733 B2 | 1/2017 | Knodel |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,803 B2 | 1/2017 | Smith et al. |
| 9,554,812 B2 | 1/2017 | Inkpen et al. |
| 9,559,624 B2 | 1/2017 | Philipp |
| 9,561,013 B2 | 2/2017 | Tsuchiya |
| 9,561,029 B2 | 2/2017 | Scheib et al. |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| 9,579,143 B2 | 2/2017 | Ullrich et al. |
| 9,579,158 B2 | 2/2017 | Brianza et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |

(56) References Cited

U.S. PATENT DOCUMENTS

| | | |
|---|---|---|
| 9,597,075 B2 | 3/2017 | Shelton, IV et al. |
| 9,597,078 B2 | 3/2017 | Scirica et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,079 B2 | 4/2017 | Kamei et al. |
| 9,610,080 B2 | 4/2017 | Whitfield et al. |
| 9,610,412 B2 | 4/2017 | Zemlok et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,622,746 B2 | 4/2017 | Simms et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,632 B2 | 4/2017 | Linder et al. |
| 9,629,652 B2 | 4/2017 | Mumaw et al. |
| 9,629,814 B2 | 4/2017 | Widenhouse et al. |
| D785,794 S | 5/2017 | Magno, Jr. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,091 B2 | 5/2017 | Beardsley et al. |
| 9,636,111 B2 | 5/2017 | Wenchell |
| 9,636,112 B2 | 5/2017 | Penna et al. |
| 9,636,113 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,642,642 B2 | 5/2017 | Lim |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,649,190 B2 | 5/2017 | Mathies |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,661,991 B2 | 5/2017 | Glossop |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,668,735 B2 | 6/2017 | Beetel |
| 9,675,344 B2 | 6/2017 | Combrowski et al. |
| 9,675,348 B2 | 6/2017 | Smith et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,368 B2 | 6/2017 | Guo et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,775 B2 | 7/2017 | Agarwal et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,706,674 B2 | 7/2017 | Collins et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,003 B2 | 7/2017 | Hoell, Jr. et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| D795,919 S | 8/2017 | Bischoff et al. |
| 9,717,497 B2 | 8/2017 | Zerkle et al. |
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,299 B2 | 8/2017 | Yan |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,503 B2 | 9/2017 | Milliman |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |

(56) References Cited

U.S. PATENT DOCUMENTS

| | | |
|---|---|---|
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,187 B2 | 10/2017 | Zergiebel et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,815,118 B1 | 11/2017 | Schmitt et al. |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,235 B2 | 12/2017 | Penna et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,850,994 B2 | 12/2017 | Schena |
| D808,989 S | 1/2018 | Ayvazian et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,366 B2 | 1/2018 | Aranyi |
| 9,861,382 B2 | 1/2018 | Smith et al. |
| 9,861,446 B2 | 1/2018 | Lang |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,722 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |

(56) References Cited

U.S. PATENT DOCUMENTS

| | | |
|---|---|---|
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,123 B2 | 7/2018 | Williams et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |

(56) References Cited

U.S. PATENT DOCUMENTS

| | | |
|---|---|---|
| 10,099,303 B2 | 10/2018 | Yoshida et al. |
| 10,101,861 B2 | 10/2018 | Kiyoto |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |
| D841,667 S | 2/2019 | Coren |
| 10,194,801 B2 | 2/2019 | Elhaway et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| D847,199 S | 4/2019 | Whitmore |
| 10,244,991 B2 | 4/2019 | Shademan et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |

(56) References Cited

U.S. PATENT DOCUMENTS

| | | |
|---|---|---|
| 10,258,336 B2 | 4/2019 | Baxter, III et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,840 B2 | 4/2019 | Sapre |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,847 B2 | 4/2019 | Racenet et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |
| 10,299,790 B2 | 5/2019 | Beardsley |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| 10,303,851 B2 | 5/2019 | Nguyen et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,582 B2 | 6/2019 | Shelton, IV et al. |
| 10,314,584 B2 | 6/2019 | Scirica et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,937 B2 | 7/2019 | Williams |
| 10,349,939 B2 | 7/2019 | Shelton, IV et al. |
| 10,349,941 B2 | 7/2019 | Marczyk et al. |
| 10,349,963 B2 | 7/2019 | Fiksen et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,867 B2 | 8/2019 | Harris et al. |
| 10,368,892 B2 | 8/2019 | Stulen et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D860,219 S | 9/2019 | Rasmussen et al. |
| D861,035 S | 9/2019 | Park et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,398,460 B2 | 9/2019 | Overmyer |
| 10,404,136 B2 | 9/2019 | Oktavec et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,405,937 B2 | 9/2019 | Black et al. |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,552 B2 | 9/2019 | Shelton, IV et al. |
| 10,420,553 B2 | 9/2019 | Shelton, IV et al. |
| 10,420,554 B2 | 9/2019 | Collings et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |

(56) References Cited

U.S. PATENT DOCUMENTS

| | | |
|---|---|---|
| 10,420,561 B2 | 9/2019 | Shelton, IV et al. |
| 10,420,577 B2 | 9/2019 | Chowaniec et al. |
| D861,707 S | 10/2019 | Yang |
| D862,518 S | 10/2019 | Niven et al. |
| D863,343 S | 10/2019 | Mazlish et al. |
| D864,388 S | 10/2019 | Barber |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,426,555 B2 | 10/2019 | Crowley et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,371 B2 | 11/2019 | Kostrzewski |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,767 B2 | 11/2019 | Gleiman et al. |
| 10,470,768 B2 | 11/2019 | Harris et al. |
| 10,470,769 B2 | 11/2019 | Shelton, IV et al. |
| 10,471,282 B2 | 11/2019 | Kirk et al. |
| 10,471,576 B2 | 11/2019 | Totsu |
| 10,471,607 B2 | 11/2019 | Butt et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,187 B2 | 11/2019 | Shelton, IV et al. |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,917 B2 | 12/2019 | Scheib et al. |
| 10,499,918 B2 | 12/2019 | Schellin et al. |
| 10,500,309 B2 | 12/2019 | Shah et al. |
| 10,508,720 B2 | 12/2019 | Nicholas |
| 10,512,461 B2 | 12/2019 | Gupta et al. |
| 10,517,590 B2 | 12/2019 | Giordano et al. |
| 10,517,592 B2 | 12/2019 | Shelton, IV et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 10,524,784 B2 | 1/2020 | Kostrzewski |
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,908 B2 | 1/2020 | Mei et al. |
| 10,542,974 B2 | 1/2020 | Yates et al. |
| 10,542,976 B2 | 1/2020 | Calderoni et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,593 B2 | 2/2020 | Shelton, IV et al. |
| 10,548,600 B2 | 2/2020 | Shelton, IV et al. |
| 10,548,673 B2 | 2/2020 | Harris et al. |
| 10,561,418 B2 | 2/2020 | Richard et al. |
| 10,561,419 B2 | 2/2020 | Beardsley |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| D879,808 S | 3/2020 | Harris et al. |
| D879,809 S | 3/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,835 B2 | 3/2020 | Kerr et al. |
| 10,595,862 B2 | 3/2020 | Shelton, IV et al. |
| 10,595,882 B2 | 3/2020 | Parfett et al. |
| 10,595,887 B2 | 3/2020 | Shelton, IV et al. |

(56) References Cited

U.S. PATENT DOCUMENTS

| | | | |
|---|---|---|---|
| 10,595,929 | B2 | 3/2020 | Boudreaux et al. |
| 10,603,036 | B2 | 3/2020 | Hunter et al. |
| 10,603,039 | B2 | 3/2020 | Vendely et al. |
| 10,603,041 | B2 | 3/2020 | Miller et al. |
| 10,603,117 | B2 | 3/2020 | Schings et al. |
| 10,603,128 | B2 | 3/2020 | Zergiebel et al. |
| 10,610,224 | B2 | 4/2020 | Shelton, IV et al. |
| 10,610,236 | B2 | 4/2020 | Baril |
| 10,610,313 | B2 | 4/2020 | Bailey et al. |
| 10,617,411 | B2 | 4/2020 | Williams |
| 10,617,412 | B2 | 4/2020 | Shelton, IV et al. |
| 10,617,413 | B2 | 4/2020 | Shelton, IV et al. |
| 10,617,414 | B2 | 4/2020 | Shelton, IV et al. |
| 10,617,416 | B2 | 4/2020 | Leimbach et al. |
| 10,617,417 | B2 | 4/2020 | Baxter, III et al. |
| 10,617,418 | B2 | 4/2020 | Barton et al. |
| 10,617,420 | B2 | 4/2020 | Shelton, IV et al. |
| 10,624,616 | B2 | 4/2020 | Mukherjee et al. |
| 10,624,630 | B2 | 4/2020 | Deville et al. |
| 10,624,633 | B2 | 4/2020 | Shelton, IV et al. |
| 10,624,634 | B2 | 4/2020 | Shelton, IV et al. |
| 10,624,635 | B2 | 4/2020 | Harris et al. |
| 10,624,709 | B2 | 4/2020 | Remm |
| 10,624,861 | B2 | 4/2020 | Widenhouse et al. |
| 10,625,062 | B2 | 4/2020 | Matlock et al. |
| 10,631,857 | B2 | 4/2020 | Kostrzewski |
| 10,631,858 | B2 | 4/2020 | Burbank |
| 10,631,859 | B2 | 4/2020 | Shelton, IV et al. |
| 10,631,860 | B2 | 4/2020 | Bakos et al. |
| 10,636,104 | B2 | 4/2020 | Mazar et al. |
| 10,639,018 | B2 | 5/2020 | Shelton, IV et al. |
| 10,639,034 | B2 | 5/2020 | Harris et al. |
| 10,639,035 | B2 | 5/2020 | Shelton, IV et al. |
| 10,639,036 | B2 | 5/2020 | Yates et al. |
| 10,639,037 | B2 | 5/2020 | Shelton, IV et al. |
| 10,639,089 | B2 | 5/2020 | Manwaring et al. |
| 10,639,115 | B2 | 5/2020 | Shelton, IV et al. |
| 10,646,220 | B2 | 5/2020 | Shelton, IV et al. |
| 10,653,413 | B2 | 5/2020 | Worthington et al. |
| 10,653,417 | B2 | 5/2020 | Shelton, IV et al. |
| 10,653,435 | B2 | 5/2020 | Shelton, IV et al. |
| 10,660,640 | B2 | 5/2020 | Yates et al. |
| 10,667,808 | B2 | 6/2020 | Baxter, III et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,028 | B2 | 6/2020 | Shelton, IV et al. |
| 10,675,035 | B2 | 6/2020 | Zingman |
| 10,677,035 | B2 | 6/2020 | Balan et al. |
| 10,682,134 | B2 | 6/2020 | Shelton, IV et al. |
| 10,682,136 | B2 | 6/2020 | Harris et al. |
| 10,682,138 | B2 | 6/2020 | Shelton, IV et al. |
| 10,682,141 | B2 | 6/2020 | Moore et al. |
| 10,682,142 | B2 | 6/2020 | Shelton, IV et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,812 | B2 | 6/2020 | Shelton, IV et al. |
| 10,687,813 | B2 | 6/2020 | Shelton, IV et al. |
| 10,687,817 | B2 | 6/2020 | Shelton, IV et al. |
| 10,687,904 | B2 | 6/2020 | Harris et al. |
| 10,695,053 | B2 | 6/2020 | Hess et al. |
| 10,695,055 | B2 | 6/2020 | Shelton, IV et al. |
| 10,695,057 | B2 | 6/2020 | Shelton, IV et al. |
| 10,695,058 | B2 | 6/2020 | Lytle, IV et al. |
| 10,695,062 | B2 | 6/2020 | Leimbach et al. |
| 10,695,063 | B2 | 6/2020 | Morgan et al. |
| 10,695,074 | B2 | 6/2020 | Carusillo |
| 10,695,081 | B2 | 6/2020 | Shelton, IV et al. |
| 10,695,123 | B2 | 6/2020 | Allen, IV |
| 10,695,187 | B2 | 6/2020 | Moskowitz et al. |
| D890,784 | S | 7/2020 | Shelton, IV et al. |
| 10,702,266 | B2 | 7/2020 | Parihar et al. |
| 10,702,267 | B2 | 7/2020 | Hess et al. |
| 10,702,270 | B2 | 7/2020 | Shelton, IV et al. |
| 10,702,271 | B2 | 7/2020 | Aranyi et al. |
| 10,705,660 | B2 | 7/2020 | Xiao |
| 10,709,446 | B2 | 7/2020 | Harris et al. |
| 10,709,468 | B2 | 7/2020 | Shelton, IV et al. |
| 10,709,469 | B2 | 7/2020 | Shelton, IV et al. |
| 10,709,496 | B2 | 7/2020 | Moua et al. |
| 10,716,563 | B2 | 7/2020 | Shelton, IV et al. |
| 10,716,565 | B2 | 7/2020 | Shelton, IV et al. |
| 10,716,568 | B2 | 7/2020 | Hall et al. |
| 10,716,614 | B2 | 7/2020 | Yates et al. |
| 10,717,179 | B2 | 7/2020 | Koenig et al. |
| 10,722,232 | B2 | 7/2020 | Yates et al. |
| 10,722,233 | B2 | 7/2020 | Wellman |
| 10,722,292 | B2 | 7/2020 | Arya et al. |
| 10,722,293 | B2 | 7/2020 | Arya et al. |
| 10,722,317 | B2 | 7/2020 | Ward et al. |
| 10,729,432 | B2 | 8/2020 | Shelton, IV et al. |
| 10,729,436 | B2 | 8/2020 | Shelton, IV et al. |
| 10,729,443 | B2 | 8/2020 | Cabrera et al. |
| 10,729,458 | B2 | 8/2020 | Stoddard et al. |
| 10,729,501 | B2 | 8/2020 | Leimbach et al. |
| 10,729,509 | B2 | 8/2020 | Shelton, IV et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,630 | B2 | 8/2020 | Huang et al. |
| 10,736,633 | B2 | 8/2020 | Vendely et al. |
| 10,736,634 | B2 | 8/2020 | Shelton, IV et al. |
| 10,736,636 | B2 | 8/2020 | Baxter, III et al. |
| 10,736,644 | B2 | 8/2020 | Windolf et al. |
| 10,743,849 | B2 | 8/2020 | Shelton, IV et al. |
| 10,743,851 | B2 | 8/2020 | Swayze et al. |
| 10,743,868 | B2 | 8/2020 | Shelton, IV et al. |
| 10,743,870 | B2 | 8/2020 | Hall et al. |
| 10,743,872 | B2 | 8/2020 | Leimbach et al. |
| 10,743,873 | B2 | 8/2020 | Overmyer et al. |
| 10,743,874 | B2 | 8/2020 | Shelton, IV et al. |
| 10,743,875 | B2 | 8/2020 | Shelton, IV et al. |
| 10,743,877 | B2 | 8/2020 | Shelton, IV et al. |
| 10,743,930 | B2 | 8/2020 | Nagtegaal |
| 10,751,048 | B2 | 8/2020 | Whitman et al. |
| 10,751,053 | B2 | 8/2020 | Harris et al. |
| 10,751,076 | B2 | 8/2020 | Laurent et al. |
| 10,751,138 | B2 | 8/2020 | Giordano et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,233 | B2 | 9/2020 | Scheib et al. |
| 10,758,259 | B2 | 9/2020 | Demmy et al. |
| 10,765,425 | B2 | 9/2020 | Yates et al. |
| 10,765,427 | B2 | 9/2020 | Shelton, IV et al. |
| 10,765,429 | B2 | 9/2020 | Leimbach et al. |
| 10,765,430 | B2 | 9/2020 | Wixey |
| 10,765,432 | B2 | 9/2020 | Moore et al. |
| 10,765,442 | B2 | 9/2020 | Strobl |
| 10,772,625 | B2 | 9/2020 | Shelton, IV et al. |
| 10,772,628 | B2 | 9/2020 | Chen et al. |
| 10,772,629 | B2 | 9/2020 | Shelton, IV et al. |
| 10,772,630 | B2 | 9/2020 | Wixey |
| 10,772,631 | B2 | 9/2020 | Zergiebel et al. |
| 10,772,632 | B2 | 9/2020 | Kostrzewski |
| 10,772,651 | B2 | 9/2020 | Shelton, IV et al. |
| 10,779,818 | B2 | 9/2020 | Zemlok et al. |
| 10,779,820 | B2 | 9/2020 | Harris et al. |
| 10,779,821 | B2 | 9/2020 | Harris et al. |
| 10,779,822 | B2 | 9/2020 | Yates et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,826 | B2 | 9/2020 | Shelton, IV et al. |
| 10,779,903 | B2 | 9/2020 | Wise et al. |
| 10,780,539 | B2 | 9/2020 | Shelton, IV et al. |
| 10,786,248 | B2 | 9/2020 | Rousseau et al. |
| 10,786,253 | B2 | 9/2020 | Shelton, IV et al. |
| 10,786,255 | B2 | 9/2020 | Hodgkinson et al. |

(56) References Cited

U.S. PATENT DOCUMENTS

| | | |
|---|---|---|
| 10,792,038 B2 | 10/2020 | Becerra et al. |
| 10,796,471 B2 | 10/2020 | Leimbach et al. |
| 10,799,240 B2 | 10/2020 | Shelton, IV et al. |
| 10,799,306 B2 | 10/2020 | Robinson et al. |
| 10,806,448 B2 | 10/2020 | Shelton, IV et al. |
| 10,806,449 B2 | 10/2020 | Shelton, IV et al. |
| 10,806,450 B2 | 10/2020 | Yates et al. |
| 10,806,451 B2 | 10/2020 | Harris et al. |
| 10,806,453 B2 | 10/2020 | Chen et al. |
| 10,806,479 B2 | 10/2020 | Shelton, IV et al. |
| 10,813,638 B2 | 10/2020 | Shelton, IV et al. |
| 10,813,639 B2 | 10/2020 | Shelton, IV et al. |
| 10,813,640 B2 | 10/2020 | Adams et al. |
| 10,813,641 B2 | 10/2020 | Setser et al. |
| 10,813,683 B2 | 10/2020 | Baxter, III et al. |
| 10,813,705 B2 | 10/2020 | Hares et al. |
| 10,813,710 B2 | 10/2020 | Grubbs |
| 10,820,939 B2 | 11/2020 | Sartor |
| 10,828,028 B2 | 11/2020 | Harris et al. |
| 10,828,030 B2 | 11/2020 | Weir et al. |
| 10,828,032 B2 | 11/2020 | Leimbach et al. |
| 10,828,033 B2 | 11/2020 | Shelton, IV et al. |
| 10,828,089 B2 | 11/2020 | Clark et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,249 B2 | 11/2020 | Schellin et al. |
| 10,835,251 B2 | 11/2020 | Shelton, IV et al. |
| 10,835,330 B2 | 11/2020 | Shelton, IV et al. |
| 10,842,357 B2 | 11/2020 | Moskowitz et al. |
| 10,842,473 B2 | 11/2020 | Scheib et al. |
| 10,842,488 B2 | 11/2020 | Swayze et al. |
| 10,842,489 B2 | 11/2020 | Shelton, IV |
| 10,842,490 B2 | 11/2020 | DiNardo et al. |
| 10,842,491 B2 | 11/2020 | Shelton, IV et al. |
| 10,842,492 B2 | 11/2020 | Shelton, IV et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,856,866 B2 | 12/2020 | Shelton, IV et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,863,981 B2 | 12/2020 | Overmyer et al. |
| 10,863,984 B2 | 12/2020 | Shelton, IV et al. |
| 10,863,986 B2 | 12/2020 | Yates et al. |
| 10,869,664 B2 | 12/2020 | Shelton, IV |
| 10,869,665 B2 | 12/2020 | Shelton, IV et al. |
| 10,869,666 B2 | 12/2020 | Shelton, IV et al. |
| 10,869,669 B2 | 12/2020 | Shelton, IV et al. |
| 10,874,290 B2 | 12/2020 | Walen et al. |
| 10,874,391 B2 | 12/2020 | Shelton, IV et al. |
| 10,874,392 B2 | 12/2020 | Scirica et al. |
| 10,874,393 B2 | 12/2020 | Satti, III et al. |
| 10,874,396 B2 | 12/2020 | Moore et al. |
| 10,874,399 B2 | 12/2020 | Zhang |
| 10,879,275 B2 | 12/2020 | Li et al. |
| D907,647 S | 1/2021 | Siebel et al. |
| D907,648 S | 1/2021 | Siebel et al. |
| 10,881,395 B2 | 1/2021 | Merchant et al. |
| 10,881,396 B2 | 1/2021 | Shelton, IV et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,888,318 B2 | 1/2021 | Parihar et al. |
| 10,888,321 B2 | 1/2021 | Shelton, IV et al. |
| 10,888,322 B2 | 1/2021 | Morgan et al. |
| 10,888,325 B2 | 1/2021 | Harris et al. |
| 10,888,328 B2 | 1/2021 | Shelton, IV et al. |
| 10,888,329 B2 | 1/2021 | Moore et al. |
| 10,888,330 B2 | 1/2021 | Moore et al. |
| 10,888,369 B2 | 1/2021 | Messerly et al. |
| 10,892,899 B2 | 1/2021 | Shelton, IV et al. |
| 10,893,853 B2 | 1/2021 | Shelton, IV et al. |
| 10,893,863 B2 | 1/2021 | Shelton, IV et al. |
| 10,893,864 B2 | 1/2021 | Harris et al. |
| 10,893,867 B2 | 1/2021 | Leimbach et al. |
| 10,898,183 B2 | 1/2021 | Shelton, IV et al. |
| 10,898,184 B2 | 1/2021 | Yates et al. |
| 10,898,185 B2 | 1/2021 | Overmyer et al. |
| 10,898,186 B2 | 1/2021 | Bakos et al. |
| 10,898,190 B2 | 1/2021 | Yates et al. |
| 10,898,193 B2 | 1/2021 | Shelton, IV et al. |
| 10,898,194 B2 | 1/2021 | Moore et al. |
| 10,898,195 B2 | 1/2021 | Moore et al. |
| 10,903,685 B2 | 1/2021 | Yates et al. |
| D910,847 S | 2/2021 | Shelton, IV et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,905,422 B2 | 2/2021 | Bakos et al. |
| 10,905,423 B2 | 2/2021 | Baber et al. |
| 10,905,426 B2 | 2/2021 | Moore et al. |
| 10,905,427 B2 | 2/2021 | Moore et al. |
| 10,911,515 B2 | 2/2021 | Biasi et al. |
| 10,912,559 B2 | 2/2021 | Harris et al. |
| 10,912,562 B2 | 2/2021 | Dunki-Jacobs et al. |
| 10,912,575 B2 | 2/2021 | Shelton, IV et al. |
| 10,918,364 B2 | 2/2021 | Applegate et al. |
| 10,918,380 B2 | 2/2021 | Morgan et al. |
| 10,918,385 B2 | 2/2021 | Overmyer et al. |
| 10,918,386 B2 | 2/2021 | Shelton, IV et al. |
| 10,925,600 B2 | 2/2021 | McCuen |
| 10,925,605 B2 | 2/2021 | Moore et al. |
| D914,878 S | 3/2021 | Shelton, IV et al. |
| 10,932,772 B2 | 3/2021 | Shelton, IV et al. |
| 10,932,774 B2 | 3/2021 | Shelton, IV |
| 10,932,775 B2 | 3/2021 | Shelton, IV et al. |
| 10,932,778 B2 | 3/2021 | Smith et al. |
| 10,932,779 B2 | 3/2021 | Vendely et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,945,728 B2 | 3/2021 | Morgan et al. |
| 10,945,729 B2 | 3/2021 | Shelton, IV et al. |
| 10,945,731 B2 | 3/2021 | Baxter, III et al. |
| 10,952,708 B2 | 3/2021 | Scheib et al. |
| 10,952,727 B2 | 3/2021 | Giordano et al. |
| 10,952,728 B2 | 3/2021 | Shelton, IV et al. |
| 10,952,759 B2 | 3/2021 | Messerly et al. |
| 10,952,767 B2 | 3/2021 | Kostrzewski et al. |
| 10,959,722 B2 | 3/2021 | Morgan et al. |
| 10,959,725 B2 | 3/2021 | Kerr et al. |
| 10,959,727 B2 | 3/2021 | Hunter et al. |
| 10,959,731 B2 | 3/2021 | Casasanta, Jr. et al. |
| 10,959,744 B2 | 3/2021 | Shelton, IV et al. |
| D917,500 S | 4/2021 | Siebel et al. |
| 10,966,627 B2 | 4/2021 | Shelton, IV et al. |
| 10,966,717 B2 | 4/2021 | Shah et al. |
| 10,966,718 B2 | 4/2021 | Shelton, IV et al. |
| 10,966,791 B2 | 4/2021 | Harris et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0034530 A1 | 10/2001 | Malackowski et al. |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0111624 A1 | 8/2002 | Witt et al. |
| 2002/0116063 A1 | 8/2002 | Giannetti et al. |
| 2002/0117534 A1 | 8/2002 | Green et al. |
| 2002/0127265 A1 | 9/2002 | Bowman et al. |

(56) References Cited

U.S. PATENT DOCUMENTS

| | | |
|---|---|---|
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0177848 A1 | 11/2002 | Truckai et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0040670 A1 | 2/2003 | Govari |
| 2003/0045835 A1 | 3/2003 | Anderson et al. |
| 2003/0047230 A1 | 3/2003 | Kim |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0121586 A1 | 7/2003 | Mitra et al. |
| 2003/0139741 A1 | 7/2003 | Goble et al. |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0164172 A1 | 9/2003 | Chumas et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092992 A1 | 5/2004 | Adams et al. |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |

(56) References Cited

U.S. PATENT DOCUMENTS

| | | |
|---|---|---|
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0235368 A1 | 10/2006 | Oz |
| 2006/0241666 A1 | 10/2006 | Briggs et al. |
| 2006/0244460 A1 | 11/2006 | Weaver |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0103437 A1 | 5/2007 | Rosenberg |
| 2007/0106113 A1 | 5/2007 | Ravo |
| 2007/0106317 A1 | 5/2007 | Shelton et al. |
| 2007/0118115 A1 | 5/2007 | Artale et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0173872 A1 | 7/2007 | Neuenfeldt |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0244496 A1 | 10/2007 | Hellenkamp |
| 2007/0246505 A1 | 10/2007 | Pace-Floridia et al. |
| 2007/0260132 A1 | 11/2007 | Sterling |
| 2007/0262592 A1 | 11/2007 | Hwang et al. |
| 2007/0270660 A1 | 11/2007 | Caylor et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0290027 A1 | 12/2007 | Maatta et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0051833 A1 | 2/2008 | Gramuglia et al. |
| 2008/0064920 A1 | 3/2008 | Bakos et al. |

(56) References Cited

U.S. PATENT DOCUMENTS

| | | |
|---|---|---|
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0077158 A1 | 3/2008 | Haider et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0149682 A1 | 6/2008 | Uhm |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0208058 A1 | 8/2008 | Sabata et al. |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0255420 A1 | 10/2008 | Lee et al. |
| 2008/0255663 A1 | 10/2008 | Akpek et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0281332 A1 | 11/2008 | Taylor |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0298784 A1 | 12/2008 | Kastner |
| 2008/0308602 A1 | 12/2008 | Timm et al. |
| 2008/0308603 A1 | 12/2008 | Shelton et al. |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0110533 A1 | 4/2009 | Jinno |
| 2009/0112234 A1 | 4/2009 | Crainich et al. |
| 2009/0118762 A1 | 5/2009 | Crainch et al. |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177218 A1 | 7/2009 | Young et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0248100 A1 | 10/2009 | Vaisnys et al. |
| 2009/0253959 A1 | 10/2009 | Yoshie et al. |
| 2009/0255974 A1 | 10/2009 | Viola |
| 2009/0261141 A1 | 10/2009 | Stratton et al. |
| 2009/0262078 A1 | 10/2009 | Pizzi |
| 2009/0270895 A1 | 10/2009 | Churchill et al. |
| 2009/0278406 A1 | 11/2009 | Hoffman |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0325859 A1 | 12/2009 | Ameer et al. |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0030239 A1 | 2/2010 | Viola et al. |
| 2010/0032179 A1 | 2/2010 | Hanspers et al. |
| 2010/0036370 A1 | 2/2010 | Mirel et al. |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100123 A1 | 4/2010 | Bennett |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0137990 A1 | 6/2010 | Apatsidis et al. |
| 2010/0138659 A1 | 6/2010 | Carmichael et al. |
| 2010/0145146 A1 | 6/2010 | Melder |
| 2010/0147921 A1 | 6/2010 | Olson |
| 2010/0147922 A1 | 6/2010 | Olson |
| 2010/0159435 A1 | 6/2010 | Mueller et al. |
| 2010/0179022 A1 | 7/2010 | Shirokoshi |

(56) References Cited

U.S. PATENT DOCUMENTS

| | | |
|---|---|---|
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0228250 A1 | 9/2010 | Brogna |
| 2010/0234687 A1 | 9/2010 | Azarbarzin et al. |
| 2010/0241137 A1 | 9/2010 | Doyle et al. |
| 2010/0245102 A1 | 9/2010 | Yokoi |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1* | 11/2010 | Castro ............... A61B 17/07207 600/104 |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0009694 A1 | 1/2011 | Schultz et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0029270 A1 | 2/2011 | Mueglitz |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0056717 A1 | 3/2011 | Herisse |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174099 A1* | 7/2011 | Ross ................... A61B 17/072 74/89.32 |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0220381 A1 | 9/2011 | Friese et al. |
| 2011/0225105 A1 | 9/2011 | Scholer et al. |
| 2011/0230713 A1 | 9/2011 | Kleemann et al. |
| 2011/0238044 A1 | 9/2011 | Main et al. |
| 2011/0241597 A1 | 10/2011 | Zhu et al. |
| 2011/0256266 A1 | 10/2011 | Orme et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0290856 A1 | 12/2011 | Shelton, IV et al. |
| 2011/0290858 A1 | 12/2011 | Whitman et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2011/0319896 A1* | 12/2011 | Papenfuss .......... A61B 17/1631 606/79 |
| 2012/0004636 A1 | 1/2012 | Lo |
| 2012/0007442 A1 | 1/2012 | Rhodes et al. |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0197272 A1 | 8/2012 | Oray et al. |
| 2012/0211542 A1 | 8/2012 | Racenet |
| 2012/0220990 A1 | 8/2012 | Mckenzie et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Wdenhouse et al. |
| 2012/0251861 A1 | 10/2012 | Liang et al. |
| 2012/0253328 A1 | 10/2012 | Cunningham et al. |
| 2012/0271327 A1 | 10/2012 | West et al. |
| 2012/0283707 A1 | 11/2012 | Giordano et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0296342 A1 | 11/2012 | Haglund Wendelschafer |
| 2012/0298722 A1 | 11/2012 | Hess et al. |
| 2012/0301498 A1 | 11/2012 | Altreuter et al. |
| 2012/0330329 A1 | 12/2012 | Harris et al. |
| 2013/0006227 A1 | 1/2013 | Takashino |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0106352 A1 | 5/2013 | Nagamine |

(56) References Cited

U.S. PATENT DOCUMENTS

| | | |
|---|---|---|
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172878 A1 | 7/2013 | Smith |
| 2013/0175317 A1 | 7/2013 | Yates et al. |
| 2013/0211244 A1 | 8/2013 | Nathaniel |
| 2013/0214025 A1 | 8/2013 | Zemlok et al. |
| 2013/0215449 A1 | 8/2013 | Yamasaki |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0306704 A1 | 11/2013 | Balbierz et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0014704 A1 | 1/2014 | Onukuri et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0022283 A1 | 1/2014 | Chan et al. |
| 2014/0039549 A1 | 2/2014 | Belsky et al. |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0115229 A1 | 4/2014 | Kothamasu et al. |
| 2014/0131418 A1 | 5/2014 | Kostrzewski |
| 2014/0135832 A1 | 5/2014 | Park et al. |
| 2014/0151433 A1 | 6/2014 | Shelton, IV et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0188091 A1 | 7/2014 | Vidal et al. |
| 2014/0188159 A1 | 7/2014 | Steege |
| 2014/0207124 A1 | 7/2014 | Aldridge et al. |
| 2014/0209658 A1 | 7/2014 | Skalla et al. |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch et al. |
| 2014/0249573 A1 | 9/2014 | Arav |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0025549 A1 | 1/2015 | Kilroy et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076211 A1 | 3/2015 | Irka et al. |
| 2015/0076212 A1 | 3/2015 | Shelton, IV |
| 2015/0082624 A1 | 3/2015 | Craig et al. |
| 2015/0083781 A1 | 3/2015 | Giordano et al. |
| 2015/0083782 A1 | 3/2015 | Scheib et al. |
| 2015/0087952 A1 | 3/2015 | Albert et al. |
| 2015/0088127 A1 | 3/2015 | Craig et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |
| 2015/0127021 A1 | 5/2015 | Harris et al. |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209045 A1 | 7/2015 | Hodgkinson et al. |
| 2015/0222212 A1 | 8/2015 | Iwata |
| 2015/0223868 A1 | 8/2015 | Brandt et al. |
| 2015/0230697 A1 | 8/2015 | Phee et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297233 A1 | 10/2015 | Huitema et al. |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0352699 A1 | 12/2015 | Sakai et al. |
| 2015/0366585 A1 | 12/2015 | Lemay et al. |
| 2015/0367497 A1 | 12/2015 | Ito et al. |

(56) References Cited

U.S. PATENT DOCUMENTS

| | | |
|---|---|---|
| 2015/0372265 A1 | 12/2015 | Morisaku et al. |
| 2015/0374372 A1 | 12/2015 | Zergiebel et al. |
| 2015/0374378 A1 | 12/2015 | Giordano et al. |
| 2016/0000431 A1 | 1/2016 | Giordano et al. |
| 2016/0000437 A1 | 1/2016 | Giordano et al. |
| 2016/0000452 A1 | 1/2016 | Yates et al. |
| 2016/0000453 A1 | 1/2016 | Yates et al. |
| 2016/0030042 A1 | 2/2016 | Heinrich et al. |
| 2016/0051316 A1 | 2/2016 | Boudreaux |
| 2016/0066913 A1 | 3/2016 | Swayze et al. |
| 2016/0069449 A1 | 3/2016 | Kanai et al. |
| 2016/0074040 A1 | 3/2016 | Wdenhouse et al. |
| 2016/0082161 A1 | 3/2016 | Zilberman et al. |
| 2016/0120545 A1 | 5/2016 | Shelton, IV et al. |
| 2016/0135835 A1 | 5/2016 | Onuma |
| 2016/0135895 A1 | 5/2016 | Faasse et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192960 A1 | 7/2016 | Bueno et al. |
| 2016/0199063 A1 | 7/2016 | Mandakolathur Vasudevan et al. |
| 2016/0199956 A1 | 7/2016 | Shelton, IV et al. |
| 2016/0235494 A1 | 8/2016 | Shelton, IV et al. |
| 2016/0242783 A1 | 8/2016 | Shelton, IV et al. |
| 2016/0249910 A1 | 9/2016 | Shelton, IV et al. |
| 2016/0249922 A1 | 9/2016 | Morgan et al. |
| 2016/0256159 A1 | 9/2016 | Pinjala et al. |
| 2016/0256221 A1 | 9/2016 | Smith |
| 2016/0256229 A1 | 9/2016 | Morgan et al. |
| 2016/0262745 A1 | 9/2016 | Morgan et al. |
| 2016/0262921 A1 | 9/2016 | Balbierz et al. |
| 2016/0287265 A1 | 10/2016 | Macdonald et al. |
| 2016/0287279 A1 | 10/2016 | Bovay et al. |
| 2016/0310143 A1 | 10/2016 | Bettuchi |
| 2016/0314716 A1 | 10/2016 | Grubbs |
| 2016/0345976 A1 | 12/2016 | Gonzalez et al. |
| 2016/0367122 A1 | 12/2016 | Ichimura et al. |
| 2017/0000553 A1 | 1/2017 | Wiener et al. |
| 2017/0007244 A1 | 1/2017 | Shelton, IV et al. |
| 2017/0007245 A1 | 1/2017 | Shelton, IV et al. |
| 2017/0007250 A1 | 1/2017 | Shelton, IV et al. |
| 2017/0007347 A1 | 1/2017 | Jaworek et al. |
| 2017/0014125 A1 | 1/2017 | Shelton, IV et al. |
| 2017/0027572 A1 | 2/2017 | Nalagatla et al. |
| 2017/0049448 A1 | 2/2017 | Widenhouse et al. |
| 2017/0055819 A1 | 3/2017 | Hansen et al. |
| 2017/0056000 A1 | 3/2017 | Nalagatla et al. |
| 2017/0056002 A1 | 3/2017 | Nalagatla et al. |
| 2017/0056005 A1 | 3/2017 | Shelton, IV et al. |
| 2017/0066054 A1 | 3/2017 | Birky |
| 2017/0079642 A1 | 3/2017 | Overmyer et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086838 A1 | 3/2017 | Harris et al. |
| 2017/0086842 A1 | 3/2017 | Shelton, IV et al. |
| 2017/0086930 A1 | 3/2017 | Thompson et al. |
| 2017/0105733 A1 | 4/2017 | Scheib et al. |
| 2017/0172382 A1 | 6/2017 | Nir et al. |
| 2017/0172662 A1 | 6/2017 | Panescu et al. |
| 2017/0182195 A1 | 6/2017 | Wagner |
| 2017/0182211 A1 | 6/2017 | Raxworthy et al. |
| 2017/0196558 A1 | 7/2017 | Morgan et al. |
| 2017/0196637 A1 | 7/2017 | Shelton, IV et al. |
| 2017/0196649 A1 | 7/2017 | Yates et al. |
| 2017/0202571 A1 | 7/2017 | Shelton, IV et al. |
| 2017/0202770 A1 | 7/2017 | Friedrich et al. |
| 2017/0209145 A1 | 7/2017 | Swayze et al. |
| 2017/0224332 A1 | 8/2017 | Hunter et al. |
| 2017/0224334 A1 | 8/2017 | Worthington et al. |
| 2017/0224339 A1 | 8/2017 | Huang et al. |
| 2017/0231627 A1 | 8/2017 | Shelton, IV et al. |
| 2017/0231628 A1 | 8/2017 | Shelton, IV et al. |
| 2017/0238962 A1 | 8/2017 | Hansen et al. |
| 2017/0249431 A1 | 8/2017 | Shelton, IV et al. |
| 2017/0262110 A1 | 9/2017 | Polishchuk et al. |
| 2017/0265774 A1 | 9/2017 | Johnson et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0333034 A1 | 11/2017 | Morgan et al. |
| 2017/0333035 A1 | 11/2017 | Morgan et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0358052 A1 | 12/2017 | Yuan |
| 2017/0360441 A1 | 12/2017 | Sgroi |
| 2017/0367695 A1 | 12/2017 | Shelton, IV et al. |
| 2018/0000545 A1 | 1/2018 | Giordano et al. |
| 2018/0008356 A1 | 1/2018 | Giordano et al. |
| 2018/0028185 A1 | 2/2018 | Shelton, IV et al. |
| 2018/0042611 A1 | 2/2018 | Swayze et al. |
| 2018/0055513 A1 | 3/2018 | Shelton, IV et al. |
| 2018/0064440 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070942 A1 | 3/2018 | Shelton, IV et al. |
| 2018/0085116 A1 | 3/2018 | Yates et al. |
| 2018/0085117 A1 | 3/2018 | Shelton, IV et al. |
| 2018/0092710 A1 | 4/2018 | Bosisio et al. |
| 2018/0110522 A1 | 4/2018 | Shelton, IV et al. |
| 2018/0110523 A1 | 4/2018 | Shelton, IV |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125590 A1 | 5/2018 | Giordano et al. |
| 2018/0125594 A1 | 5/2018 | Beardsley |
| 2018/0126504 A1 | 5/2018 | Shelton, IV et al. |
| 2018/0132845 A1 | 5/2018 | Schmid et al. |
| 2018/0132849 A1 | 5/2018 | Miller et al. |
| 2018/0132850 A1 | 5/2018 | Leimbach et al. |
| 2018/0132926 A1 | 5/2018 | Asher et al. |
| 2018/0132952 A1 | 5/2018 | Spivey et al. |
| 2018/0140299 A1 | 5/2018 | Weaner et al. |
| 2018/0146960 A1 | 5/2018 | Shelton, IV et al. |
| 2018/0150153 A1 | 5/2018 | Yoon et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168590 A1 | 6/2018 | Overmyer et al. |
| 2018/0168592 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |

(56) References Cited

U.S. PATENT DOCUMENTS

| | | |
|---|---|---|
| 2018/0168650 A1 | 6/2018 | Shelton, IV et al. |
| 2018/0168651 A1 | 6/2018 | Shelton, IV et al. |
| 2018/0228490 A1 | 8/2018 | Richard et al. |
| 2018/0250001 A1 | 9/2018 | Aronhalt et al. |
| 2018/0271520 A1 | 9/2018 | Shelton, IV et al. |
| 2018/0271604 A1 | 9/2018 | Grout et al. |
| 2018/0273597 A1 | 9/2018 | Stimson |
| 2018/0289369 A1 | 10/2018 | Shelton, IV et al. |
| 2018/0289371 A1 | 10/2018 | Wang et al. |
| 2018/0296211 A1 | 10/2018 | Timm et al. |
| 2018/0296216 A1 | 10/2018 | Shelton, IV et al. |
| 2018/0310935 A1 | 11/2018 | Wixey |
| 2018/0317919 A1 | 11/2018 | Shelton, IV et al. |
| 2018/0333155 A1 | 11/2018 | Hall et al. |
| 2018/0333169 A1 | 11/2018 | Leimbach et al. |
| 2018/0344319 A1 | 12/2018 | Shelton, IV et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360445 A1 | 12/2018 | Shelton, IV et al. |
| 2018/0360446 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0360471 A1 | 12/2018 | Parfett et al. |
| 2018/0360472 A1 | 12/2018 | Harris et al. |
| 2018/0360473 A1 | 12/2018 | Shelton, IV et al. |
| 2018/0368833 A1 | 12/2018 | Shelton, IV et al. |
| 2018/0368838 A1 | 12/2018 | Shelton, IV et al. |
| 2018/0368839 A1 | 12/2018 | Shelton, IV et al. |
| 2018/0368841 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2019/0000457 A1 | 1/2019 | Shelton, IV et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000469 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000481 A1 | 1/2019 | Harris et al. |
| 2019/0000525 A1 | 1/2019 | Messerly et al. |
| 2019/0000531 A1 | 1/2019 | Messerly et al. |
| 2019/0000538 A1 | 1/2019 | Widenhouse et al. |
| 2019/0000565 A1 | 1/2019 | Shelton, IV et al. |
| 2019/0015096 A1 | 1/2019 | Shelton, IV et al. |
| 2019/0015102 A1 | 1/2019 | Baber et al. |
| 2019/0015165 A1 | 1/2019 | Giordano et al. |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038371 A1 | 2/2019 | Wixey et al. |
| 2019/0076143 A1 | 3/2019 | Smith |
| 2019/0090871 A1 | 3/2019 | Shelton, IV et al. |
| 2019/0091183 A1 | 3/2019 | Tomat et al. |
| 2019/0099177 A1 | 4/2019 | Yates et al. |
| 2019/0099179 A1 | 4/2019 | Leimbach et al. |
| 2019/0099181 A1 | 4/2019 | Shelton, IV et al. |
| 2019/0099229 A1 | 4/2019 | Spivey et al. |
| 2019/0104919 A1 | 4/2019 | Shelton, IV et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105038 A1 | 4/2019 | Schmid et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0110791 A1 | 4/2019 | Shelton, IV et al. |
| 2019/0110792 A1 | 4/2019 | Shelton, IV et al. |
| 2019/0117216 A1 | 4/2019 | Overmyer et al. |
| 2019/0117222 A1 | 4/2019 | Shelton, IV et al. |
| 2019/0117224 A1 | 4/2019 | Setser et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125339 A1 | 5/2019 | Shelton, IV et al. |
| 2019/0125343 A1 | 5/2019 | Wise et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125384 A1 | 5/2019 | Scheib et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133422 A1 | 5/2019 | Nakamura |
| 2019/0142421 A1 | 5/2019 | Shelton, IV |
| 2019/0142449 A1 | 5/2019 | Shelton, IV et al. |
| 2019/0150925 A1 | 5/2019 | Marczyk et al. |
| 2019/0159778 A1 | 5/2019 | Shelton, IV et al. |
| 2019/0183491 A1 | 6/2019 | Shelton, IV et al. |
| 2019/0183496 A1 | 6/2019 | Shelton, IV et al. |
| 2019/0183498 A1 | 6/2019 | Shelton, IV et al. |
| 2019/0183499 A1 | 6/2019 | Shelton, IV et al. |
| 2019/0183501 A1 | 6/2019 | Shelton, IV et al. |
| 2019/0183502 A1 | 6/2019 | Shelton, IV et al. |
| 2019/0183594 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192144 A1 | 6/2019 | Parfett et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192149 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192152 A1 | 6/2019 | Morgan et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192156 A1 | 6/2019 | Simms et al. |
| 2019/0192157 A1 | 6/2019 | Scott et al. |
| 2019/0192158 A1 | 6/2019 | Scott et al. |
| 2019/0192159 A1 | 6/2019 | Simms et al. |
| 2019/0192227 A1 | 6/2019 | Shelton, IV et al. |

(56) References Cited

U.S. PATENT DOCUMENTS

| | | |
|---|---|---|
| 2019/0192235 A1 | 6/2019 | Harris et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200998 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201145 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0209164 A1 | 7/2019 | Timm et al. |
| 2019/0209165 A1 | 7/2019 | Timm et al. |
| 2019/0209171 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0223865 A1 | 7/2019 | Shelton, IV et al. |
| 2019/0261984 A1 | 8/2019 | Nelson et al. |
| 2019/0261991 A1 | 8/2019 | Beckman et al. |
| 2019/0269400 A1 | 9/2019 | Mandakolathur Vasudevan et al. |
| 2019/0269402 A1 | 9/2019 | Murray et al. |
| 2019/0269407 A1 | 9/2019 | Swensgard et al. |
| 2019/0269428 A1 | 9/2019 | Allen et al. |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0274685 A1 | 9/2019 | Olson et al. |
| 2019/0290263 A1 | 9/2019 | Morgan et al. |
| 2019/0290264 A1 | 9/2019 | Morgan et al. |
| 2019/0290265 A1 | 9/2019 | Shelton, IV et al. |
| 2019/0290266 A1 | 9/2019 | Scheib et al. |
| 2019/0290267 A1 | 9/2019 | Baxter, III et al. |
| 2019/0290281 A1 | 9/2019 | Aronhalt et al. |
| 2019/0290297 A1 | 9/2019 | Haider et al. |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298348 A1 | 10/2019 | Harris et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307455 A1 | 10/2019 | Shelton, IV et al. |
| 2019/0307456 A1 | 10/2019 | Shelton, IV et al. |
| 2019/0307476 A1 | 10/2019 | Shelton, IV et al. |
| 2019/0307477 A1 | 10/2019 | Shelton, IV et al. |
| 2019/0307478 A1 | 10/2019 | Shelton, IV et al. |
| 2019/0307479 A1 | 10/2019 | Shelton, IV et al. |
| 2019/0314016 A1 | 10/2019 | Huitema et al. |
| 2019/0314017 A1 | 10/2019 | Huitema et al. |
| 2019/0314018 A1 | 10/2019 | Huitema et al. |
| 2019/0321039 A1 | 10/2019 | Harris et al. |
| 2019/0321040 A1 | 10/2019 | Shelton, IV |
| 2019/0321041 A1 | 10/2019 | Shelton, IV |
| 2019/0328386 A1 | 10/2019 | Harris et al. |
| 2019/0328387 A1 | 10/2019 | Overmyer et al. |
| 2019/0328390 A1 | 10/2019 | Harris et al. |
| 2019/0336128 A1 | 11/2019 | Harris et al. |
| 2019/0343514 A1 | 11/2019 | Shelton, IV et al. |
| 2019/0343515 A1 | 11/2019 | Morgan et al. |
| 2019/0343518 A1 | 11/2019 | Shelton, IV |
| 2019/0343525 A1 | 11/2019 | Shelton, IV et al. |
| 2019/0350581 A1 | 11/2019 | Baxter, III et al. |
| 2019/0350582 A1 | 11/2019 | Shelton, IV et al. |
| 2019/0357909 A1 | 11/2019 | Huitema et al. |
| 2019/0365384 A1 | 12/2019 | Baxter, III et al. |
| 2019/0374224 A1 | 12/2019 | Huitema et al. |
| 2020/0000461 A1 | 1/2020 | Yates et al. |
| 2020/0000468 A1 | 1/2020 | Shelton, IV et al. |
| 2020/0000469 A1 | 1/2020 | Shelton, IV et al. |
| 2020/0000471 A1 | 1/2020 | Shelton, IV et al. |
| 2020/0000531 A1 | 1/2020 | Giordano et al. |
| 2020/0008800 A1 | 1/2020 | Shelton, IV et al. |
| 2020/0008802 A1 | 1/2020 | Aronhalt et al. |
| 2020/0008809 A1 | 1/2020 | Shelton, IV et al. |
| 2020/0015815 A1 | 1/2020 | Harris et al. |
| 2020/0015819 A1 | 1/2020 | Shelton, IV et al. |
| 2020/0022702 A1 | 1/2020 | Shelton, IV et al. |
| 2020/0029964 A1 | 1/2020 | Overmyer et al. |
| 2020/0030050 A1 | 1/2020 | Shelton, IV et al. |
| 2020/0038016 A1 | 2/2020 | Shelton, IV et al. |
| 2020/0038018 A1 | 2/2020 | Shelton, IV et al. |
| 2020/0038020 A1 | 2/2020 | Yates et al. |
| 2020/0046348 A1 | 2/2020 | Shelton, IV et al. |
| 2020/0046893 A1 | 2/2020 | Shelton, IV et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |

(56) References Cited

U.S. PATENT DOCUMENTS

| | | |
|---|---|---|
| 2020/0054324 A1 | 2/2020 | Shelton, IV et al. |
| 2020/0054326 A1 | 2/2020 | Harris et al. |
| 2020/0054328 A1 | 2/2020 | Harris et al. |
| 2020/0054330 A1 | 2/2020 | Harris et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060680 A1 | 2/2020 | Shelton, IV et al. |
| 2020/0060681 A1 | 2/2020 | Shelton, IV et al. |
| 2020/0060713 A1 | 2/2020 | Leimbach et al. |
| 2020/0077994 A1 | 3/2020 | Shelton, IV et al. |
| 2020/0078015 A1 | 3/2020 | Miller et al. |
| 2020/0078016 A1 | 3/2020 | Swayze et al. |
| 2020/0085427 A1 | 3/2020 | Giordano et al. |
| 2020/0085431 A1 | 3/2020 | Swayze et al. |
| 2020/0085435 A1 | 3/2020 | Shelton, IV et al. |
| 2020/0085436 A1 | 3/2020 | Beckman et al. |
| 2020/0085518 A1 | 3/2020 | Giordano et al. |
| 2020/0093484 A1 | 3/2020 | Shelton, IV et al. |
| 2020/0093485 A1 | 3/2020 | Shelton, IV et al. |
| 2020/0093487 A1 | 3/2020 | Baber et al. |
| 2020/0093488 A1 | 3/2020 | Baber et al. |
| 2020/0093506 A1 | 3/2020 | Leimbach et al. |
| 2020/0093550 A1 | 3/2020 | Spivey et al. |
| 2020/0100699 A1 | 4/2020 | Shelton, IV et al. |
| 2020/0100783 A1 | 4/2020 | Yates et al. |
| 2020/0100787 A1 | 4/2020 | Shelton, IV et al. |
| 2020/0107829 A1 | 4/2020 | Shelton, IV et al. |
| 2020/0138434 A1 | 5/2020 | Miller et al. |
| 2020/0138435 A1 | 5/2020 | Shelton, IV et al. |
| 2020/0138436 A1 | 5/2020 | Yates et al. |
| 2020/0138437 A1 | 5/2020 | Vendely et al. |
| 2020/0138534 A1 | 5/2020 | Garcia Kilroy et al. |
| 2020/0146678 A1 | 5/2020 | Leimbach et al. |
| 2020/0146741 A1 | 5/2020 | Long et al. |
| 2020/0155151 A1 | 5/2020 | Overmyer et al. |
| 2020/0155155 A1 | 5/2020 | Shelton, IV et al. |
| 2020/0178958 A1 | 6/2020 | Overmyer et al. |
| 2020/0178960 A1 | 6/2020 | Overmyer et al. |
| 2020/0187943 A1 | 6/2020 | Shelton, IV et al. |
| 2020/0214706 A1 | 7/2020 | Vendely et al. |
| 2020/0214731 A1 | 7/2020 | Shelton, IV et al. |
| 2020/0222047 A1 | 7/2020 | Shelton, IV et al. |
| 2020/0229812 A1 | 7/2020 | Parihar et al. |
| 2020/0229816 A1 | 7/2020 | Bakos et al. |
| 2020/0237371 A1 | 7/2020 | Huitema et al. |
| 2020/0246001 A1 | 8/2020 | Ming et al. |
| 2020/0253605 A1 | 8/2020 | Swayze et al. |
| 2020/0261106 A1 | 8/2020 | Hess et al. |
| 2020/0268377 A1 | 8/2020 | Schmid et al. |
| 2020/0268394 A1 | 8/2020 | Parfett et al. |
| 2020/0275926 A1 | 9/2020 | Shelton, IV et al. |
| 2020/0275927 A1 | 9/2020 | Shelton, IV et al. |
| 2020/0275928 A1 | 9/2020 | Shelton, IV et al. |
| 2020/0275930 A1 | 9/2020 | Harris et al. |
| 2020/0281585 A1 | 9/2020 | Timm et al. |
| 2020/0281587 A1 | 9/2020 | Schmid et al. |
| 2020/0281590 A1 | 9/2020 | Shelton, IV et al. |
| 2020/0289112 A1 | 9/2020 | Whitfield et al. |
| 2020/0297340 A1 | 9/2020 | Hess et al. |
| 2020/0297341 A1 | 9/2020 | Yates et al. |
| 2020/0297346 A1 | 9/2020 | Shelton, IV et al. |
| 2020/0297438 A1 | 9/2020 | Shelton, IV et al. |
| 2020/0305862 A1 | 10/2020 | Yates et al. |
| 2020/0305863 A1 | 10/2020 | Yates et al. |
| 2020/0305864 A1 | 10/2020 | Yates et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305870 A1 | 10/2020 | Shelton, IV |
| 2020/0305871 A1 | 10/2020 | Shelton, IV et al. |
| 2020/0305874 A1 | 10/2020 | Huitema et al. |
| 2020/0315612 A1 | 10/2020 | Shelton, IV et al. |
| 2020/0315615 A1 | 10/2020 | Yates et al. |
| 2020/0315616 A1 | 10/2020 | Yates et al. |
| 2020/0315625 A1 | 10/2020 | Hall et al. |
| 2020/0315983 A1 | 10/2020 | Widenhouse et al. |
| 2020/0323526 A1 | 10/2020 | Huang et al. |
| 2020/0330092 A1 | 10/2020 | Shelton, IV et al. |
| 2020/0330093 A1 | 10/2020 | Shelton, IV et al. |
| 2020/0330094 A1 | 10/2020 | Baxter, III et al. |
| 2020/0330096 A1 | 10/2020 | Shelton, IV et al. |
| 2020/0337693 A1 | 10/2020 | Shelton, IV et al. |
| 2020/0337702 A1 | 10/2020 | Shelton, IV et al. |
| 2020/0337703 A1 | 10/2020 | Shelton, IV et al. |
| 2020/0337791 A1 | 10/2020 | Shelton, IV et al. |
| 2020/0345346 A1 | 11/2020 | Shelton, IV et al. |
| 2020/0345349 A1 | 11/2020 | Kimball et al. |
| 2020/0345352 A1 | 11/2020 | Shelton, IV et al. |
| 2020/0345353 A1 | 11/2020 | Leimbach et al. |
| 2020/0345354 A1 | 11/2020 | Leimbach et al. |
| 2020/0345355 A1 | 11/2020 | Baxter, III et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345360 A1 | 11/2020 | Leimbach et al. |
| 2020/0345446 A1 | 11/2020 | Kimball et al. |
| 2020/0352562 A1 | 11/2020 | Timm et al. |
| 2020/0367885 A1 | 11/2020 | Yates et al. |
| 2020/0367886 A1 | 11/2020 | Shelton, IV et al. |
| 2020/0375585 A1 | 12/2020 | Swayze et al. |
| 2020/0375592 A1 | 12/2020 | Hall et al. |
| 2020/0375593 A1 | 12/2020 | Hunter et al. |
| 2020/0375597 A1 | 12/2020 | Shelton, IV et al. |
| 2020/0390444 A1 | 12/2020 | Harris et al. |
| 2020/0397433 A1 | 12/2020 | Lytle, IV et al. |
| 2020/0397434 A1 | 12/2020 | Overmyer et al. |
| 2020/0405290 A1 | 12/2020 | Shelton, IV et al. |
| 2020/0405291 A1 | 12/2020 | Shelton, IV et al. |
| 2020/0405292 A1 | 12/2020 | Shelton, IV et al. |
| 2020/0405293 A1 | 12/2020 | Shelton, IV et al. |
| 2020/0405294 A1 | 12/2020 | Shelton, IV |
| 2020/0405295 A1 | 12/2020 | Shelton, IV et al. |
| 2020/0405296 A1 | 12/2020 | Shelton, IV et al. |
| 2020/0405297 A1 | 12/2020 | Shelton, IV et al. |
| 2020/0405301 A1 | 12/2020 | Shelton, IV et al. |
| 2020/0405302 A1 | 12/2020 | Shelton, IV et al. |
| 2020/0405303 A1 | 12/2020 | Shelton, IV |
| 2020/0405305 A1 | 12/2020 | Shelton, IV et al. |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405309 A1 | 12/2020 | Shelton, IV et al. |
| 2020/0405311 A1 | 12/2020 | Shelton, IV et al. |
| 2020/0405312 A1 | 12/2020 | Shelton, IV et al. |
| 2020/0405313 A1 | 12/2020 | Shelton, IV |
| 2020/0405314 A1 | 12/2020 | Shelton, IV et al. |
| 2020/0405316 A1 | 12/2020 | Shelton, IV et al. |
| 2020/0405341 A1 | 12/2020 | Hess et al. |
| 2020/0405409 A1 | 12/2020 | Shelton, IV et al. |
| 2020/0405410 A1 | 12/2020 | Shelton, IV |
| 2020/0405416 A1 | 12/2020 | Shelton, IV et al. |
| 2020/0405422 A1 | 12/2020 | Shelton, IV et al. |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0405440 A1 | 12/2020 | Shelton, IV et al. |
| 2020/0405441 A1 | 12/2020 | Shelton, IV et al. |
| 2020/0410177 A1 | 12/2020 | Shelton, IV |
| 2020/0410180 A1 | 12/2020 | Shelton, IV et al. |
| 2021/0000466 A1 | 1/2021 | Leimbach et al. |
| 2021/0000467 A1 | 1/2021 | Shelton, IV et al. |
| 2021/0000470 A1 | 1/2021 | Leimbach et al. |
| 2021/0015480 A1 | 1/2021 | Shelton, IV et al. |
| 2021/0022741 A1 | 1/2021 | Baxter, III et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059666 A1 | 3/2021 | Schmid et al. |

(56) References Cited

U.S. PATENT DOCUMENTS

| | | |
|---|---|---|
| 2021/0059669 A1 | 3/2021 | Yates et al. |
| 2021/0059670 A1 | 3/2021 | Overmyer et al. |
| 2021/0059671 A1 | 3/2021 | Shelton, IV et al. |
| 2021/0059672 A1 | 3/2021 | Giordano et al. |
| 2021/0059673 A1 | 3/2021 | Shelton, IV et al. |
| 2021/0068817 A1 | 3/2021 | Shelton, IV et al. |
| 2021/0068818 A1 | 3/2021 | Overmyer et al. |
| 2021/0068820 A1 | 3/2021 | Parihar et al. |
| 2021/0068830 A1 | 3/2021 | Baber et al. |
| 2021/0068831 A1 | 3/2021 | Baber et al. |
| 2021/0068832 A1 | 3/2021 | Yates et al. |
| 2021/0068835 A1 | 3/2021 | Shelton, IV et al. |
| 2021/0077092 A1 | 3/2021 | Parihar et al. |
| 2021/0077099 A1 | 3/2021 | Shelton, IV et al. |
| 2021/0077100 A1 | 3/2021 | Shelton, IV et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085317 A1 | 3/2021 | Miller et al. |
| 2021/0085318 A1 | 3/2021 | Swayze et al. |
| 2021/0085319 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0085326 A1 | 3/2021 | Vendely et al. |
| 2021/0093323 A1 | 4/2021 | Scirica et al. |
| 2021/0100541 A1 | 4/2021 | Shelton, IV et al. |
| 2021/0100550 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |

FOREIGN PATENT DOCUMENTS

| | | |
|---|---|---|
| AU | 2011218702 B2 | 6/2013 |
| AU | 2012200178 B2 | 7/2013 |
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 1777406 A | 5/2006 |
| CN | 2796654 Y | 7/2006 |
| CN | 2868212 Y | 2/2007 |
| CN | 200942099 Y | 9/2007 |
| CN | 200984209 Y | 12/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101188900 A | 5/2008 |
| CN | 101203085 A | 6/2008 |
| CN | 101378791 A | 3/2009 |
| CN | 101507635 A | 8/2009 |
| CN | 101522120 A | 9/2009 |
| CN | 101669833 A | 3/2010 |
| CN | 101721236 A | 6/2010 |
| CN | 101828940 A | 9/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 102217961 A | 10/2011 |
| CN | 102217963 A | 10/2011 |
| CN | 102243850 A | 11/2011 |
| CN | 102247183 A | 11/2011 |
| CN | 101779977 B | 12/2011 |
| CN | 101912284 B | 7/2012 |
| CN | 102125450 B | 7/2012 |
| CN | 202313537 U | 7/2012 |
| CN | 202397539 U | 8/2012 |
| CN | 202426586 U | 9/2012 |
| CN | 202489990 U | 10/2012 |
| CN | 102228387 B | 11/2012 |
| CN | 102835977 A | 12/2012 |
| CN | 202568350 U | 12/2012 |
| CN | 103037781 A | 4/2013 |
| CN | 103083053 A | 5/2013 |
| CN | 103391037 A | 11/2013 |
| CN | 203328751 U | 12/2013 |
| CN | 103505264 A | 1/2014 |
| CN | 103584893 A | 2/2014 |
| CN | 103690212 A | 4/2014 |
| CN | 203564285 U | 4/2014 |
| CN | 203564287 U | 4/2014 |
| CN | 203597997 U | 5/2014 |
| CN | 103829981 A | 6/2014 |
| CN | 103829983 A | 6/2014 |
| CN | 103908313 A | 7/2014 |
| CN | 203693685 U | 7/2014 |
| CN | 203736251 U | 7/2014 |
| CN | 103981635 A | 8/2014 |
| CN | 203815517 U | 9/2014 |
| CN | 102783741 B | 10/2014 |
| CN | 102973300 B | 10/2014 |
| CN | 204092074 U | 1/2015 |
| CN | 104337556 A | 2/2015 |
| CN | 204158440 U | 2/2015 |
| CN | 204158441 U | 2/2015 |
| CN | 102469995 B | 3/2015 |
| CN | 104422849 A | 3/2015 |
| CN | 104586463 A | 5/2015 |
| CN | 204520822 U | 8/2015 |
| CN | 204636451 U | 9/2015 |
| CN | 103860225 B | 3/2016 |
| CN | 103750872 B | 5/2016 |
| CN | 103648410 B | 10/2016 |
| CN | 106344091 A | 1/2017 |
| CN | 104349800 B | 11/2017 |
| CN | 107635483 A | 1/2018 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004063606 A1 | 7/2006 |
| DE | 202007003114 U1 | 6/2007 |
| DE | 102010013150 A1 | 9/2011 |
| DE | 102012213322 A1 | 1/2014 |
| DE | 102013101158 A1 | 8/2014 |
| EM | 002220467-0008 | 4/2013 |
| EP | 0000756 A1 | 2/1979 |
| EP | 0122046 A1 | 10/1984 |
| EP | 0129442 B1 | 11/1987 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |

(56) References Cited

FOREIGN PATENT DOCUMENTS

| | | |
|---|---|---|
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1064882 A1 | 1/2001 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1558161 A1 | 8/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2789299 A1 | 10/2014 |
| EP | 2842500 A1 | 3/2015 |
| EP | 2853220 A1 | 4/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 3120781 A2 | 1/2017 |
| EP | 3135225 A2 | 3/2017 |
| EP | 2789299 B1 | 5/2017 |
| EP | 3225190 A2 | 10/2017 |
| EP | 3326548 A1 | 5/2018 |
| EP | 3363378 A1 | 8/2018 |
| EP | 3275378 B1 | 7/2019 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | S63270040 A | 11/1988 |
| JP | S63318824 A | 12/1988 |
| JP | H0129503 B2 | 6/1989 |
| JP | H02106189 A | 4/1990 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H06237937 A | 8/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000210299 A | 8/2000 |
| JP | 2000271141 A | 10/2000 |
| JP | 2000287987 A | 10/2000 |
| JP | 2000325303 A | 11/2000 |
| JP | 2001-69758 A | 3/2001 |
| JP | 2001087272 A | 4/2001 |
| JP | 2001208655 A | 8/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |

(56) References Cited

FOREIGN PATENT DOCUMENTS

| | | |
|---|---|---|
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006291180 A | 10/2006 |
| JP | 2006346445 A | 12/2006 |
| JP | 2007-97252 A | 4/2007 |
| JP | 2007289715 A | 11/2007 |
| JP | 2007304057 A | 11/2007 |
| JP | 2007306710 A | 11/2007 |
| JP | D1322057 | 2/2008 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | D1383743 | 2/2010 |
| JP | 2010065594 A | 3/2010 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |
| JP | D1432094 | 12/2011 |
| JP | 2012115542 A | 6/2012 |
| JP | 2012143283 A | 8/2012 |
| JP | 5154710 B1 | 2/2013 |
| JP | 2013099551 A | 5/2013 |
| JP | 2013126430 A | 6/2013 |
| JP | D1481426 | 9/2013 |
| JP | 2013541983 A | 11/2013 |
| JP | 2013541997 A | 11/2013 |
| JP | D1492363 | 2/2014 |
| JP | 2014121599 A | 7/2014 |
| JP | 2014171879 A | 9/2014 |
| JP | 1517663 S | 2/2015 |
| JP | 2015512725 A | 4/2015 |
| JP | 2015513956 A | 5/2015 |
| JP | 2015513958 A | 5/2015 |
| JP | 2015514471 A | 5/2015 |
| JP | 2015521525 A | 7/2015 |
| JP | 2016007800 A | 1/2016 |
| JP | 2016512057 A | 4/2016 |
| JP | 2016530949 A | 10/2016 |
| JP | 1601498 S | 4/2018 |
| KR | 20100110134 A | 10/2010 |
| KR | 20110003229 A | 1/2011 |
| KR | 300631507 | 3/2012 |
| KR | 300747646 | 6/2014 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9308754 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0024448 A2 | 10/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |

(56) References Cited

FOREIGN PATENT DOCUMENTS

| | | |
|---|---|---|
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2014175894 A1 | 10/2014 |
| WO | WO-2015032797 A1 | 3/2015 |
| WO | WO-2015076780 A1 | 5/2015 |
| WO | WO-2015137040 A1 | 9/2015 |
| WO | WO-2015138760 A1 | 9/2015 |
| WO | WO-2015187107 A1 | 12/2015 |
| WO | WO-2016100682 A1 | 6/2016 |
| WO | WO-2016107448 A1 | 7/2016 |
| WO | WO-2019036490 A1 | 2/2019 |

OTHER PUBLICATIONS

ASTM procedure D2240-05, "Standard Test Method for Rubber Property-Durometer Hardness," (Published Apr. 2010).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).

(56) References Cited

OTHER PUBLICATIONS

The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al—2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press Ltd, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "*Demystifying UHF Gen 2 RFID, HF RFID*," Online Article, Jun. 2, 2008, pp. 1-3, <https://www.edn.com/design/industrial-control/4019123/Demystifying-UHF-Gen-2-RFID-HF-RFID>.
Adeeb, et al., "*An Inductive Link-Based Wireless Power Transfer System for Biomedical Applications*," Research Article, Nov. 14, 2011, pp. 1-12, vol. 2012, Article ID 879294, *Hindawi Publishing Corporation*.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed Is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/

(56) References Cited

OTHER PUBLICATIONS

20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L.&C. Ligislation and Competition, S, No. L 169, Jun. 14, 1993, pp. 1-43.

\* cited by examiner

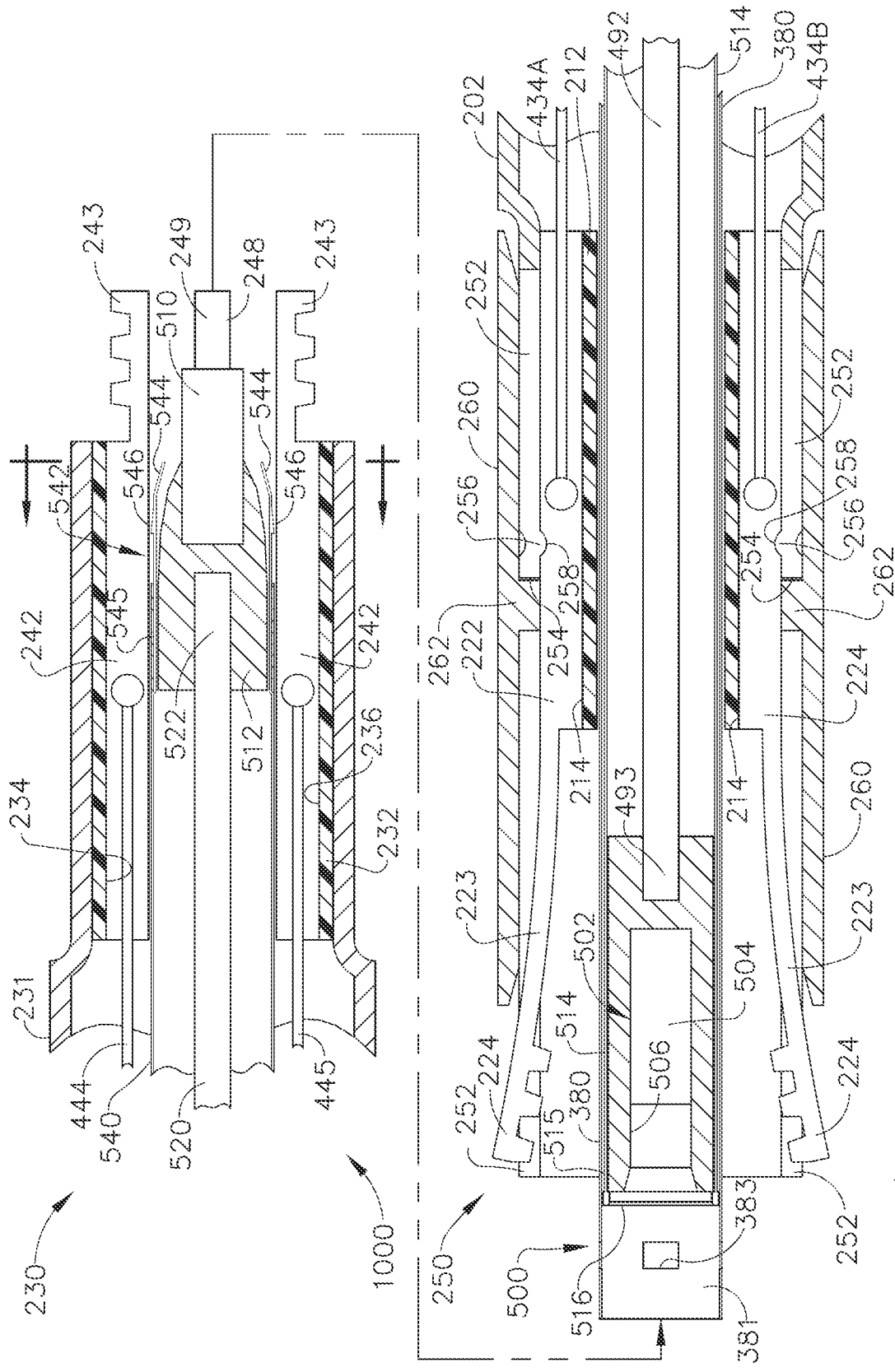

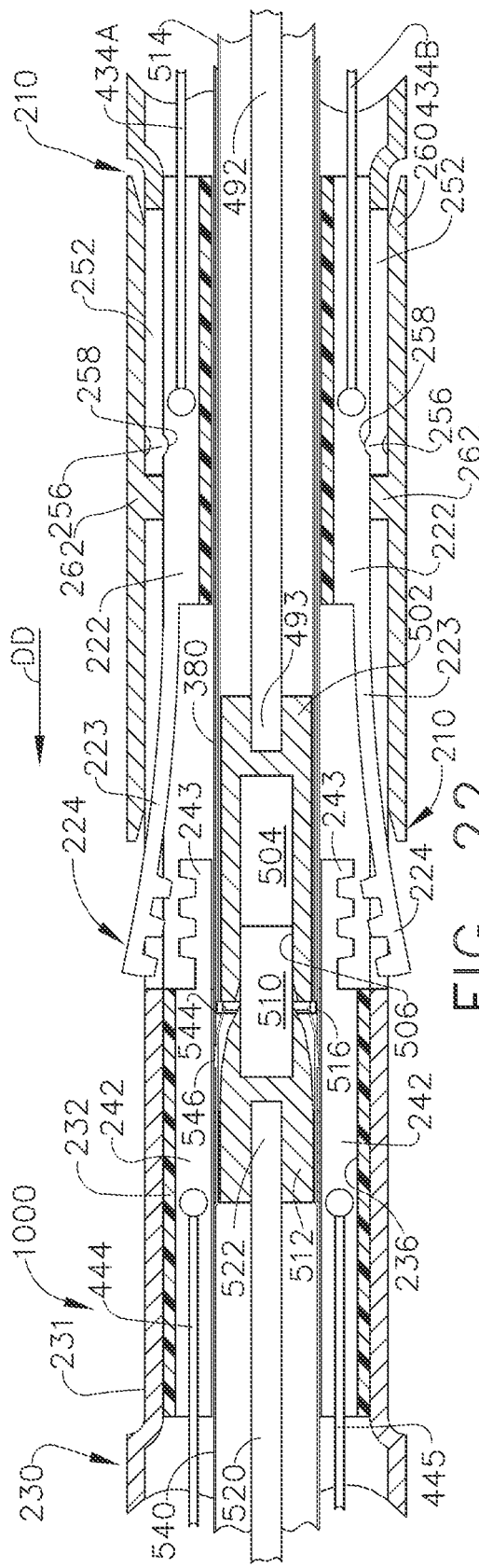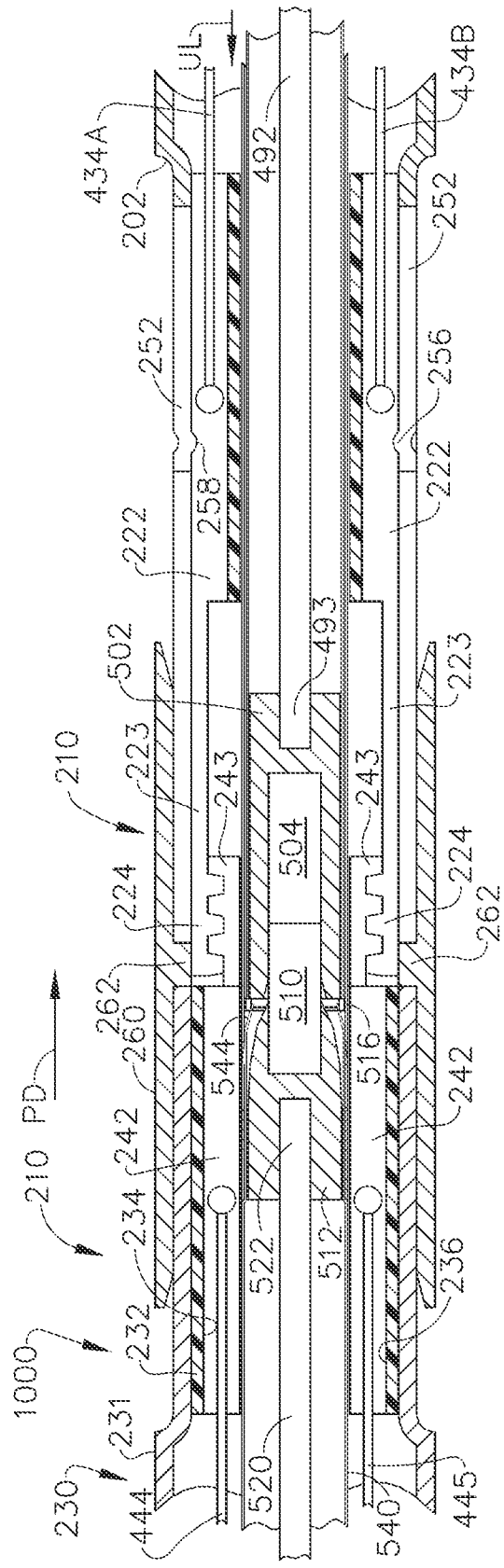

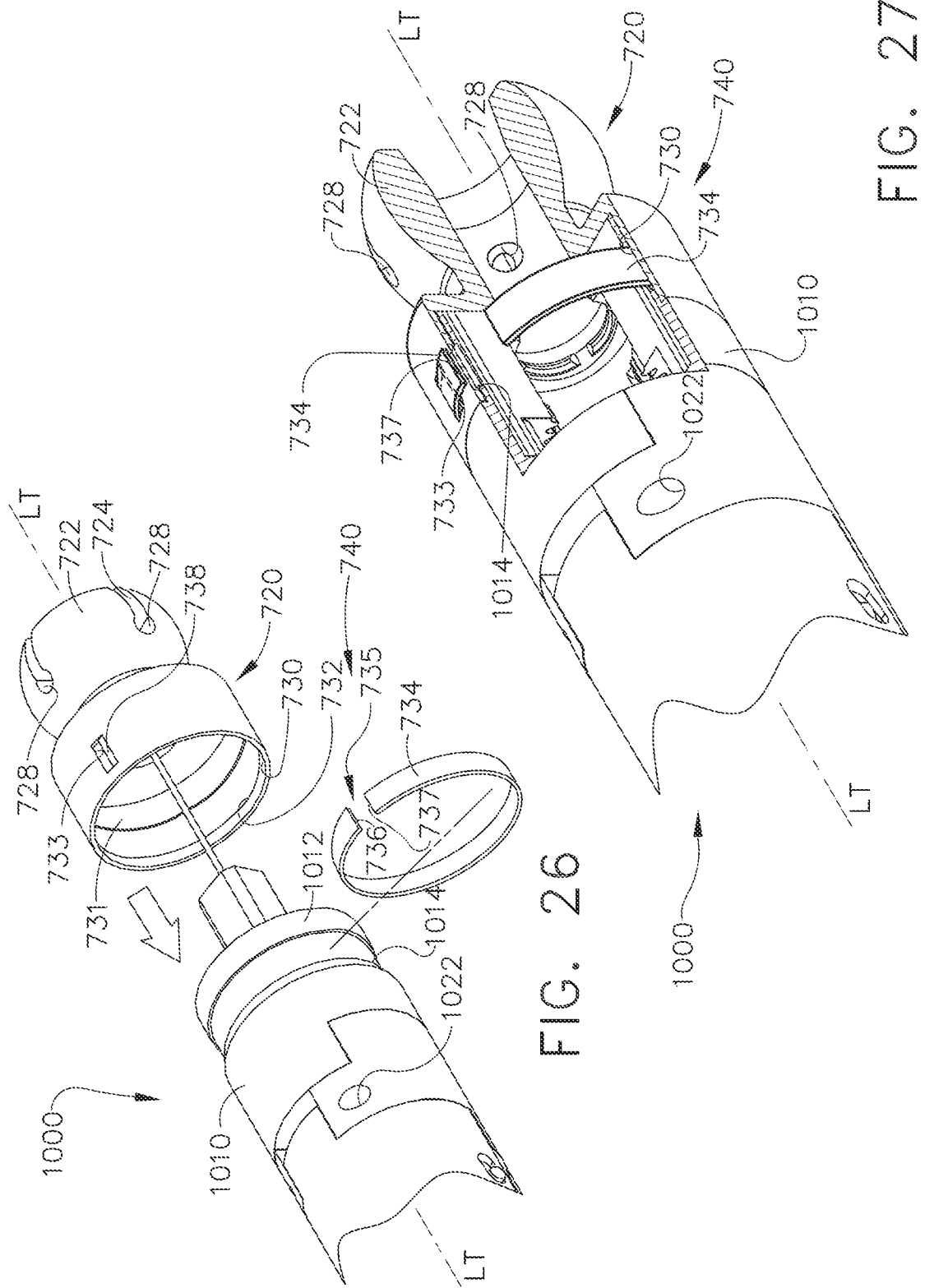

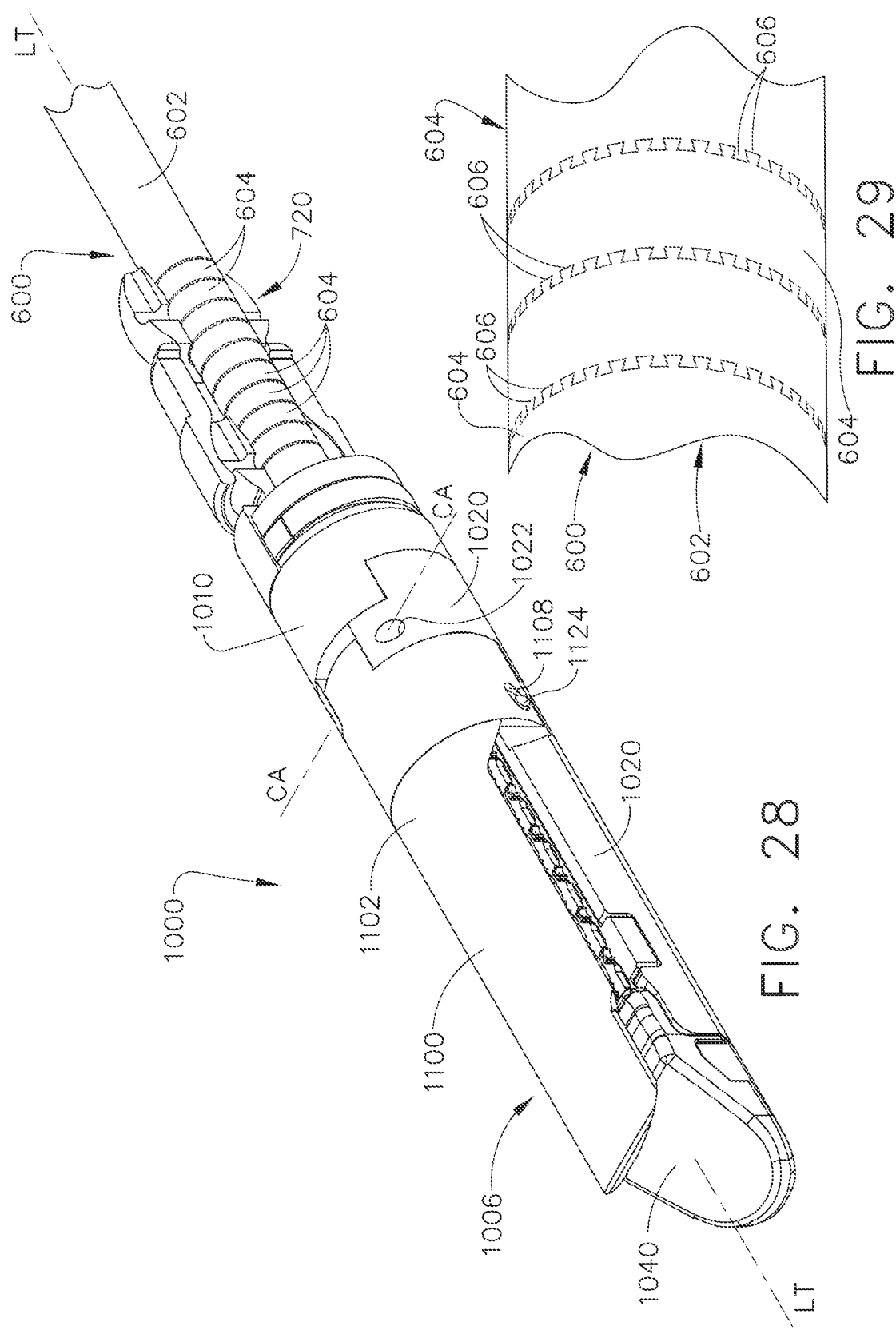

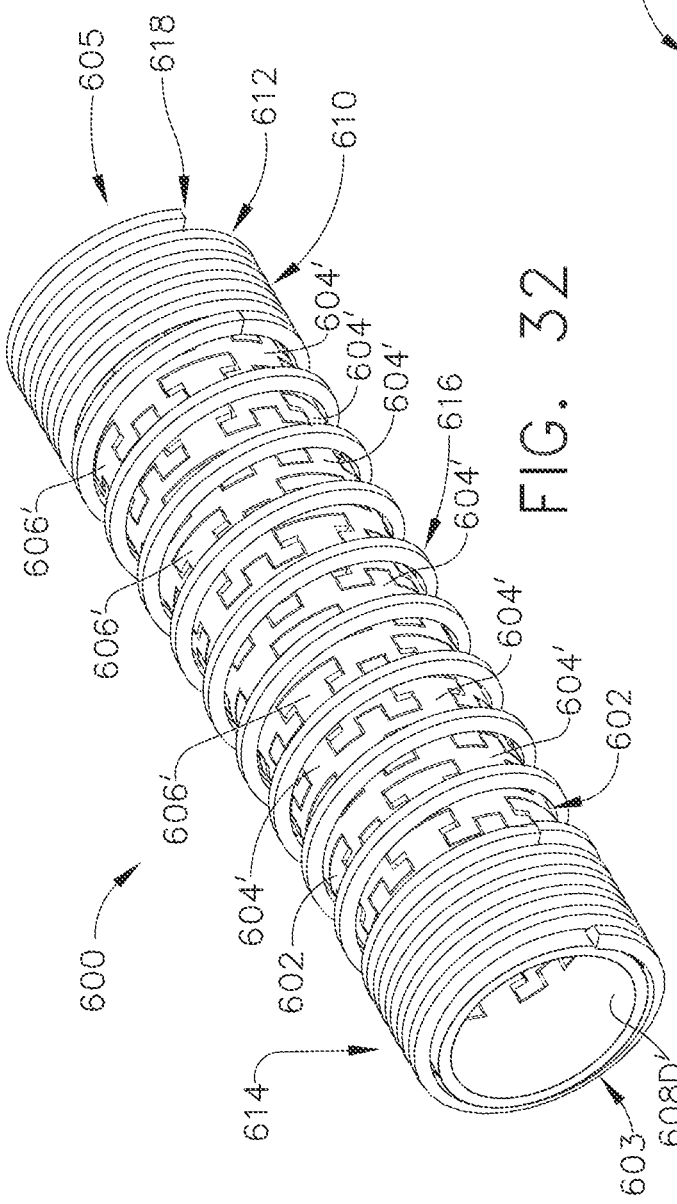
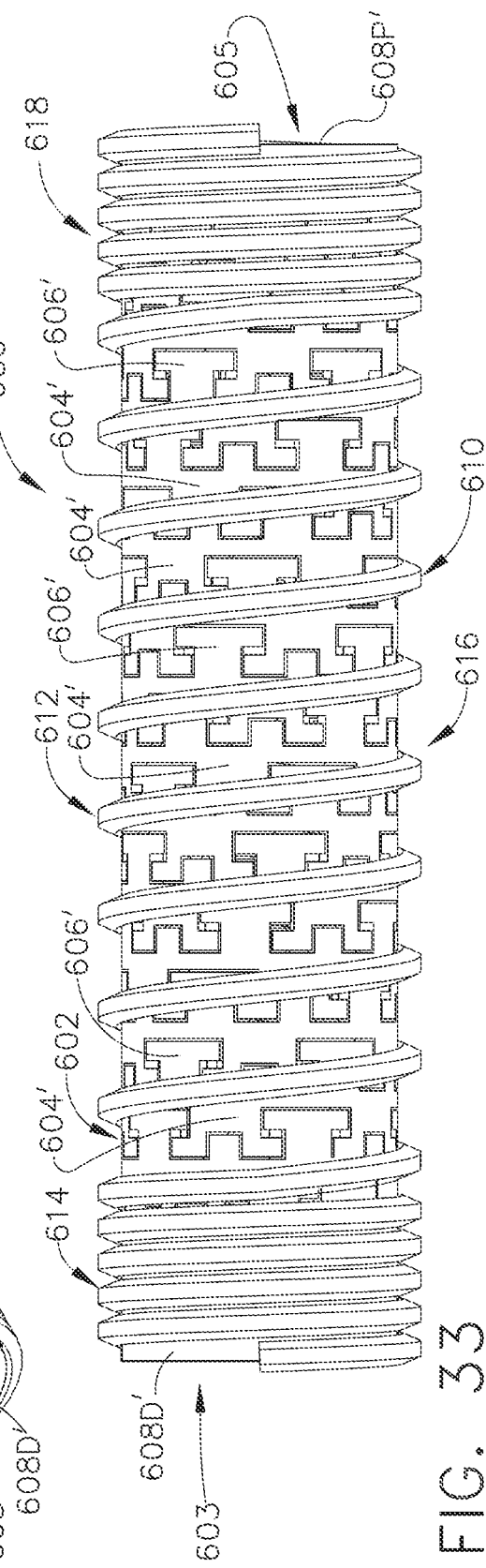
FIG. 32
FIG. 33

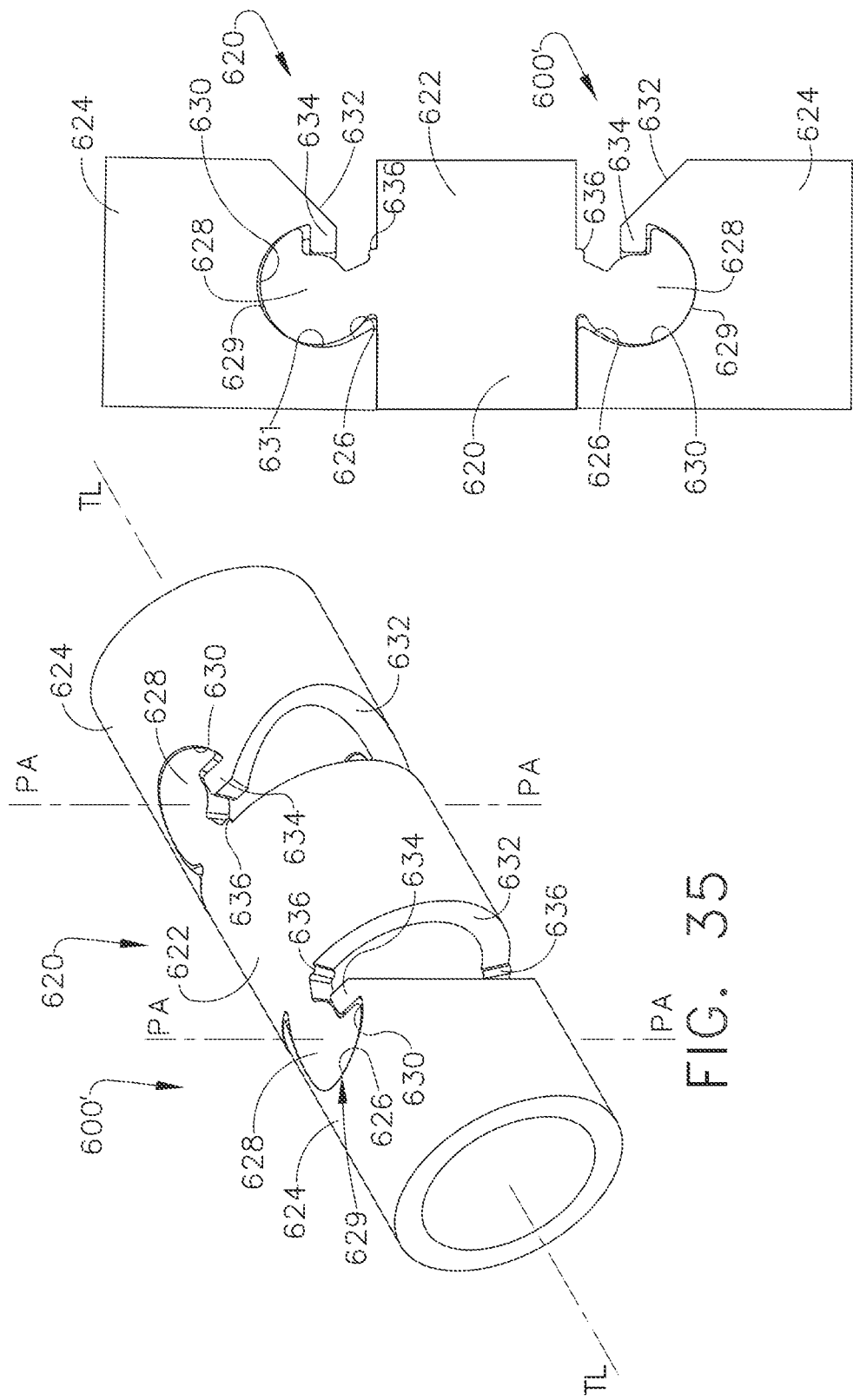

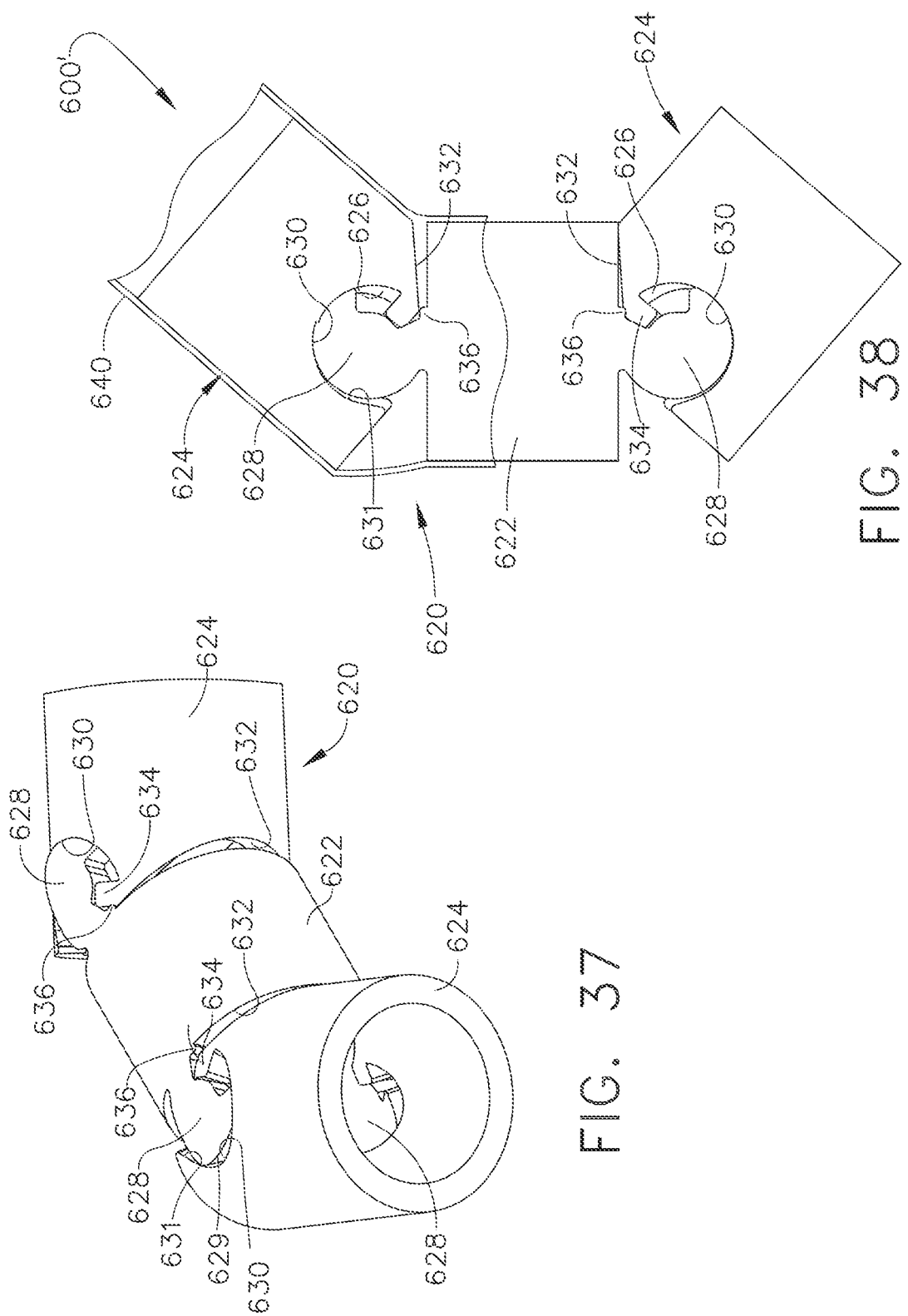

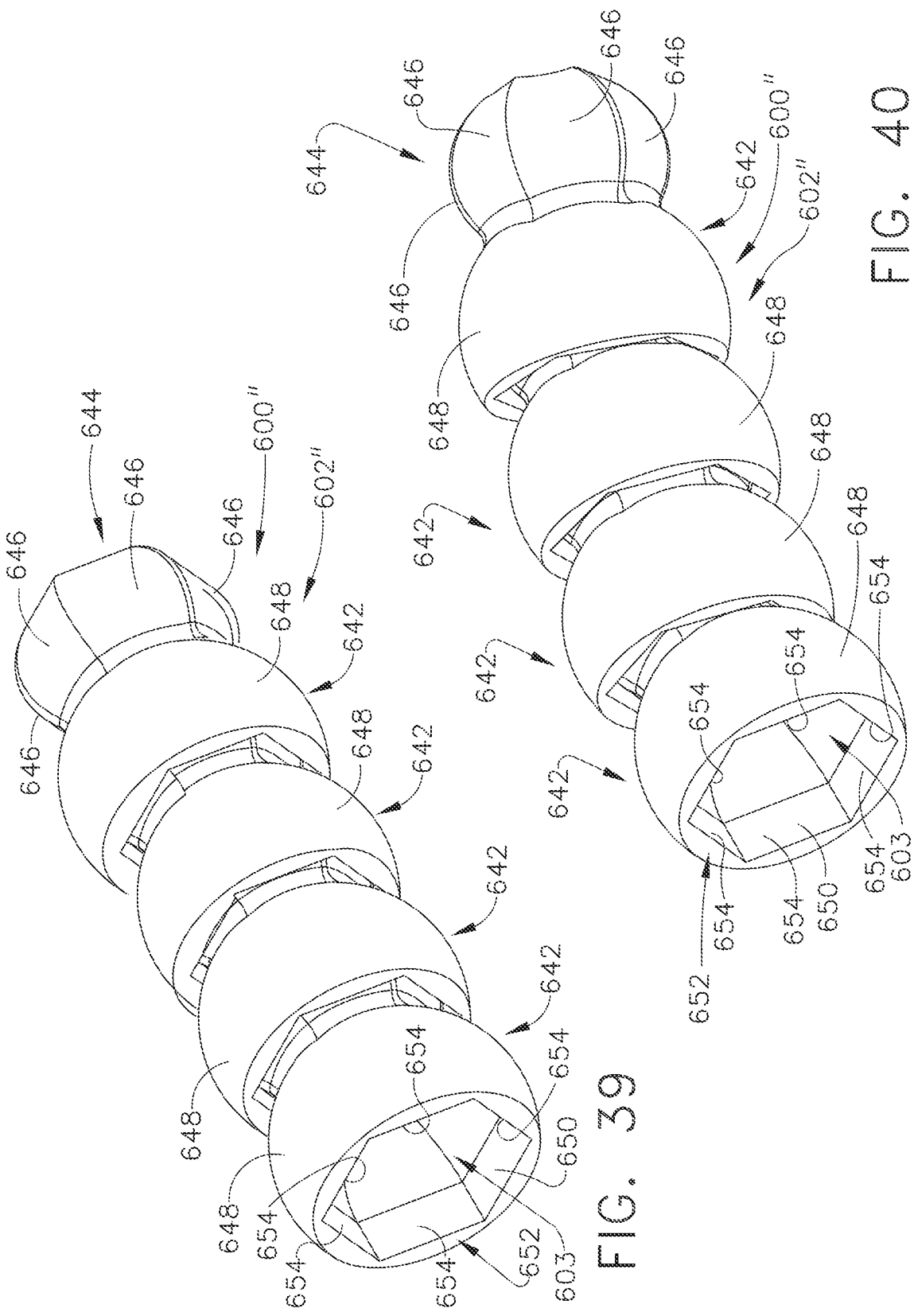

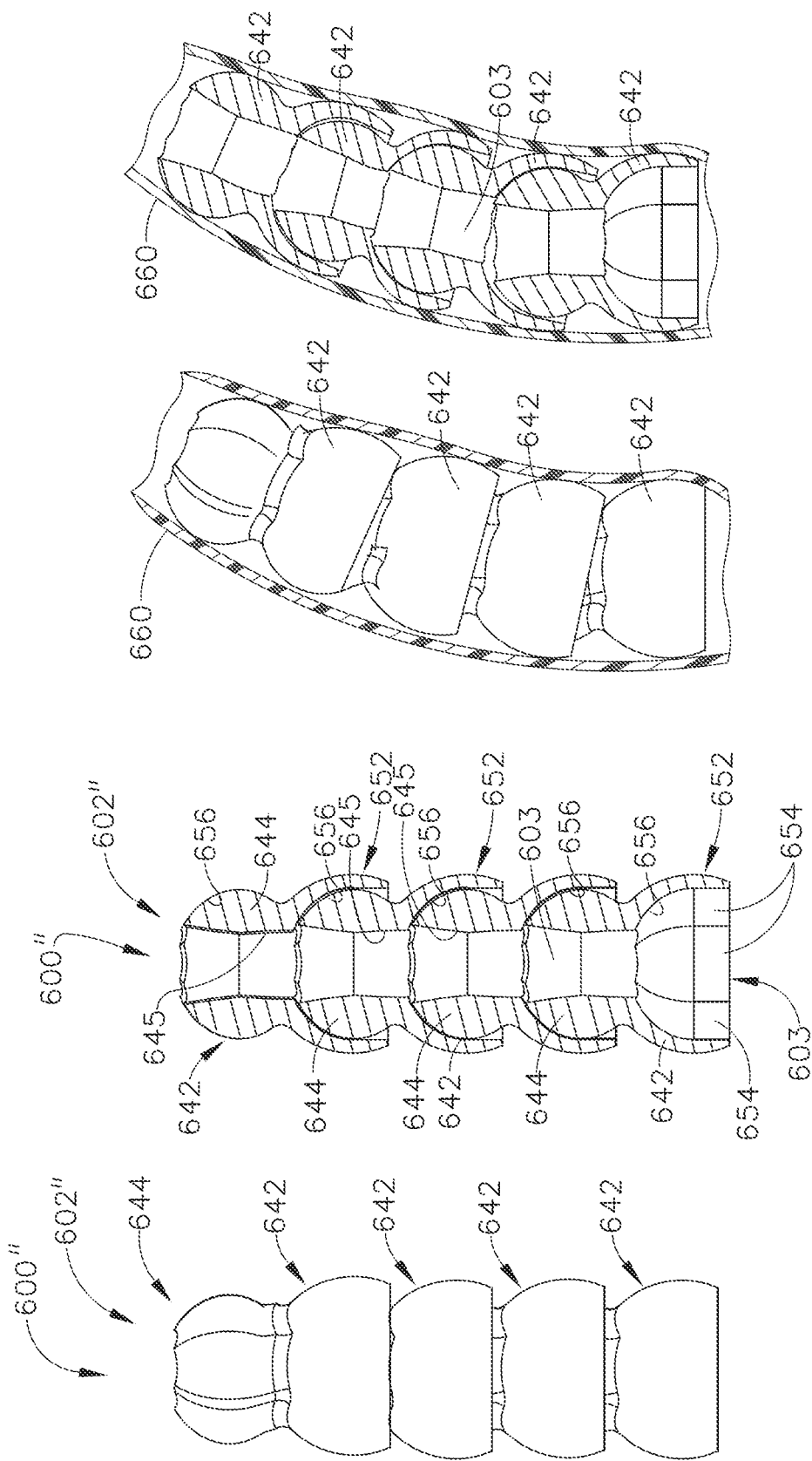

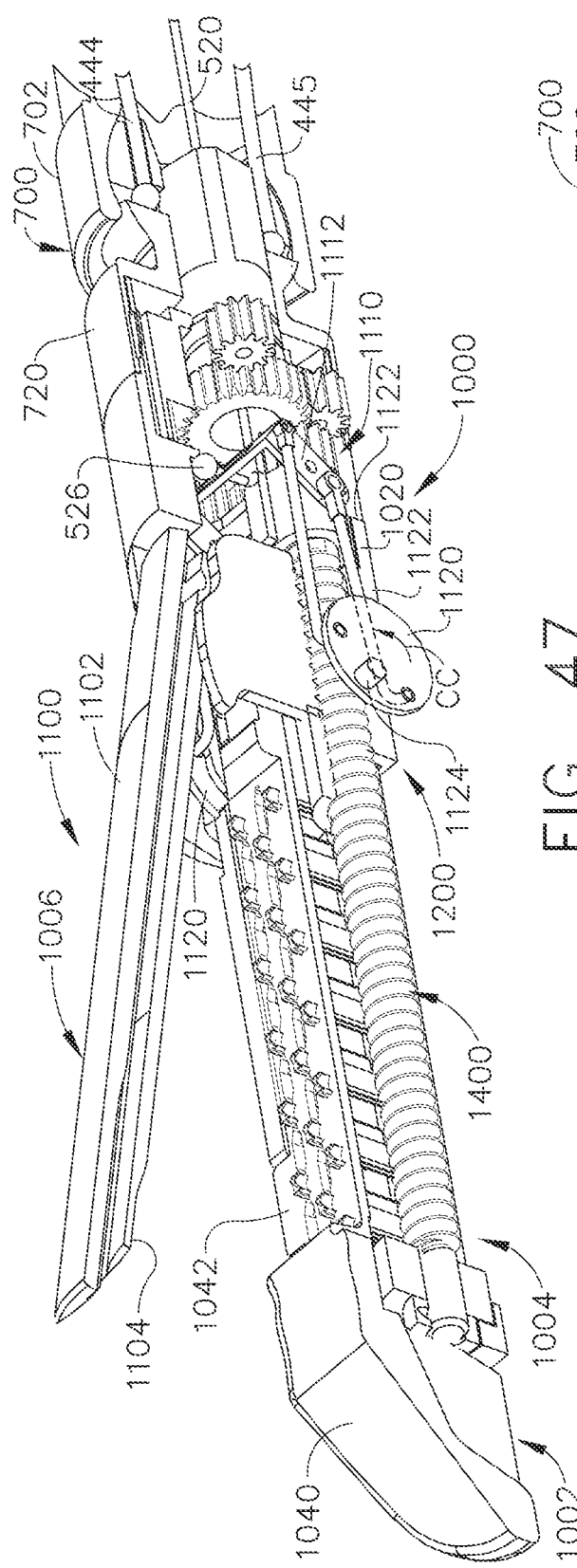
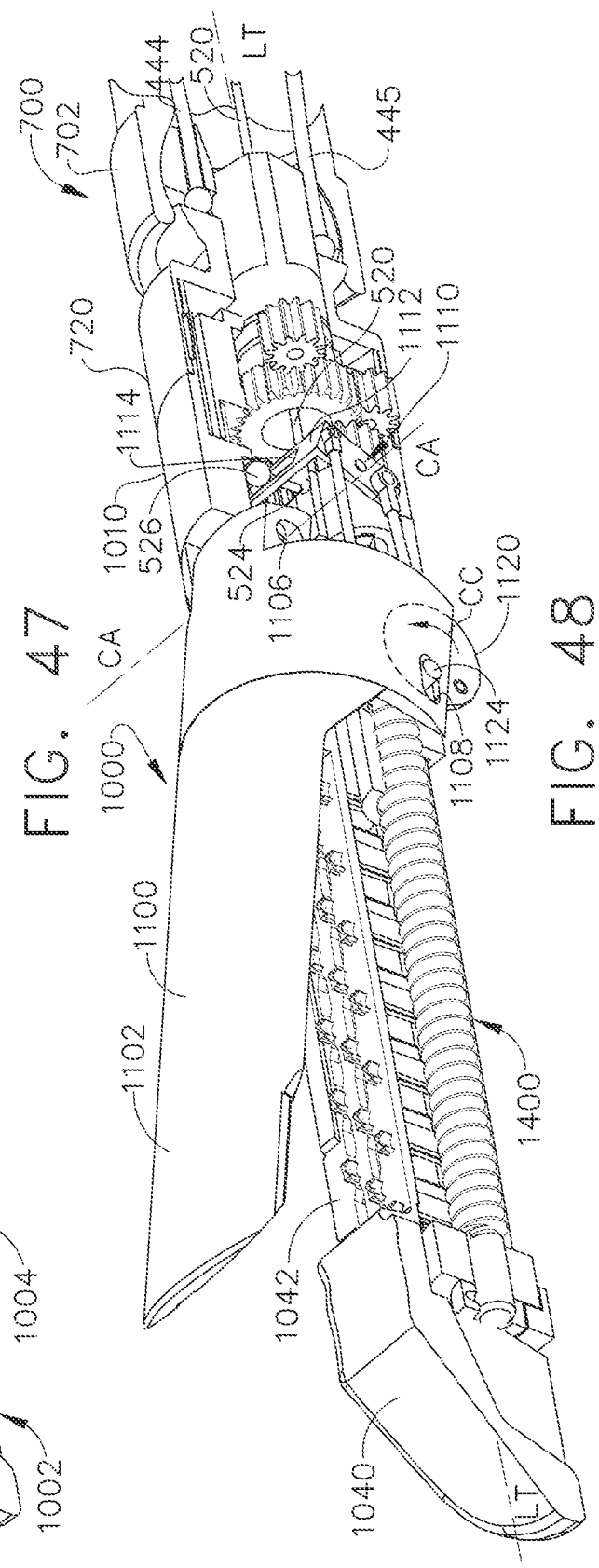

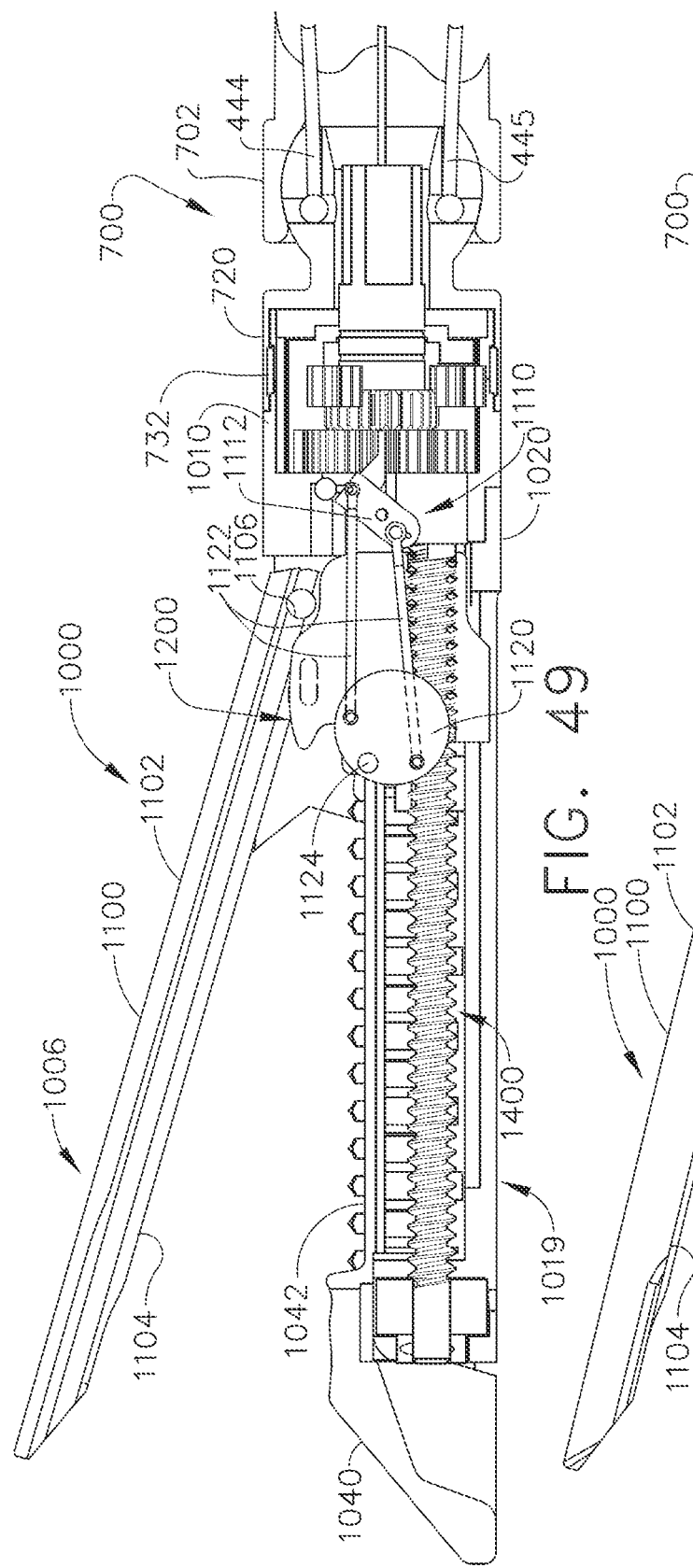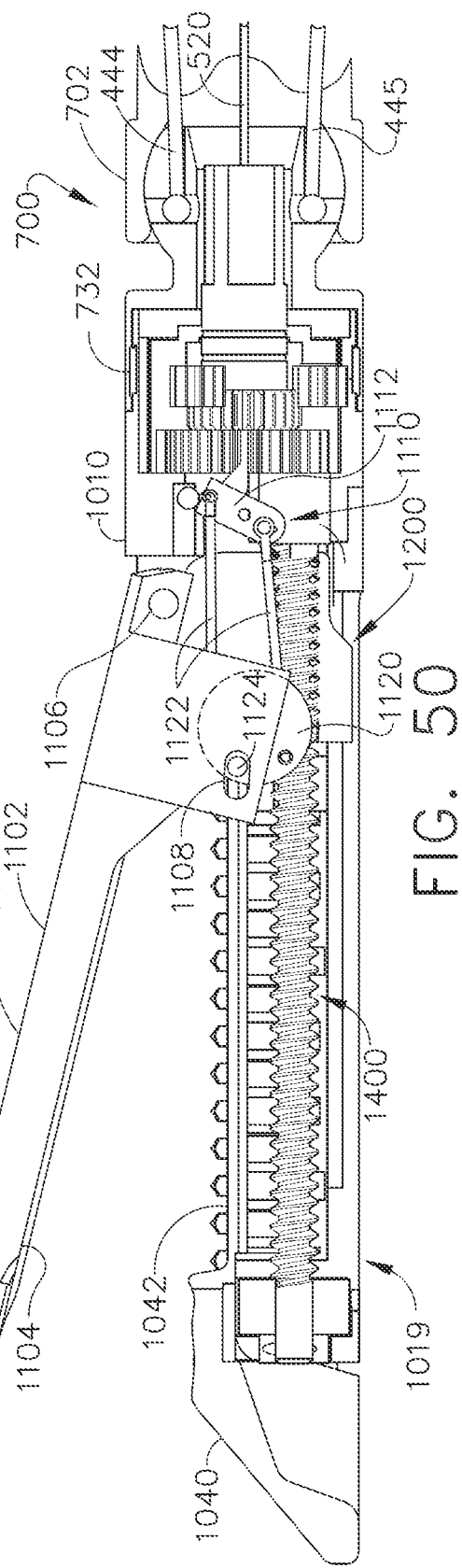

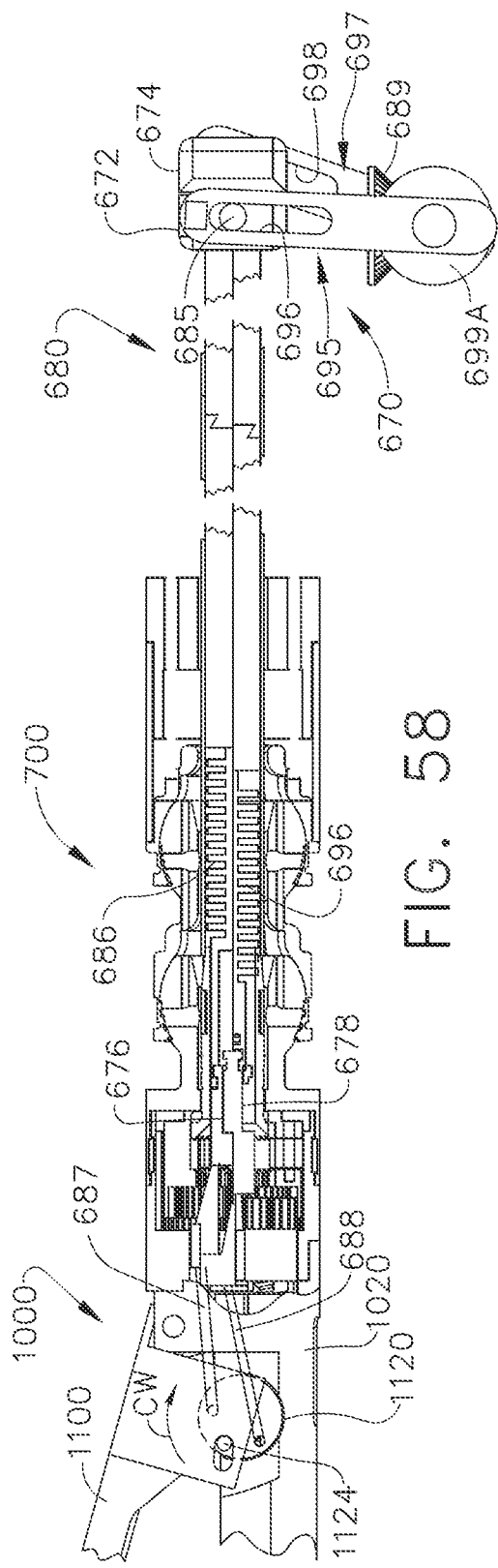
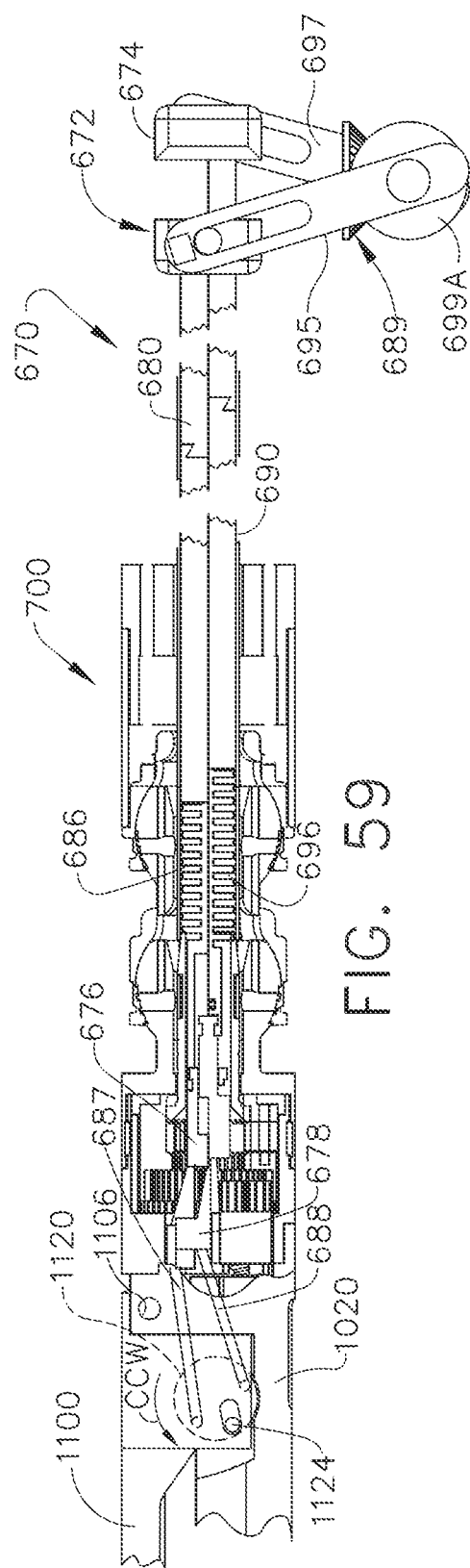

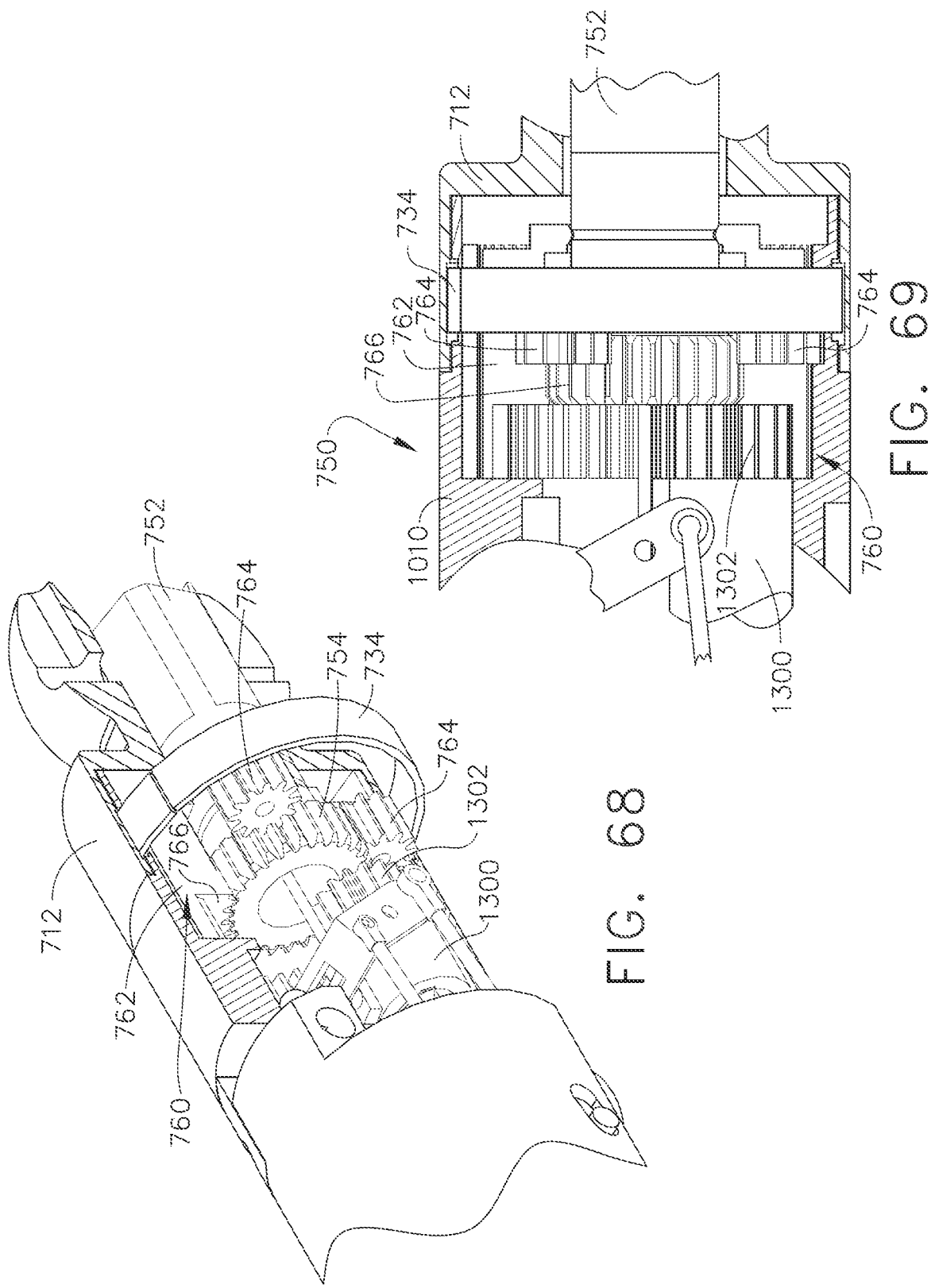

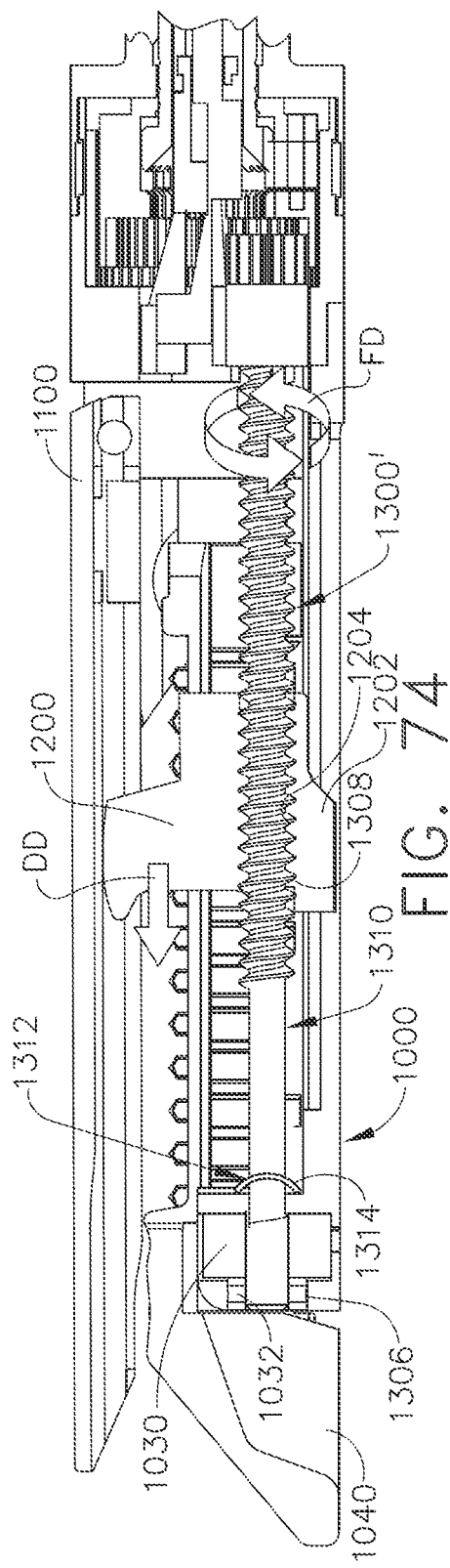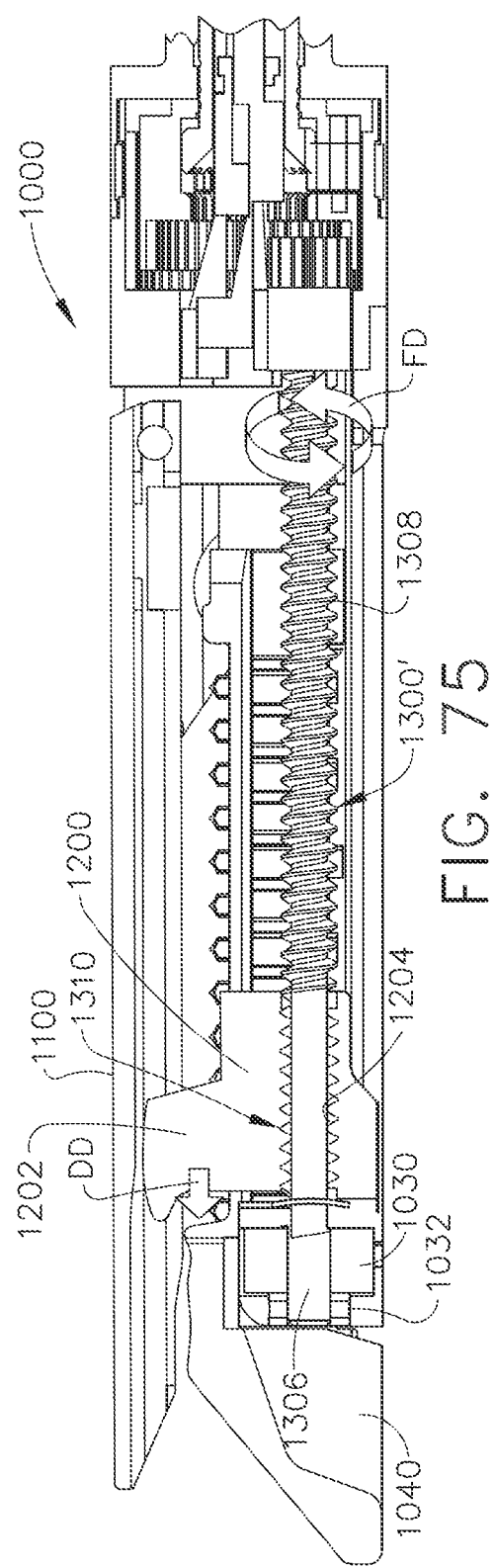

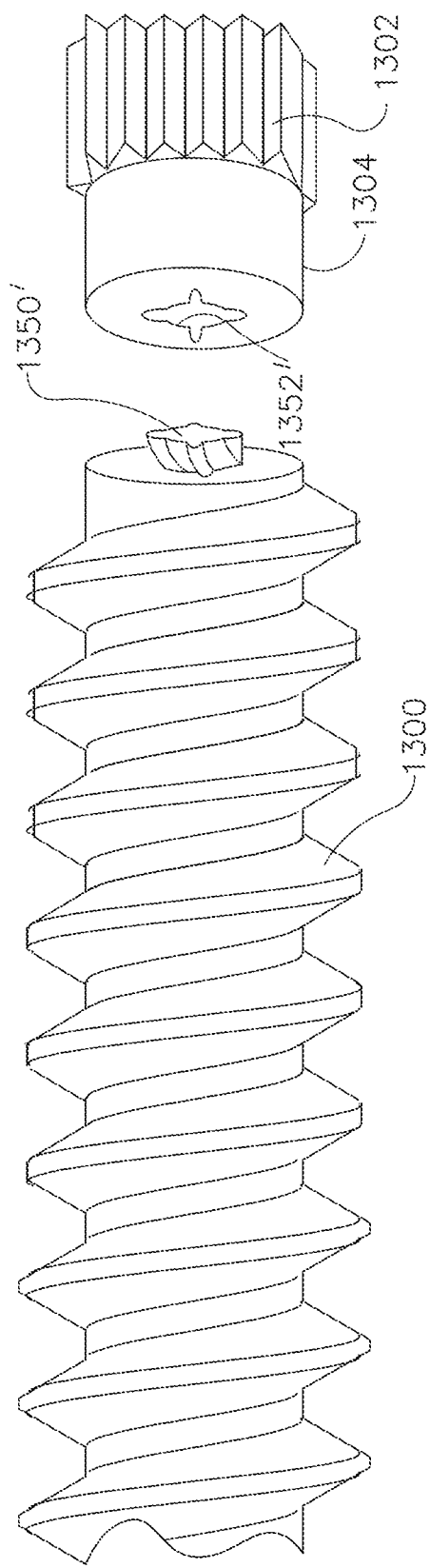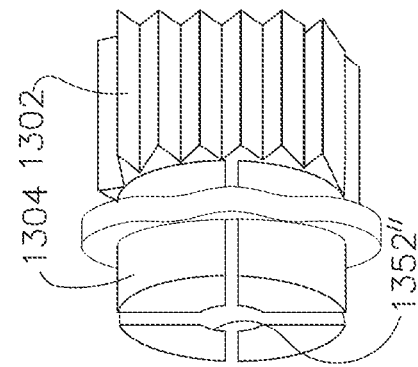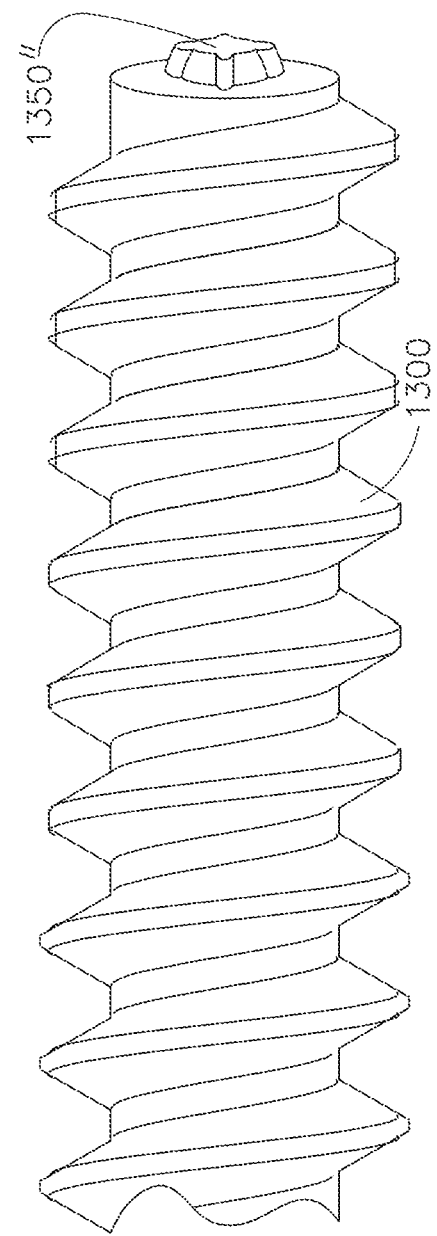
FIG. 81A
FIG. 81B

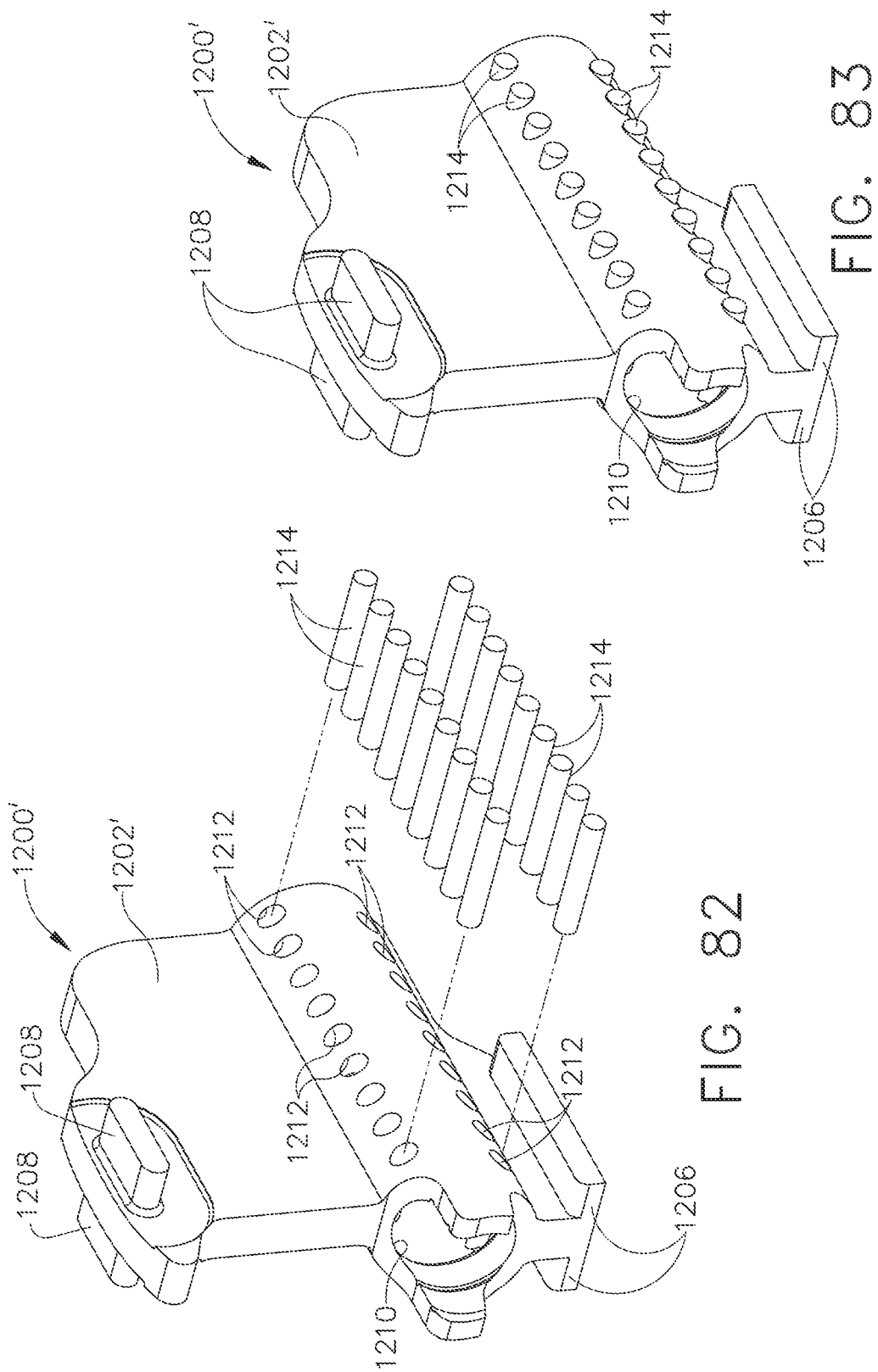

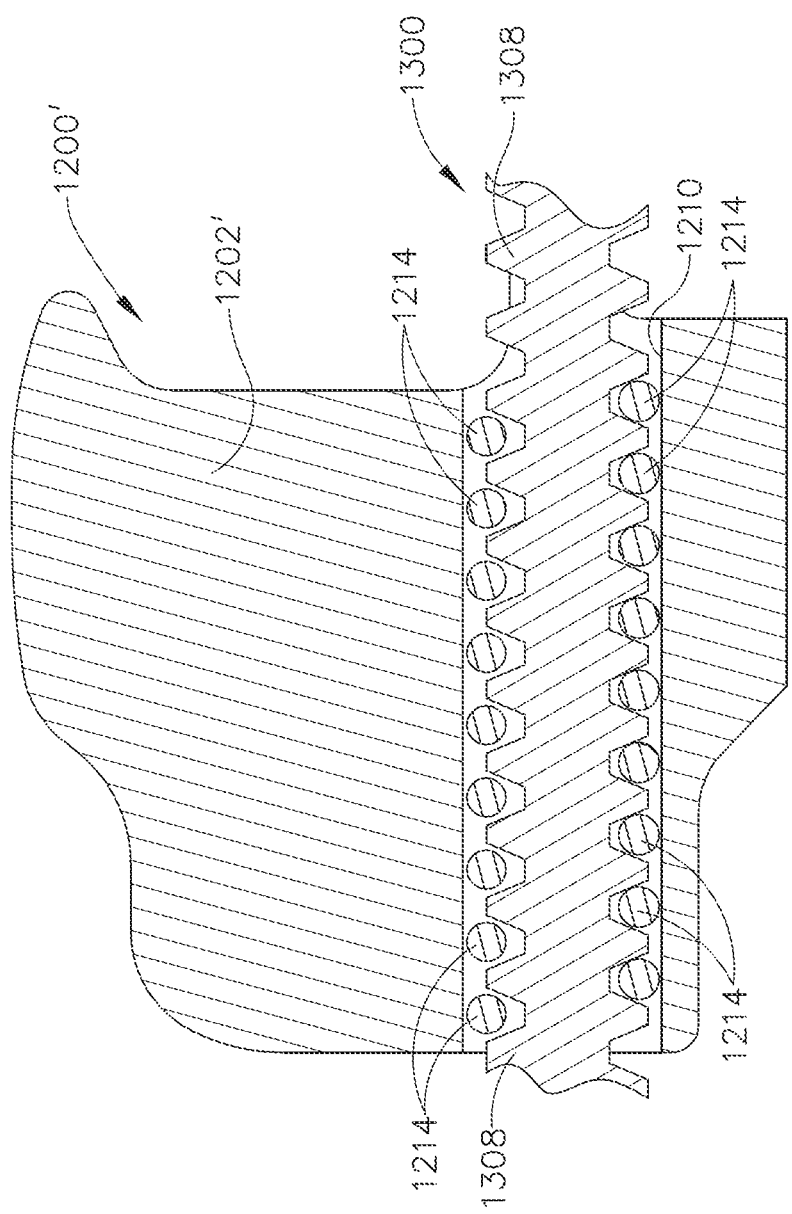

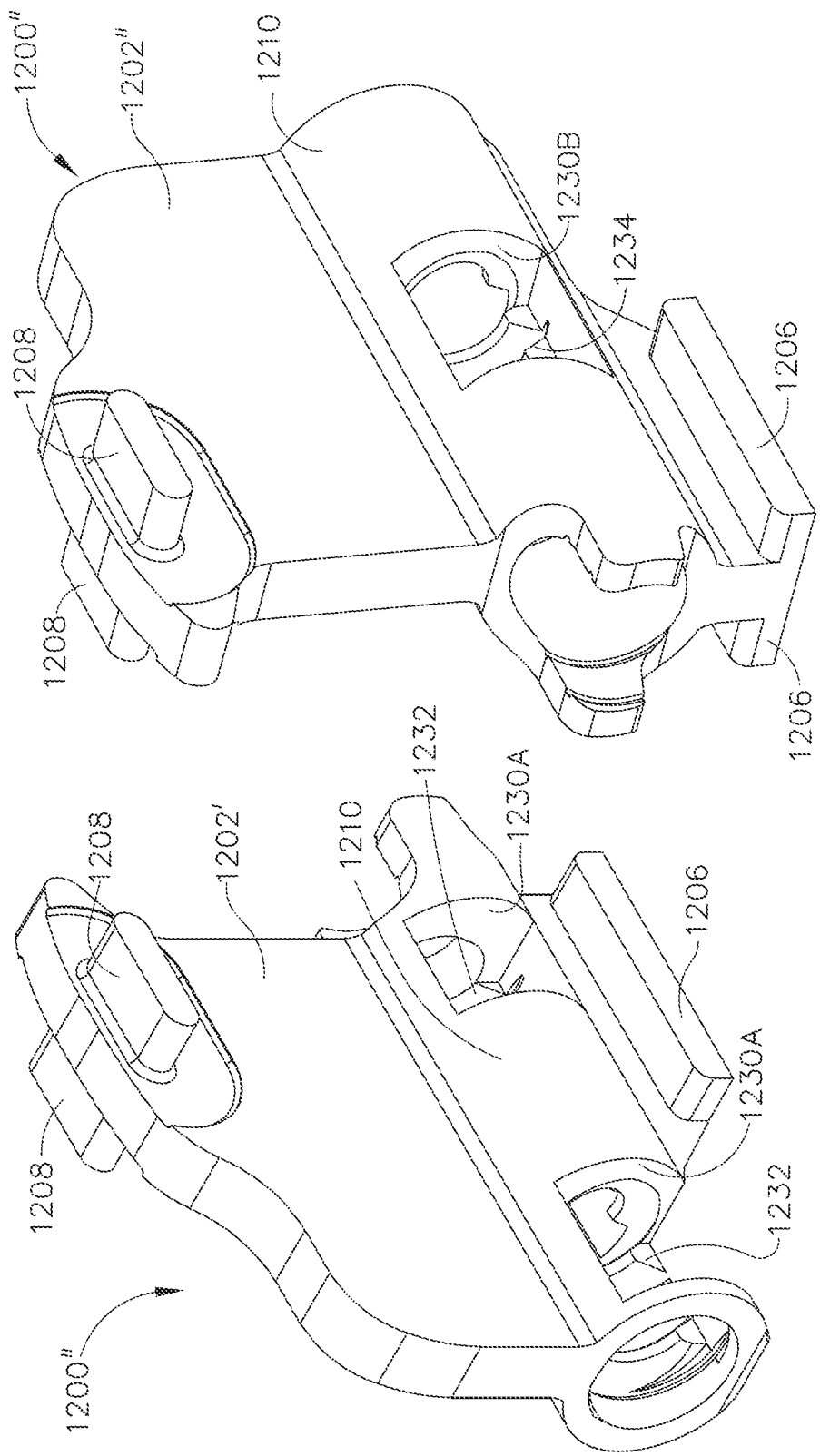

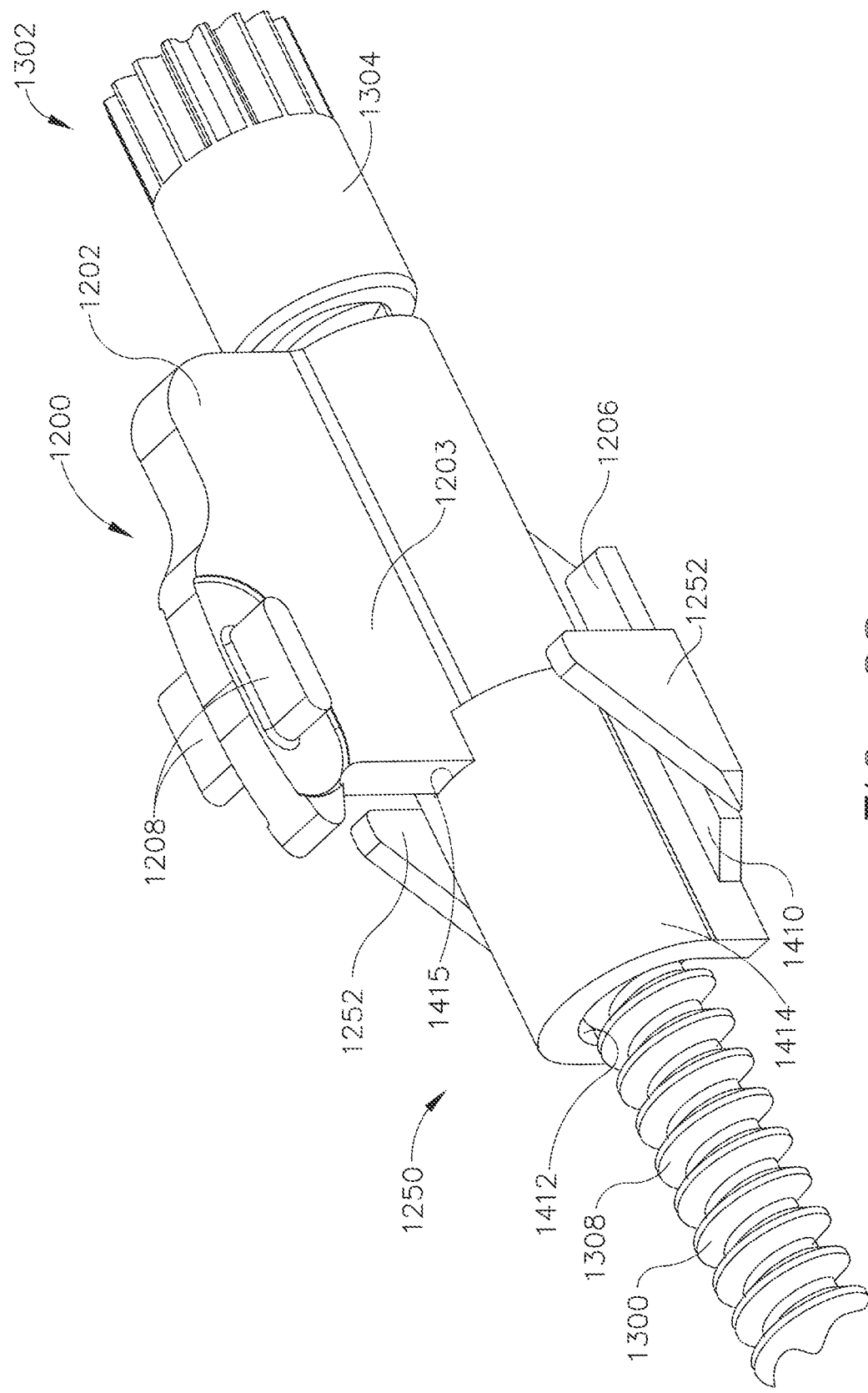

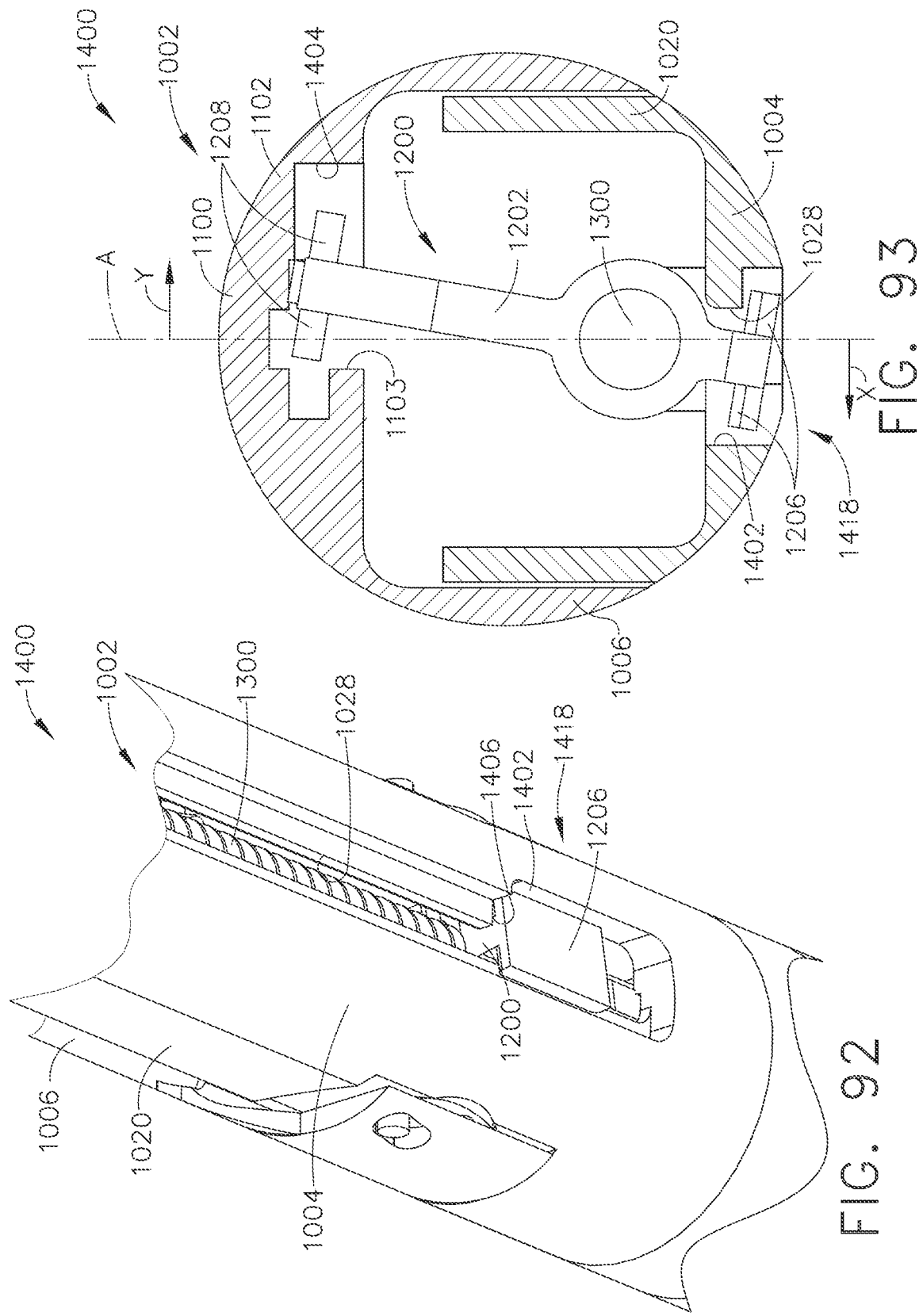

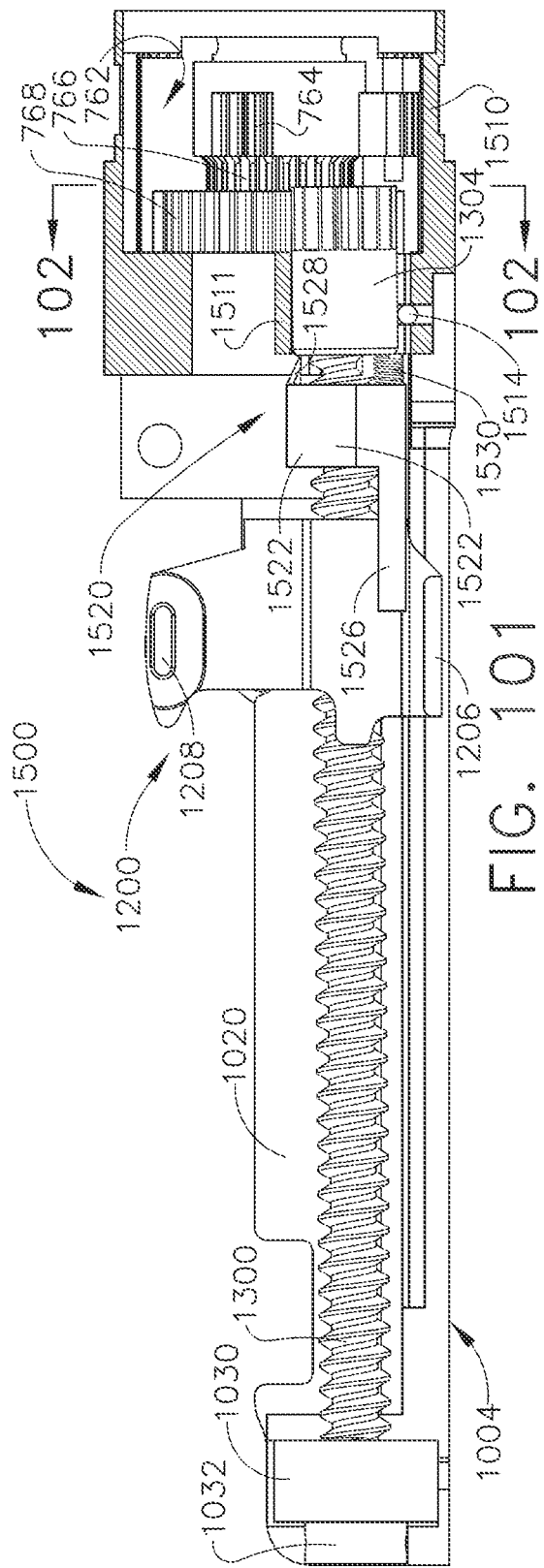
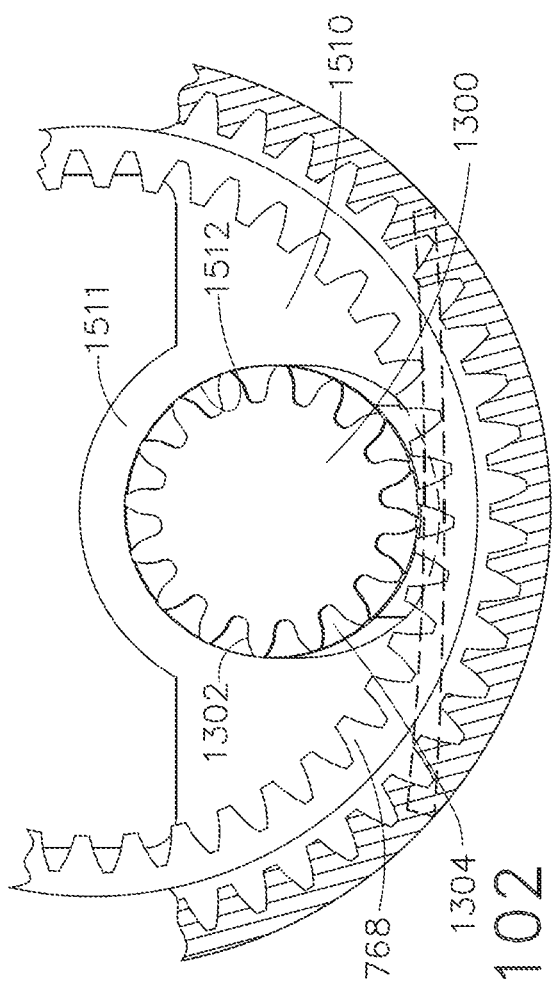

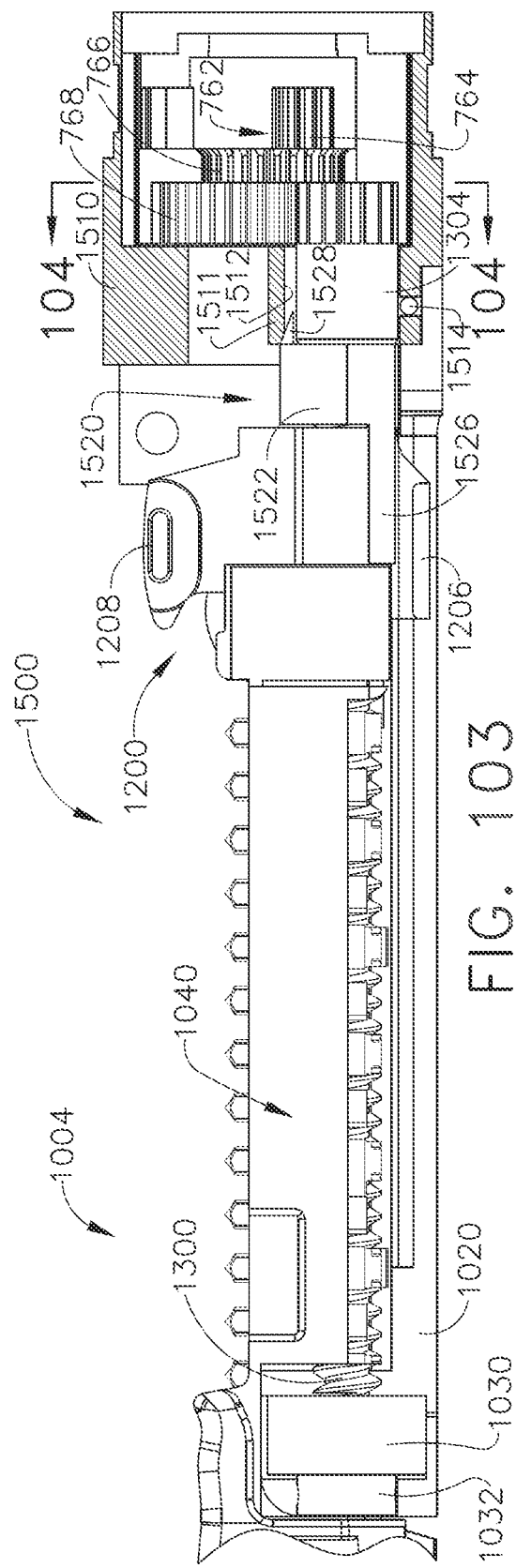
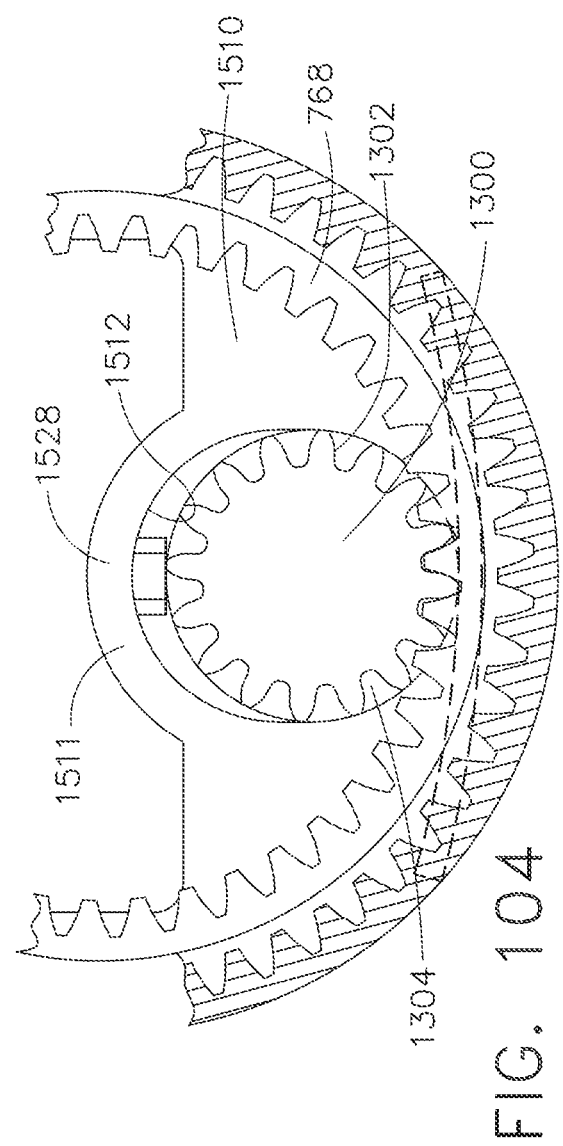
FIG. 103
FIG. 104

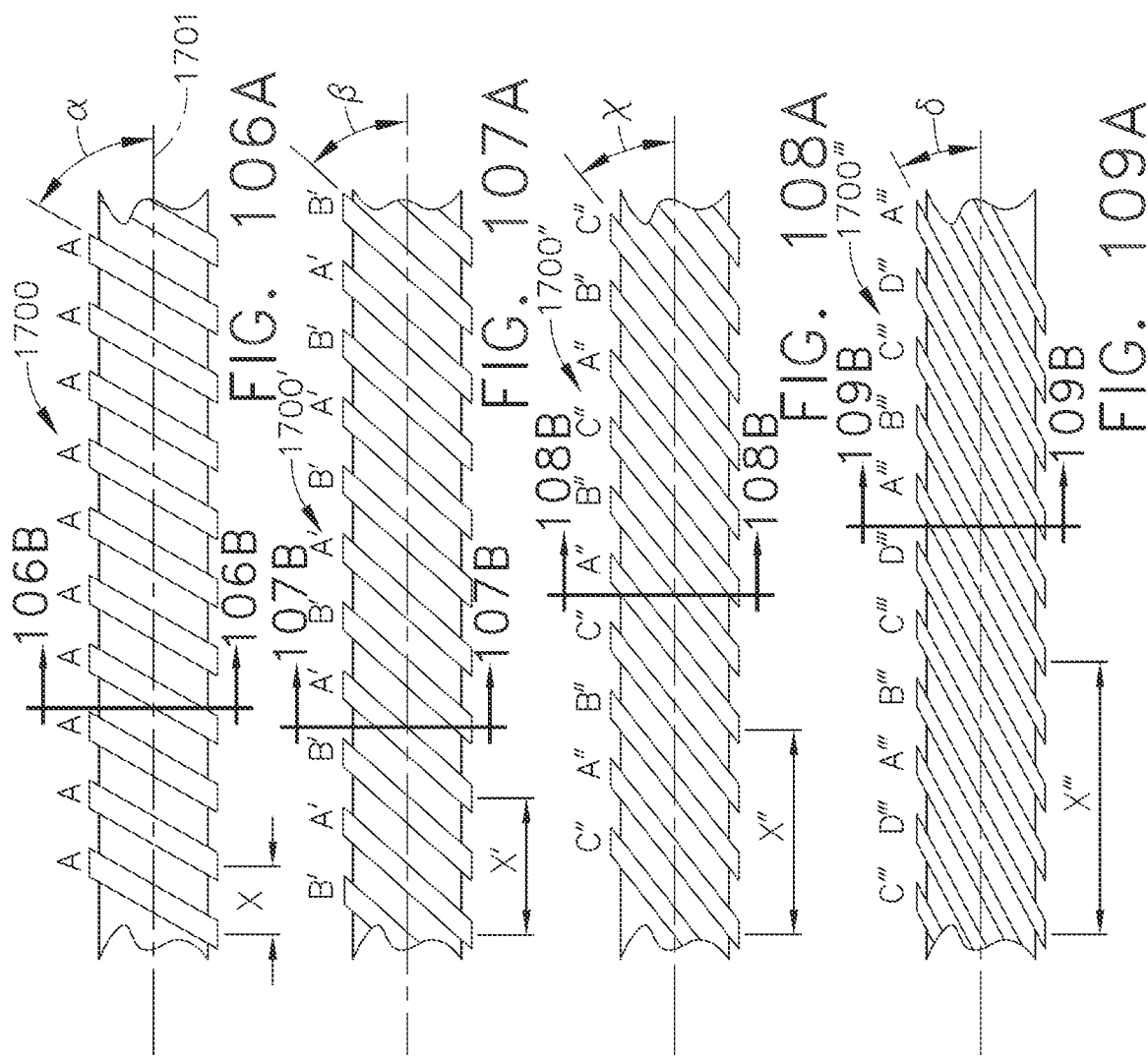
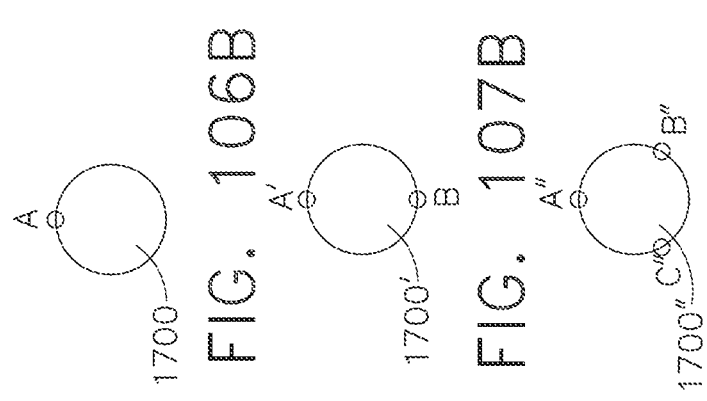

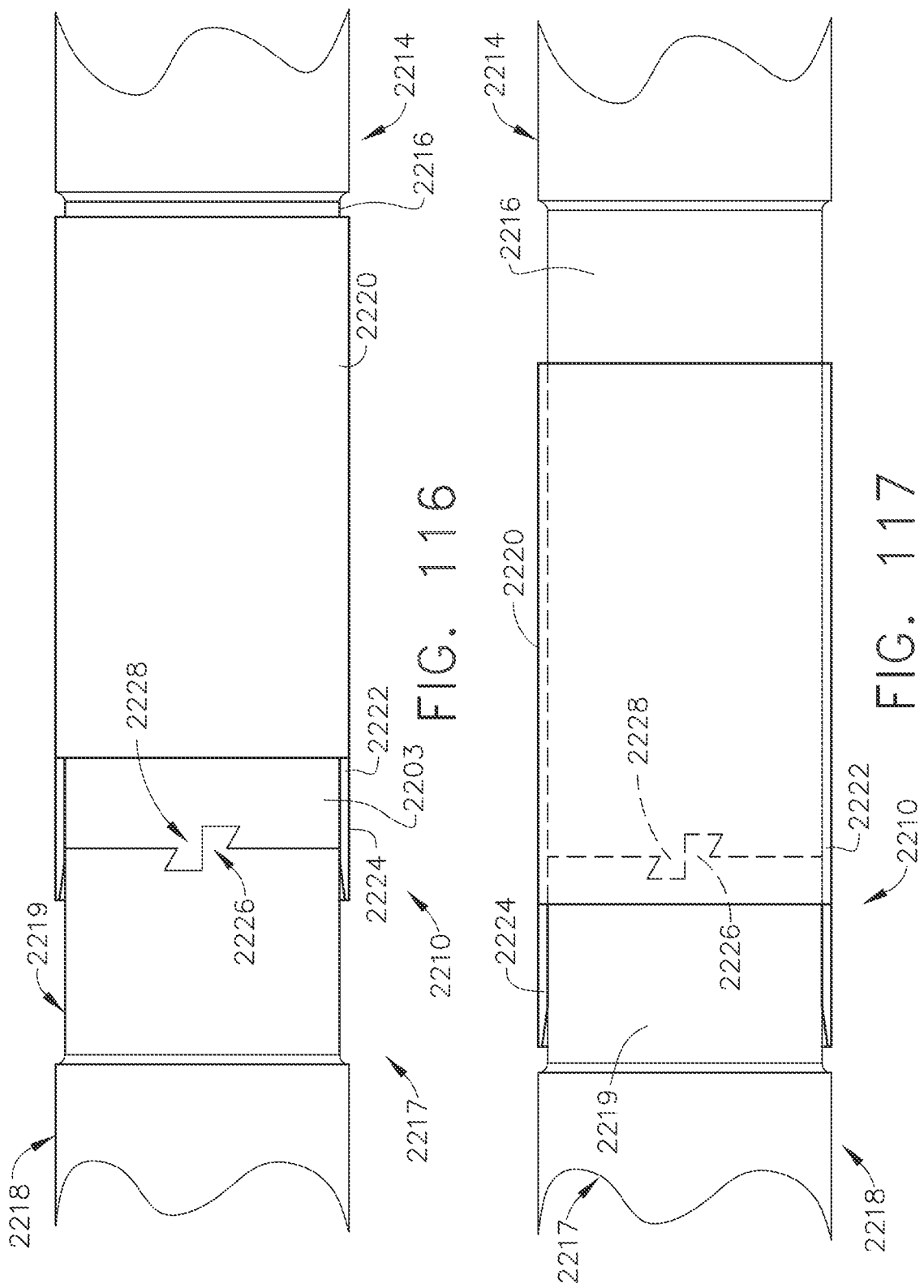

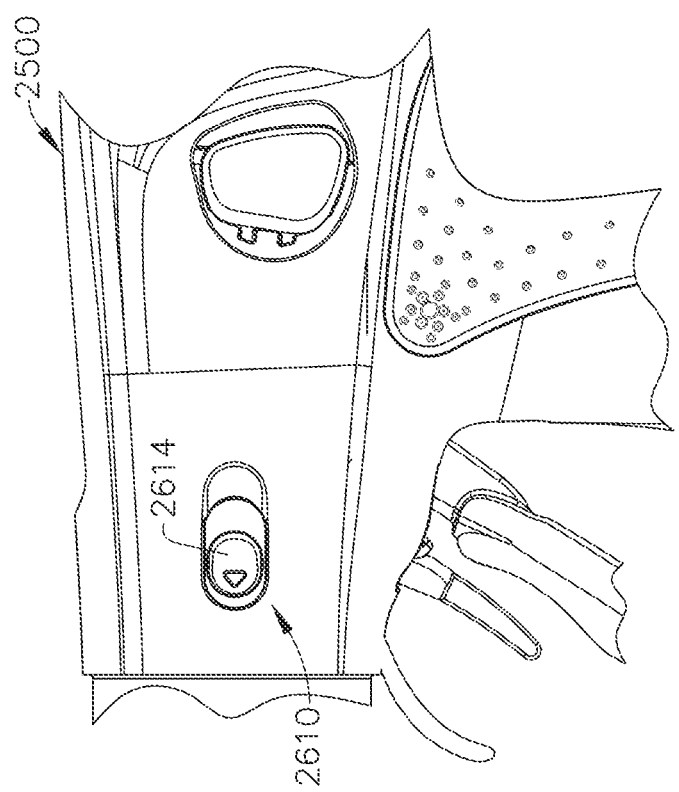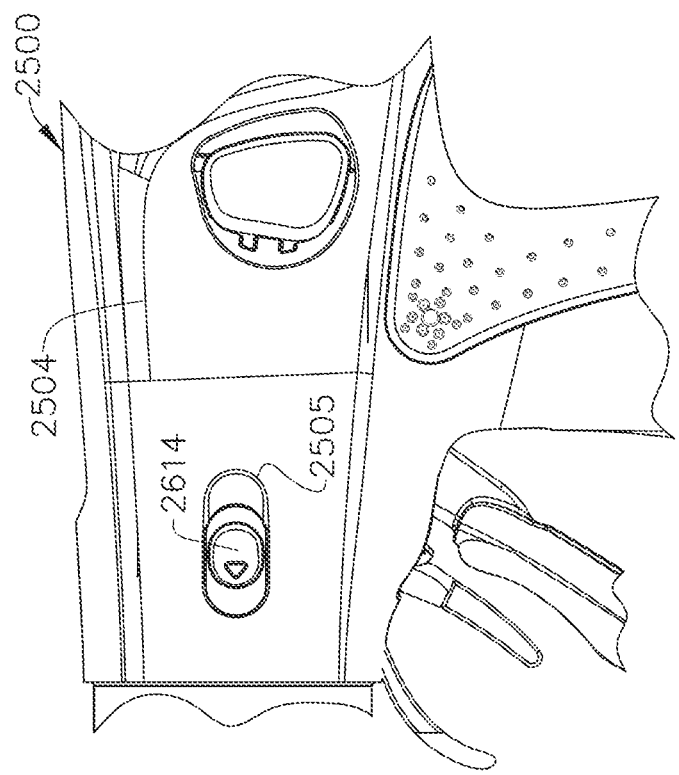

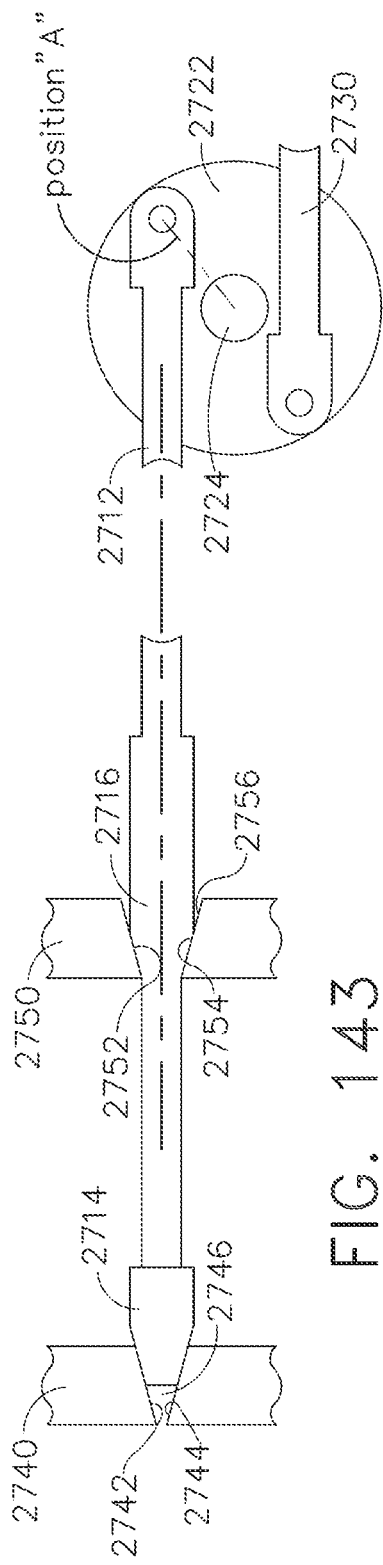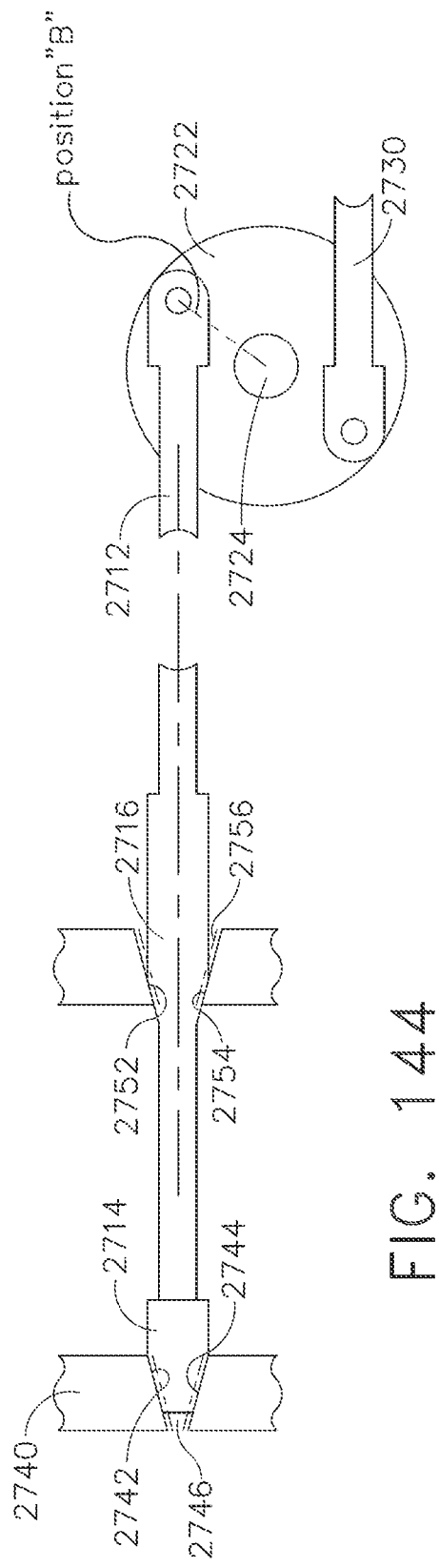

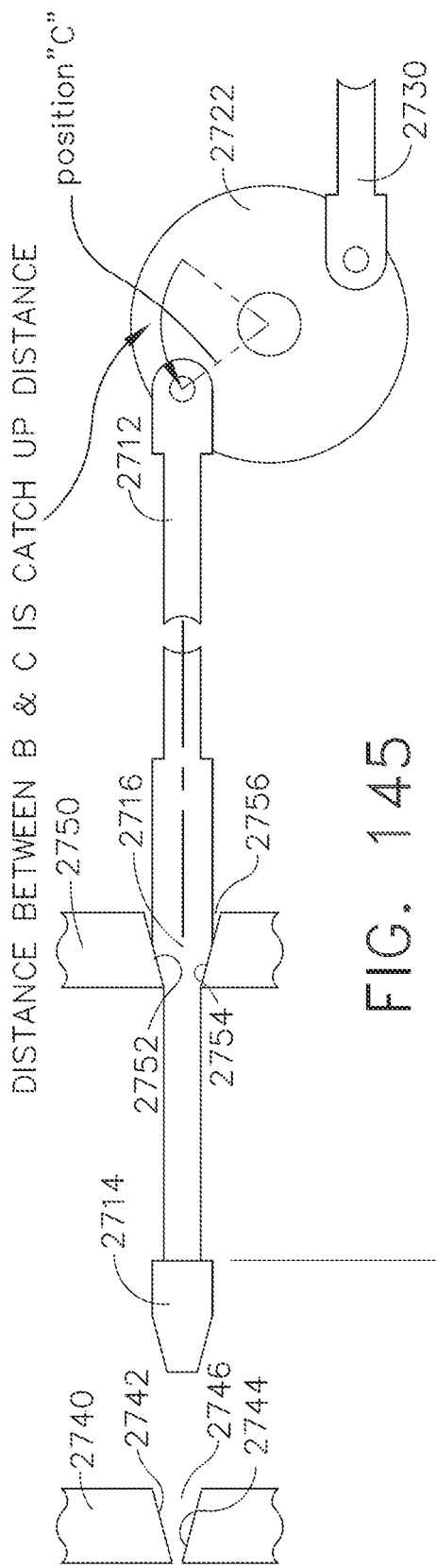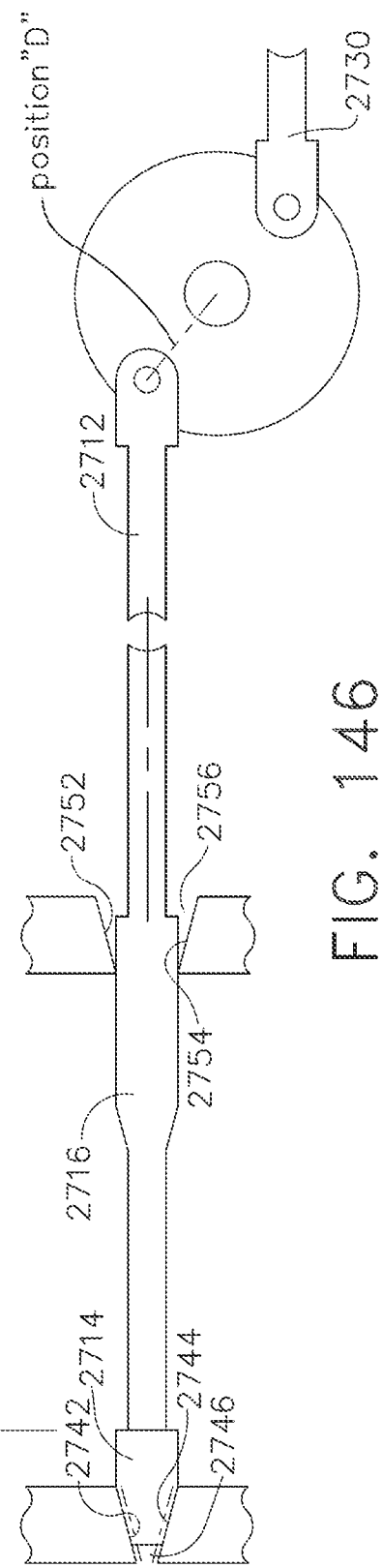

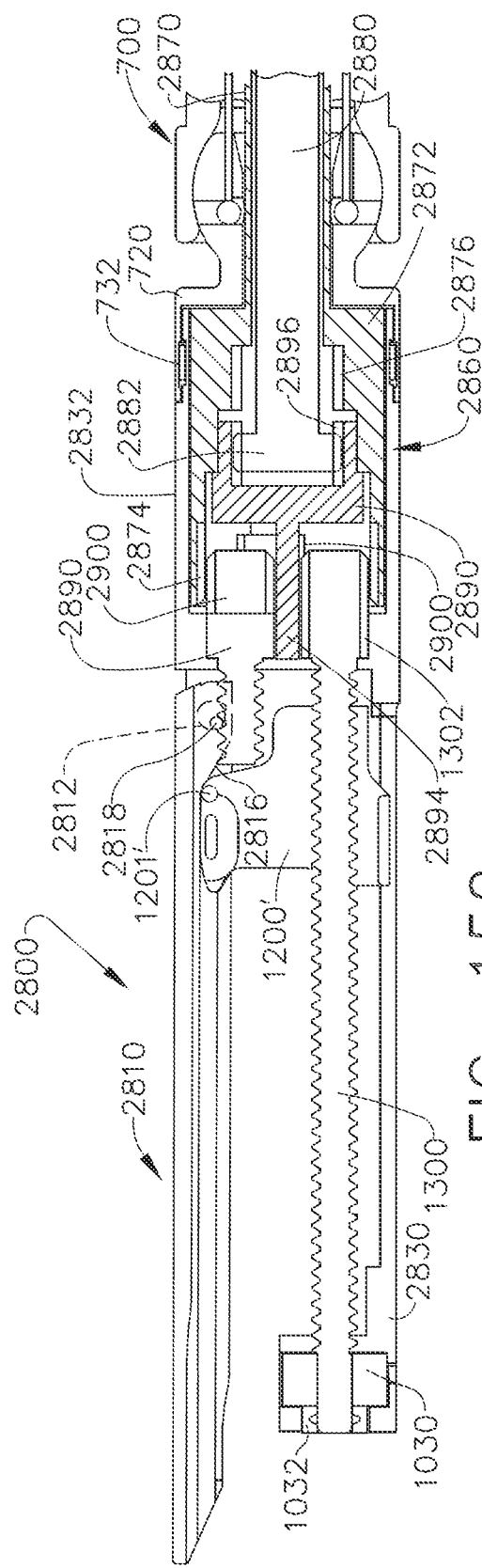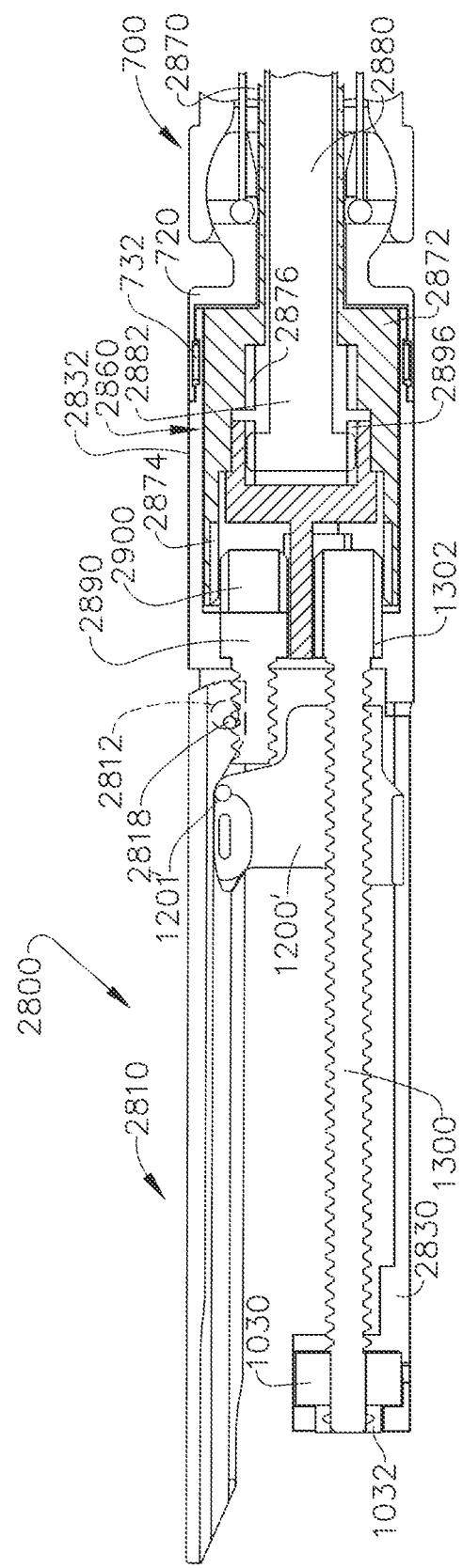

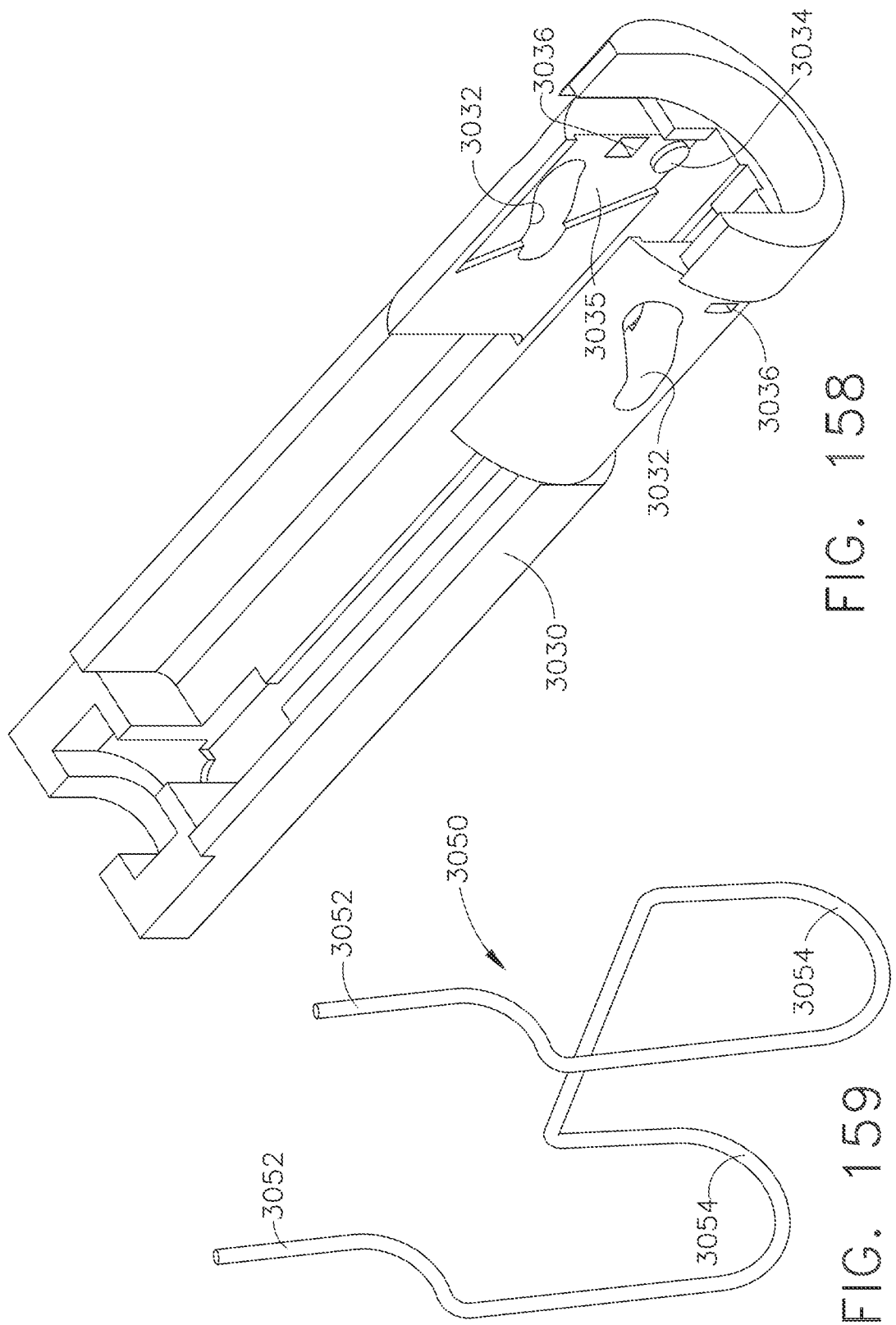

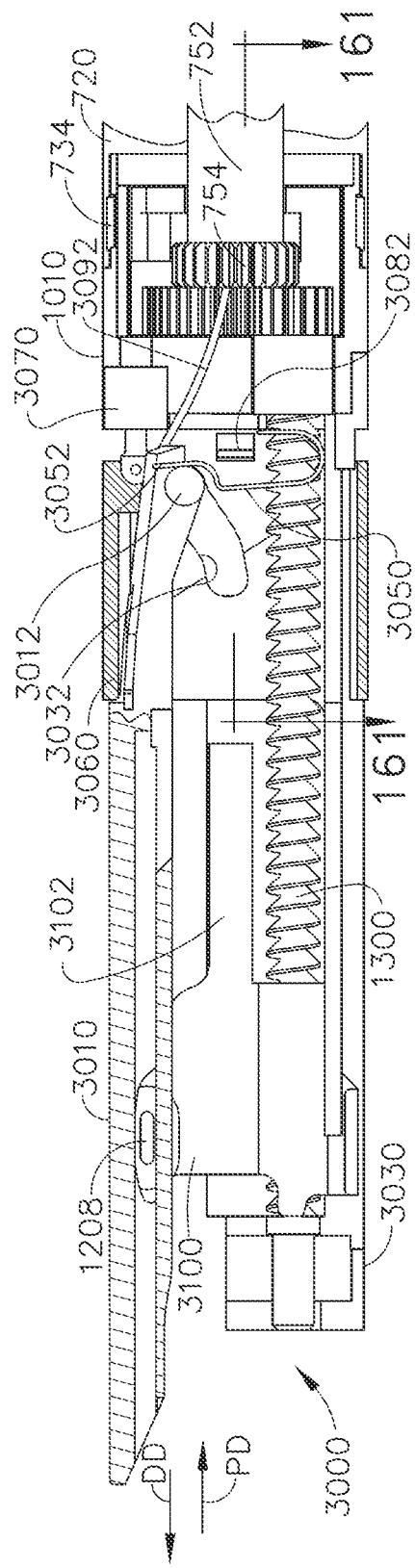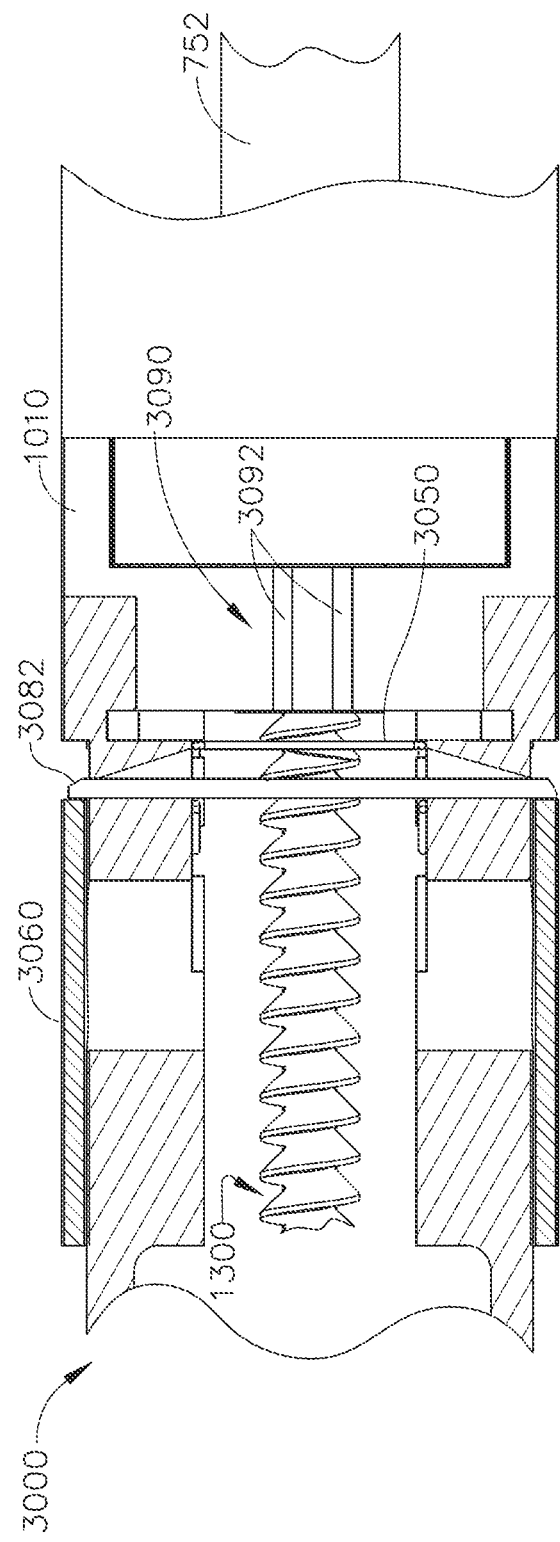

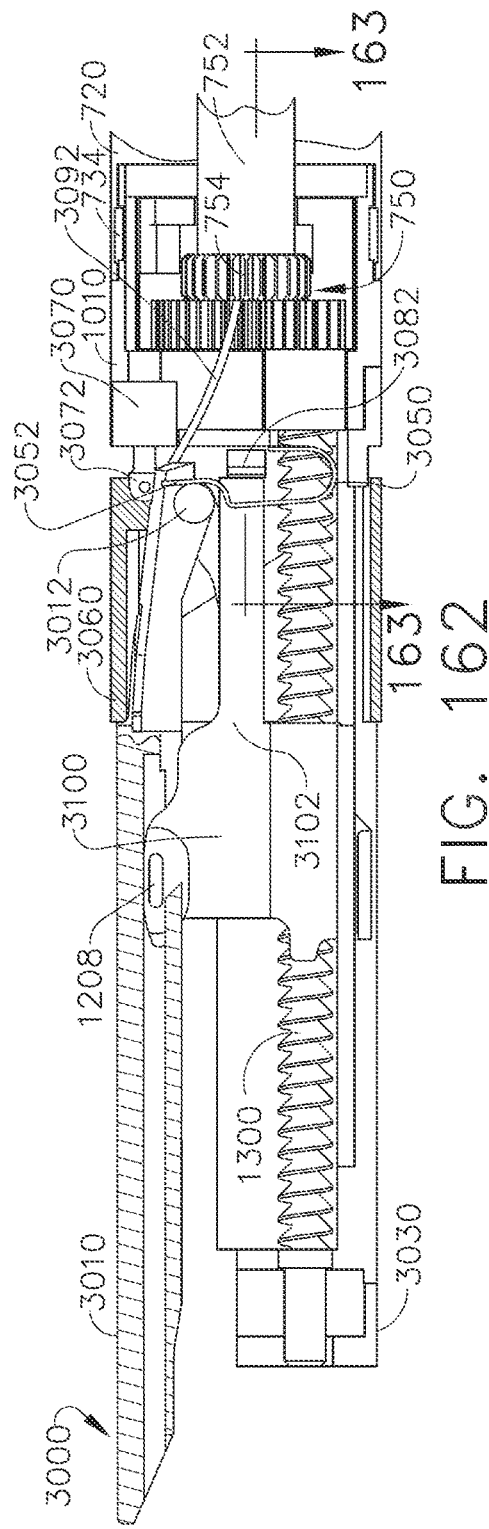
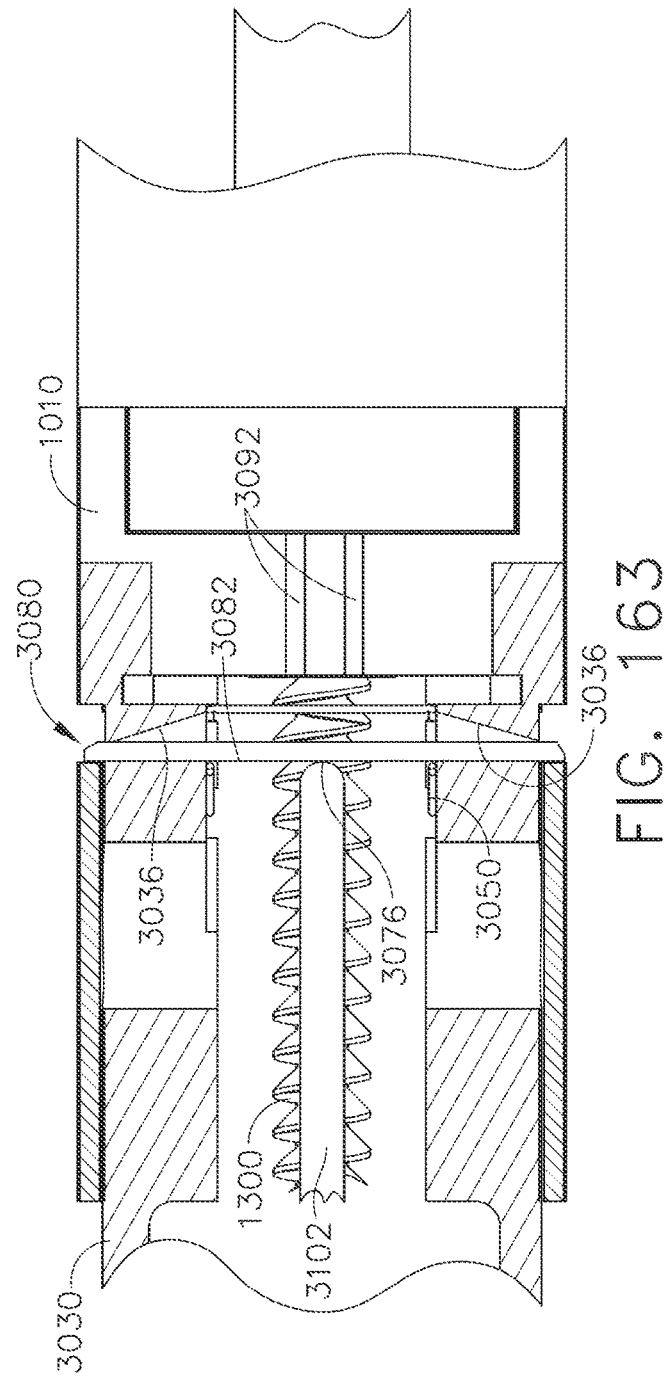

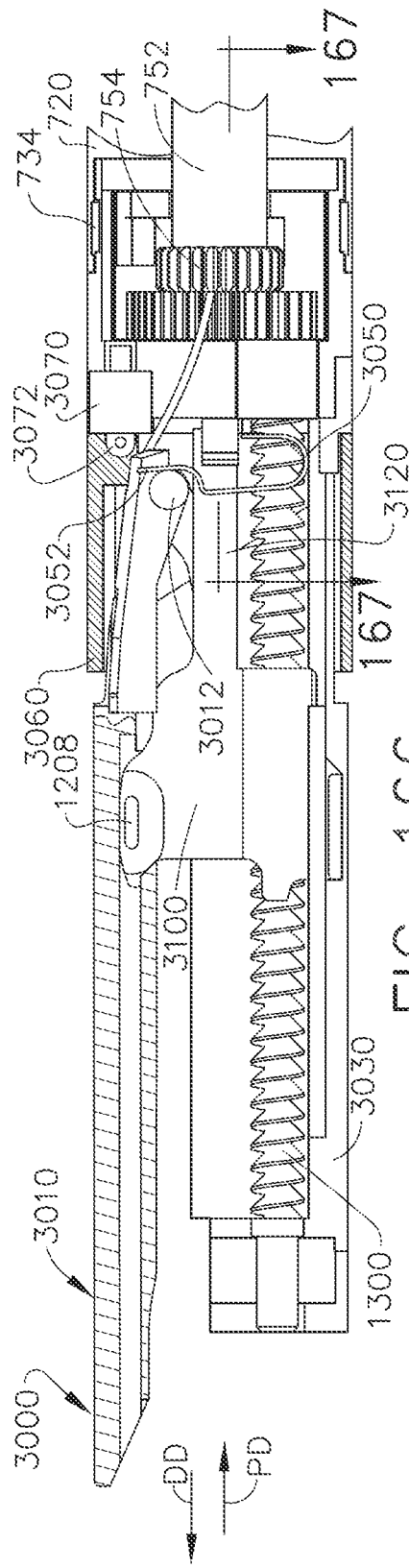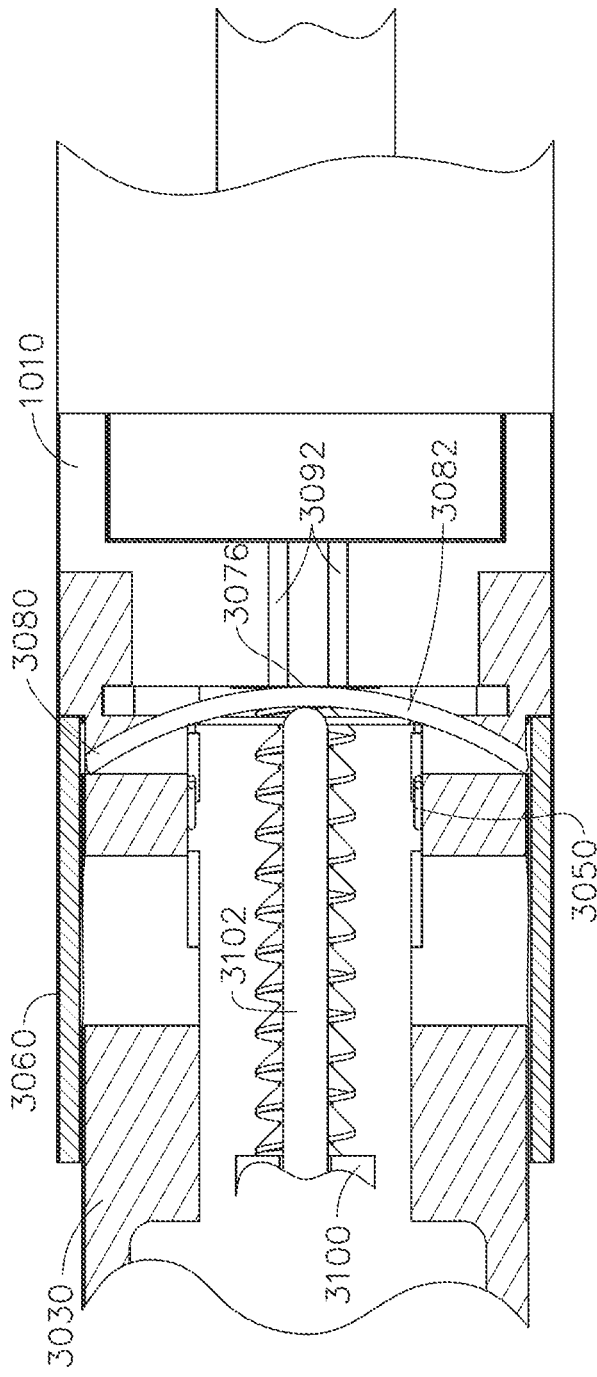

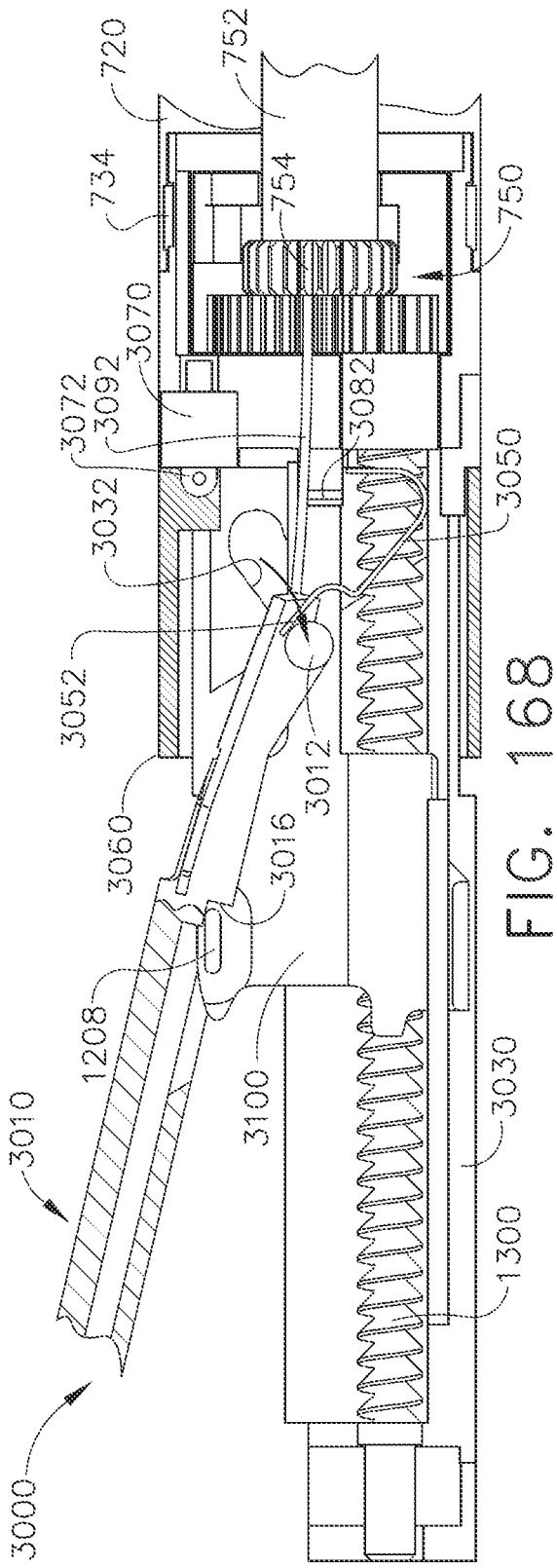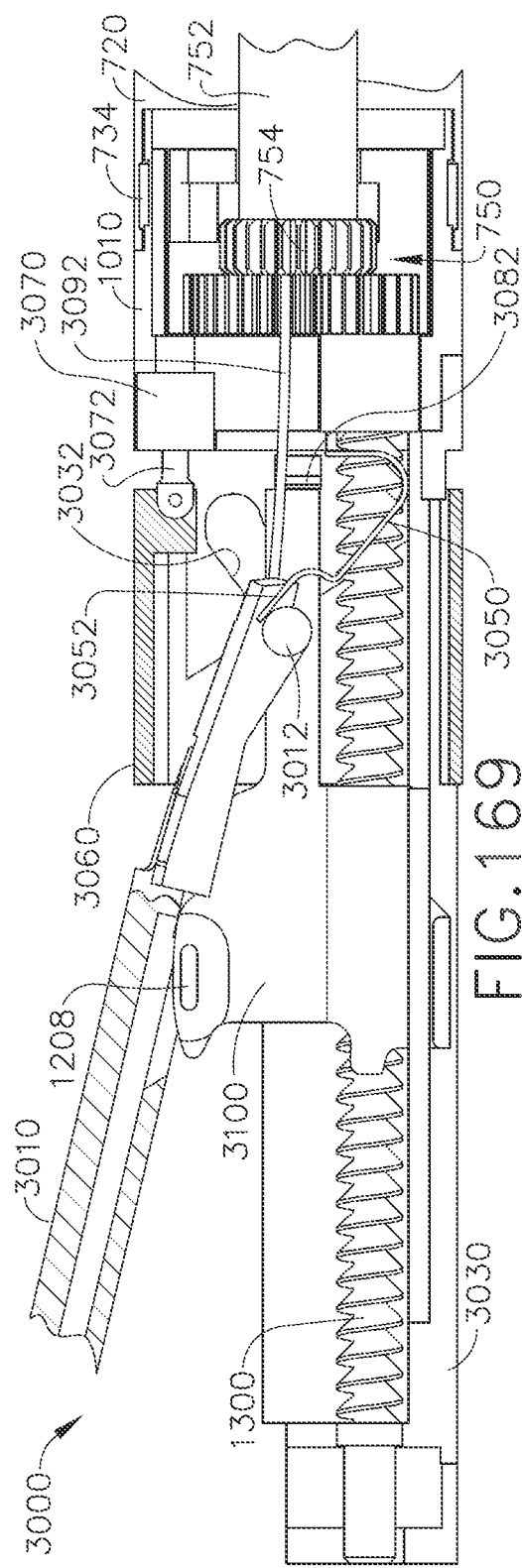

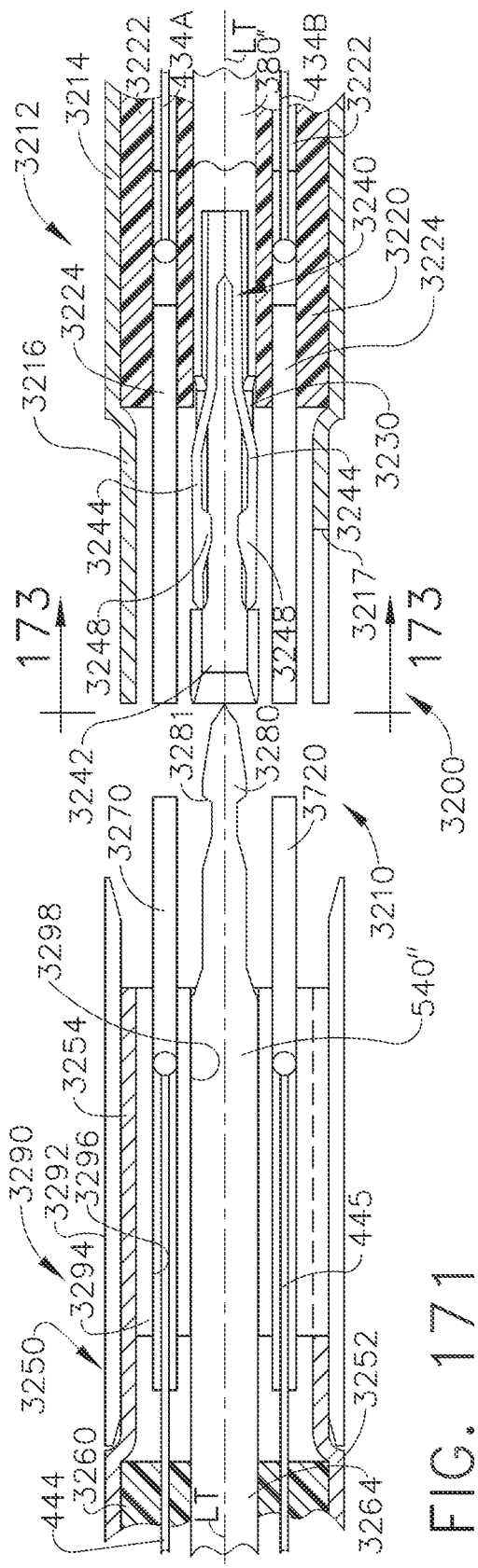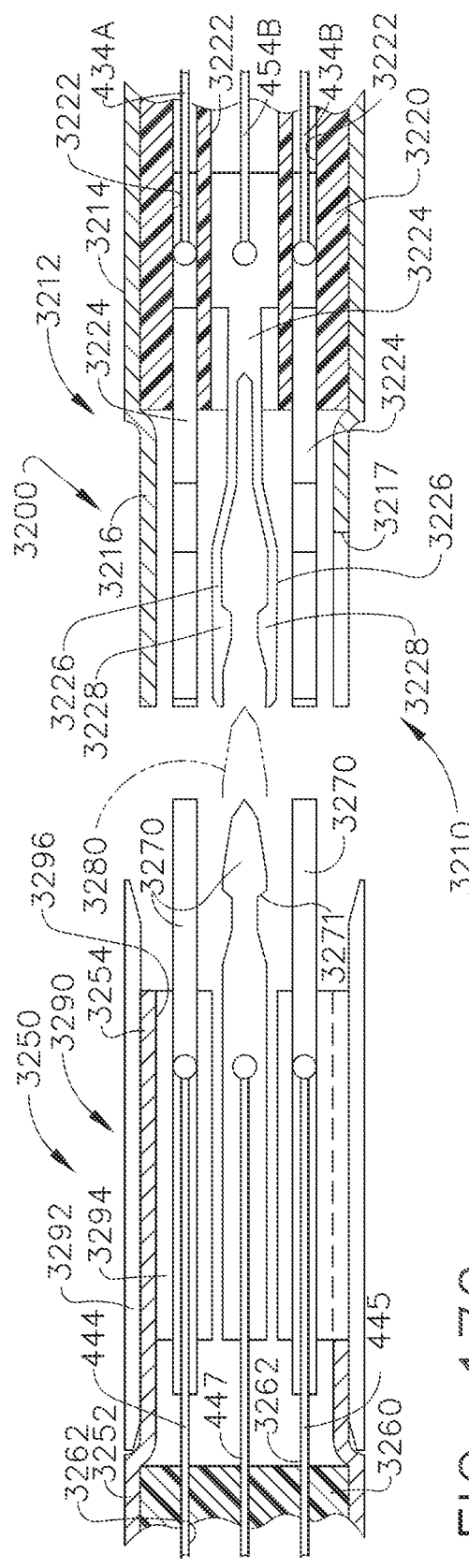

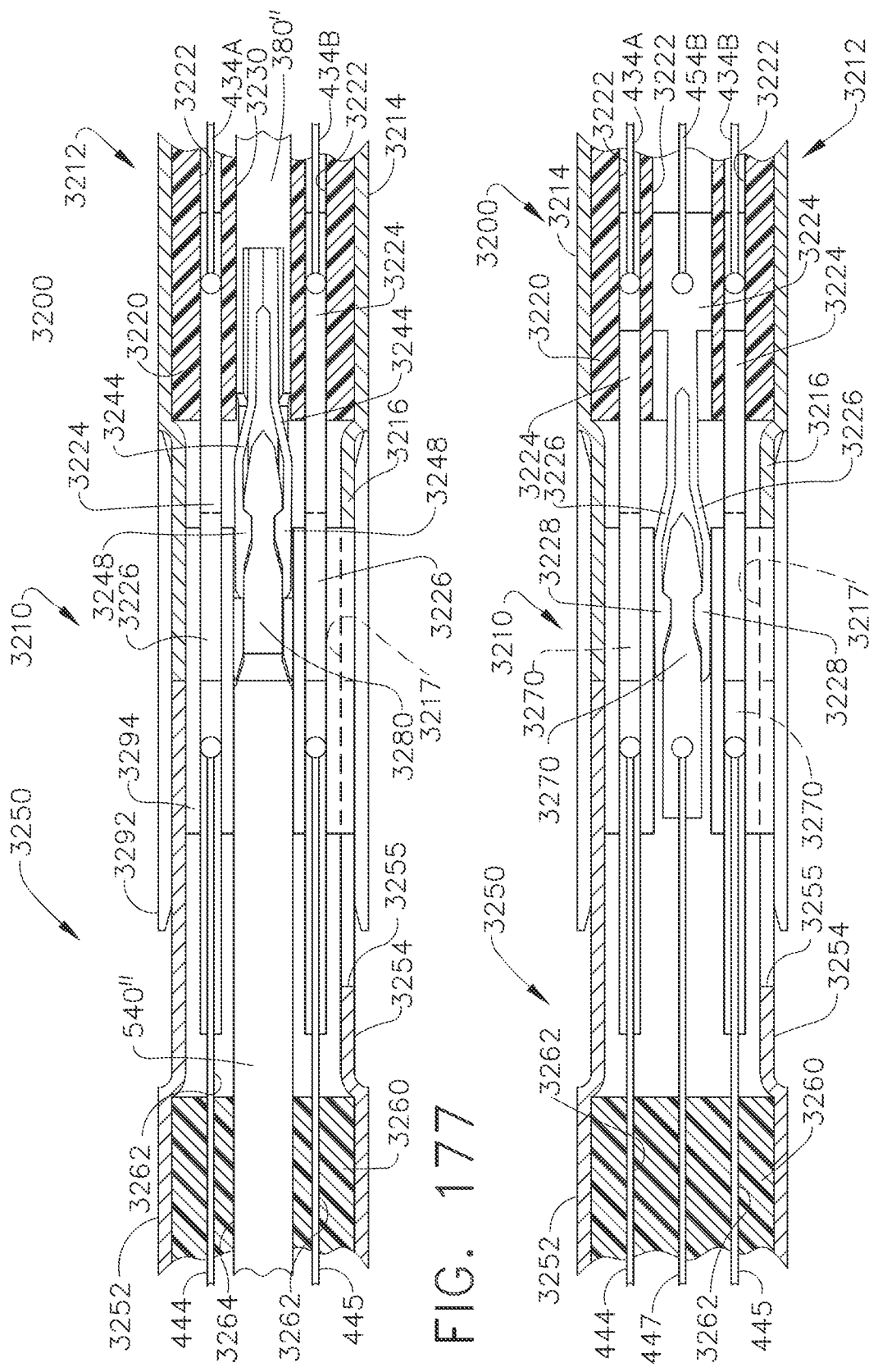

SURGICAL STAPLING ASSEMBLY COMPRISING FLEXIBLE OUTPUT SHAFT

CROSS REFERENCE TO RELATED APPLICATIONS

This application is a continuation application claiming priority under 35 U.S.C. § 120 to U.S. patent application Ser. No. 15/079,526, entitled ROBOTICALLY POWERED SURGICAL DEVICE WITH MANUALLY-ACTUATABLE REVERSING SYSTEM, filed on Mar. 24, 2016, which issued on Nov. 26, 2019 as U.S. Pat. No. 10,485,541, which is a continuation application claiming priority under 35 U.S.C. § 120 to U.S. patent application Ser. No. 13/536,323, entitled ROBOTICALLY POWERED SURGICAL DEVICE WITH MANUALLY-ACTUATABLE REVERSING SYSTEM, filed on Jun. 28, 2012, which issued on Aug. 9, 2016 as U.S. Pat. No. 9,408,606, the entire disclosures of which are hereby incorporated by reference herein.

BACKGROUND

Over the years a variety of minimally invasive robotic (or "telesurgical") systems have been developed to increase surgical dexterity as well as to permit a surgeon to operate on a patient in an intuitive manner. Many of such systems are disclosed in the following U.S. patents which are each herein incorporated by reference in their respective entirety: U.S. Pat. No. 5,792,135, entitled ARTICULATED SURGICAL INSTRUMENT FOR PERFORMING MINIMALLY INVASIVE SURGERY WITH ENHANCED DEXTERITY AND SENSITIVITY, U.S. Pat. No. 6,231,565, entitled ROBOTIC ARM DLUS FOR PERFORMING SURGICAL TASKS, U.S. Pat. No. 6,783,524, entitled ROBOTIC SURGICAL TOOL WITH ULTRASOUND CAUTERIZING AND CUTTING INSTRUMENT, U.S. Pat. No. 6,364,888, entitled ALIGNMENT OF MASTER AND SLAVE IN A MINIMALLY INVASIVE SURGICAL APPARATUS, U.S. Pat. No. 7,524,320, entitled MECHANICAL ACTUATOR INTERFACE SYSTEM FOR ROBOTIC SURGICAL TOOLS, U.S. Pat. No. 7,691,098, entitled PLATFORM LINK WRIST MECHANISM, U.S. Pat. No. 7,806,891, entitled REPOSITIONING AND REORIENTATION OF MASTER/SLAVE RELATIONSHIP IN MINIMALLY INVASIVE TELESURGERY, and U.S. Pat. No. 7,824,401, entitled SURGICAL TOOL WITH WRISTED MONOPOLAR ELECTROSURGICAL END EFFECTORS. Many of such systems, however, have in the past been unable to generate the magnitude of forces required to effectively cut and fasten tissue. In addition, existing robotic surgical systems are limited in the number of different types of surgical devices that they may operate.

BRIEF DESCRIPTION OF THE DRAWINGS

The features and advantages of this invention, and the manner of attaining them, will become more apparent and the invention itself will be better understood by reference to the following description of exemplary embodiments of the invention taken in conjunction with the accompanying drawings, wherein:

Various exemplary embodiments are described herein by way of example in conjunction with the following Figures wherein:

FIG. 21 is a cross-sectional view of a quick disconnect joint embodiment with the distal shaft portion of the end effector detached from the proximal shaft portion;

FIG. 22 is another cross-sectional view of the quick disconnect joint embodiment of FIGS. 19-21 wherein the distal shaft portion has been initially engaged with the proximal shaft portion;

FIG. 23 is another cross-sectional view of the quick disconnect joint embodiment of FIGS. 19-22 wherein the distal shaft portion has been attached to the proximal shaft portion;

FIG. 26 is an exploded assembly view of a portion of the articulation joint and end effector of FIG. 25;

FIG. 27 is a partial cross-sectional perspective view of the articulation joint and end effector portions depicted in FIG. 26;

FIG. 28 is a partial perspective view of an end effector and drive shaft assembly embodiment;

FIG. 29 is a partial side view of a drive shaft assembly embodiment;

FIG. 32 is a perspective view of a composite drive shaft assembly embodiment;

FIG. 33 is a side view of the composite drive shaft assembly of FIG. 33;

FIG. 35 is a perspective view of a portion of another drive shaft assembly embodiment;

FIG. 36 is a top view of the drive shaft assembly embodiment of FIG. 35;

FIG. 37 is another perspective view of the drive shaft assembly embodiment of FIGS. 35 and 36 in an arcuate configuration;

FIG. 38 is a top view of the drive shaft assembly embodiment depicted in FIG. 37;

FIG. 39 is a perspective view of another drive shaft assembly embodiment;

FIG. 40 is another perspective view of the drive shaft assembly embodiment of FIG. 39 in an arcuate configuration;

FIG. 41 is a top view of the drive shaft assembly embodiment of FIGS. 39 and 40;

FIG. 42 is a cross-sectional view of the drive shaft assembly embodiment of FIG. 41;

FIG. 43 is a partial cross-sectional view of another drive shaft assembly embodiment;

FIG. 44 is another cross-sectional view of the drive shaft assembly embodiment of FIG. 43;

FIG. 47 is a partial cross-sectional perspective view of an end effector embodiment with the anvil thereof in an open position;

FIG. 48 is another partial cross-sectional perspective view of the end effector embodiment of FIG. 47;

FIG. 49 is a side cross-sectional view of the end effector embodiment of FIGS. 47 and 48;

FIG. 50 is another side cross-sectional view of the end effector embodiment of FIGS. 47-49;

FIG. 58 is a side cross-sectional view of the closure system embodiment of FIGS. 57 and 57 within an end effector embodiment wherein the anvil thereof is in an open position;

FIG. 59 is another cross-sectional view of the closure system and end effector embodiment of FIG. 58 with the anvil thereof in a closed position;

FIG. 68 is a cross-sectional perspective view of a portion of an end effector embodiment and articulation joint embodiment;

FIG. 69 is a cross-sectional side view of the end effector and articulation joint embodiment depicted in FIG. 68;

FIG. 74 is a cross-sectional side view of another end effector embodiment wherein the firing member thereof has been partially driven through the firing stroke;

FIG. 75 is another cross-sectional side view of the end effector embodiment of FIG. 74 wherein the firing member has been driven to the end of its firing stroke;

FIG. 81A is an exploded assembly view of an implement drive shaft and bearing segment embodiment;

FIG. 81B is an exploded assembly view of another implement drive shaft and bearing segment embodiment;

FIG. 82 is an exploded assembly view of a firing member embodiment;

FIG. 83 is a perspective view of the firing member of FIG. 82;

FIG. 84 is a cross-sectional view of the firing member of FIGS. 82 and 83 installed on a portion of an exemplary implement drive shaft embodiment;

FIG. 86 is a rear perspective view of another firing member embodiment;

FIG. 87 is a front perspective view of the firing member embodiment of FIG. 86;

FIG. 88 is a perspective view of a firing member, implement drive shaft, wedge sled assembly and alignment portion for a surgical end effector;

FIG. 92 is a perspective view of a portion of the bottom of the surgical end effector of FIG. 91 in a closed and inoperable configuration;

FIG. 93 is a cross-sectional elevational view of the surgical end effector of FIG. 91 in a closed and inoperable configuration;

FIG. 101 is a cross-sectional elevational view of the surgical end effector of FIG. 98 illustrating the biasing element in a second set of positions;

FIG. 102 is a cross-sectional view of a portion of the surgical end effector of FIG. 98 illustrating the implement drive shaft in an inoperable position;

FIG. 103 is a cross-sectional view of a portion of the surgical end effector of FIG. 98 illustrating the biasing element in a first set of positions;

FIG. 104 is a cross-sectional view of a portion of the surgical end effector of FIG. 98 illustrating the biasing element in a first set of positions and the implement drive shaft in an operable position;

FIG. 106A is a side view of a portion of a first drive screw for an end effector comprising a first length, wherein the first drive screw includes a single thread;

FIG. 106B is a cross-sectional end view of the first drive screw of FIG. 106A;

FIG. 107A is a side view of a portion of a second drive screw for an end effector comprising a second length, wherein the second drive screw includes two threads;

FIG. 107B is a cross-sectional end view of the second drive screw of FIG. 107A;

FIG. 108A is a side view of a portion of a third drive screw for an end effector comprising a third length, wherein the third drive screw includes three threads;

FIG. 108B is a cross-sectional end view of the third drive screw of FIG. 108A;

FIG. 109A is a side view of a portion of a fourth drive screw for an end effector comprising a fourth length, wherein the fourth drive screw includes four threads;

FIG. 109B is a cross-sectional end view of the fourth drive screw of FIG. 109A;

FIG. 110 is a exploded perspective view of a cutting blade for use with an end effector having a drive screw;

FIG. 111 is a perspective view of a gearing arrangement for transmitting rotation from a drive shaft to a drive screw of an end effector, wherein the gearing arrangement is shown with portions thereof removed for the purposes of illustration;

FIG. 112 is a perspective view of another surgical tool embodiment;

FIG. 112A is a perspective view of the end effector arrangement of the surgical tool of FIG. 112;

FIG. 113 is an exploded assembly view of a portion of the elongate shaft assembly and quick disconnect coupler arrangement depicted in FIG. 112;

FIG. 114 is a perspective view of a portion of the elongate shaft assembly of FIGS. 112 and 113;

FIG. 115 is an enlarged exploded perspective view of the exemplary quick disconnect coupler arrangement depicted in FIGS. 112-114;

FIG. 116 is a side elevational view of the quick disconnect coupler arrangement of FIGS. 112-115 with the locking collar thereof in an unlocked position;

Figure 20:
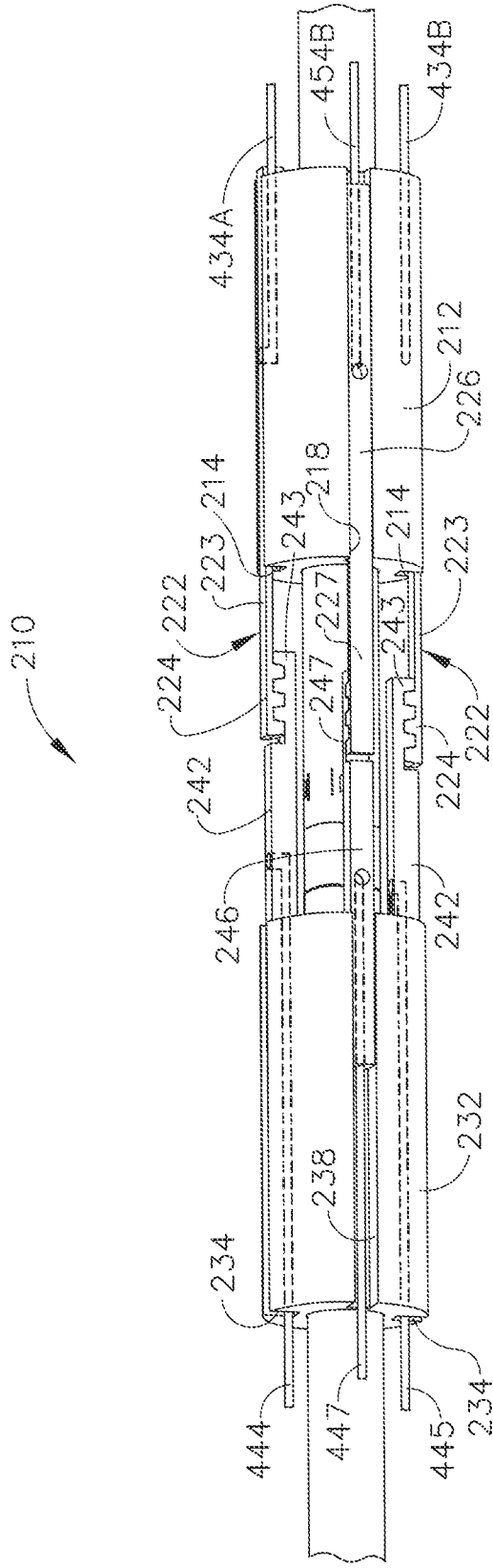
FIG. 20 is a side perspective view showing a portion of a interconnected quick disconnect joint embodiment.
Figure 118:
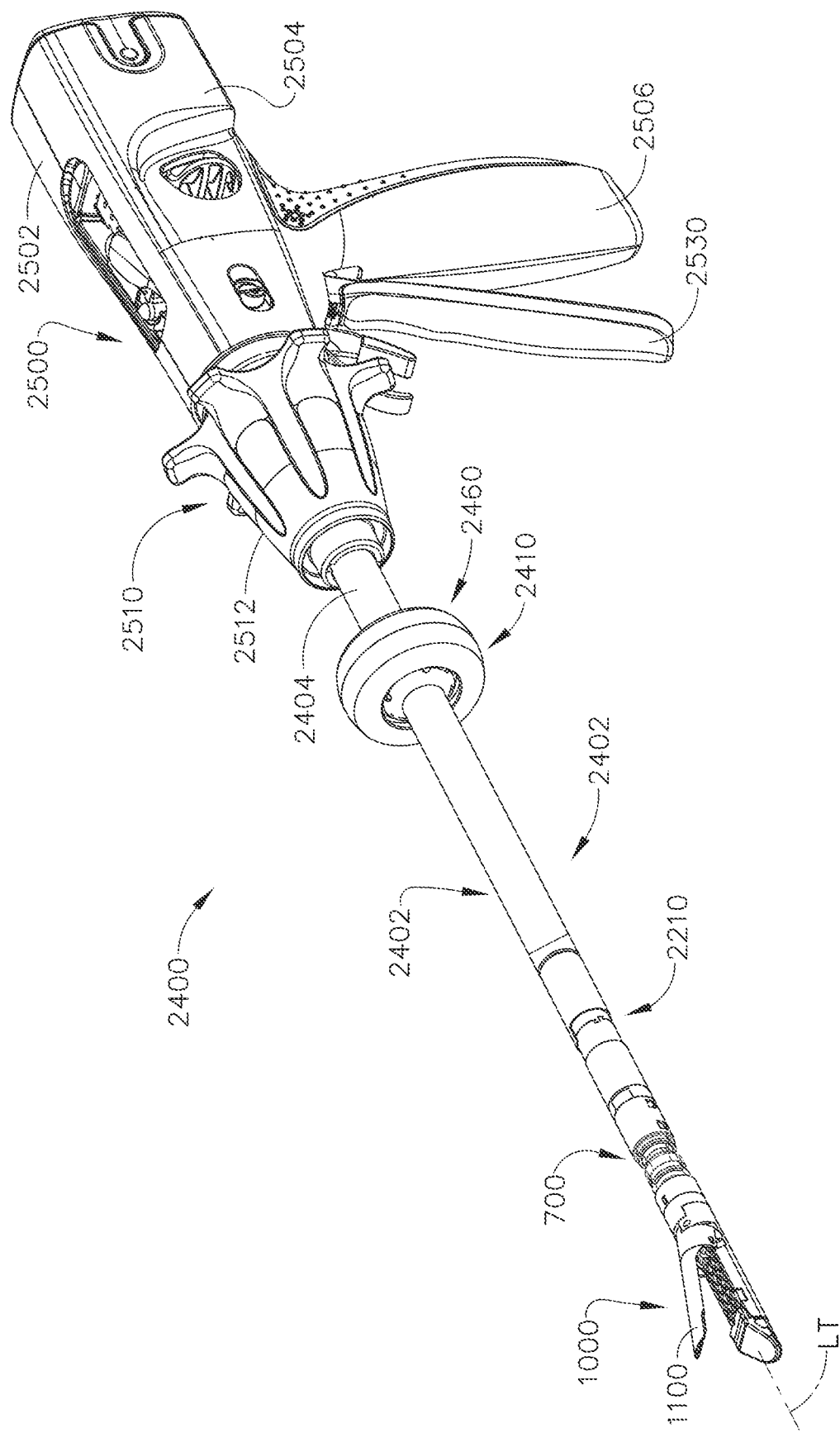
Figure 119:
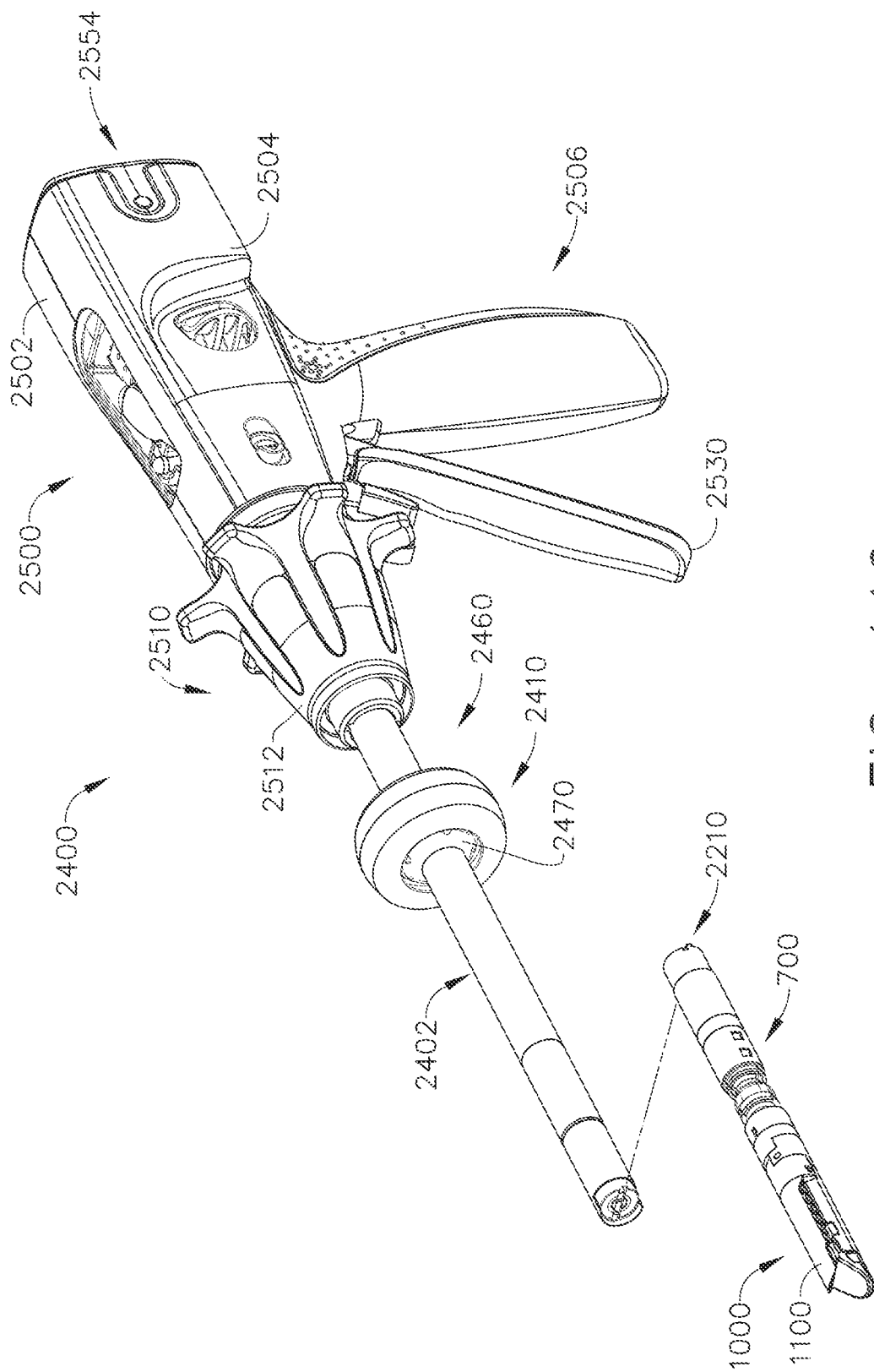
Figure 120:
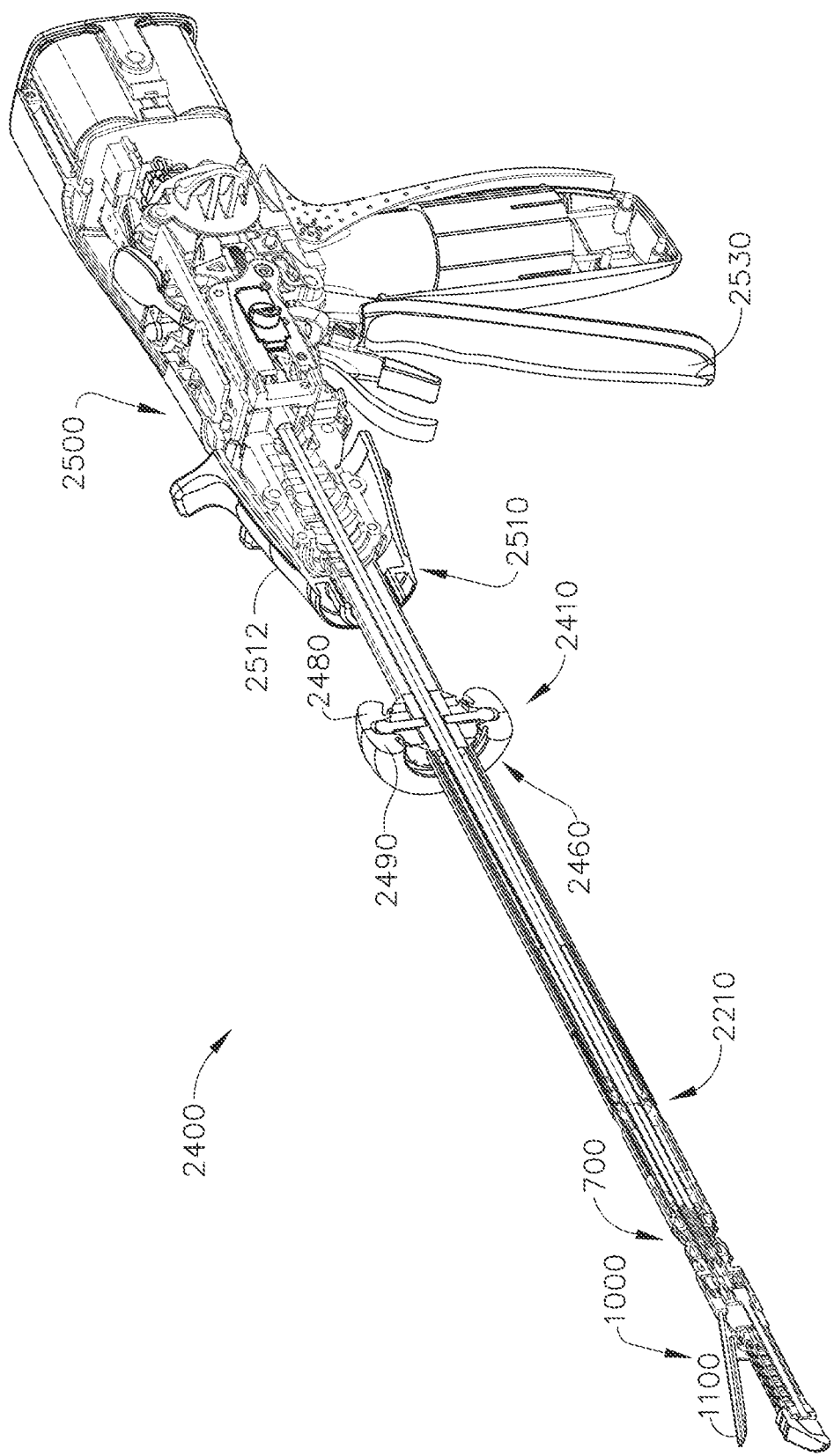
Figure 121:
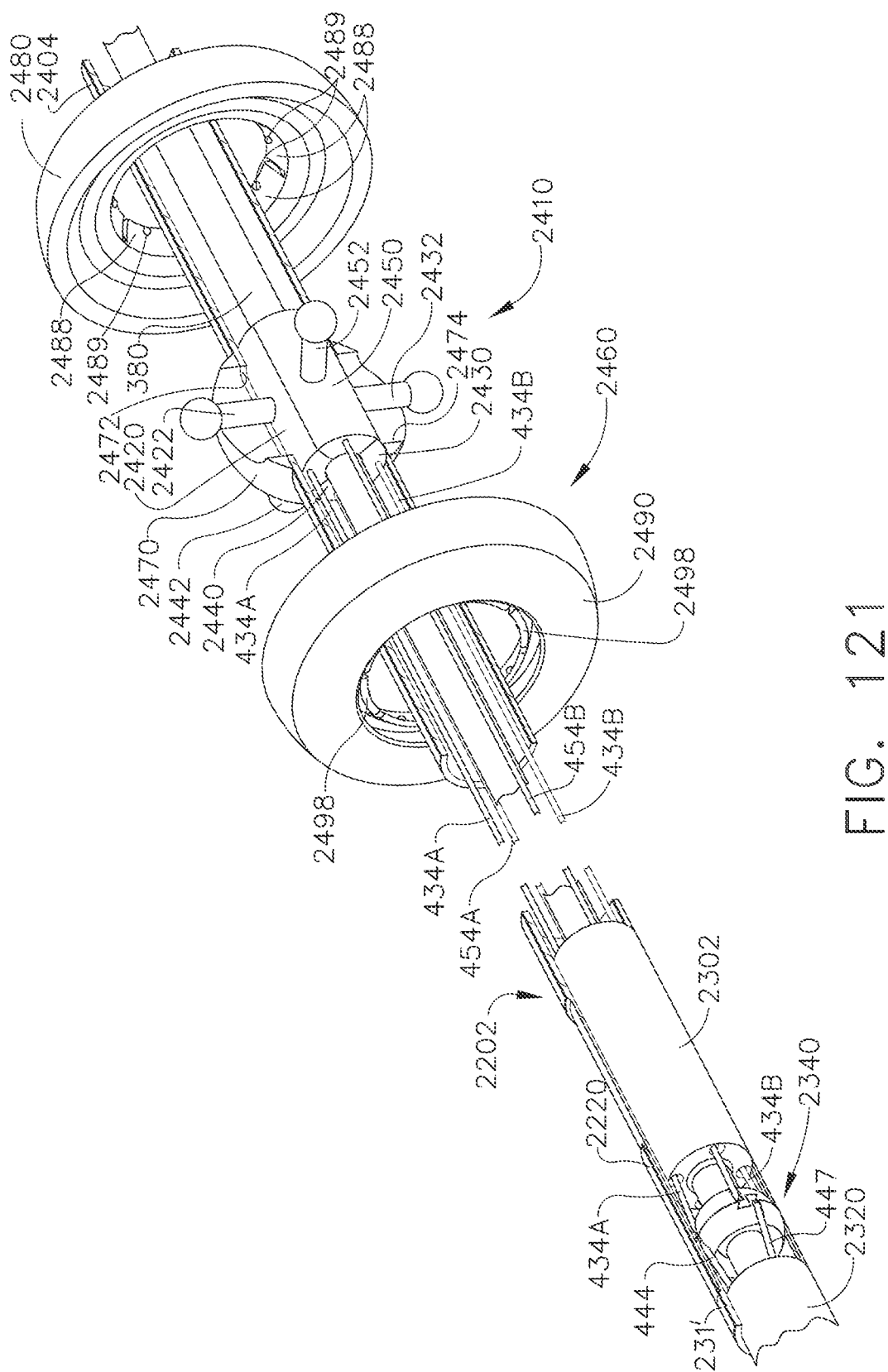
Figure 122:
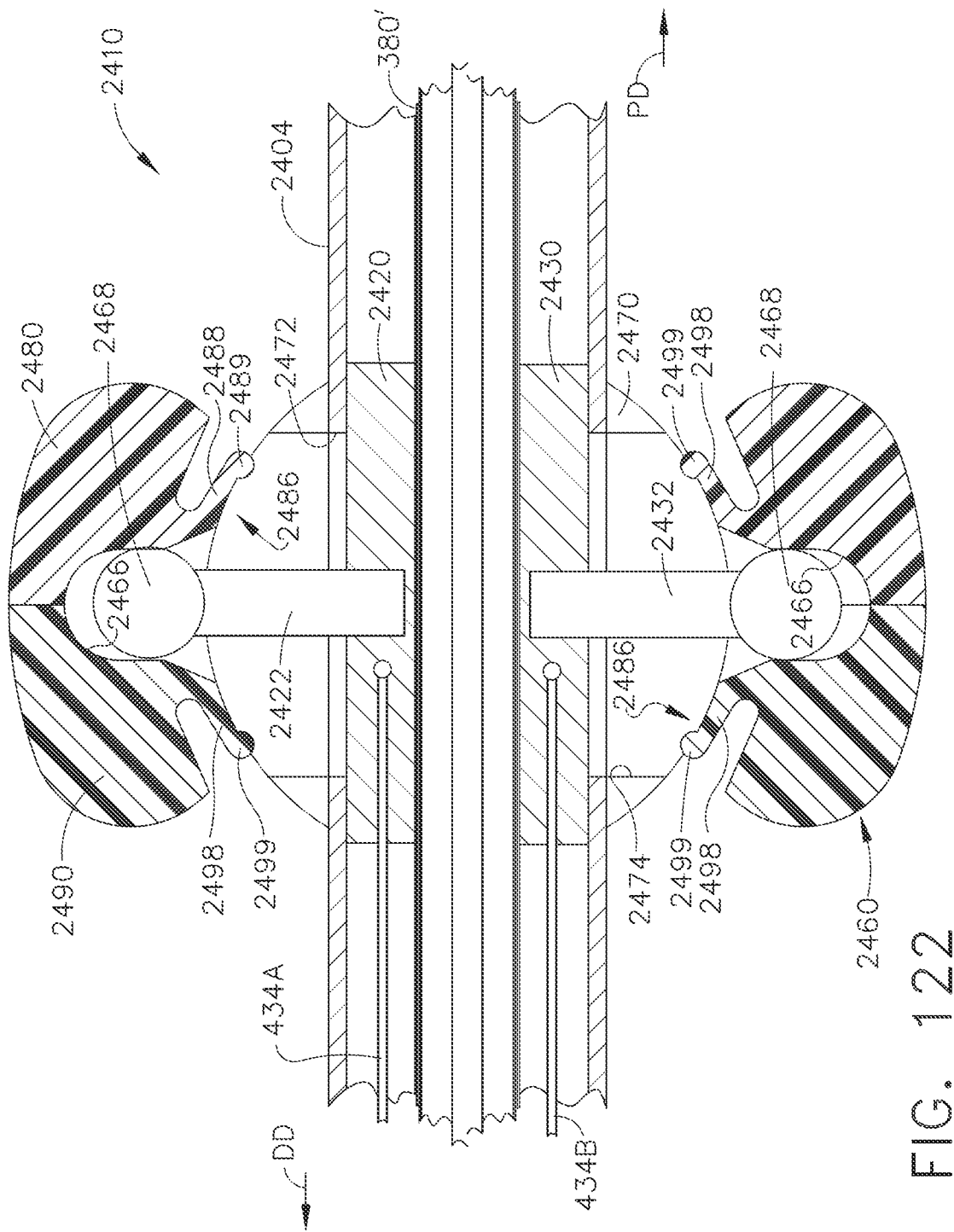
Figure 123:
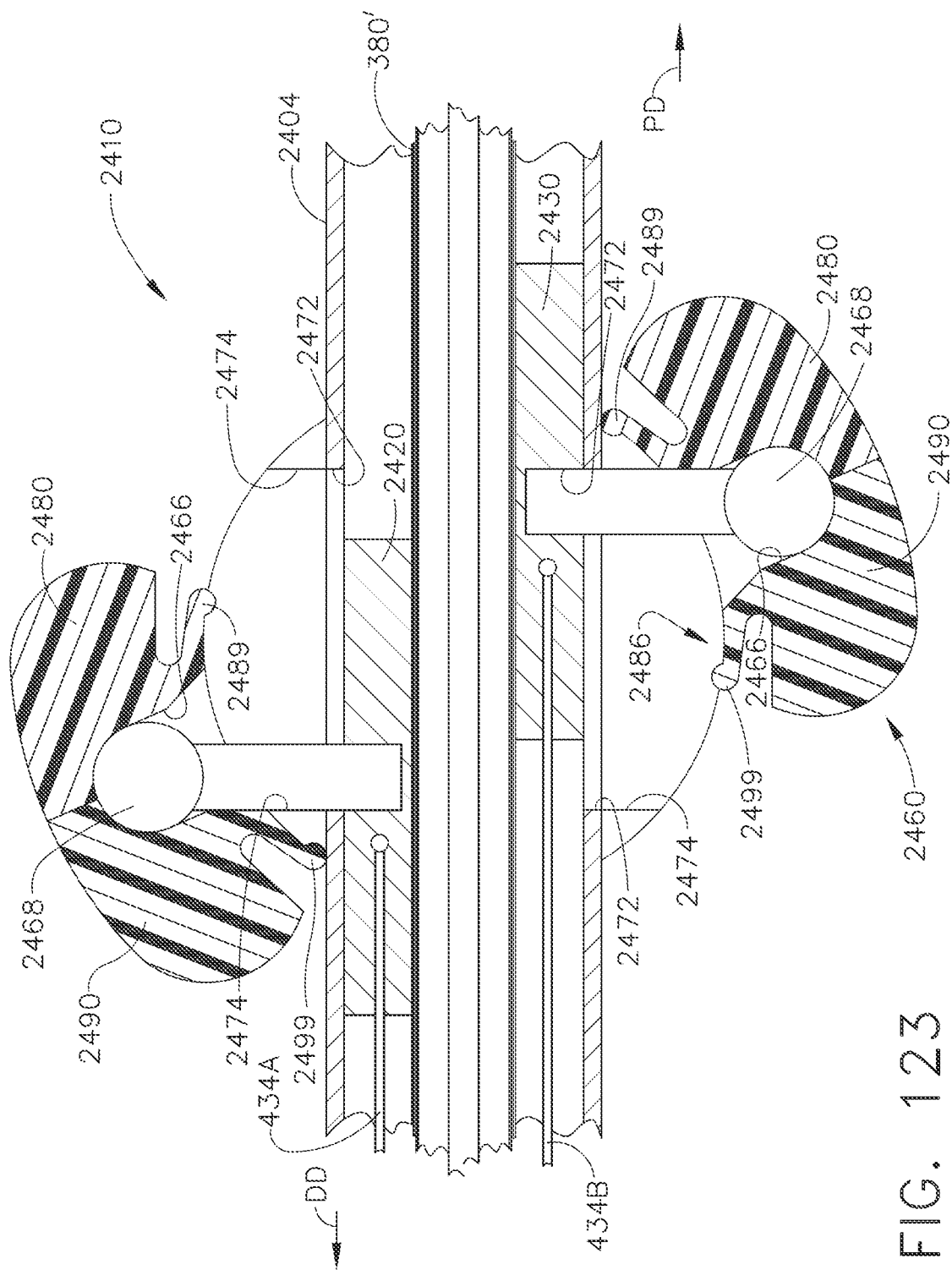
Figure 124:
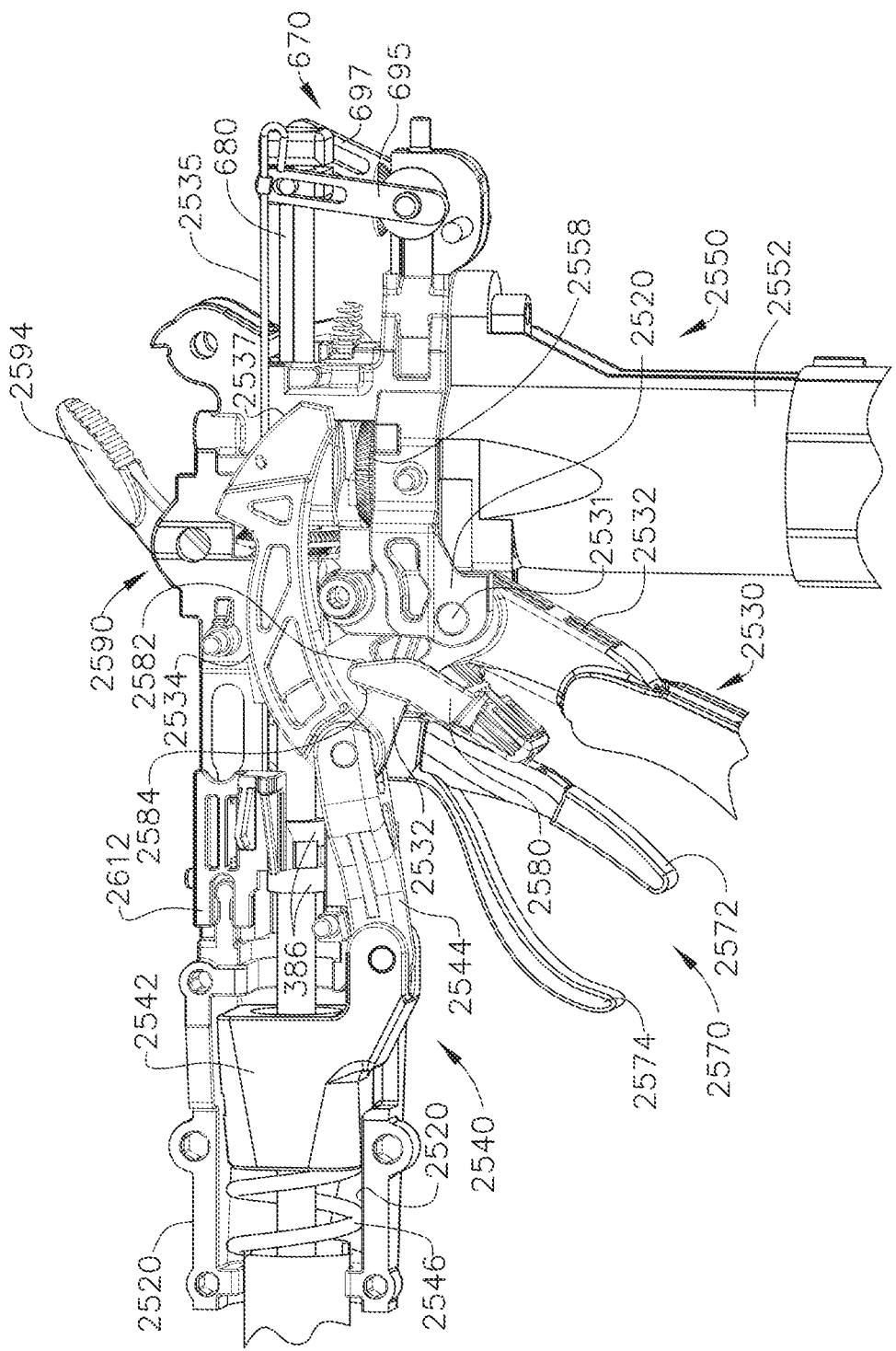
Figure 125:
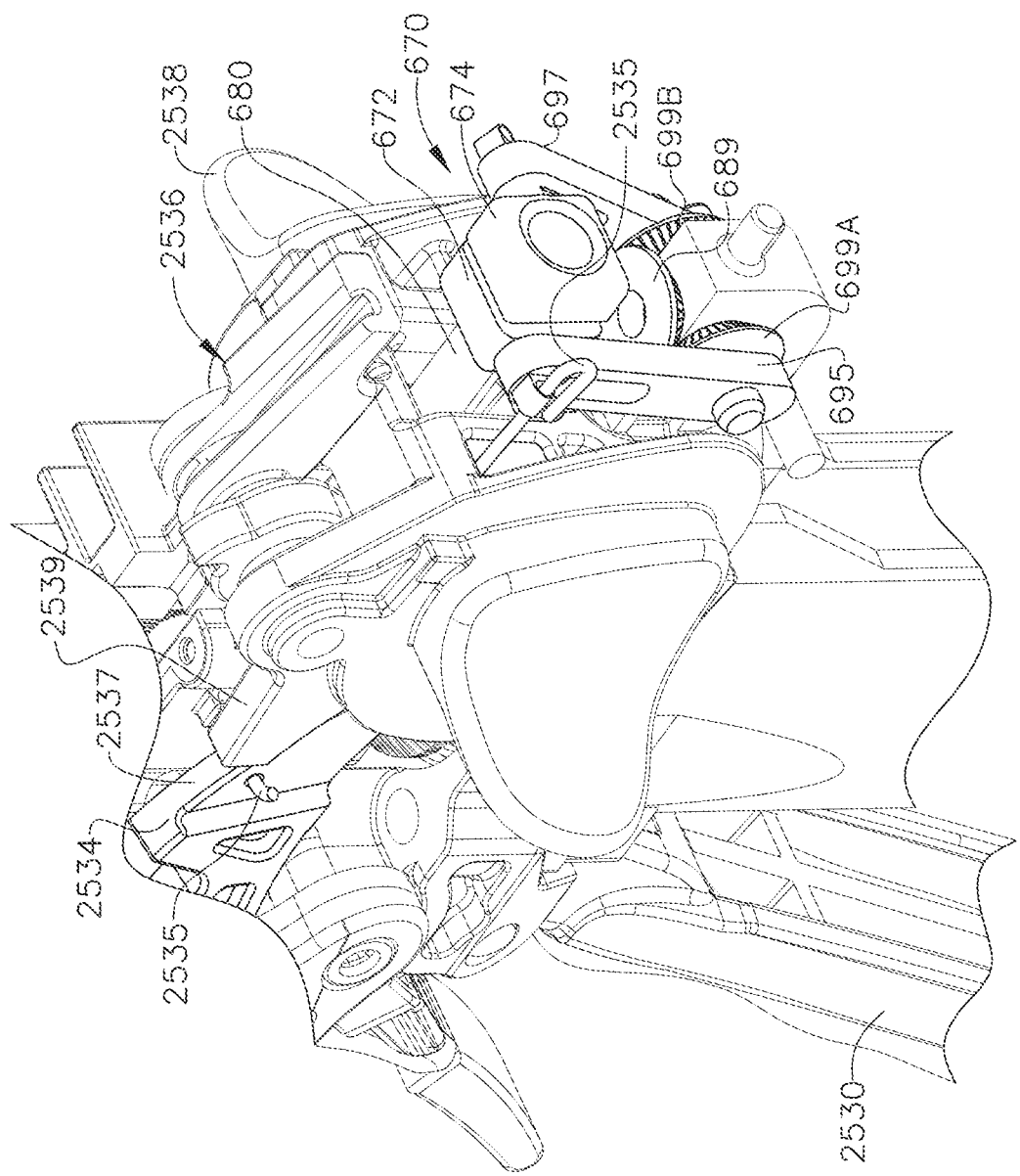
Figure 126:
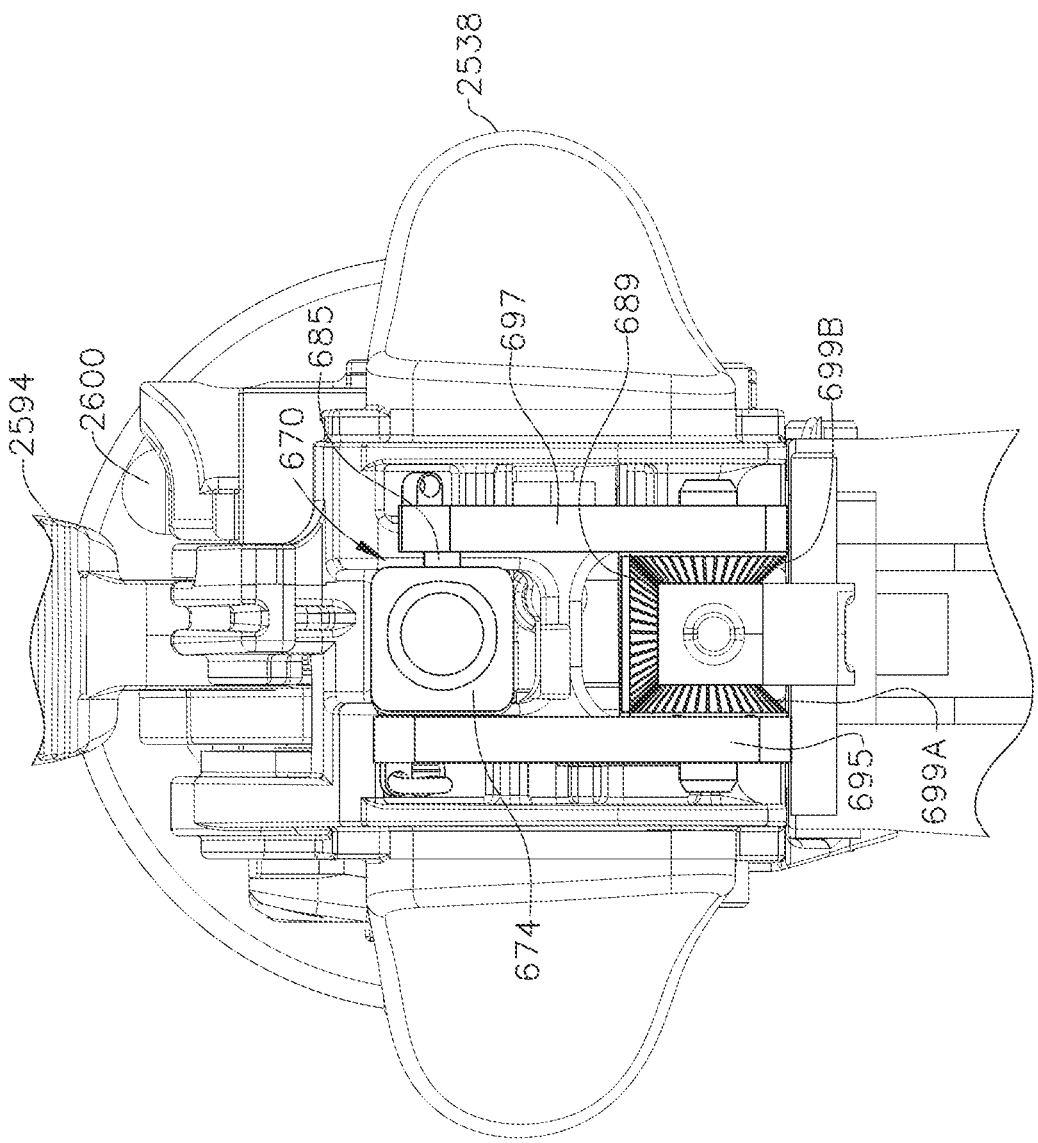
Figure 127:
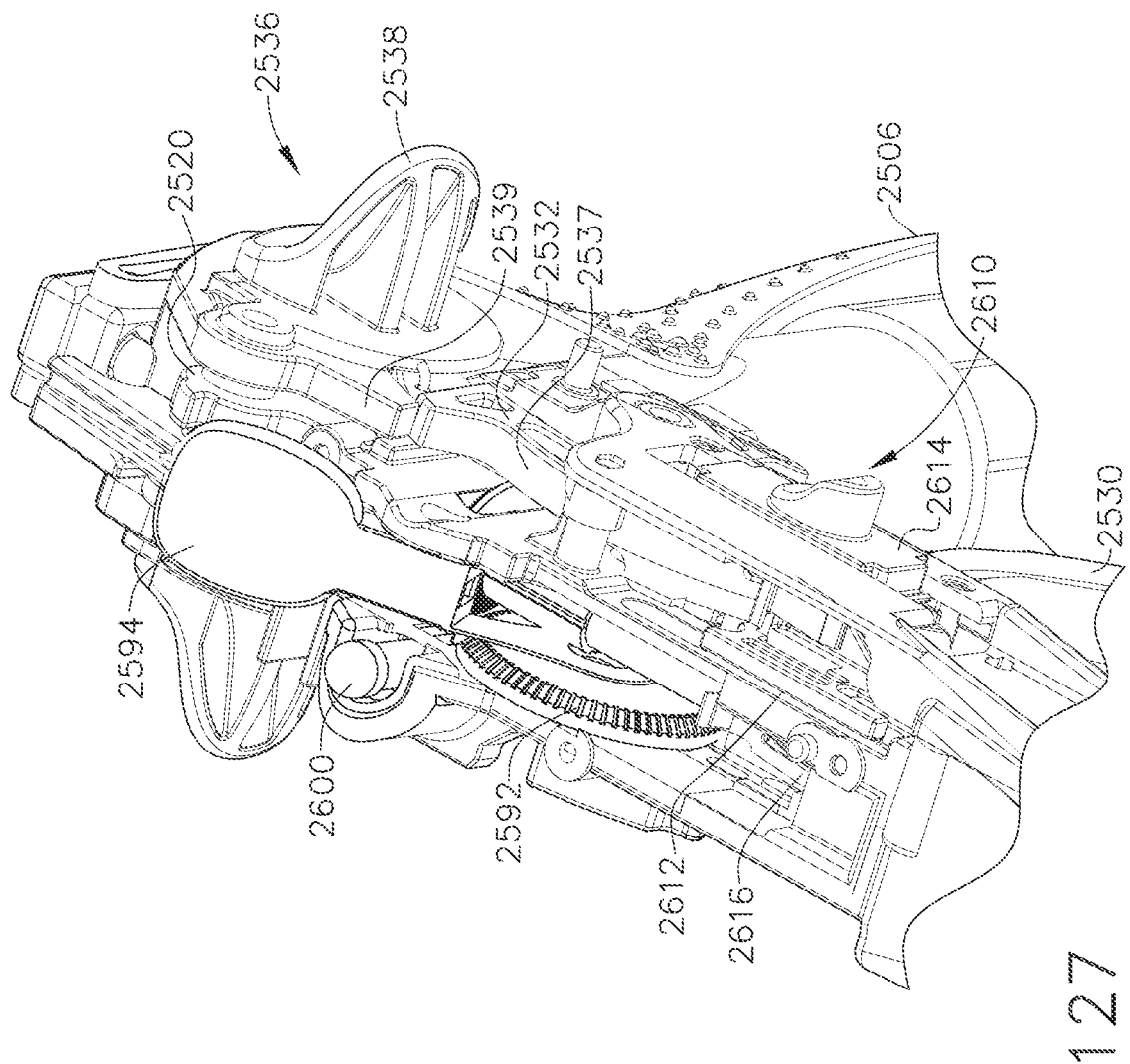
Figure 128:
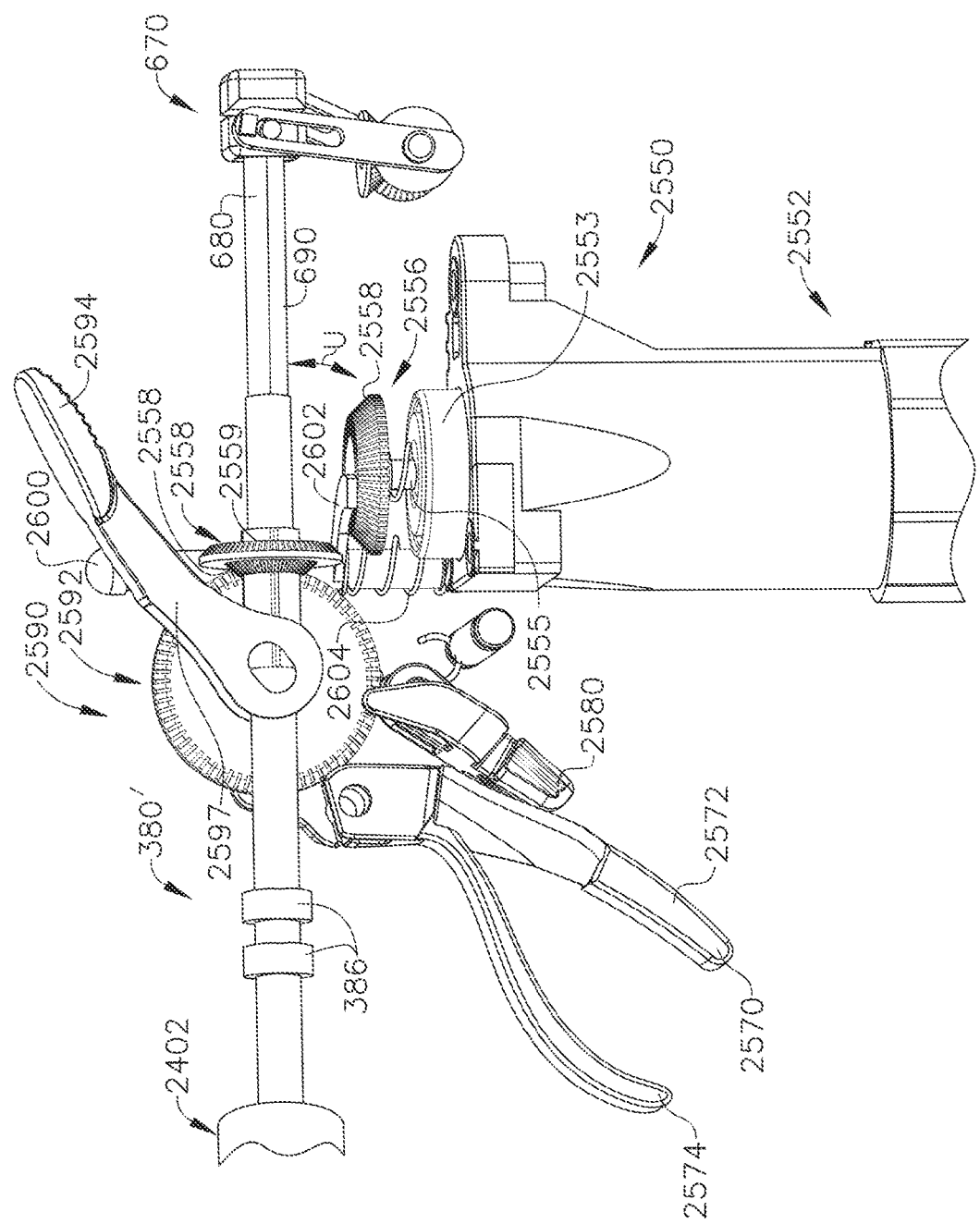
Figure 129:
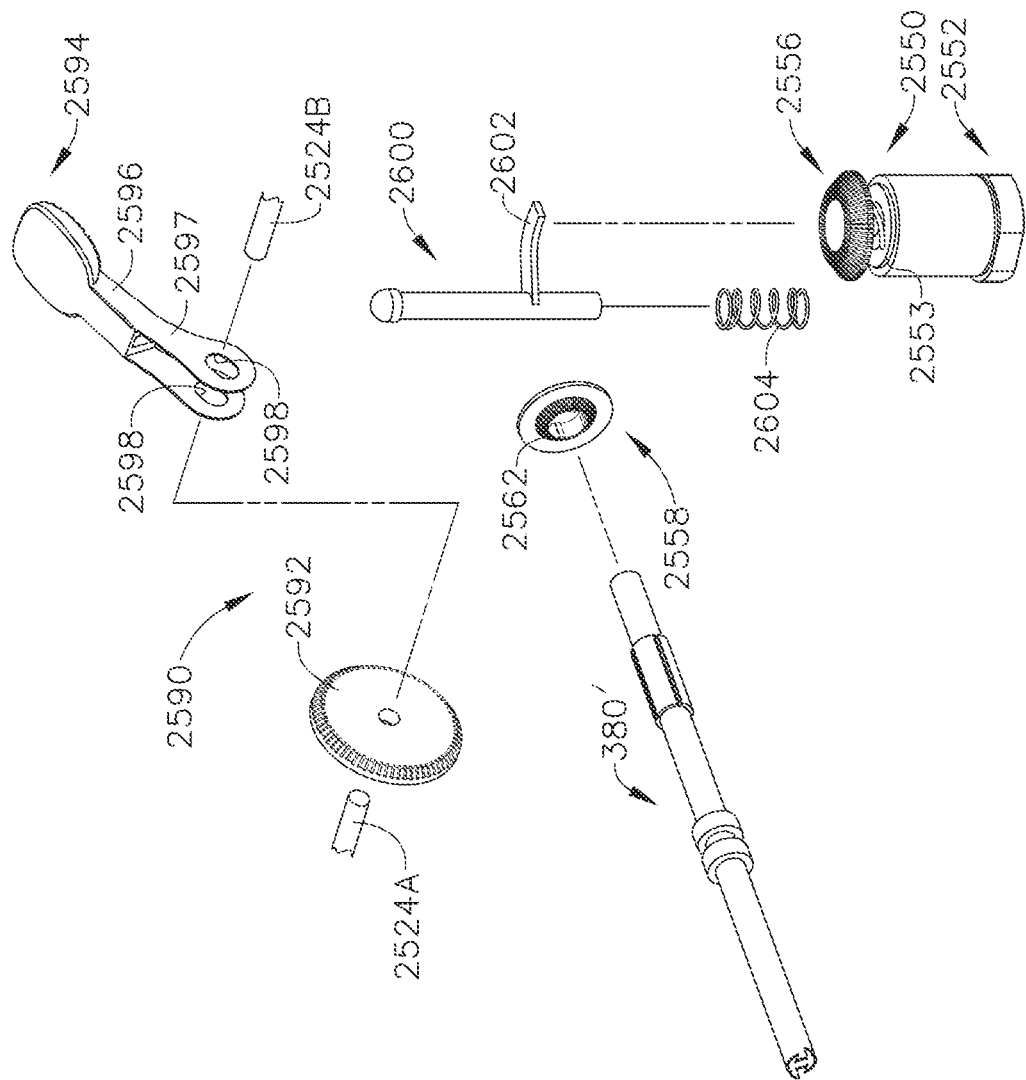
Figure 131:
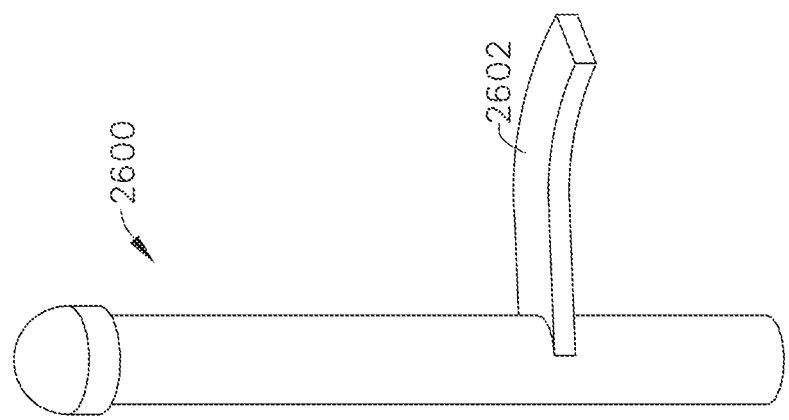
Figure 130:
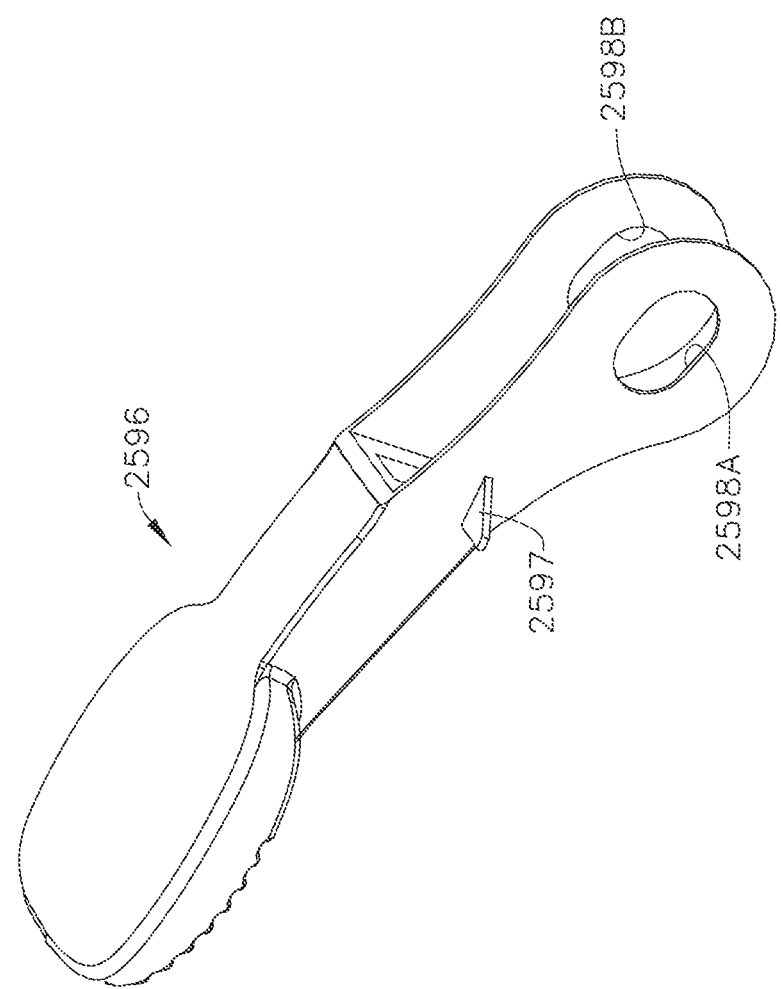
Figure 132:
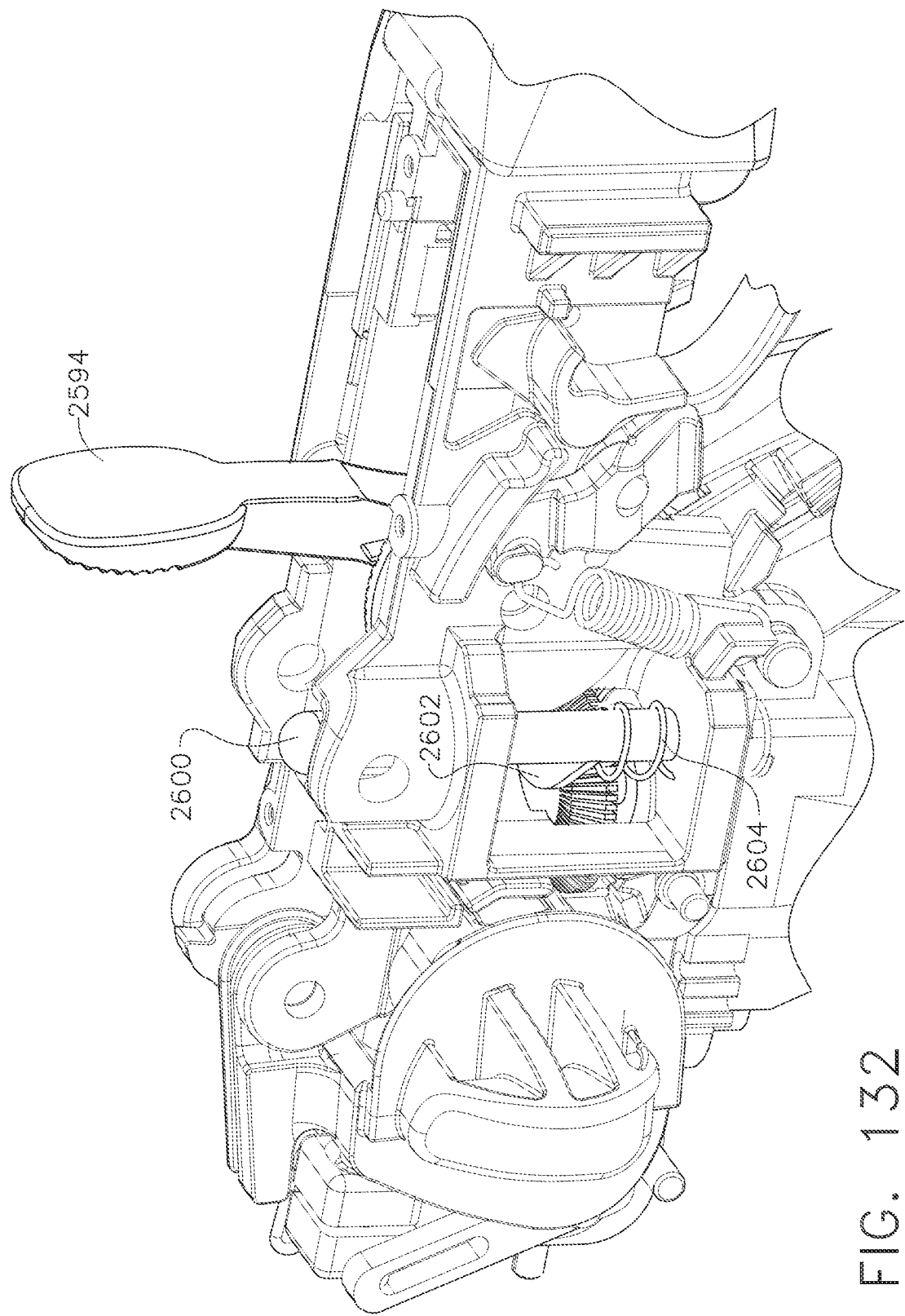
Figure 133:
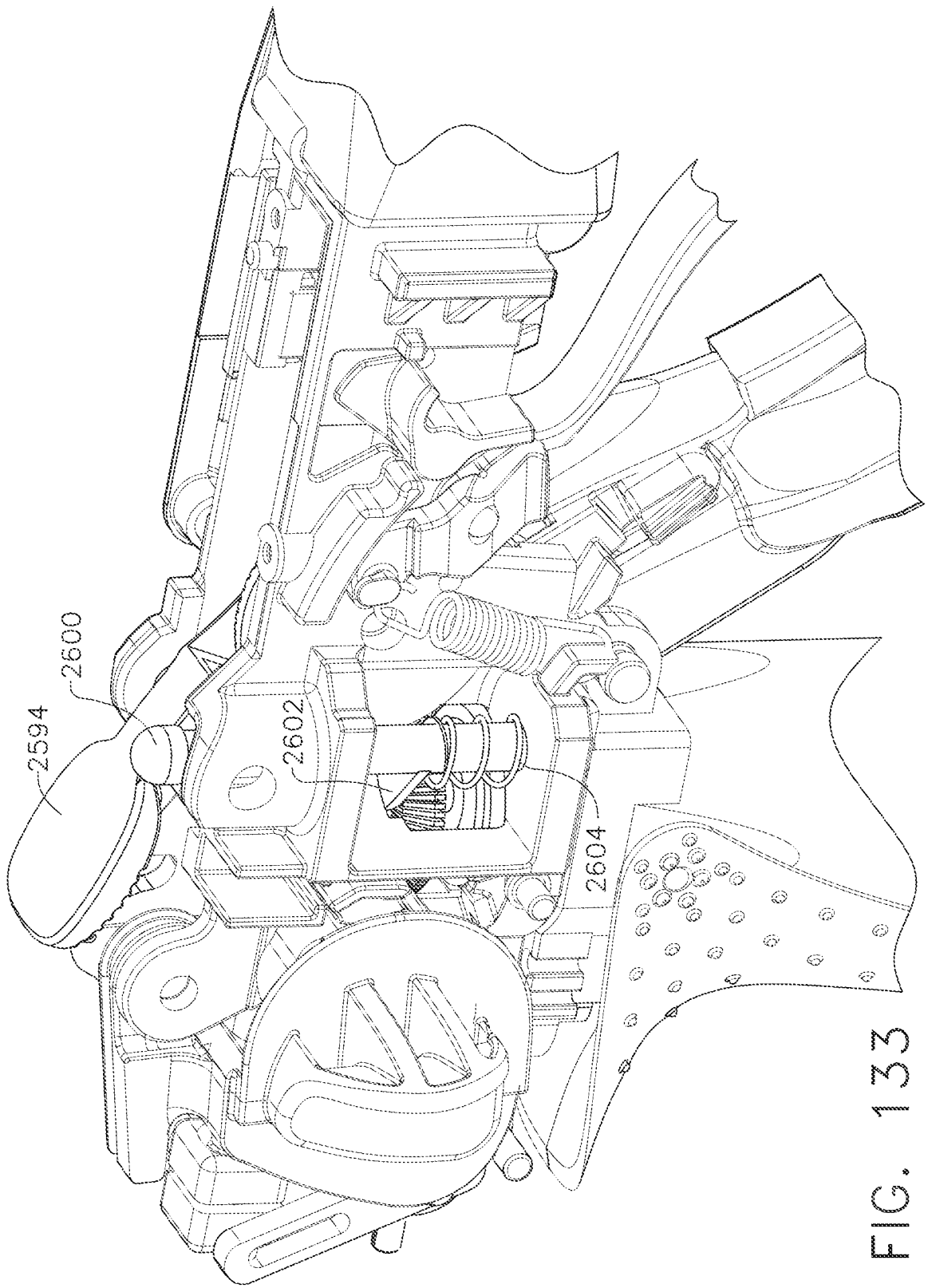
Figure 134:
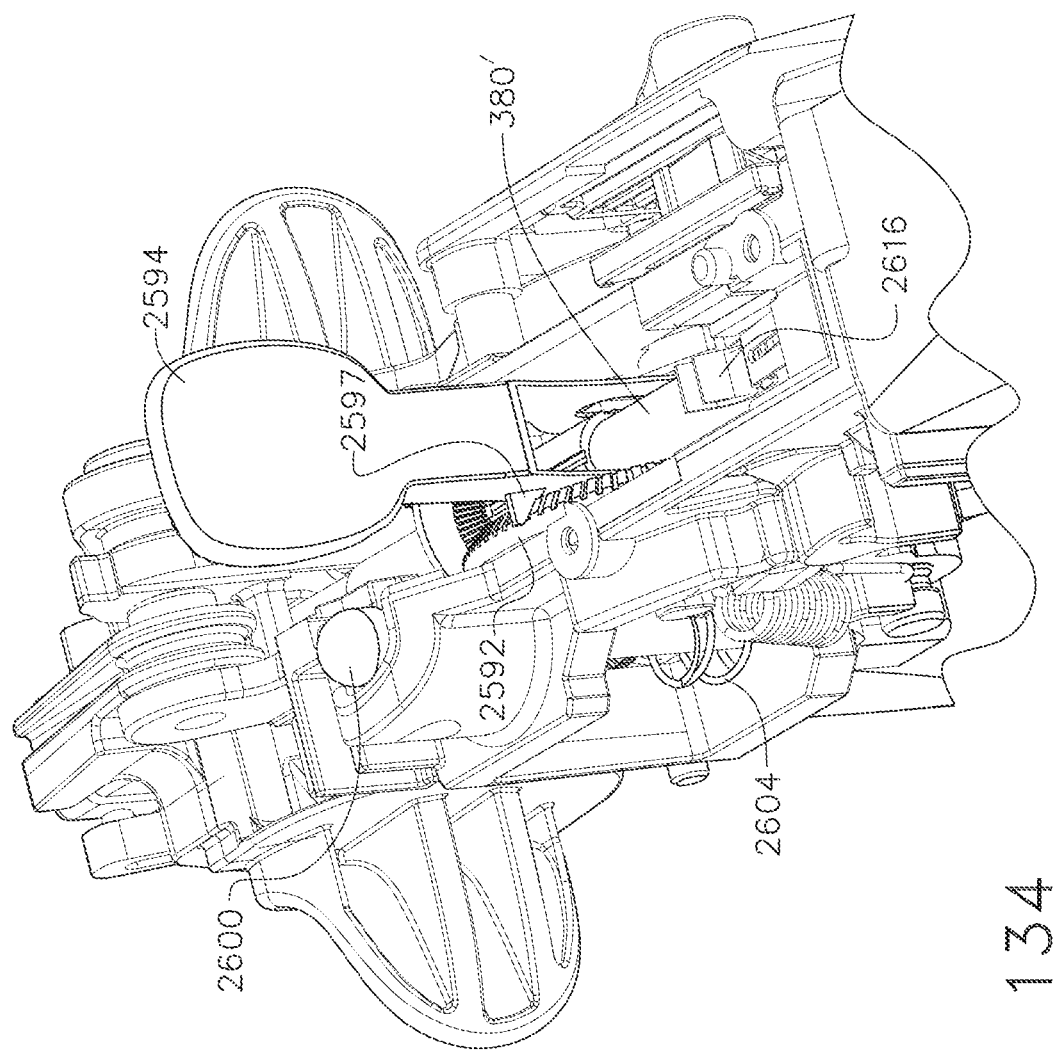
Figure 137:
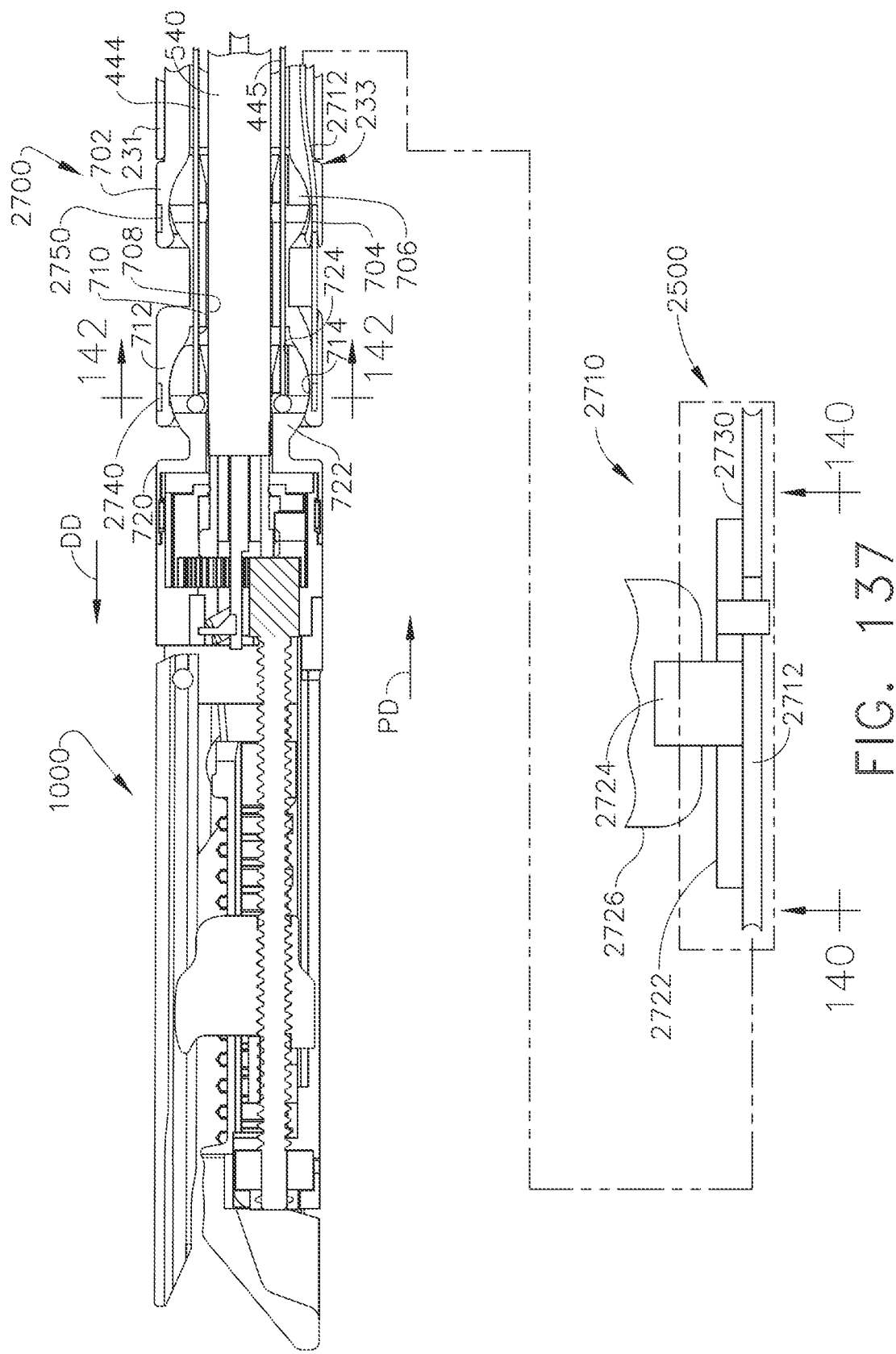
Figure 138:
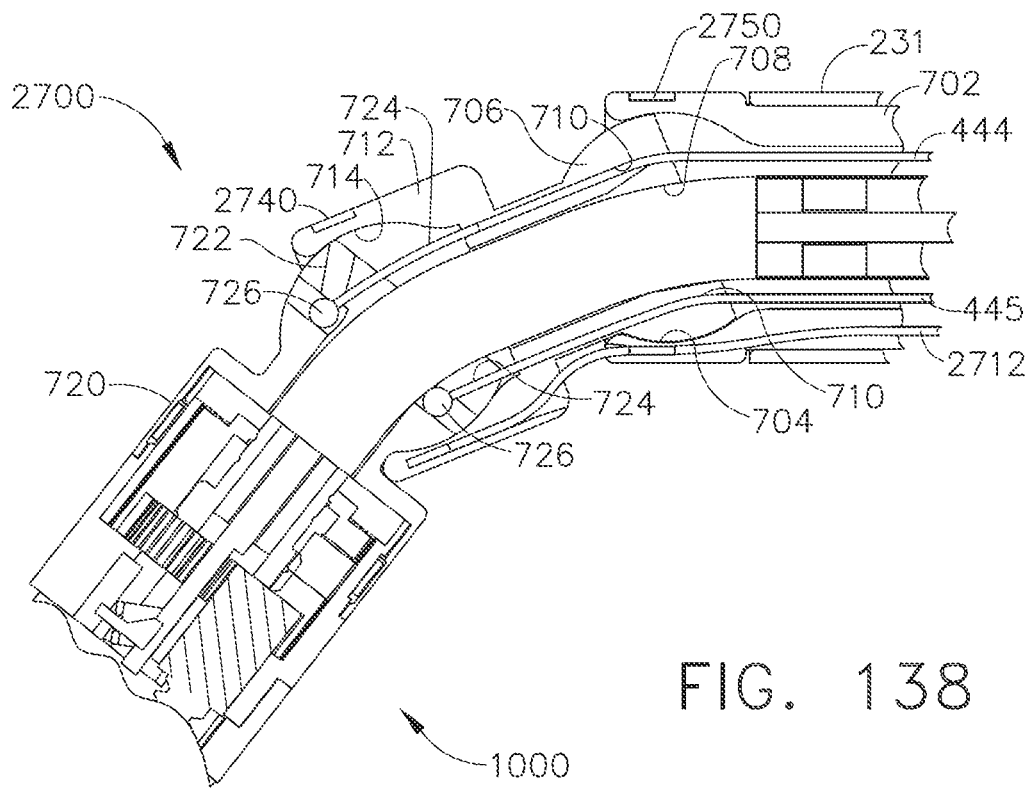
Figure 139:
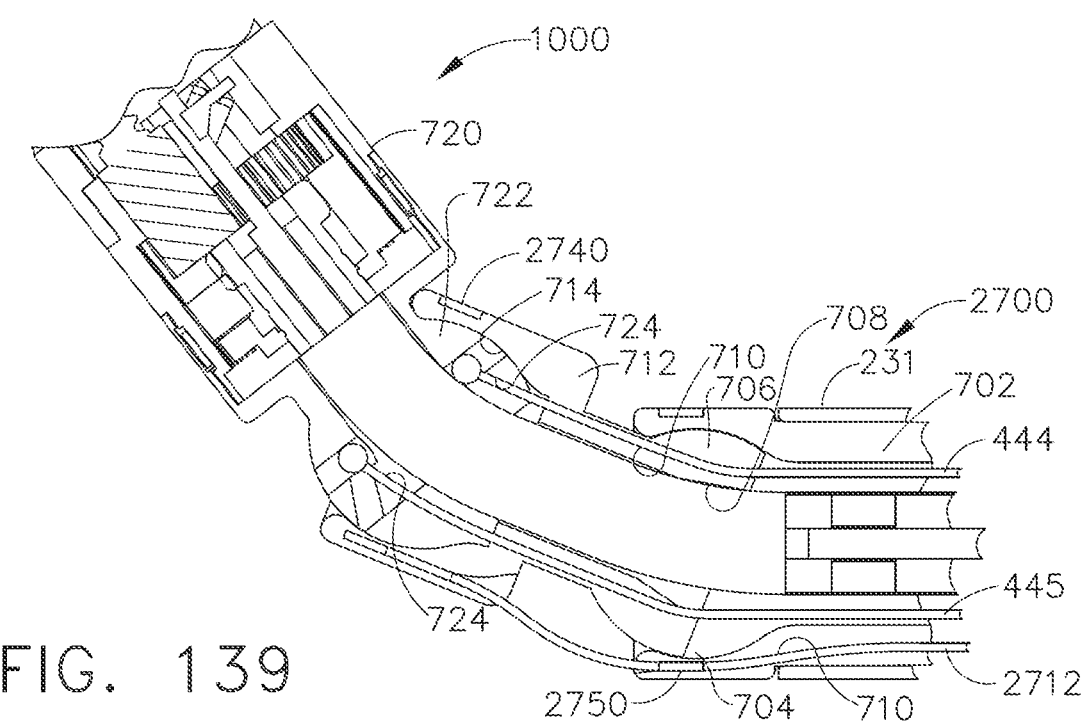
Figure 140:
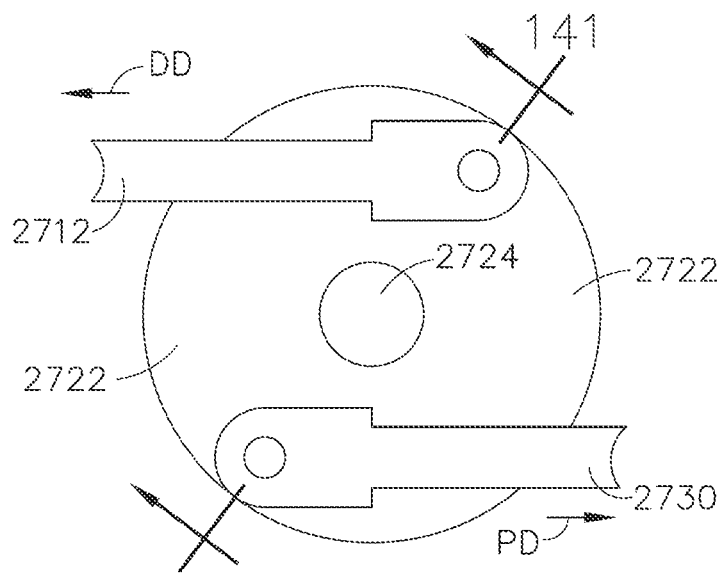
Figure 141:
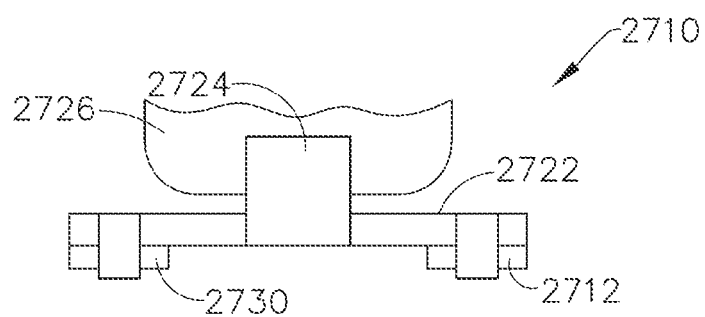
Figure 142:
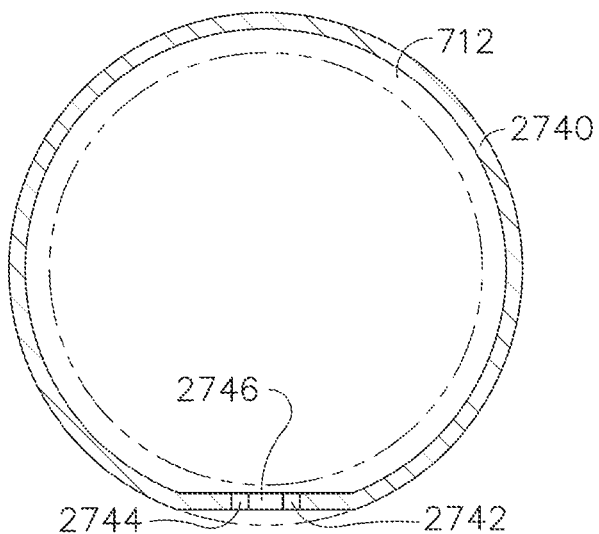
Figure 147:
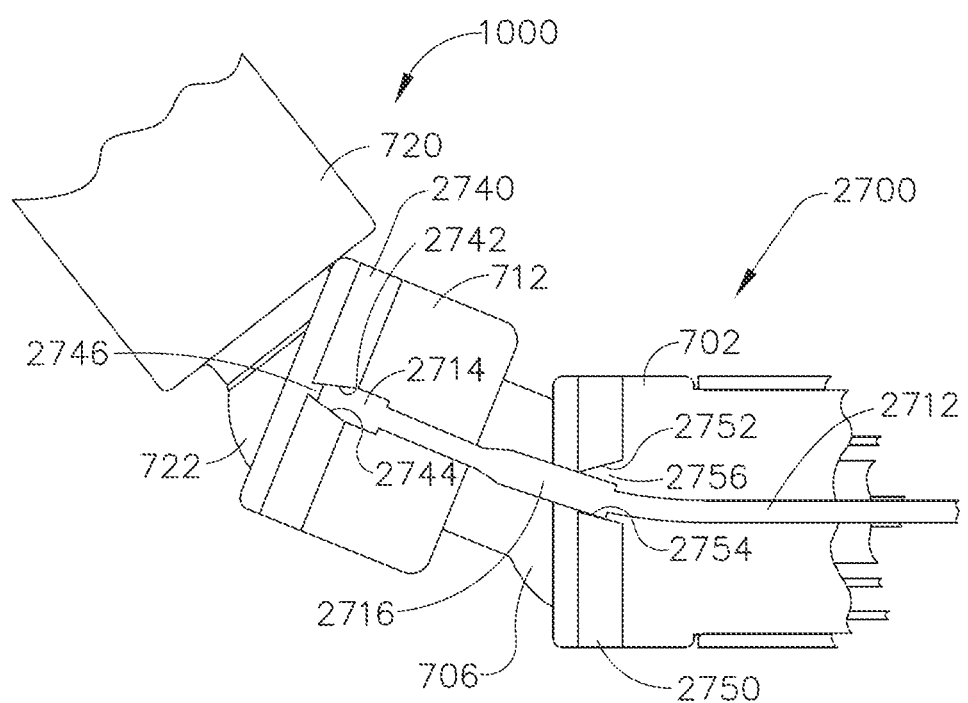
Figure 148:
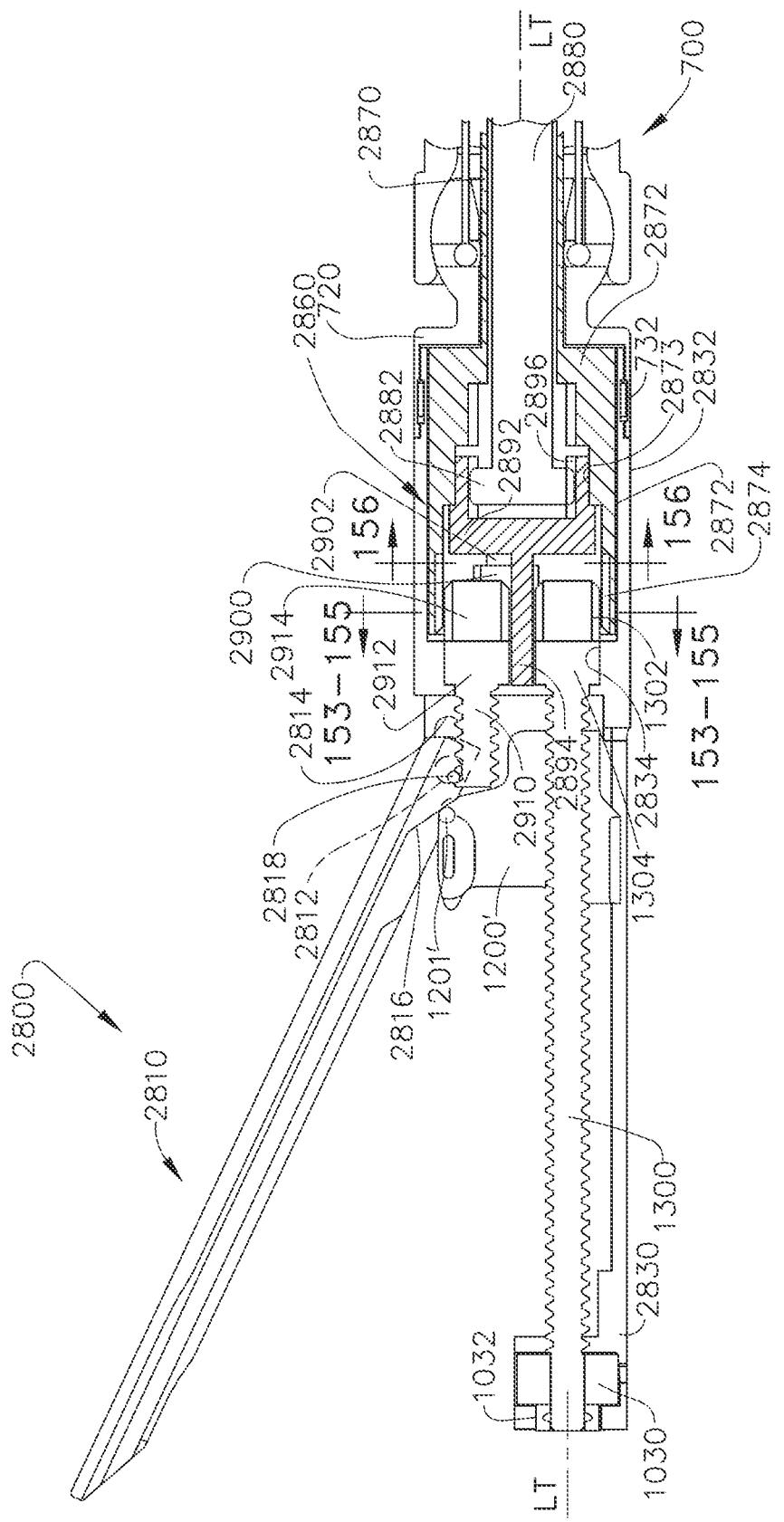
Figure 149:
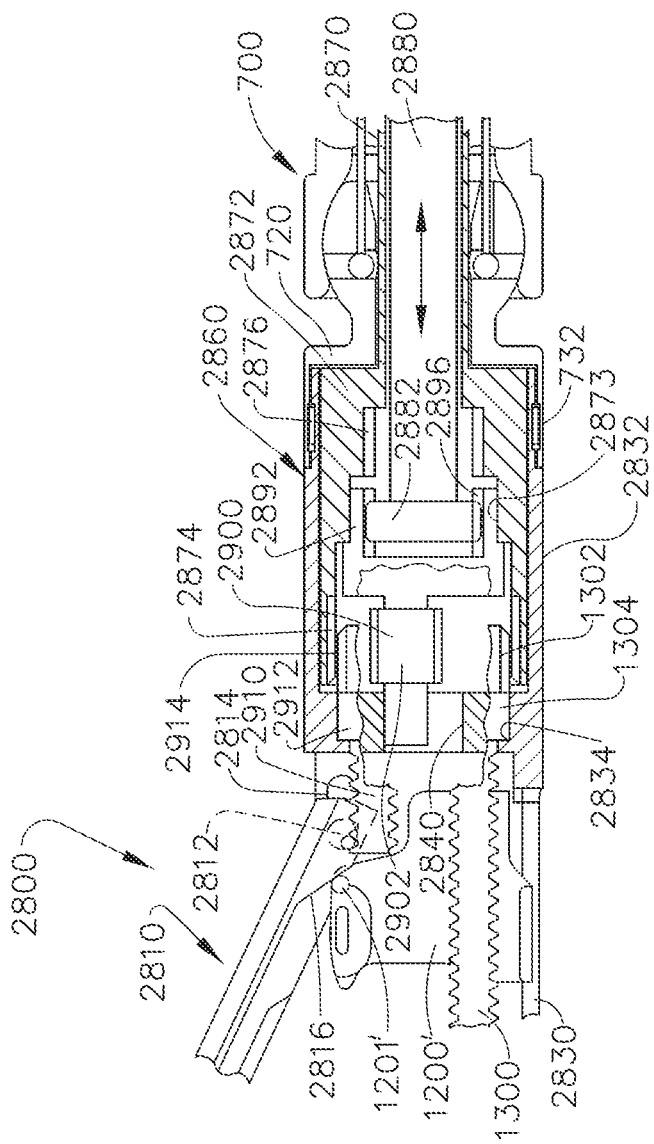
Figure 152:
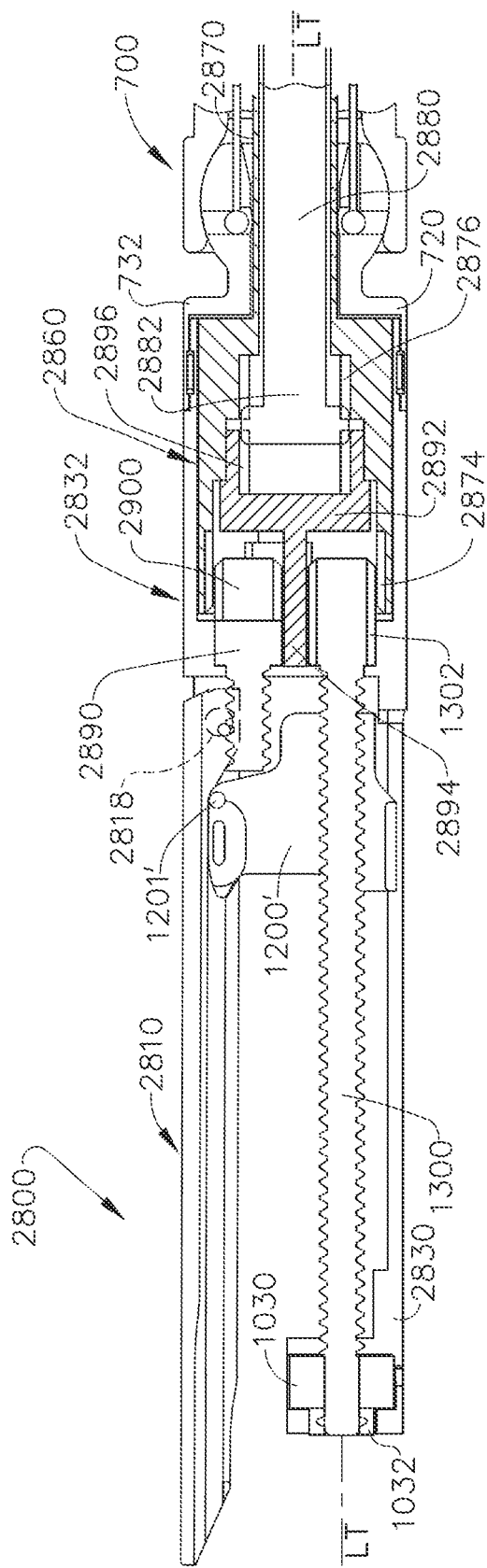
Figure 153:
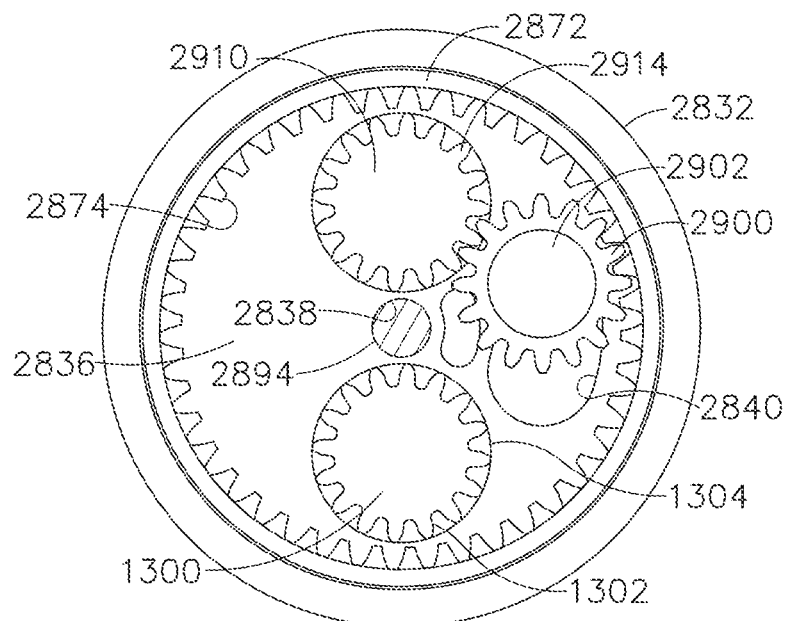
Figure 154:
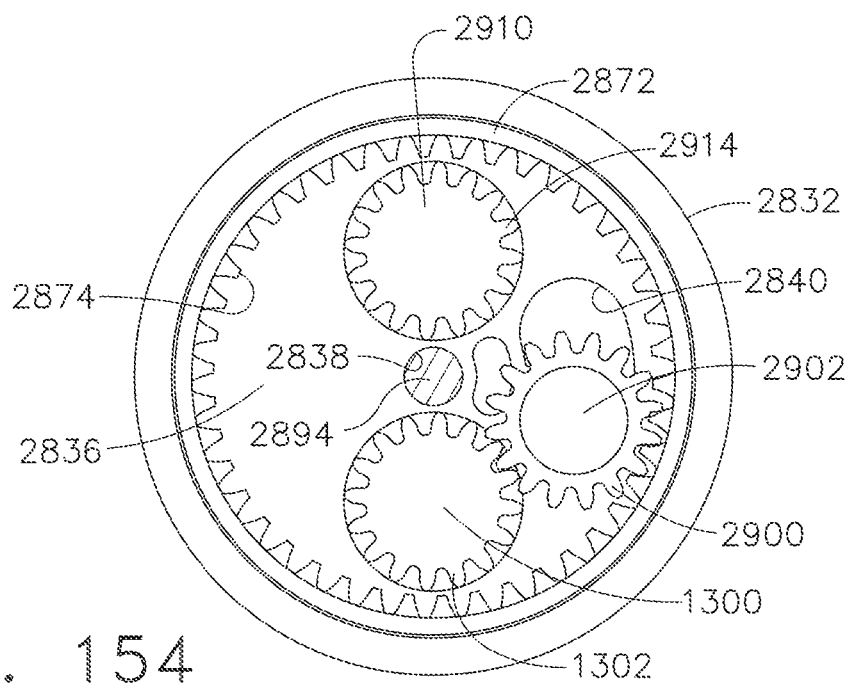
Figure 155:
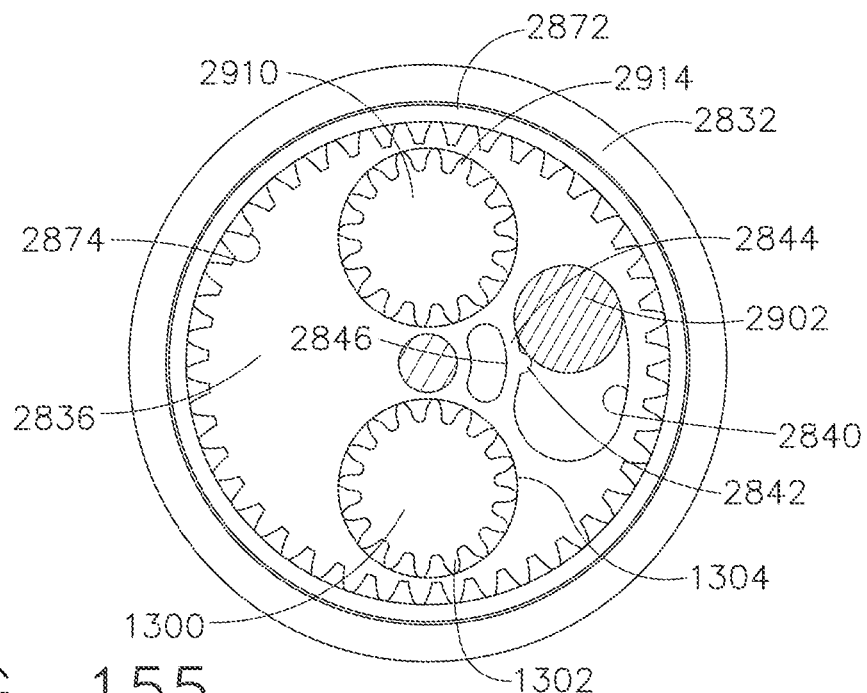
Figure 156:
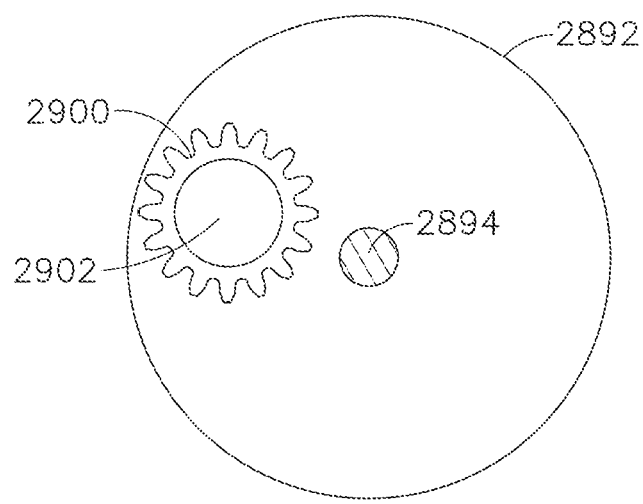
Figure 157:
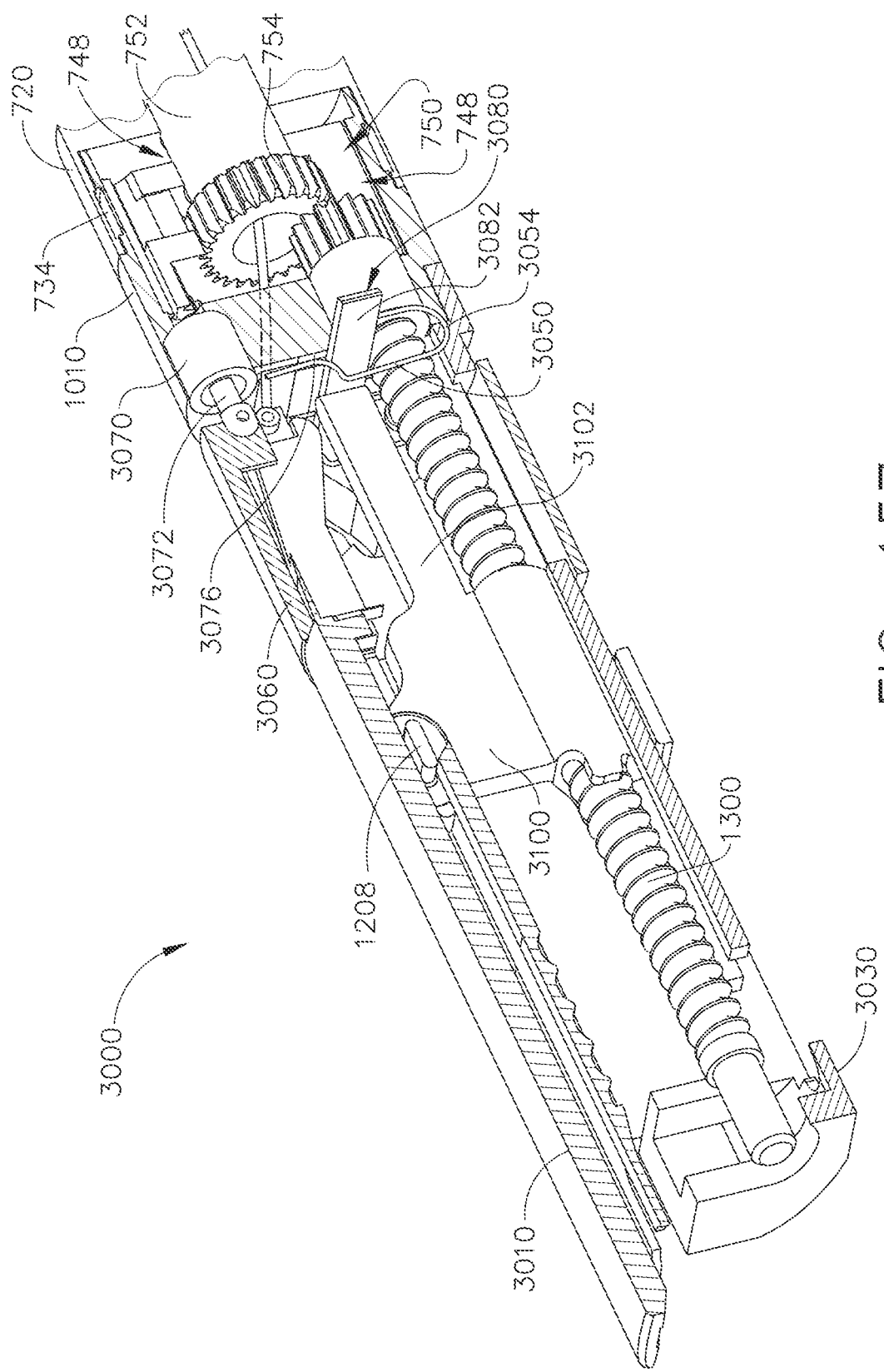
Figure 164:
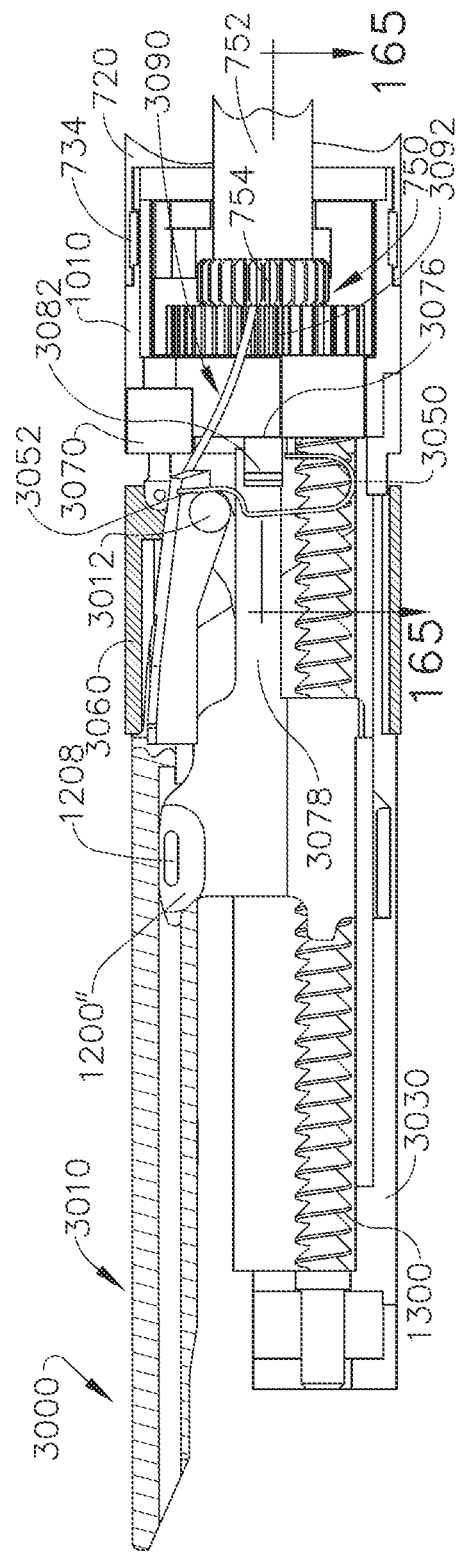
Figure 165:
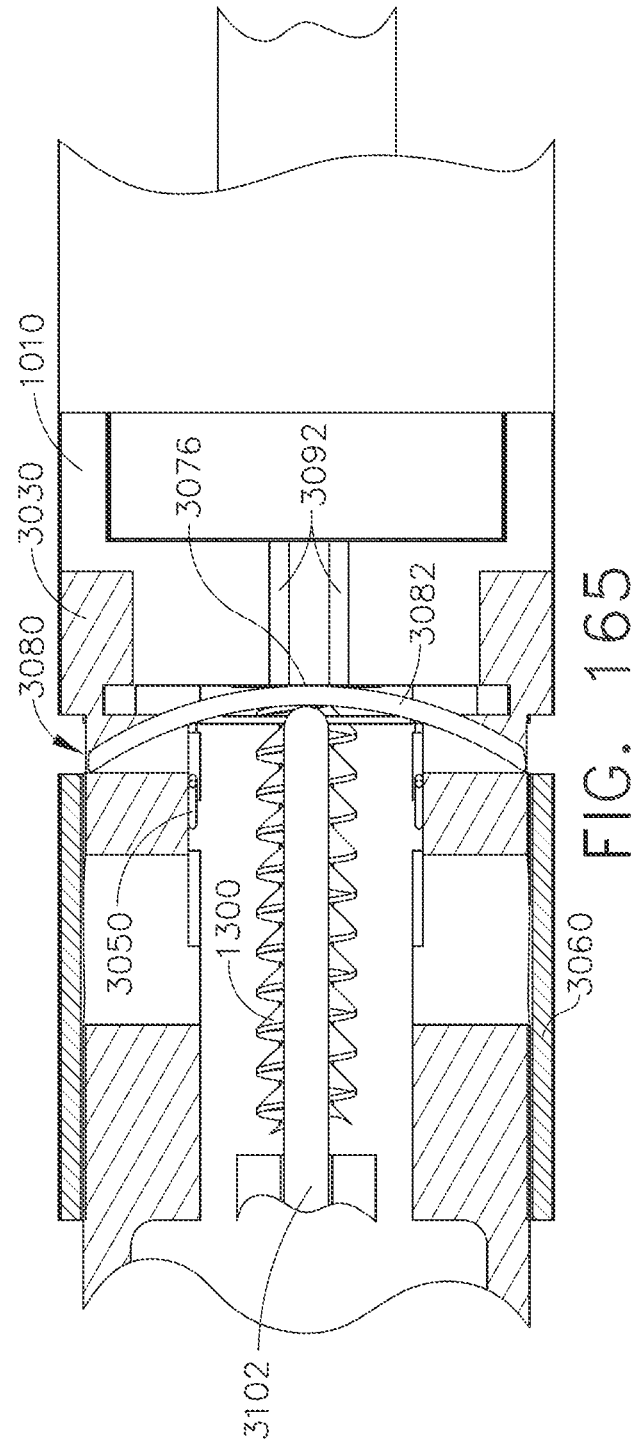
Figure 170:
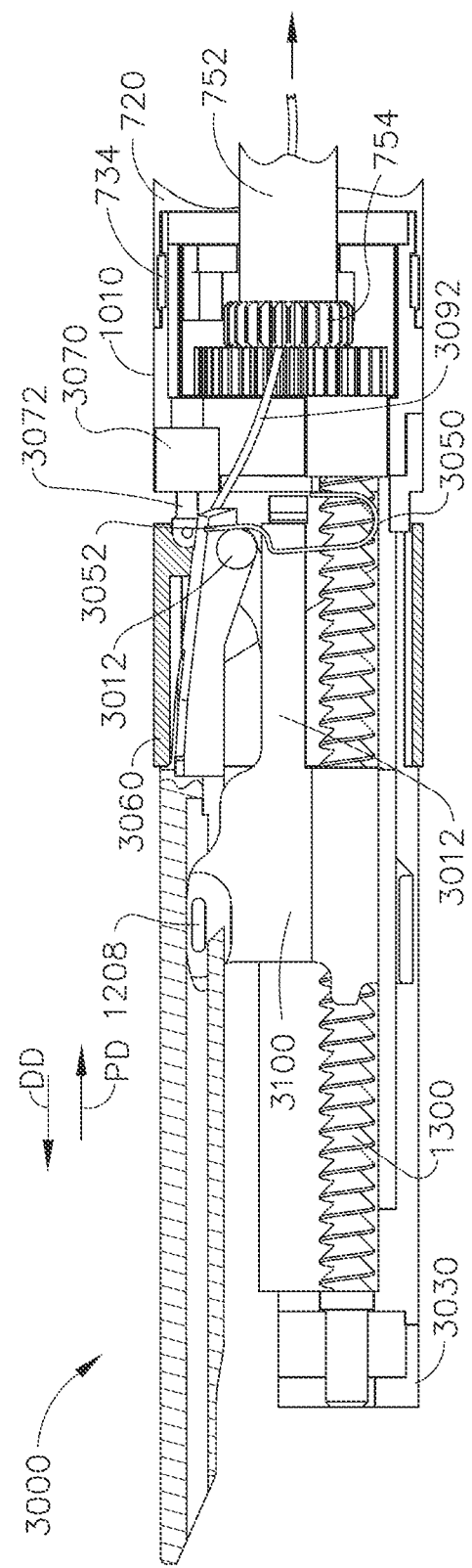
Figures 173, 174:
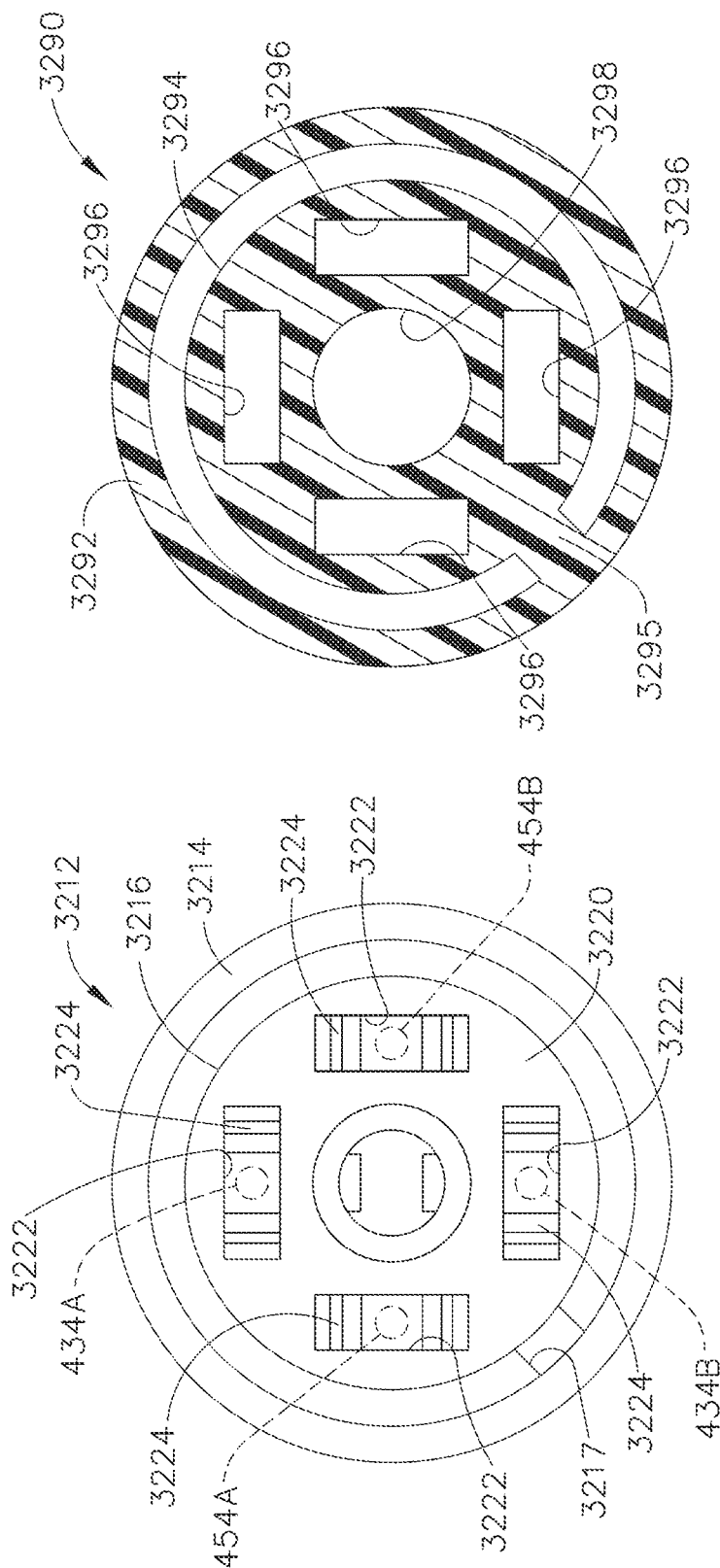
Figure 174A:
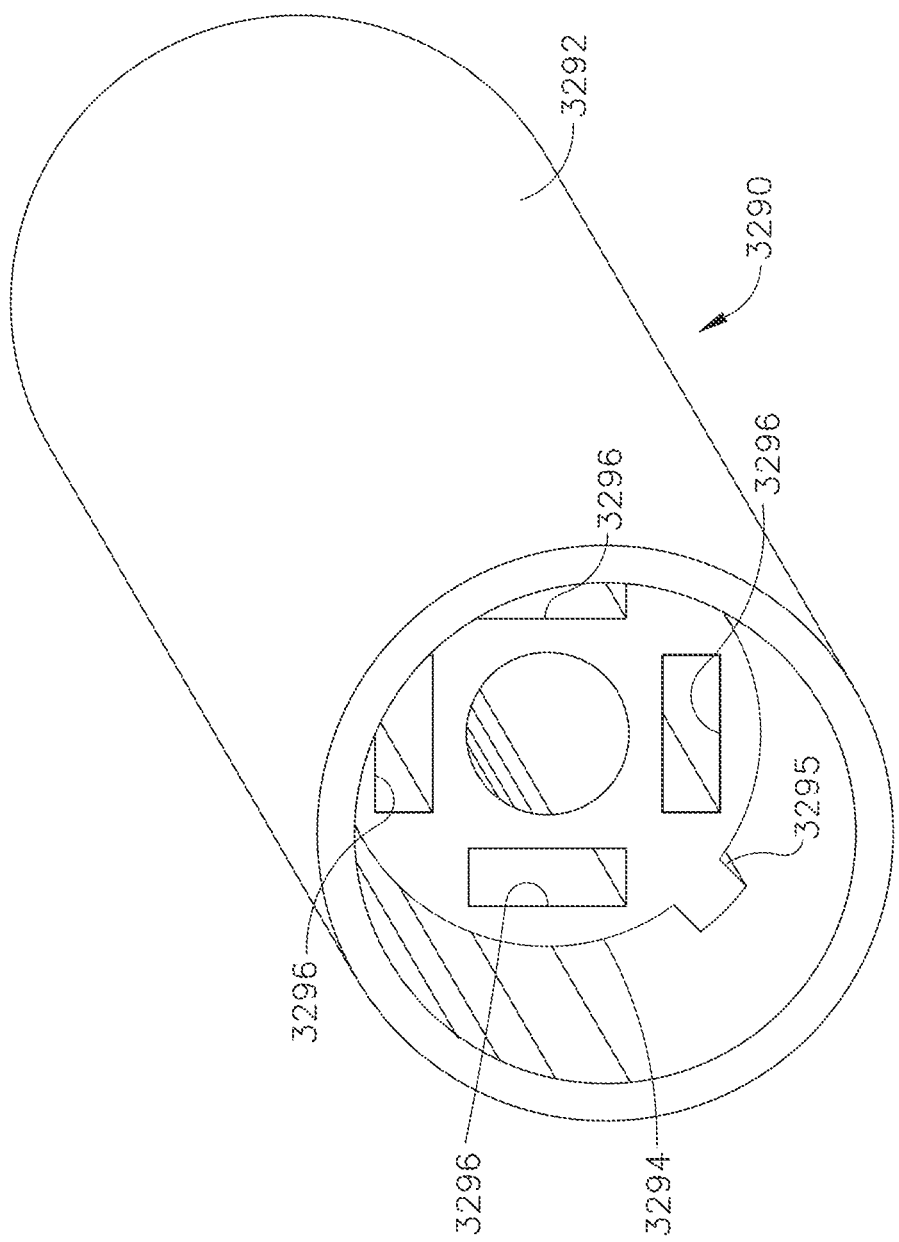
Figure 175:
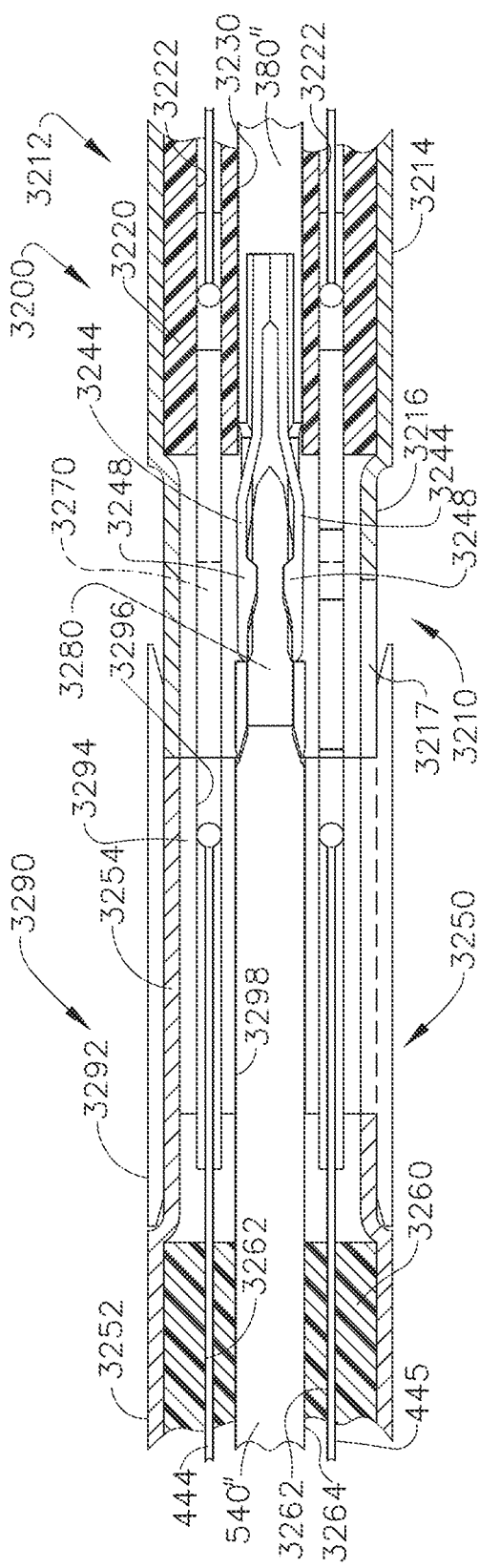
Figure 176:
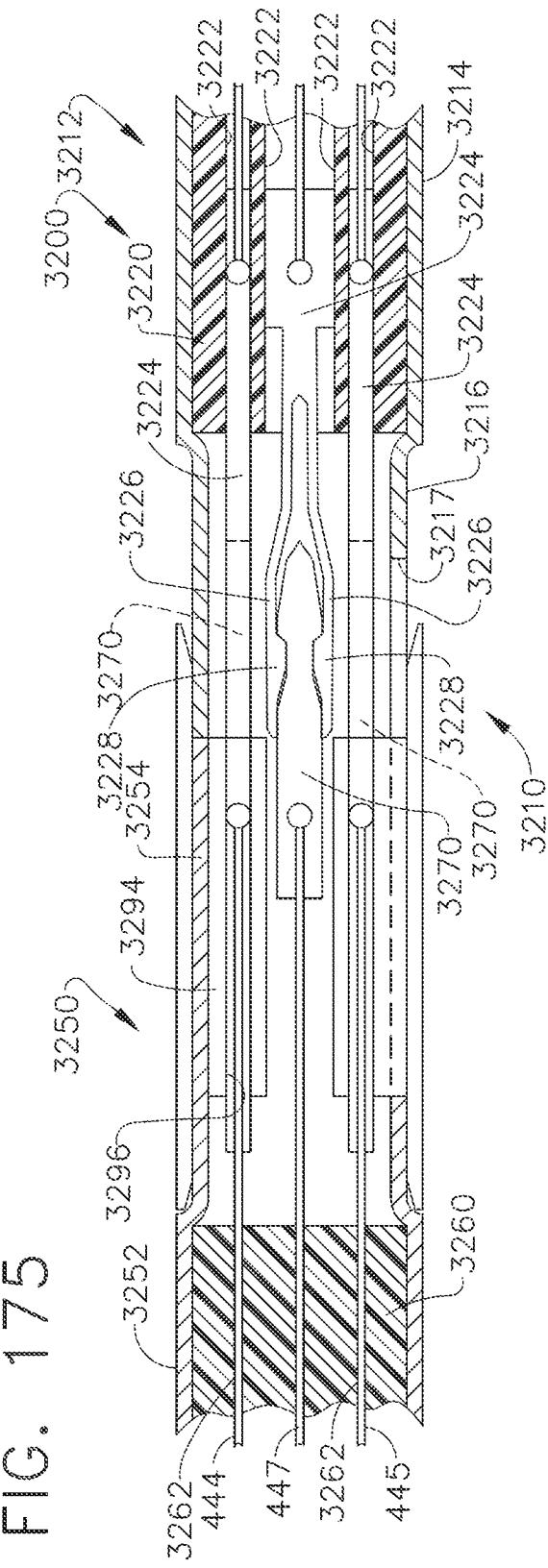

FIG. 117 is another side elevational view of the quick disconnect coupler arrangement of FIGS. 112-116 with the locking collar thereof in a locked position;

FIG. 118 is a perspective view of another surgical tool embodiment;

FIG. 119 is another perspective view of the surgical tool embodiment of FIG. 118;

FIG. 120 is a cross-sectional perspective view of the surgical tool embodiment of FIGS. 118 and 119;

FIG. 121 is a cross-sectional perspective view of a portion of an articulation system;

FIG. 122 is a cross-sectional view of the articulation system of FIG. 121 in a neutral position;

FIG. 123 is another cross-sectional view of the articulation system of FIGS. 121 and 122 in an articulated position;

FIG. 124 is a side elevational view of a portion of the surgical instrument embodiment of FIGS. 118-120 with portions thereof omitted for clarity;

FIG. 125 is a rear perspective view of a portion of the surgical instrument embodiment of FIGS. 118-120 with portions thereof omitted for clarity;

FIG. 126 is a rear elevational view of a portion of the surgical instrument embodiment of FIGS. 118-120 with portions thereof omitted for clarity;

FIG. 127 is a front perspective view of a portion of the surgical instrument embodiment of FIGS. 118-120 with portions thereof omitted for clarity;

FIG. 128 is a side elevational view of a portion of the surgical instrument embodiment of FIGS. 118-120 with portions thereof omitted for clarity;

FIG. 129 is an exploded assembly view of an exemplary reversing system embodiment of the surgical instrument embodiment of FIGS. 118-120;

FIG. 130 is a perspective view of a lever arm embodiment of the reversing system of FIG. 129;

FIG. 131 is a perspective view of a knife retractor button of the reversing system of FIG. 129;

FIG. 132 is a perspective view of a portion of the surgical instrument embodiment of FIGS. 118-120 with portions thereof omitted for clarity and with the lever arm in actuatable engagement with the reversing gear;

FIG. 133 is a perspective view of a portion of the surgical instrument embodiment of FIGS. 118-120 with portions thereof omitted for clarity and with the lever arm in an unactuated position;

FIG. 134 is another perspective view of a portion of the surgical instrument embodiment of FIGS. 118-120 with portions thereof omitted for clarity and with the lever arm in actuatable engagement with the reversing gear;

FIG. 135 is a side elevational view of a portion of a handle assembly portion of the surgical instrument embodiment of FIGS. 118-20 with the a shifter button assembly moved into a position which will result in the rotation of the end effector when the drive shaft assembly is actuated;

FIG. 136 is another side elevational view of a portion of a handle assembly portion of the surgical instrument embodiment of FIGS. 118-120 with the a shifter button assembly moved into another position which will result in the firing of the firing member in the end effector when the drive shaft assembly is actuated;

FIG. 137 is a cross-sectional view of a portion of another surgical tool embodiment with a lockable articulation joint embodiment;

FIG. 138 is another cross-sectional view of the portion of surgical tool of FIG. 137 articulated in one configuration;

FIG. 139 is another cross-sectional view of the portion of surgical tool of FIGS. 137 and 138 articulated in another configuration;

FIG. 140 is a cross-sectional of an articulation locking system embodiment depicted in FIG. 137 taken along line 140-140 in FIG. 137;

FIG. 141 is a cross-sectional view of the articulation locking system of FIG. 140 taken along line 141-141 in FIG. 140;

FIG. 142 is a cross-sectional view of a portion of the surgical tool of FIG. 137 taken along line 142-142 in FIG. 137;

FIG. 143 illustrates the position of the locking wire when the first and second locking rings are in a clamped or locked configuration when the end effector has been articulated into a first articulation position illustrated in FIG. 138;

FIG. 144 illustrates a position of the locking wire when the first and second locking rings have been sprung to their respective unclamped or unlocked positions when the end effector has been articulated to the first articulation position illustrated in FIG. 138;

FIG. 145 illustrates a position of the locking wire when the first and second locking rings are in a clamped or locked configuration when the end effector has been articulated into a second articulation position illustrated in FIG. 139;

FIG. 146 illustrates the position of the locking wire when the first and second locking rings have been sprung to their respective unclamped or unlocked positions when the end effector has been articulated to the first articulation position illustrated in FIG. 139;

FIG. 147 is another view of the locking wire when the end effector has been articulated relative to the elongate shaft assembly;

FIG. 148 is a cross-sectional view of another end effector embodiment with the anvil assembly thereof in the closed position;

FIG. 149 is another cross-sectional view of the end effector embodiment of FIG. 148;

FIG. 150 is another cross-sectional view of the end effector embodiment of FIGS. 148 and 149 with the anvil assembly in the closed position;

FIG. 151 is another cross-sectional view of the end effector embodiment of FIGS. 148-150 illustrating the drive transmission configured to drive the firing member;

FIG. 152 is another cross-sectional view of the end effector embodiment of FIGS. 148-151 with the drive transmission configured to rotate the entire end effector about the longitudinal tool axis;

FIG. 153 is a cross-sectional view of the end effector of FIGS. 148-152 taken along line 153-153 in FIG. 148 with the drive transmission configured to actuate the anvil assembly;

FIG. 154 is a cross-sectional view of the end effector of FIGS. 148-153 taken along line 154-154 in FIG. 148 with the drive transmission configured to fire the firing member;

FIG. 155 is a cross-sectional view of the end effector of FIGS. 148-154 taken along line 155-155 in FIG. 148 with the drive transmission configured to actuate the anvil assembly;

FIG. 156 is a cross-sectional view of the end effector of FIGS. 148-155 taken along line 156-156 in FIG. 148;

FIG. 157 is a cross-sectional perspective view of another end effector embodiment;

FIG. 158 is a perspective view of an elongate channel of the end effector of FIG. 157;

FIG. 159 is a perspective view of an anvil spring embodiment;

FIG. 160 is a side cross-sectional view of the end effector of FIG. 157 with the anvil in a closed position after the firing member has been driven to its distal-most position;

FIG. 161 is a cross-sectional view of a portion of the end effector of FIG. 160 taken along line 161-161 in FIG. 160;

FIG. 162 is another side cross-sectional view of the end effector of FIGS. 157, 160 and 161 with the firing member being retracted;

FIG. 163 is a cross-sectional view of a portion of the end effector of FIG. 162 taken along line 163-163;

FIG. 164 is another side cross-sectional view of the end effector of FIGS. 157 and 160-163 with the firing member in its proximal-most position;

FIG. 165 is a cross-sectional view of the end effector of FIGS. 157 and 160-164 taken along line 165-165 in FIG. 164;

FIG. 166 is another side cross-sectional view of the end effector of FIGS. 157 and 160-165 after the solenoid has pulled the closure tube to its proximal-most position;

FIG. 167 is a cross-sectional view of the end effector of FIGS. 157 and 160-166 taken along line 167-167 in FIG. 166;

FIG. 168 is another side cross-sectional view of the end effector of FIGS. 157 and 160-167 with the anvil in an open position and the after the solenoid has pulled the closure tube to its proximal-most position;

FIG. 169 is another side cross-sectional view of the end effector of FIGS. 157 and 160-168 after the firing member has moved to its starting position;

FIG. 170 is another side cross-sectional view of the end effector of FIGS. 157 and 160-169 with the anvil assembly closed and the firing member ready to fire;

FIG. 171 is a partial cross-sectional view of another quick disconnect arrangement for coupling a distal shaft portion that may be attached to an end effector to a proximal shaft portion that may be coupled to a tool mounting portion for a robotic system or to a handle assembly;

FIG. 172 is another partial cross-sectional view of the quick disconnect arrangement of FIG. 171;

FIG. 173 is an end view of the proximal shaft portion of the quick disconnect arrangement of FIGS. 171 and 172;

FIG. 174 is cross-sectional view of an axially movable lock collar embodiment of the quick disconnect arrangement of FIGS. 171 and 172;

FIG. 174A is a perspective view of the lock collar embodiment of FIG. 174;

FIG. 175 is another cross-sectional view of the quick disconnect arrangement of FIGS. 171 and 172 illustrating the initial coupling of the distal and proximal drive shaft portions;

FIG. 176 is another cross-sectional view of the quick disconnect arrangement of FIGS. 171, 172 and 175 illustrating the initial coupling of the corresponding articulation cable segments;

FIG. 177 is another cross-sectional view of the quick disconnect arrangement of FIG. 175 after the distal drive shaft portion has been locked to the proximal drive shaft portion; and FIG. 178 is another cross-sectional view of the quick disconnect arrangement of FIG. 176 after the corresponding articulation cable segments have been locked together.

DETAILED DESCRIPTION

Applicant of the present application also owns the following patent applications that have been filed on Jun. 28, 2012 and which are each herein incorporated by reference in their respective entireties:

1. U.S. patent application Ser. No. 13/536,271, entitled FLEXIBLE DRIVE MEMBER, now U.S. Pat. No. 9,204,879.

2. U.S. patent application Ser. No. 13/536,288, entitled MULTI-FUNCTIONAL POWERED SURGICAL DEVICE WITH EXTERNAL DISSECTION FEATURES, now U.S. Patent Application Publication No. 2014/0005718.

3. U.S. patent application Ser. No. 13/536,277, entitled COUPLING ARRANGEMENTS FOR ATTACHING SURGICAL END EFFECTORS TO DRIVE SYSTEMS THEREFOR, now U.S. Patent Application Publication No. 2014/0001234.

4. U.S. patent application Ser. No. 13/536,295, entitled ROTARY ACTUATABLE CLOSURE ARRANGEMENT FOR SURGICAL END EFFECTOR, now U.S. Pat. No. 9,119,657.

5. U.S. patent application Ser. No. 13/536,326, entitled SURGICAL END EFFECTORS HAVING ANGLED TISSUE-CONTACTING SURFACES, now U.S. Pat. No. 9,289,256.

6. U.S. patent application Ser. No. 13/536,303 entitled INTERCHANGEABLE END EFFECTOR COUPLING ARRANGEMENT, now U.S. Pat. No. 9,028,494.

7. U.S. patent application Ser. No. 13/536,393, entitled SURGICAL END EFFECTOR JAW AND ELECTRODE CONFIGURATIONS, now U.S. Patent Application Publication No. 2014/0005640.

8. U.S. patent application Ser. No. 13/536,362, entitled MULTI-AXIS ARTICULATING AND ROTATING SURGICAL TOOLS, now U.S. Pat. No. 9,125,662.

9. U.S. patent application Ser. No. 13/536,284, entitled DIFFERENTIAL LOCKING ARRANGEMENTS FOR ROTARY POWERED SURGICAL INSTRUMENTS, now U.S. Pat. No. 9,072,536.

10. U.S. patent application Ser. No. 13/536,374, entitled INTERCHANGEABLE CLIP APPLIER, now U.S. Pat. No. 9,561,038.

11. U.S. patent application Ser. No. 13/536,292, entitled FIRING SYSTEM LOCKOUT ARRANGEMENTS FOR SURGICAL INSTRUMENTS, now U.S. Patent Application Publication No. 2014/0001231.

12. U.S. patent application Ser. No. 13/536,301 entitled ROTARY DRIVE SHAFT ASSEMBLIES FOR SURGICAL INSTRUMENTS WITH ARTICULATABLE END EFFECTORS, now U.S. Pat. No. 8,747,238.

13. U.S. patent application Ser. No. 13/536,313, entitled ROTARY DRIVE ARRANGEMENTS FOR SURGICAL INSTRUMENTS, now U.S. Patent Application Publication No. 2014/0005678.

14. U.S. patent application Ser. No. 13/536,379, entitled REPLACEABLE CLIP CARTRIDGE FOR A CLIP APPLIER, now U.S. Pat. No. 9,649,111.

15. U.S. patent application Ser. No. 13/536,386 entitled EMPTY CLIP CARTRIDGE LOCKOUT, now U.S. Pat. No. 9,282,974.

16. U.S. patent application Ser. No. 13/536,360, entitled SURGICAL INSTRUMENT SYSTEM INCLUDING REPLACEABLE END EFFECTORS, now U.S. Pat. No. 9,226,751.

17. U.S. patent application Ser. No. 13/536,335, entitled SURGERY STAPLING INSTRUMENTS WITH ROTARY JOINT ASSEMBLIES, now U.S. Pat. No. 9,364,230.

18. U.S. patent application Ser. No. 13/536,417, entitled ELECTRODE CONNECTIONS FOR ROTARY DRIVEN SURGICAL TOOLS, now U.S. Pat. No. 9,101,385.

Applicant also owns the following patent applications that are each incorporated by reference in their respective entireties:

U.S. patent application Ser. No. 13/118,259, entitled SURGICAL INSTRUMENT WITH WIRELESS COMMUNICATION BETWEEN A CONTROL UNIT OF A ROBOTIC SYSTEM AND REMOTE SENSOR, now U.S. Pat. No. 8,684,253.

U.S. patent application Ser. No. 13/118,210, entitled ROBOTICALLY-CONTROLLED DISPOSABLE MOTOR DRIVEN LOADING UNIT, now U.S. Pat. No. 8,752,749.

U.S. patent application Ser. No. 13/118,194, entitled ROBOTICALLY-CONTROLLED ENDOSCOPIC ACCESSORY CHANNEL, now U.S. Pat. No. 8,992,422.

U.S. patent application Ser. No. 13/118,253, entitled ROBOTICALLY-CONTROLLED MOTORIZED SURGICAL INSTRUMENT, now U.S. Pat. No. 9,386,983.

U.S. patent application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Pat. No. 9,237,891.

U.S. patent application Ser. No. 13/118,190, entitled ROBOTICALLY-CONTROLLED MOTORIZED CUTTING AND FASTENING INSTRUMENT, now U.S. Pat. No. 9,179,912.

U.S. patent application Ser. No. 13/118,223, entitled ROBOTICALLY-CONTROLLED SHAFT BASED ROTARY DRIVE SYSTEMS FOR SURGICAL INSTRUMENTS, now U.S. Pat. No. 8,931,682.

U.S. patent application Ser. No. 13/118,263, entitled ROBOTICALLY-CONTROLLED SURGICAL INSTRUMENT HAVING RECORDING CAPABILITIES, now U.S. Patent Application Publication No. 2011-0295295.

U.S. patent application Ser. No. 13/118,272, entitled ROBOTICALLY-CONTROLLED SURGICAL INSTRUMENT WITH FORCE FEEDBACK CAPABILITIES, now U.S. Patent Application Publication No. 2011-0290856.

U.S. patent application Ser. No. 13/118,246, entitled ROBOTICALLY-DRIVEN SURGICAL INSTRUMENT WITH E-BEAM DRIVER, U.S. Pat. No. 9,060,770.

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535.

Certain exemplary embodiments will now be described to provide an overall understanding of the principles of the structure, function, manufacture, and use of the devices and methods disclosed herein. One or more examples of these exemplary embodiments are illustrated in the accompanying drawings. Those of ordinary skill in the art will understand that the devices and methods specifically described herein and illustrated in the accompanying drawings are non-limiting exemplary embodiments and that the scope of the various exemplary embodiments of the present invention is defined solely by the claims. The features illustrated or described in connection with one exemplary embodiment may be combined with the features of other exemplary embodiments. Such modifications and variations are intended to be included within the scope of the present invention.

Figure 1:
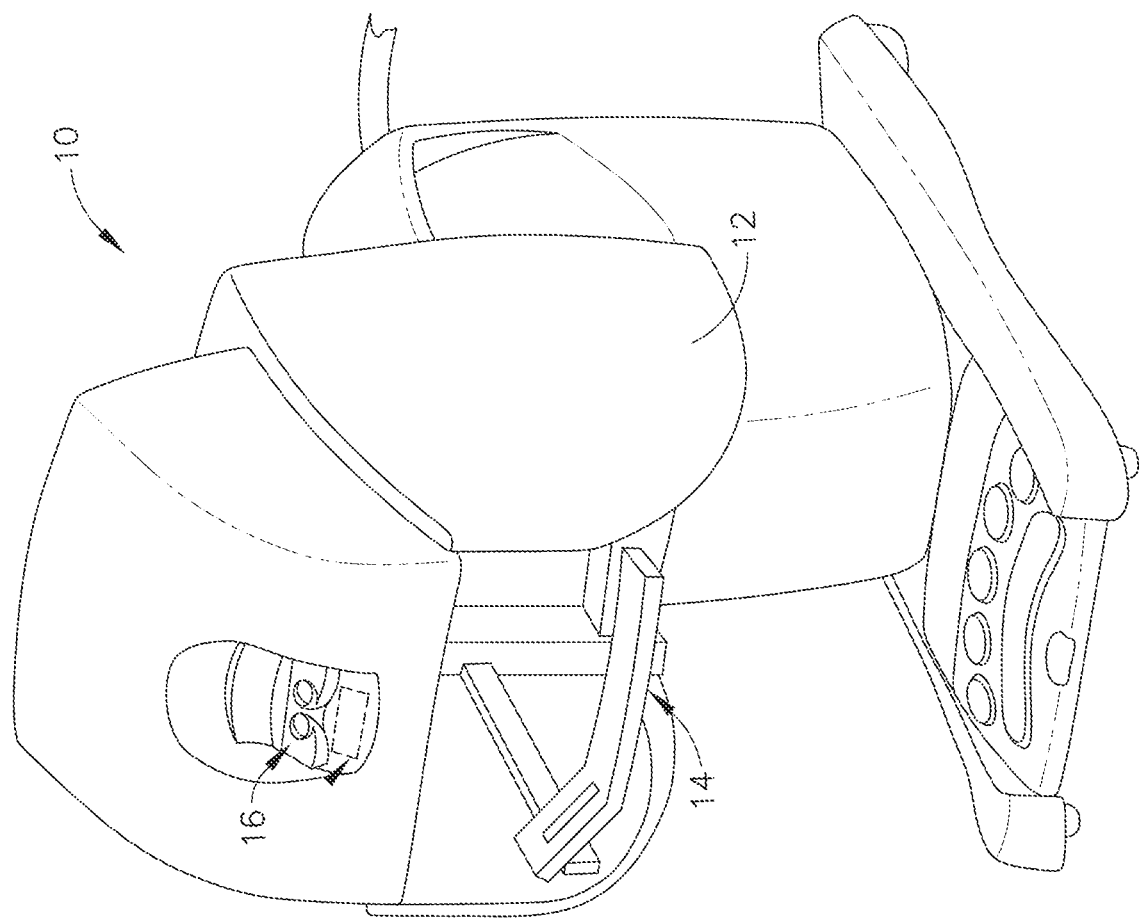
FIG. 1 is a perspective view of one robotic controller embodiment.
Figure 2:
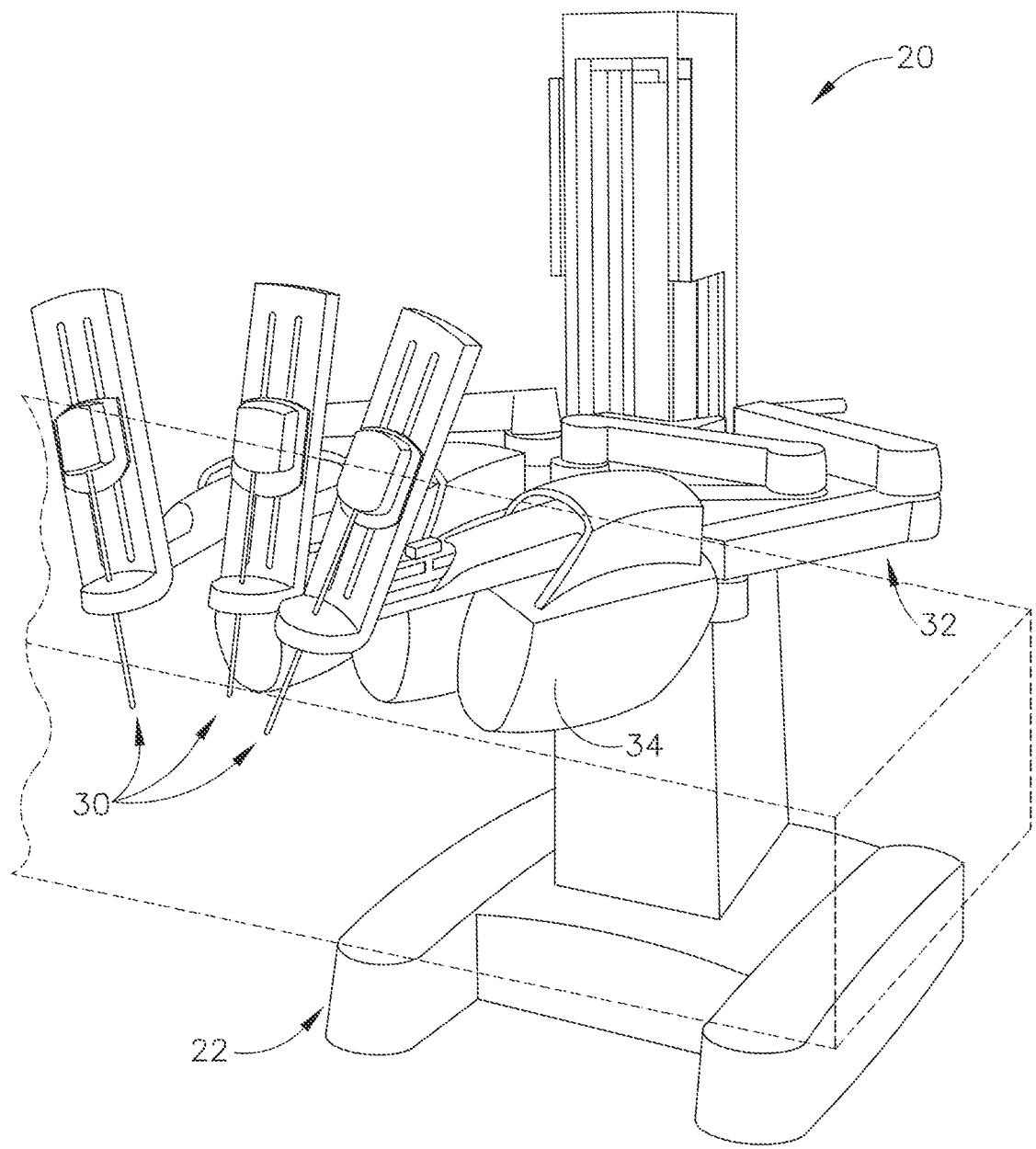
FIG. 2 is a perspective view of one robotic surgical arm cart/manipulator of a robotic system operably supporting a plurality of surgical tool embodiments.

FIG. 1 depicts a master controller 12 that is used in connection with a robotic arm slave cart 20 of the type depicted in FIG. 2. Master controller 12 and robotic arm slave cart 20, as well as their respective components and control systems are collectively referred to herein as a robotic system 10. Examples of such systems and devices are disclosed in U.S. Pat. No. 7,524,320 which has been herein incorporated by reference. Thus, various details of such devices will not be described in detail herein beyond that which may be necessary to understand various exemplary embodiments disclosed herein. As is known, the master controller 12 generally includes master controllers (generally represented as 14 in FIG. 1) which are grasped by the surgeon and manipulated in space while the surgeon views the procedure via a stereo display 16. The master controllers 12 generally comprise manual input devices which preferably move with multiple degrees of freedom, and which often further have an actuatable handle for actuating tools (for example, for closing grasping jaws, applying an electrical potential to an electrode, or the like).

As can be seen in FIG. 2, the robotic arm cart 20 is configured to actuate a plurality of surgical tools, generally designated as 30. Various robotic surgery systems and methods employing master controller and robotic arm cart arrangements are disclosed in U.S. Pat. No. 6,132,368, entitled MULTI-COMPONENT TELEPRESENCE SYSTEM AND METHOD, the full disclosure of which is incorporated herein by reference. As shown, the robotic arm cart 20 includes a base 22 from which, in the illustrated embodiment, three surgical tools 30 are supported. The surgical tools 30 are each supported by a series of manually articulatable linkages, generally referred to as set-up joints 32, and a robotic manipulator 34. These structures are herein illustrated with protective covers extending over much of the robotic linkage. These protective covers may be optional, and may be limited in size or entirely eliminated to minimize the inertia that is encountered by the servo mechanisms used to manipulate such devices, to limit the volume of moving components so as to avoid collisions, and to limit the overall weight of the cart 20. The cart 20 generally has dimensions suitable for transporting the cart 20 between operating rooms. The cart 20 is configured to typically fit through standard operating room doors and onto standard hospital elevators. The cart 20 would preferably have a weight and include a wheel (or other transportation) system that allows the cart 20 to be positioned adjacent an operating table by a single attendant.

Figure 3:
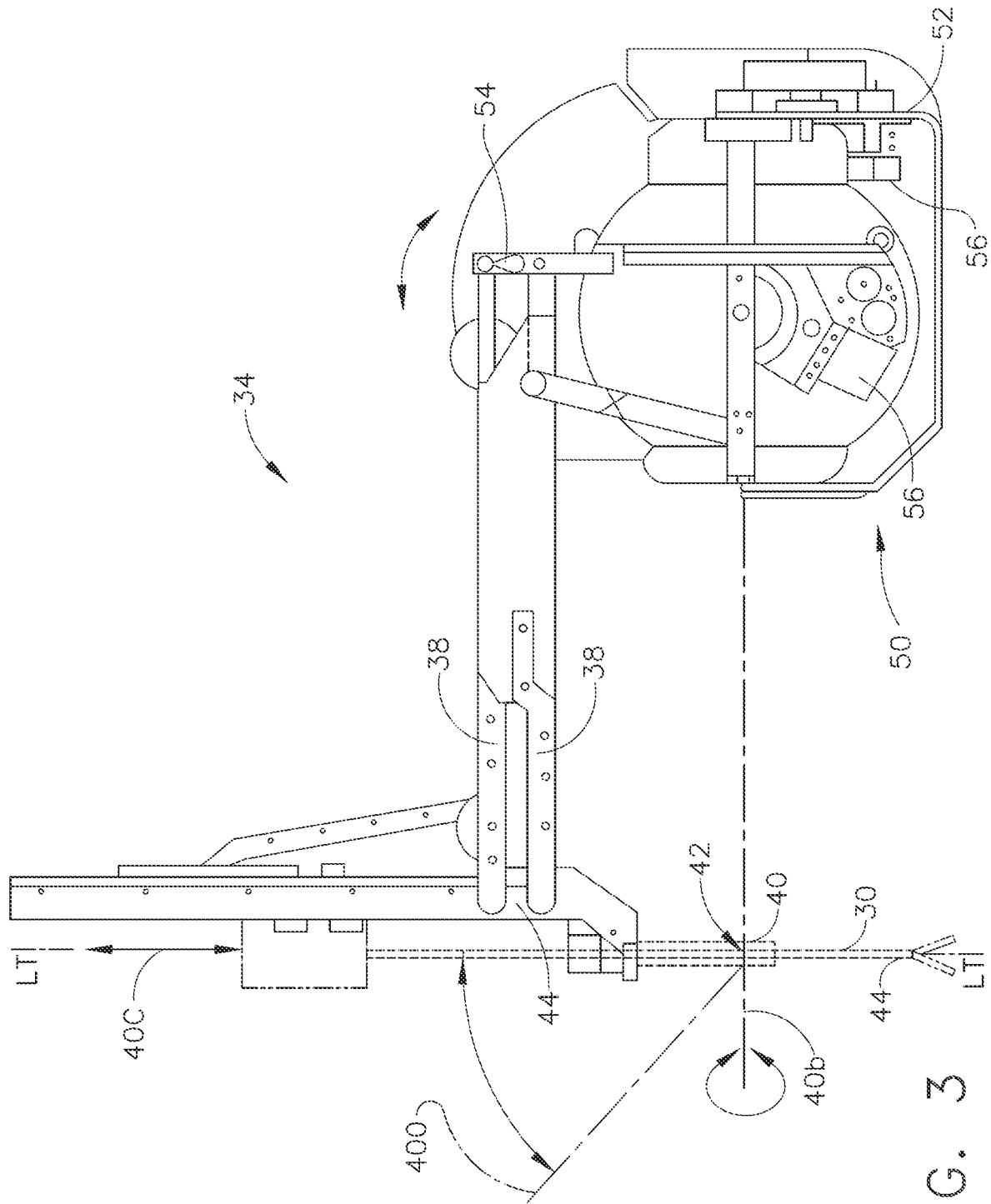
FIG. 3 is a side view of the robotic surgical arm cart/manipulator depicted in FIG. 2.
Figure 4:
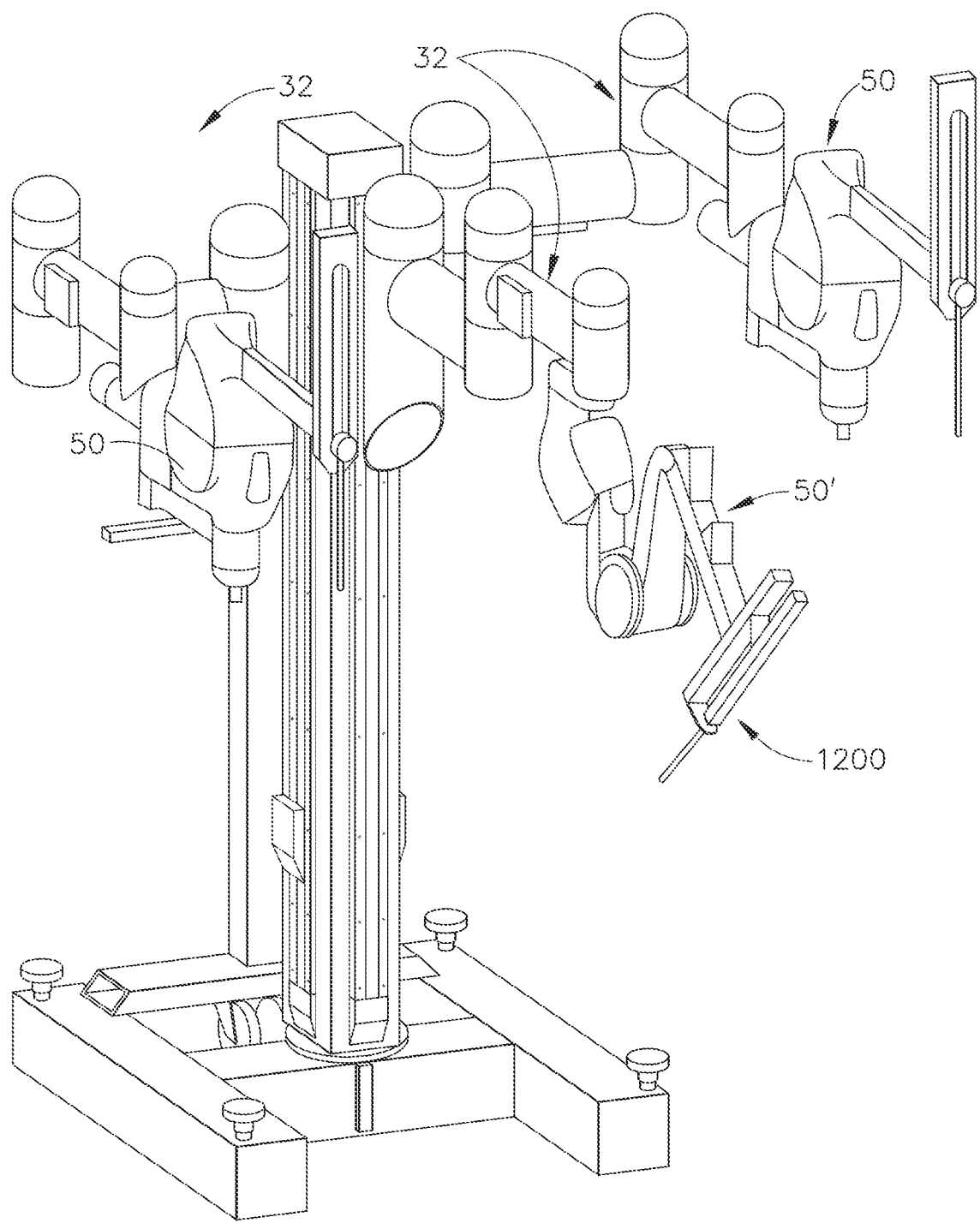
FIG. 4 is a perspective view of a cart structure with positioning linkages for operably supporting robotic manipulators that may be used with surgical tool embodiments.

Referring now to FIG. 3, robotic manipulators 34 as shown include a linkage 38 that constrains movement of the surgical tool 30. Linkage 38 includes rigid links coupled together by rotational joints in a parallelogram arrangement so that the surgical tool 30 rotates around a point in space 40, as more fully described in U.S. Pat. No. 5,817,084, the full disclosure of which is herein incorporated by reference. The parallelogram arrangement constrains rotation to pivoting about an axis 40a, sometimes called the pitch axis. The links supporting the parallelogram linkage are pivotally mounted to set-up joints 32 (FIG. 2) so that the surgical tool 30 further rotates about an axis 40b, sometimes called the yaw axis. The pitch and yaw axes 40a, 40b intersect at the remote center 42, which is aligned along a shaft 44 of the surgical tool 30. The surgical tool 30 may have further degrees of driven freedom as supported by manipulator 50, including sliding motion of the surgical tool 30 along the longitudinal tool axis "LT-LT". As the surgical tool 30 slides along the tool axis LT-LT relative to manipulator 50 (arrow 40c), remote center 42 remains fixed relative to base 52 of manipulator 50. Hence, the entire manipulator is generally moved to re-position remote center 42. Linkage 54 of manipulator 50 is driven by a series of motors 56. These motors actively move linkage 54 in response to commands from a processor of a control system. Motors 56 are also employed to manipulate the surgical tool 30. An alternative set-up joint structure is illustrated in FIG. 4. In this embodiment, a surgical tool 30 is supported by an alternative manipulator structure 50' between two tissue manipulation tools.

Other embodiments may incorporate a wide variety of alternative robotic structures, including those described in U.S. Pat. No. 5,878,193, entitled AUTOMATED ENDOSCOPE SYSTEM FOR OPTIMAL POSITIONING, the full disclosure of which is incorporated herein by reference. Additionally, while the data communication between a robotic component and the processor of the robotic surgical system is described with reference to communication between the surgical tool 30 and the master controller 12, similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 5:
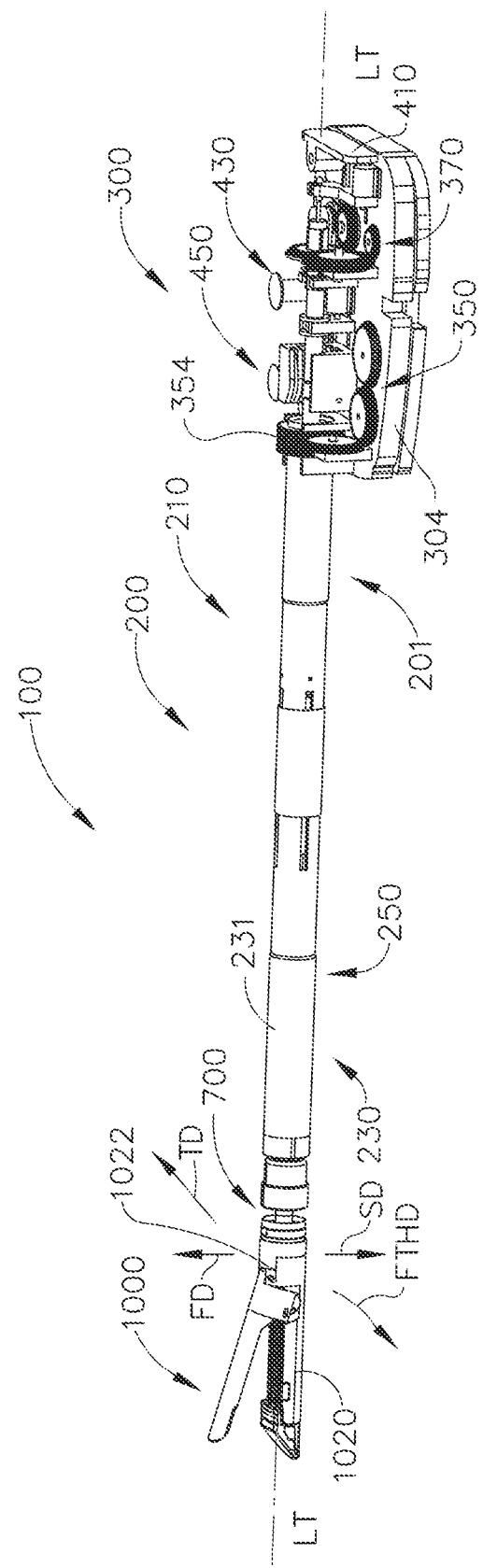
FIG. 5 is a perspective view of a surgical tool embodiment and a surgical end effector embodiment.
Figure 10:
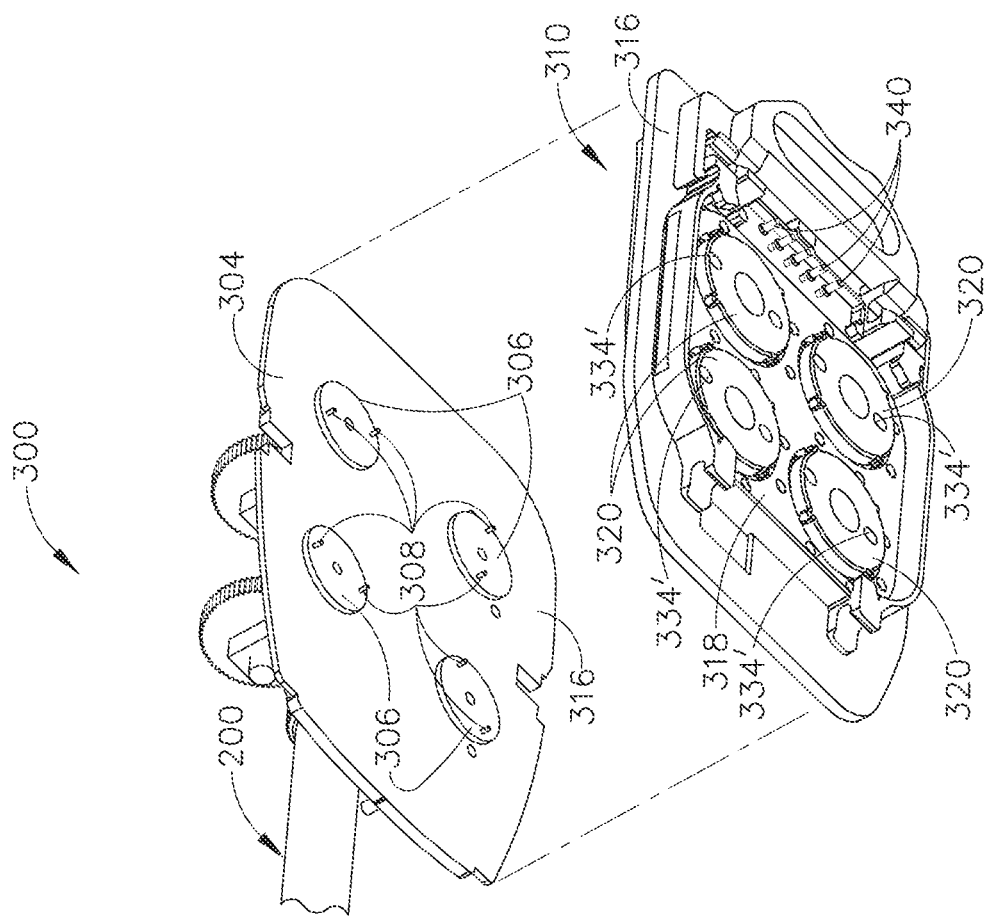
FIG. 10 is a partial bottom perspective view of a surgical tool embodiment.

A surgical tool 100 that is well-adapted for use with a robotic system 10 is depicted in FIG. 5. As can be seen in that Figure, the surgical tool 100 includes a surgical end effector 1000 that comprises an endocutter. The surgical tool 100 generally includes an elongate shaft assembly 200 that is operably coupled to the manipulator 50 by a tool mounting portion, generally designated as 300. The surgical tool 100 further includes an interface 302 which mechanically and electrically couples the tool mounting portion 300 to the manipulator. One interface 302 is illustrated in FIGS. 6-10. In the embodiment depicted in FIGS. 6-10, the tool mounting portion 300 includes a tool mounting plate 304 that operably supports a plurality of (four are shown in FIG. 10) rotatable body portions, driven discs or elements 306, that each include a pair of pins 308 that extend from a surface of the driven element 306. One pin 308 is closer to an axis of rotation of each driven elements 306 than the other pin 308 on the same driven element 306, which helps to ensure positive angular alignment of the driven element 306. Interface 302 may include an adaptor portion 310 that is configured to mountingly engage a mounting plate 304 as will be further discussed below. The illustrated adaptor portion 310 includes an array of electrical connecting pins 312 (FIG. 8) which may be coupled to a memory structure by a circuit board within the tool mounting portion 300. While interface 302 is described herein with reference to mechanical, electrical, and magnetic coupling elements, it should be understood that a wide variety of telemetry modalities might be used, including infrared, inductive coupling, or the like in other embodiments.

As can be seen in FIGS. 6-9, the adapter portion 310 generally includes a tool side 314 and a holder side 316. A plurality of rotatable bodies 320 are mounted to a floating plate 318 which has a limited range of movement relative to the surrounding adaptor structure normal to the major surfaces of the adaptor 310. Axial movement of the floating plate 318 helps decouple the rotatable bodies 320 from the tool mounting portion 300 when levers or other latch formations along the sides of the tool mounting portion housing (not shown) are actuated. Other embodiments may employ other mechanisms/arrangements for releasably coupling the tool mounting portion 300 to the adaptor 310. In the embodiment of FIGS. 6-10, rotatable bodies 320 are resiliently mounted to floating plate 318 by resilient radial members which extend into a circumferential indentation about the rotatable bodies 320. The rotatable bodies 320 can move axially relative to plate 318 by deflection of these resilient structures. When disposed in a first axial position (toward tool side 314) the rotatable bodies 320 are free to rotate without angular limitation. However, as the rotatable bodies 320 move axially toward tool side 314, tabs 322 (extending radially from the rotatable bodies 320) laterally engage detents on the floating plates so as to limit angular rotation of the rotatable bodies 320 about their axes. This limited rotation can be used to help drivingly engage the rotatable bodies 320 with drive pins 332 of a corresponding tool holder portion 330 of the robotic system 10, as the drive pins 332 will push the rotatable bodies 320 into the limited rotation position until the pins 332 are aligned with (and slide into) openings 334'. Openings 334 on the tool side 314 and openings 334' on the holder side 316 of rotatable bodies 320 are configured to accurately align the driven elements 306 (FIG. 10) of the tool mounting portion 300 with the drive elements 336 of the tool holder 330. As described above regarding inner and outer pins 308 of driven elements 306, the openings 334, 334' are at differing distances from the axis of rotation on their respective rotatable bodies 306 so as to ensure that the alignment is not 180 degrees from its intended position. Additionally, each of the openings 334 may be slightly radially elongate so as to fittingly receive the pins 308 in the circumferential orientation. This allows the pins 308 to slide radially within the openings 334 and accommodate some axial misalignment between the tool 100 and tool holder 330, while minimizing any angular misalignment and backlash between the drive and driven elements. Openings 334 on the tool side 314 may be offset by about 90 degrees from the openings 334' (shown in broken lines) on the holder side 316, as can be seen most clearly in FIG. 9.

In the embodiment of FIGS. 6-10, an array of electrical connector pins 340 are located on holder side 316 of adaptor 310 and the tool side 314 of the adaptor 310 includes slots 342 (FIG. 9) for receiving a pin array (not shown) from the tool mounting portion 300. In addition to transmitting electrical signals between the surgical tool 100 and the tool holder 330, at least some of these electrical connections may be coupled to an adaptor memory device 344 (FIG. 8) by a circuit board of the adaptor 310.

Figure 6:
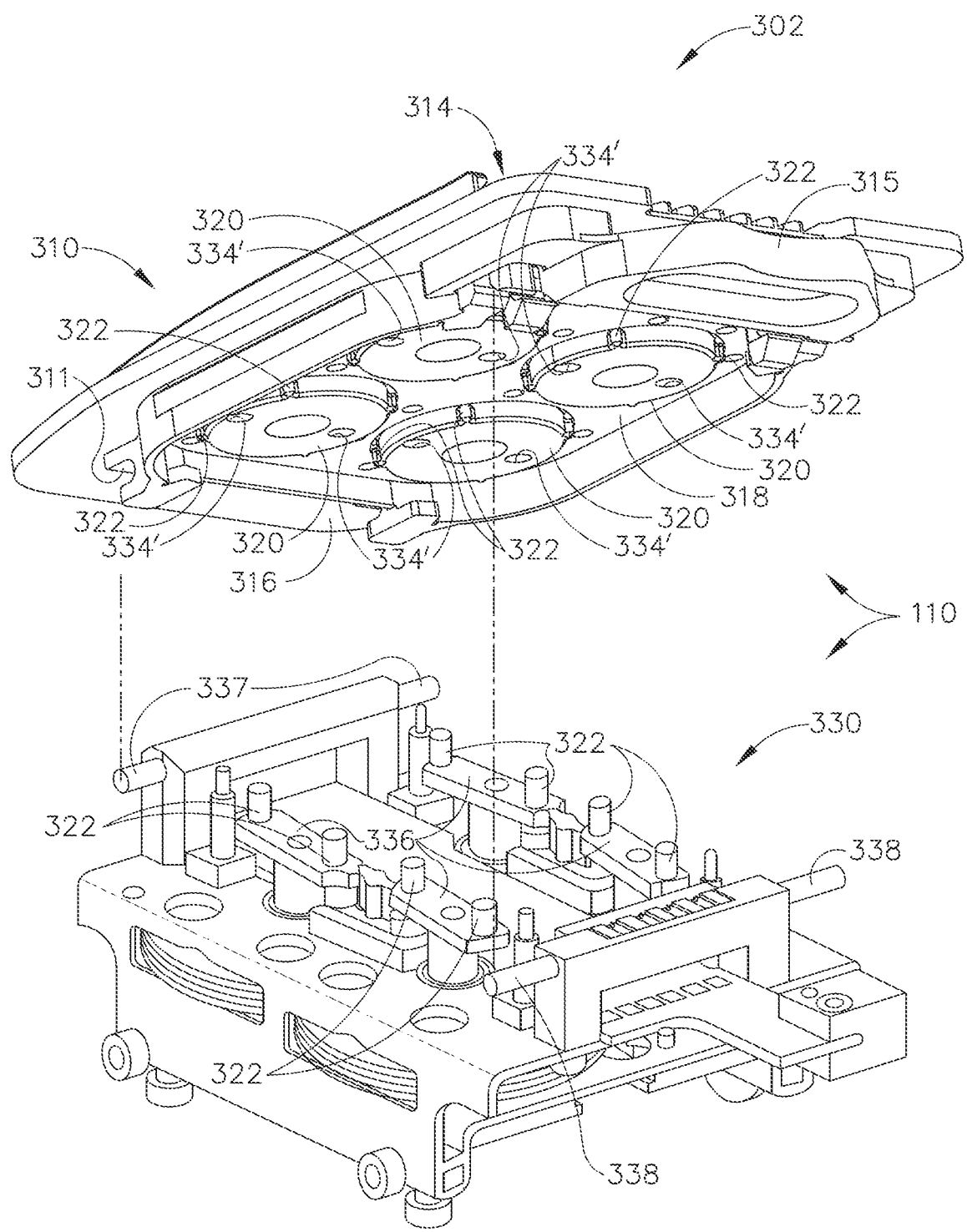
FIG. 6 is an exploded assembly view of an adapter and tool holder arrangement for attaching various surgical tool embodiments to a robotic system.
Figure 7:
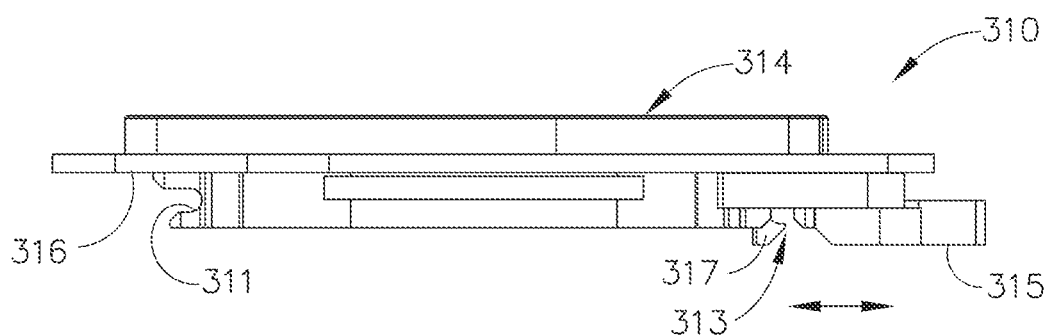
FIG. 7 is a side view of the adapter shown in FIG. 6.
Figure 8:
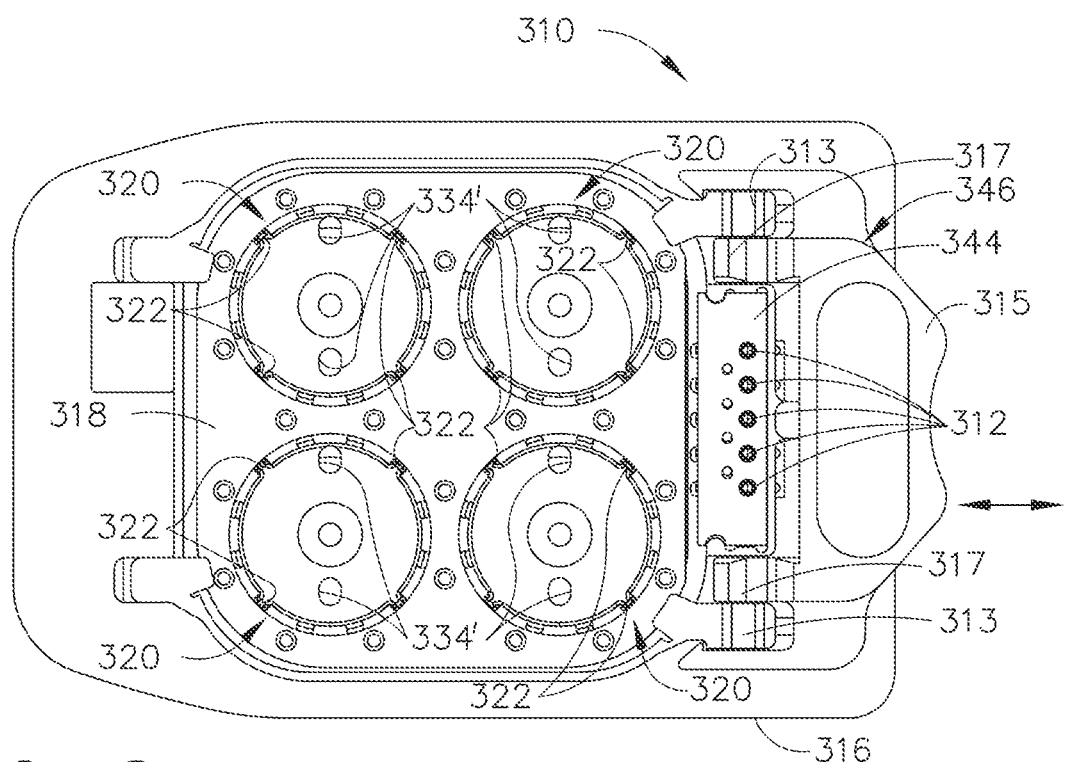
FIG. 8 is a bottom view of the adapter shown in FIG. 6.
Figure 9:
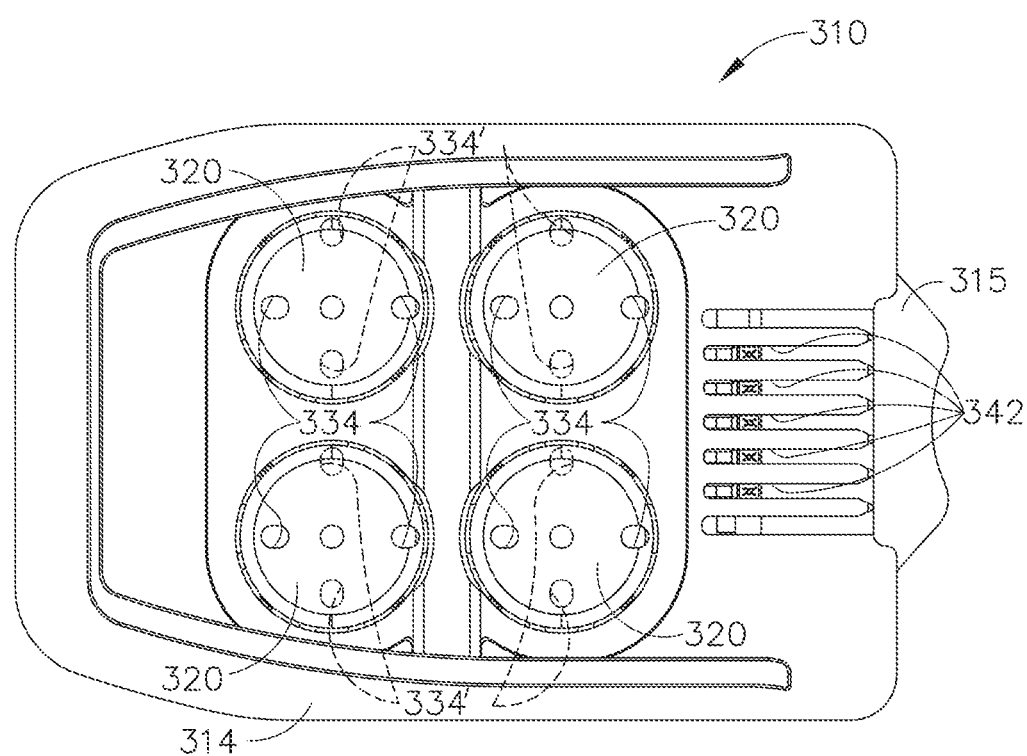
FIG. 9 is a top view of the adapter of FIGS. 6 and 7.

In the embodiment of FIGS. 6-10, a detachable latch arrangement 346 is employed to releasably affix the adaptor 310 to the tool holder 330. As used herein, the term "tool drive assembly" when used in the context of the robotic system 10, at least encompasses the adapter 310 and tool holder 330 and which have been collectively generally designated as 110 in FIG. 6. As can be seen in FIG. 6, the tool holder 330 includes a first latch pin arrangement 337 that is sized to be received in corresponding clevis slots 311 provided in the adaptor 310. In addition, the tool holder 330 further has second latch pins 338 that are sized to be retained in corresponding latch clevises 313 in the adaptor 310. See FIG. 8. A latch assembly 315 is movably supported on the adapter 310 and has a pair of latch clevises 317 formed therein that is biasable from a first latched position wherein the latch pins 338 are retained within their respective latch clevis 313 and an unlatched position wherein the clevises 317 are aligned with clevises 313 to enable the second latch pins 338 may be inserted into or removed from the latch clevises 313. A spring or springs (not shown) are employed to bias the latch assembly into the latched position. A lip on the tool side 314 of adaptor 310 slidably receives laterally extending tabs of the tool mounting housing (not shown).

Referring now to FIGS. 5 and 11-16, the tool mounting portion 300 operably supports a plurality of drive systems for generating various forms of control motions necessary to operate a particular type of end effector that is coupled to the distal end of the elongate shaft assembly 200. As shown in FIGS. 5 and 11-13, the tool mounting portion 300 includes a first drive system generally designated as 350 that is configured to receive a corresponding "first" rotary output motion from the tool drive assembly 110 of the robotic system 10 and convert that first rotary output motion to a first rotary control motion to be applied to the surgical end effector. In the illustrated embodiment, the first rotary control motion is employed to rotate the elongate shaft assembly 200 (and surgical end effector 1000) about a longitudinal tool axis LT-LT.

Figure 11:
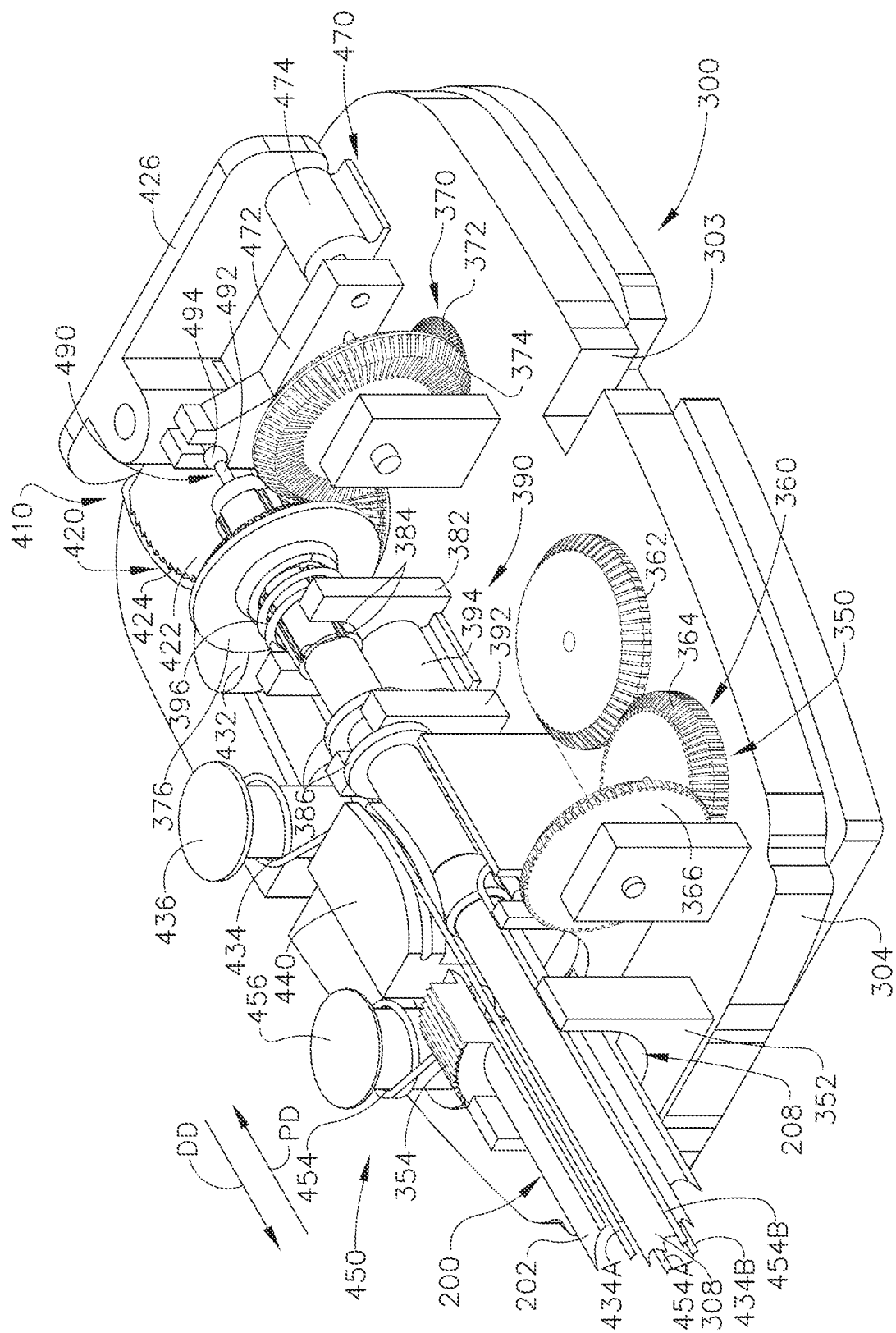
FIG. 11 is a front perspective view of a portion of a surgical tool embodiment with some elements thereof omitted for clarity.

In the embodiment of FIGS. 5 and 11-13, the first drive system 350 includes a tube gear segment 354 that is formed on (or attached to) the proximal end 208 of a proximal closure tube segment 202 of the elongate shaft assembly 200. The proximal end 208 of the proximal tube segment 202 is rotatably supported on the tool mounting plate 304 of the tool mounting portion 300 by a forward support cradle 352 that is mounted on the tool mounting plate 304. See FIG. 11. The tube gear segment 354 is supported in meshing engagement with a first rotational gear assembly 360 that is operably supported on the tool mounting plate 304. As can be seen in FIG. 11, the rotational gear assembly 360 comprises a first rotation drive gear 362 that is coupled to a corresponding first one of the driven discs or elements 306 on the holder side 316 of the tool mounting plate 304 when the tool mounting portion 300 is coupled to the tool drive assembly 110. See FIG. 10. The rotational gear assembly 360 further comprises a first rotary driven gear 364 that is rotatably supported on the tool mounting plate 304. The first rotary driven gear 364 is in meshing engagement with a second rotary driven gear 366 which, in turn, is in meshing engagement with the tube gear segment 354. Application of a first rotary output motion from the tool drive assembly 110 of the robotic system 10 to the corresponding driven element 306 will thereby cause rotation of the rotation drive gear 362. Rotation of the rotation drive gear 362 ultimately results in the rotation of the elongate shaft assembly 200 (and the surgical end effector 1000) about the longitudinal tool axis LT-LT (represented by arrow "R" in FIG. 5). It will be appreciated that the application of a rotary output motion from the tool drive assembly 110 in one direction will result in the rotation of the elongate shaft assembly 200 and surgical end effector 1000 about the longitudinal tool axis LT-LT in a first rotary direction and an application of the rotary output motion in an opposite direction will result in the rotation of the elongate shaft assembly 200 and surgical end effector 1000 in a second rotary direction that is opposite to the first rotary direction.

In embodiment of FIGS. 5 and 11-16, the tool mounting portion 300 further includes a second drive system generally designated as 370 that is configured to receive a corresponding "second" rotary output motion from the tool drive assembly 110 of the robotic system 10 and convert that second rotary output motion to a second rotary control motion for application to the surgical end effector. The second drive system 370 includes a second rotation drive gear 372 that is coupled to a corresponding second one of the driven discs or elements 306 on the holder side 316 of the tool mounting plate 304 when the tool mounting portion 300 is coupled to the tool drive assembly 110. See FIG. 10. The second drive system 370 further comprises a first rotary driven gear 374 that is rotatably supported on the tool mounting plate 304. The first rotary driven gear 374 is in meshing engagement with a shaft gear 376 that is movably and non-rotatably mounted onto a proximal drive shaft segment 380. In this illustrated embodiment, the shaft gear 376 is non-rotatably mounted onto the proximal drive shaft segment 380 by a series of axial keyways 384 that enable the shaft gear 376 to axially move on the proximal drive shaft segment 380 while being non-rotatably affixed thereto. Rotation of the proximal drive shaft segment 380 results in the transmission of a second rotary control motion to the surgical end effector 1000.

Figure 12:
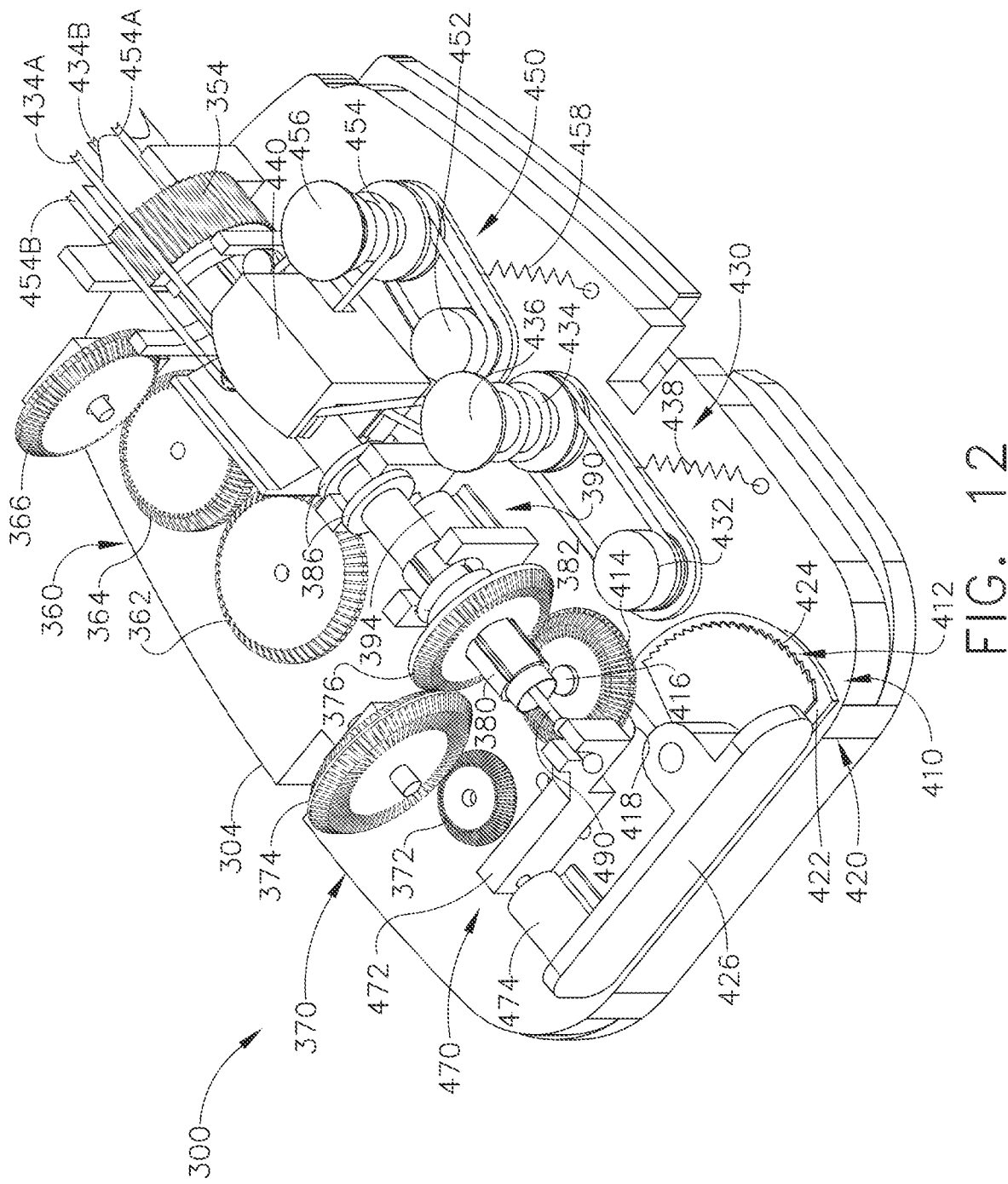
FIG. 12 is a rear perspective view of the surgical tool embodiment of FIG. 11.
Figure 13:
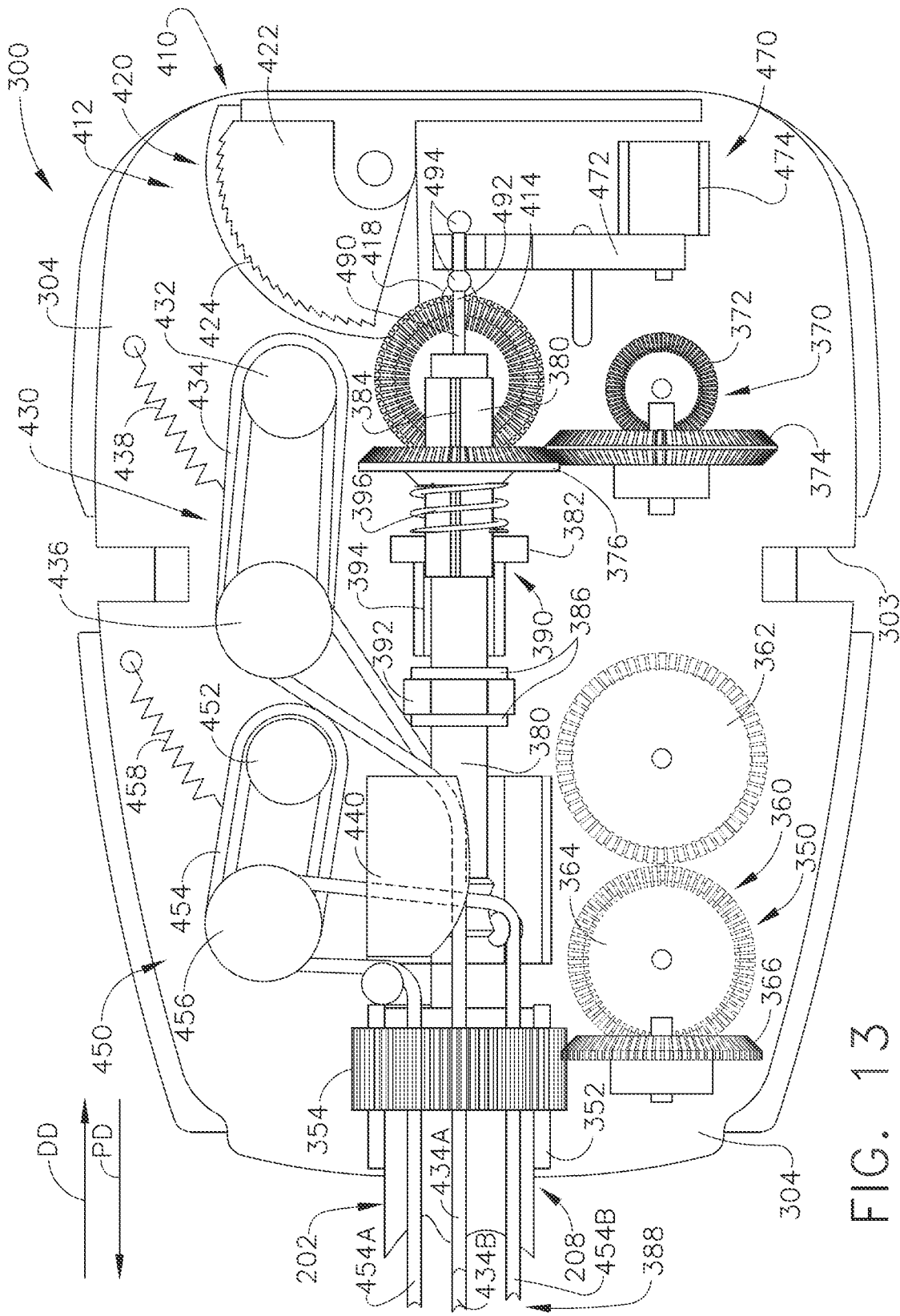
FIG. 13 is a top view of the surgical tool embodiment of FIGS. 11 and 12.
Figure 15:
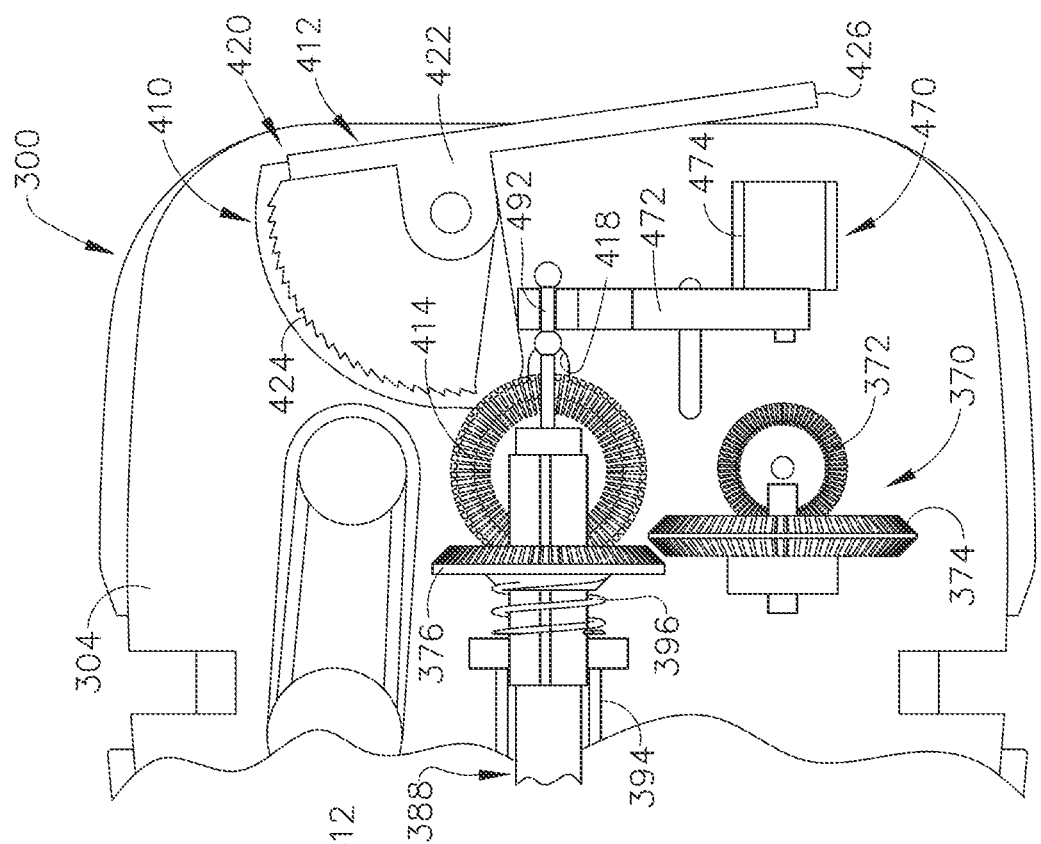
FIG. 15 is another partial top view of the surgical tool embodiment of FIGS. 11-14 with the manually actuatable drive gear in an initially actuated position.
Figure 14:
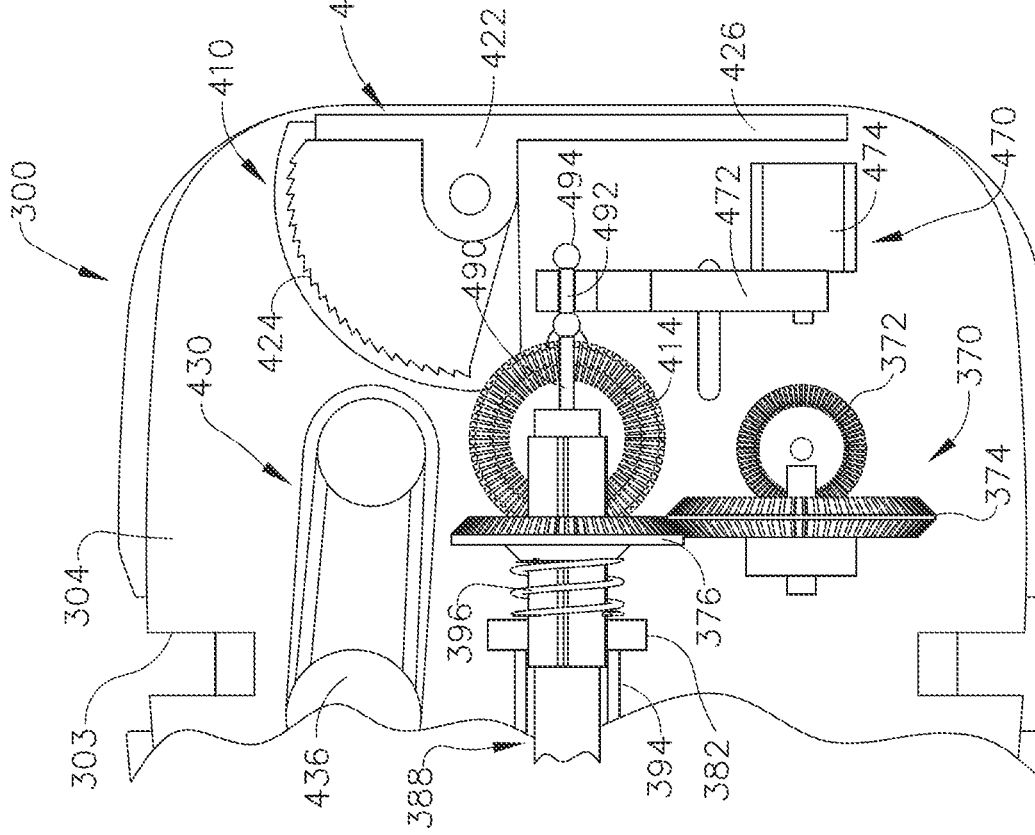
FIG. 14 is a partial top view of the surgical tool embodiment of FIGS. 11-13 with the manually actuatable drive gear in an unactuated position.
Figure 16:
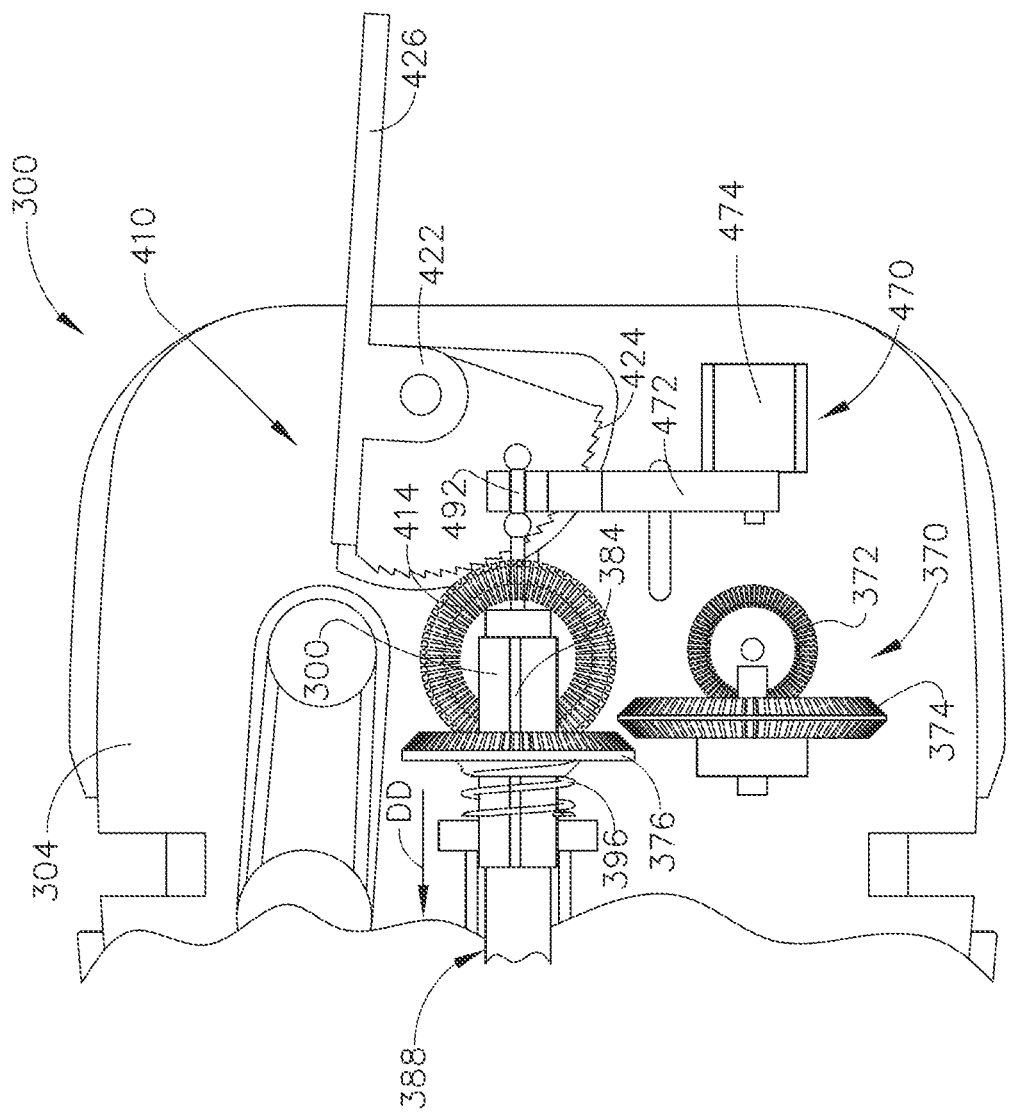
FIG. 16 is another partial top view of the surgical tool embodiment of FIGS. 11-15 with the manually actuatable drive gear in an actuated position.

The second drive system 370 in the embodiment of FIGS. 5 and 11-16 includes a shifting system 390 for selectively axially shifting the proximal drive shaft segment 380 which moves the shaft gear 376 into and out of meshing engagement with the first rotary driven gear 374. For example, as can be seen in FIGS. 11-13, the proximal drive shaft segment 380 is supported within a second support cradle 382 that is attached to the tool mounting plate 304 such that the proximal drive shaft segment 380 may move axially and rotate relative to the second support cradle 382. In at least one form, the shifting system 390 further includes a shifter yoke 392 that is slidably supported on the tool mounting plate 304. The proximal drive shaft segment 380 is supported in the shifter yoke 392 and has a pair of collars 386 thereon such that shifting of the shifter yoke 392 on the tool mounting plate 304 results in the axial movement of the proximal drive shaft segment 380. In at least one form, the shifting system 390 further includes a shifter solenoid 394 that operably interfaces with the shifter yoke 392. The shifter solenoid 394 receives control power from the robotic controller 12 such that when the shifter solenoid 394 is activated, the shifter yoke 392 is moved in the distal direction "DD".

In this illustrated embodiment, a shaft spring 396 is journaled on the proximal drive shaft segment 380 between the shaft gear 376 and the second support cradle 382 to bias the shaft gear 376 in the proximal direction "PD" and into meshing engagement with the first rotary driven gear 374. See FIGS. 11, 13 and 14. Rotation of the second rotation drive gear 372 in response to rotary output motions generated by the robotic system 10 ultimately results in the rotation of the proximal drive shaft segment 380 and other drive shaft components coupled thereto (drive shaft assembly 388) about the longitudinal tool axis LT-LT. It will be appreciated that the application of a rotary output motion from the tool drive assembly 110 in one direction will result in the rotation of the proximal drive shaft segment 380 and ultimately of the other drive shaft components attached thereto in a first direction and an application of the rotary output motion in an opposite direction will result in the rotation of the proximal drive shaft segment 380 in a second direction that is opposite to the first direction. When it is desirable to shift the proximal drive shaft segment 380 in the distal direction "DD" as will be discussed in further detail below, the robotic controller 12 activates the shifter solenoid 394 to shift the shifter yoke 392 in the distal direction "DD".

Figure 17:
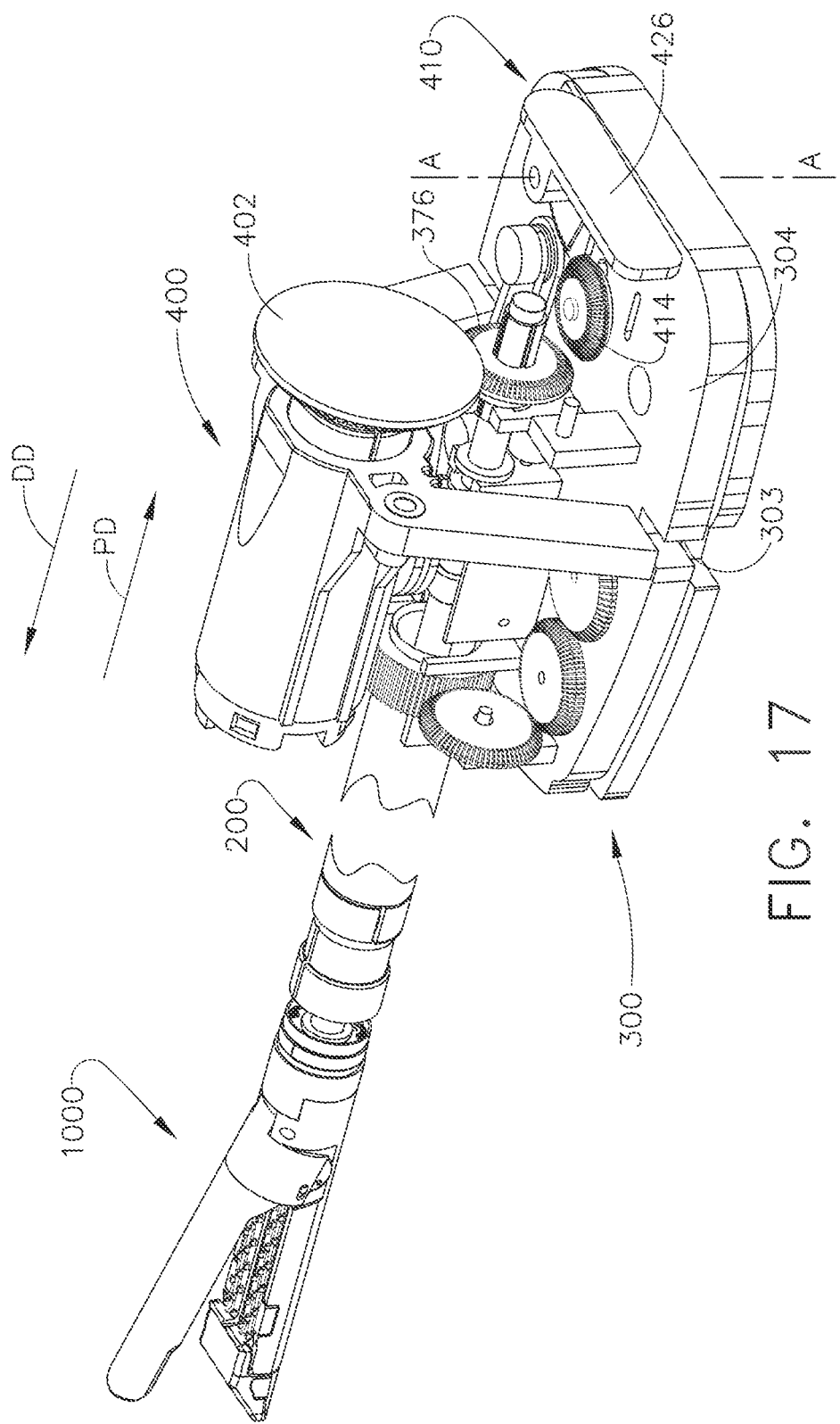
FIG. 17 is a rear perspective view of another surgical tool embodiment.
Figure 18:
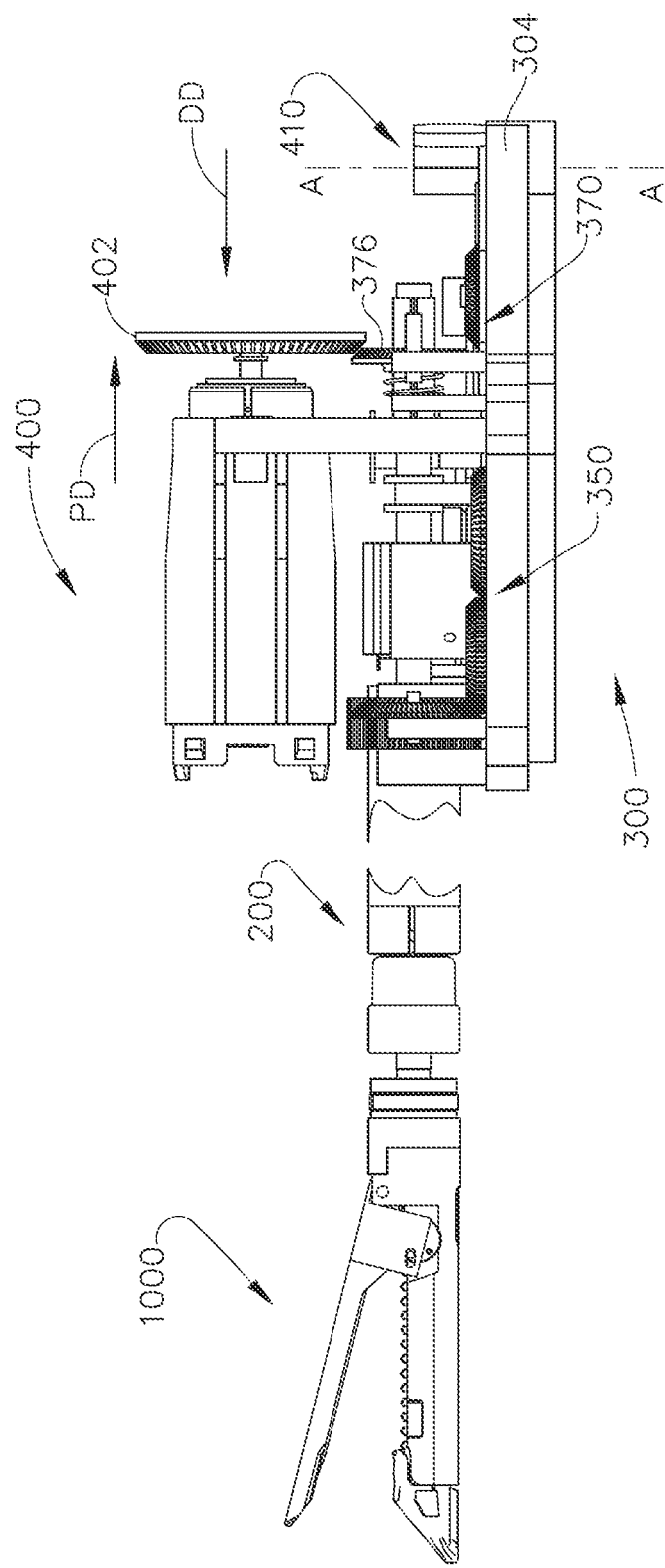
FIG. 18 is a side elevational view of the surgical tool embodiment of FIG. 17.

FIGS. 17 and 18 illustrate another embodiment that employs the same components of the embodiment depicted in FIGS. 5 and 11-16 except that this embodiment employs a battery-powered drive motor 400 for supplying rotary drive motions to the proximal drive shaft segment 380. Such arrangement enables the tool mounting portion to generate higher rotary output motions and torque which may be advantageous when different forms of end effectors are employed. As can be seen in those Figures, the motor 400 is attached to the tool mounting plate 304 by a support structure 402 such that a driver gear 404 that is coupled to the motor 400 is retained in meshing engagement with the shaft gear 376. In the embodiment of FIGS. 17 and 18, the support structure 402 is configured to removably engage latch notches 303 formed in the tool mounting plate 304 that are designed to facilitate attachment of a housing member (not shown) to the mounting plate 304 when the motor 400 is not employed. Thus, to employ the motor 400, the clinician removes the housing from the tool mounting plate 304 and then inserts the legs 403 of the support structure into the latch notches 303 in the tool mounting plate 304. The proximal drive shaft segment 380 and the other drive shaft components attached thereto are rotated about the longitudinal tool axis LT-LT by powering the motor 400. As illustrated, the motor 400 is battery powered. In such arrangement, however, the motor 400 interface with the robotic controller 12 such that the robotic system 10 controls the activation of the motor 400. In alternative embodiments, the motor 400 is manually actuatable by an on/off switch (not shown) mounted on the motor 400 itself or on the tool mounting portion 300. In still other embodiments, the motor 400 may receive power and control signals from the robotic system.

The embodiment illustrated in FIGS. 5 and 11-16 includes a manually-actuatable reversing system, generally designated as 410, for manually applying a reverse rotary motion to the proximal drive shaft segment 380 in the event that the motor fails or power to the robotic system is lost or interrupted. Such manually-actuatable reversing system 410 may also be particularly useful, for example, when the drive shaft assembly 388 becomes jammed or otherwise bound in such a way that would prevent reverse rotation of the drive shaft components under the motor power alone. In the illustrated embodiment, the mechanically-actuatable reversing system 410 includes a drive gear assembly 412 that is selectively engageable with the second rotary driven gear 376 and is manually actuatable to apply a reversing rotary motion to the proximal drive shaft segment 380. The drive gear assembly 412 includes a reversing gear 414 that is movably mounted to the tool mounting plate 304. The reversing gear 414 is rotatably journaled on a pivot shaft 416 that is movably mounted to the tool mounting plate 304 through a slot 418. See FIG. 12. In the embodiment of FIGS. 5 and 11-16, the manually-actuatable reversing system 410 further includes a manually actuatable drive gear 420 that includes a body portion 422 that has an arcuate gear segment 424 formed thereon. The body portion 422 is pivotally coupled to the tool mounting plate 304 for selective pivotal travel about an actuator axis A-A (FIG. 11) that is substantially normal to the tool mounting plate 304.

FIGS. 11-14 depict the manually-actuatable reversing system 410 in a first unactuated position. In one exemplary form, an actuator handle portion 426 is formed on or otherwise attached to the body portion 422. The actuator handle portion 426 is sized relative to the tool mounting plate 304 such that a small amount of interference is established between the handle portion 426 and the tool mounting plate 304 to retain the handle portion 426 in the first unactuated position. However, when the clinician desires to manually actuate the drive gear assembly 412, the clinician can easily overcome the interference fit by applying a pivoting motion to the handle portion 426. As can also be seen in FIGS. 11-14, when the drive gear assembly 412 is in the first unactuated position, the arcuate gear segment 424 is out of meshing engagement with the reversing gear 414. When the clinician desires to apply a reverse rotary drive motion to the proximal drive shaft segment 380, the clinician begins to apply a pivotal ratcheting motion to drive gear 420. As the drive gear 420 begins to pivot about the actuation axis A-A, a portion of the body 422 contacts a portion of the reversing gear 414 and axially moves the reversing gear 414 in the distal direction DD taking the drive shaft gear 376 out of meshing engagement with the first rotary driven gear 374 of the second drive system 370. See FIG. 15. As the drive gear 420 is pivoted, the arcuate gear segment 424 is brought into meshing engagement with the reversing gear 414. Continued ratcheting of the drive gear 420 results in the application of a reverse rotary drive motion to the drive shaft gear 376 and ultimately to the proximal drive shaft segment 380. The clinician may continue to ratchet the drive gear assembly 412 for as many times as are necessary to fully release or reverse the associated end effector component(s). Once a desired amount of reverse rotary motion has been applied to the proximal drive shaft segment 380, the clinician returns the drive gear 420 to the starting or unactuated position wherein the arcuate gear segment 416 is out of meshing engagement with the drive shaft gear 376. When in that position, the shaft spring 396 once again biases the shaft gear 376 into meshing engagement with first rotary driven gear 374 of the second drive system 370.

In use, the clinician may input control commands to the controller or control unit of the robotic system 10 which "robotically-generates" output motions that are ultimately transferred to the various components of the second drive system 370. As used herein, the terms "robotically-generates" or "robotically-generated" refer to motions that are created by powering and controlling the robotic system motors and other powered drive components. These terms are distinguishable from the terms "manually-actuatable" or "manually generated" which refer to actions taken by the clinician which result in control motions that are generated independent from those motions that are generated by powering the robotic system motors. Application of robotically-generated control motions to the second drive system in a first direction results in the application of a first rotary drive motion to the drive shaft assembly 388. When the drive shaft assembly 388 is rotated in a first rotary direction, the firing member 1200 is driven in the distal direction "DD" from its starting position toward its ending position in the end effector 1000. Application of robotically-generated control motions to the second drive system in a second direction results in the application of a second rotary drive motion to the drive shaft assembly 388. When the drive shaft assembly 388 is rotated in a second rotary direction, the firing member 1200 is driven in the proximal direction "PD" from its ending position toward its starting position in the end effector 1000. When the clinician desires to manually-apply rotary control motion to the drive shaft assembly 388, the drive shaft assembly 388 is rotated in the second rotary direction which causes the firing member 1200 to move in the proximal direction "PD" in the end effector. Other embodiments containing the same components are configured such that the manual-application of a rotary control motion to the drive shaft assembly could cause the drive shaft assembly to rotate in the first rotary direction which could be used to assist the robotically-generated control motions to drive the firing member 1200 in the distal direction.

The drive shaft assembly that is used to fire, close and rotate the end effector can be actuated and shifted manually allowing the end effector to release and be extracted from the surgical site as well as the abdomen even in the event that the motor(s) fail, the robotic system loses power or other electronic failure occurs. Actuation of the handle portion 426 results in the manual generation of actuation or control forces that are applied to the drive shaft assembly 388' by the various components of the manually-actuatable reversing system 410. If the handle portion 426 is in its unactuated state, it is biased out of actuatable engagement with the reversing gear 414. The beginning of the actuation of the handle portion 426 shifts the bias. The handle 426 is configured for repeated actuation for as many times as are necessary to fully release the firing member 1200 and the end effector 1000.

As illustrated in FIGS. 5 and 11-16, the tool mounting portion 300 includes a third drive system 430 that is configured to receive a corresponding "third" rotary output motion from the tool drive assembly 110 of the robotic system 10 and convert that third rotary output motion to a third rotary control motion. The third drive system 430 includes a third drive pulley 432 that is coupled to a corresponding third one of the driven discs or elements 306 on the holder side 316 of the tool mounting plate 304 when the tool mounting portion 300 is coupled to the tool drive assembly 110. See FIG. 10. The third drive pulley 432 is configured to apply a third rotary control motion (in response to corresponding rotary output motions applied thereto by the robotic system 10) to a corresponding third drive cable 434 that may be used to apply various control or manipulation motions to the end effector that is operably coupled to the shaft assembly 200. As can be most particularly seen in FIGS. 11 and 12, the third drive cable 434 extends around a third drive spindle assembly 436. The third drive spindle assembly 436 is pivotally mounted to the tool mounting plate 304 and a third tension spring 438 is attached between the third drive spindle assembly 436 and the tool mounting plate 304 to maintain a desired amount of tension in the third drive cable 434. As can be seen in the Figures, cable end portion 434A of the third drive cable 434 extends around an upper portion of a pulley block 440 that is attached to the tool mounting plate 304 and cable end portion 434B extends around a sheave pulley or standoff 442 on the pulley block 440. It will be appreciated that the application of a third rotary output motion from the tool drive assembly 110 in one direction will result in the rotation of the third drive pulley 432 in a first direction and cause the cable end portions 434A and 434B to move in opposite directions to apply control motions to the end effector 1000 or elongate shaft assembly 200 as will be discussed in further detail below. That is, when the third drive pulley 432 is rotated in a first rotary direction, the cable end portion 434A moves in a distal direction "DD" and cable end portion 434B moves in a proximal direction "PD". Rotation of the third drive pulley 432 in an opposite rotary direction result in the cable end portion 434A moving in a proximal direction "PD" and cable end portion 434B moving in a distal direction "DD".

The tool mounting portion 300 illustrated in FIGS. 5 and 11-16 includes a fourth drive system 450 that is configured to receive a corresponding "fourth" rotary output motion from the tool drive assembly 110 of the robotic system 10 and convert that fourth rotary output motion to a fourth rotary control motion. The fourth drive system 450 includes a fourth drive pulley 452 that is coupled to a corresponding fourth one of the driven discs or elements 306 on the holder side 316 of the tool mounting plate 304 when the tool mounting portion 300 is coupled to the tool drive assembly 110. See FIG. 10. The fourth drive pulley 452 is configured to apply a fourth rotary control motion (in response to corresponding rotary output motions applied thereto by the robotic system 10) to a corresponding fourth drive cable 454 that may be used to apply various control or manipulation motions to the end effector that is operably coupled to the shaft assembly 200. As can be most particularly seen in FIGS. 11 and 12, the fourth drive cable 454 extends around a fourth drive spindle assembly 456. The fourth drive spindle assembly 456 is pivotally mounted to the tool mounting plate 304 and a fourth tension spring 458 is attached between the fourth drive spindle assembly 456 and the tool mounting plate 304 to maintain a desired amount of tension in the fourth drive cable 454. Cable end portion 454A of the fourth drive cable 454 extends around a bottom portion of the pulley block 440 that is attached to the tool mounting plate 304 and cable end portion 454B extends around a sheave pulley or fourth standoff 462 on the pulley block 440. It will be appreciated that the application of a rotary output motion from the tool drive assembly 110 in one direction will result in the rotation of the fourth drive pulley 452 in a first direction and cause the cable end portions 454A and 454B to move in opposite directions to apply control motions to the end effector or elongate shaft assembly 200 as will be discussed in further detail below. That is, when the fourth drive pulley 434 is rotated in a first rotary direction, the cable end portion 454A moves in a distal direction "DD" and cable end portion 454B moves in a proximal direction "PD". Rotation of the fourth drive pulley 452 in an opposite rotary direction result in the cable end portion 454A moving in a proximal direction "PD" and cable end portion 454B to move in a distal direction "DD".

The surgical tool 100 as depicted in FIG. 5 includes an articulation joint 700. In such embodiment, the third drive system 430 may also be referred to as a "first articulation drive system" and the fourth drive system 450 may be referred to herein as a "second articulation drive system". Likewise, the third drive cable 434 may be referred to as a "first proximal articulation cable" and the fourth drive cable 454 may be referred to herein as a "second proximal articulation cable".

The tool mounting portion 300 of the embodiment illustrated in FIGS. 5 and 11-16 includes a fifth drive system generally designated as 470 that is configured to axially displace a drive rod assembly 490. The drive rod assembly 490 includes a proximal drive rod segment 492 that extends through the proximal drive shaft segment 380 and the drive shaft assembly 388. See FIG. 13. The fifth drive system 470 includes a movable drive yoke 472 that is slidably supported on the tool mounting plate 304. The proximal drive rod segment 492 is supported in the drive yoke 472 and has a pair of retainer balls 494 thereon such that shifting of the drive yoke 472 on the tool mounting plate 304 results in the axial movement of the proximal drive rod segment 492. In at least one exemplary form, the fifth drive system 470 further includes a drive solenoid 474 that operably interfaces with the drive yoke 472. The drive solenoid 474 receives control power from the robotic controller 12. Actuation of the drive solenoid 474 in a first direction will cause the drive rod assembly 490 to move in the distal direction "DD" and actuation of the drive solenoid 474 in a second direction will cause the drive rod assembly 490 to move in the proximal direction "PD". As can be seen in FIG. 5, the end effector 1000 includes an anvil portion that is movable between open and closed positions upon application of axial closure motions to a closure system. In the illustrated embodiment of FIGS. 5 and 11-16, the fifth drive system 470 is employed to generate such closure motions. Thus, the fifth drive system 470 may also be referred to as a "closure drive".

The embodiment depicted in FIG. 5, includes a surgical end effector 1000 that is attached to the tool mounting portion 300 by the elongate shaft assembly 200. In that illustrated embodiment, the elongate shaft assembly includes a coupling arrangement in the form of a quick disconnect arrangement or joint 210 that facilitates quick attachment of a distal portion 230 of the shaft assembly 200 to a proximal shaft portion 201 of the shaft assembly 200. The quick disconnect joint 210 serves to facilitate the quick attachment and detachment of a plurality of drive train components used to provide control motions from a source of drive motions to an end effector that is operably coupled thereto. In the embodiment illustrated in FIGS. 5 and 19, for example, the quick disconnect joint 210 is employed to couple a distal shaft portion 230 of end effector 1000 to a proximal shaft portion 201.

Figure 19:
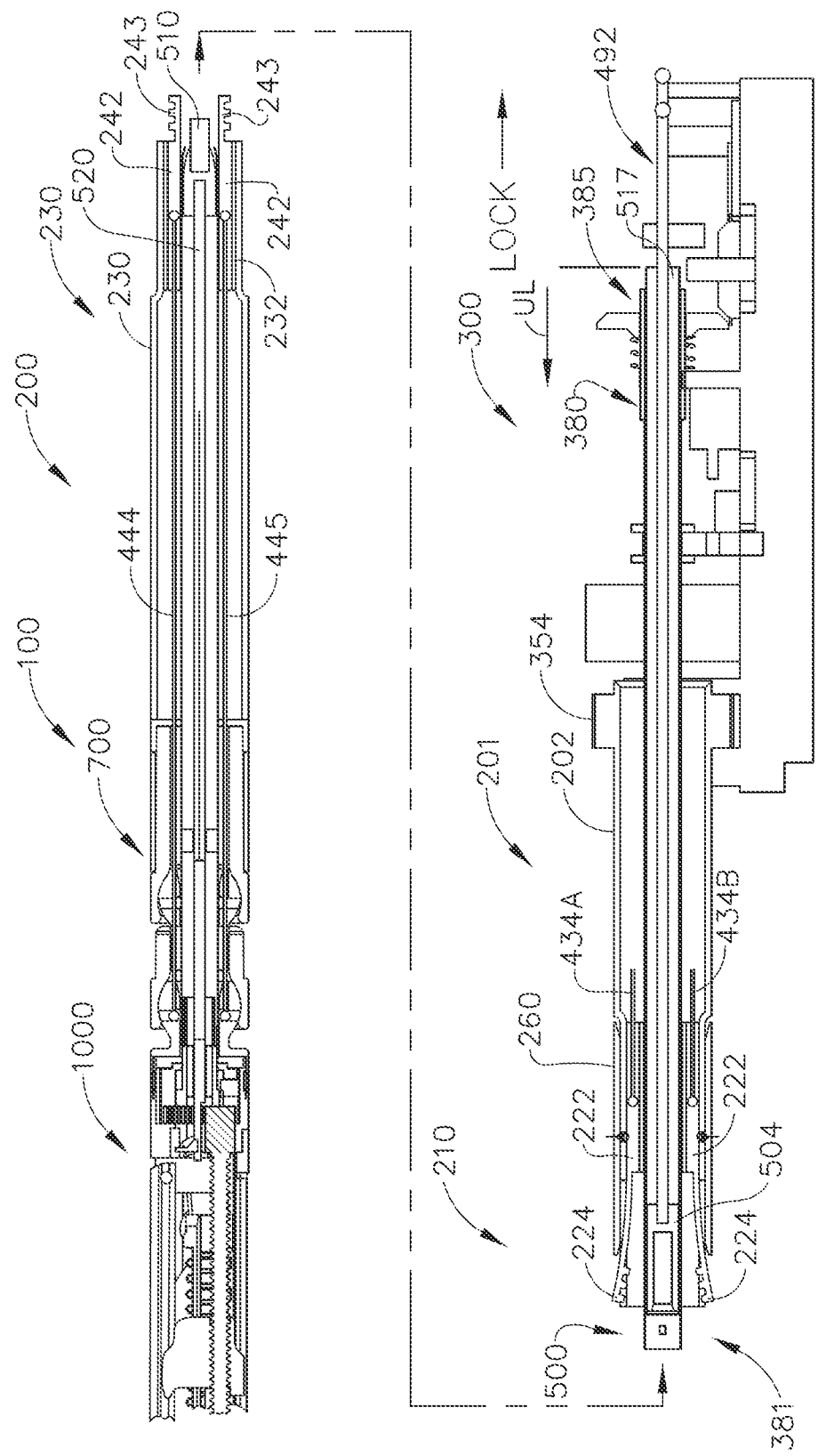
FIG. 19 is a cross-sectional view of the surgical tool embodiment of FIG. 5 with the end effector detached from the proximal shaft portion of the surgical tool.

Referring now to FIGS. 19-23, the coupling arrangement or quick disconnect joint 210 includes a proximal coupler member 212 that is configured to operably support proximal drive train assemblies and a distal coupler member 232 that is configured to operably support at least one and preferably a plurality of distal drive train assemblies. In the embodiment of FIGS. 5 and 19, the third drive system 430 (i.e., a first articulation drive system) and the fourth drive system 450 (i.e., a second articulation drive system) are employed to apply articulation motions to the articulation joint 700. For example, the third drive system 430 serves to apply control motions to the first proximal articulation cable 434 that has cable end portions 434A, 434B to articulate the end effector 1000 in first and second articulation directions about the articulation joint 700. Likewise, the fourth drive system 450 serves to apply control motions to the second proximal articulation cable 454 that has cable end portions 454A, 454B to articulate the end effector 1000 in the third and fourth articulation directions.

Referring to FIG. 20, the proximal coupler member 212 has a first pair of diametrically-opposed first slots 214 therein and a second pair of diametrically-opposed second slots 218 therein (only one slot 218 can be seen in FIG. 20). A first proximal articulation formation or link 222 is supported in each of the opposed first slots 214. A second proximal articulation formation or link 226 is supported in each of the second slots 218. The cable end portion 434A extends through a slot in one of the proximal articulation links 222 and is attached thereto. Likewise, the cable end portion 434B extends through a slot in the other proximal articulation link 222 and is attached thereto. Cable end portion 434A and its corresponding proximal articulation formation or link 222 and cable end portion 434B and its corresponding proximal articulation formation or link 222 are collectively referred to as a "first proximal articulation drive train assembly" 217. The end cable portion 454A extends through a slot in one of the proximal articulation links 226 and is attached thereto. The cable end portion 454B extends through a slot in the other proximal articulation link 226 and is attached thereto. Cable end portion 454A and its corresponding proximal articulation formation or link 226 and the cable end portion 454B and its corresponding proximal articulation formation or link 226 are collectively referred to as a "second proximal articulation drive train assembly" 221.

As can be seen in FIG. 21, the distal shaft portion 230 includes a distal outer tube portion 231 that supports the distal coupler member 232. The distal coupler member 232 has a first pair of diametrically opposed first slots 234 therein and a second pair of diametrically opposed second slots 238 therein. See FIG. 20. A first pair of distal articulation formations or links 242 are supported in the opposed first slots 234. A second pair of distal articulation formations or links 246 are supported in the second pair of slots 238. A first distal cable segment 444 extends through one of the first slots 234 and a slot in one of the distal articulation links 242 to be attached thereto. A primary distal cable segment 445 extends through the other one of the first slots 234 and through a slot in the other distal articulation link 242 and to be attached thereto. The first distal cable segment 444 and its corresponding distal articulation link 242 and the primary distal cable segment 445 and its corresponding distal articulation link 242 are collectively referred to as a "first distal articulation drive train assembly" 237. A second distal cable segment 446 extends through one of the second slots 238 and a slot in one of the distal articulation links 246 and to be attached thereto. A secondary distal cable segment 447 extends through the other second slot 238 and through a slot in the other distal articulation link 246 to be attached thereto. The second distal cable segment 446 and its corresponding distal articulation link 246 and the secondary distal cable segment 447 and its corresponding distal articulation link 246 are collectively referred to as a "second distal articulation drive train assembly" 241.

Each of the proximal articulation links 222 has a toothed end 224 formed on a spring arm portion 223 thereof. Each proximal articulation link 226 has a toothed end 227' formed on a spring arm portion 227. Each distal articulation link 242 has a toothed end 243 that is configured to be meshingly coupled with the toothed end 224 of a corresponding one of the proximal articulation links 222. Each distal articulation link 246 has a toothed end 247 that is configured to be meshingly coupled with the toothed end 228 of a corresponding proximal articulation link 226. When the proximal articulation formations or links 222, 226 are meshingly linked with the distal articulation links 242, 246, respectively, the first and second proximal articulation drive train assemblies 217 and 221 are operably coupled to the first and second distal articulation drive train assemblies 237 and 241, respectively. Thus, actuation of the third and fourth drive systems 430, 450 will apply actuation motions to the distal cable segments 444, 445, 446, 447 as will be discussed in further detail below.

In the embodiment of FIGS. 19-23, a distal end 250 of proximal outer tube segment 202 has a series of spring fingers 252 therein that extend distally into slots 254 configured to receive corresponding spring arm portions 223, 227 therein. See FIG. 21 (spring arm portion 227 is not depicted in FIG. 21 but can be seen in FIG. 20). Each spring finger 252 has a detent 256 therein that is adapted to engage corresponding dimples 258 formed in the proximal articulation links 222, 226 when the proximal articulation links 222, 226 are in the neutral position (FIG. 23). When the clinician desires to remove or attach an end effector 1000 to the proximal shaft portion 201, the third and fourth drive systems 430, 450 are parked in their neutral unactuated positions.

The proximal coupler member 212 and the distal coupler member 232 of the quick disconnect joint 210 operably support corresponding portions of a drive member coupling assembly 500 for releasably coupling the proximal drive rod segment 492 to a distal drive rod segment 520. The proximal drive rod segment 492 comprises a proximal axial drive train assembly 496 and the distal drive rod segment 520 comprises a distal axial drive train assembly 528. The drive member coupling assembly 500 comprises a drive rod coupler or formation 502 that comprises a receiving formation or first magnet 504 such as, for example, a rare earth magnet, etc. that is attached to the distal end 493 of the distal drive rod segment 520. The first magnet 504 has a receiving cavity 506 formed therein for receiving a second formation or distal magnet 510. As can be seen in FIG. 21, the distal magnet 510 is attached to a tapered mounting member 512 that is attached to a proximal end 522 of the distal drive rod segment 520.

The proximal coupler member 212 and the distal coupler member 232 of the quick disconnect joint 210 operably support other corresponding portions of a drive member coupling assembly 500 for releasably coupling the proximal drive shaft segment 380 with a distal drive shaft segment 540. The proximal drive shaft segment 380, in at least one exemplary form, comprises a proximal rotary drive train assembly 387 and the distal drive shaft segment 540 comprises a distal rotary drive train assembly 548. When the proximal rotary drive train assembly 387 is operably coupled to the distal rotary drive train assembly 548, the drive shaft assembly 388 is formed to transmit rotary control motions to the end effector 1000. In the illustrated exemplary embodiment, a proximal end 542 of the distal drive shaft segment 540 has a plurality (e.g., four—only two can be seen in FIG. 21) formations or cleated fingers 544 formed thereon. Each cleated finger 544 has an attachment cleat 546 formed thereon that are sized to be received in corresponding lock formations or holes or slots 383 in a distal end 381 of the proximal drive shaft segment 380. The fingers 544 extend through a reinforcing ring 545 journaled onto the proximal end 542 of the distal drive shaft segment 540.

In the embodiment depicted in FIGS. 19-23, the drive member coupling assembly 500 further includes an unlocking tube 514 for assisting in the disengagement of the first and second magnets 504, 510 when the clinician detaches the end effector 1000 from the proximal shaft portion 201 of the surgical tool 100. The unlocking tube 514 extends through the proximal drive shaft segment 380 and its proximal end 517 protrudes out of the proximal end 385 of the proximal drive shaft segment 380 as shown in FIG. 19. The unlocking tube 514 is sized relative to the proximal drive shaft segment 380 so as to be axially movable therein upon application of an unlocking motion "UL" applied to the proximal end 517 thereof. A handle (not shown) is attached to the proximal end 517 of the unlocking tube to facilitate the manual application of the unlocking motion "UL" to the unlocking tube 514 or the unlocking motion "UL". Other embodiments that are otherwise identical to the embodiment of FIGS. 19-23 employ an unlocking solenoid (not shown) that is attached to the tool mounting plate 304 and powered by the robotic controller 12 or a separate battery attached thereto is employed to apply the unlocking motion.

In the illustrated exemplary embodiment, the coupling arrangement or quick disconnect joint 210 also includes an outer lock collar 260 that is slidably journaled on the distal end 204 of the proximal outer tube portion 202. The outer lock collar 260 has four inwardly extending detents 262 that extend into a corresponding one of the slots 254 in the proximal outer tube portion 202. Use of the quick disconnect joint 210 can be understood from reference to FIGS. 21-23. FIG. 21 illustrates the conditions of the proximal shaft portion 201 and the distal shaft portion 230 prior to being coupled together. As can be seen in that Figure, the spring arm portions 223, 227 of the proximal articulation links 224, 226, respectively are naturally radially sprung outward. The locking collar 260 is moved to its proximal-most position on the proximal outer tube 202 wherein the detents 262 are at the proximal end of the slots 254 therein. When the clinician desires to attach the end effector 1000 to the proximal shaft portion 201 of the surgical tool 100, the clinician brings the distal shaft portion 230 into axial alignment and coupling engagement with the proximal shaft portion 201 as shown in FIG. 22. As can be seen in that Figure, the distal magnet 510 is seated within the cavity 506 in the drive rod coupler 502 and is magnetically attached to the proximal magnet 504 to thereby couple the distal drive rod segment 520 to the proximal drive rod segment 492. Such action thereby operably couples the distal axial drive train assembly 528 to the proximal axial drive train assembly 496. In addition, as the shaft portions 201, 230 are joined together, the cleated fingers 544 flex inward until the cleats 546 formed thereon enter the lock openings 383 in the distal end portion 381 of the proximal drive shaft segment 380. When the cleats 546 are seated within their respective locking holes 383, the distal drive shaft segment 540 is coupled to the proximal drive shaft segment 380. Thus, such action thereby operably couples the distal rotary drive train assembly 548 to the proximal rotary drive train assembly 387. As such, when distal coupler member 232 and the proximal coupler member 212 are brought into axial alignment and engagement in the manner described above and the locking collar 260 is moved to its proximal-most position on the proximal outer tube 202, the distal drive train assemblies are operably coupled to the proximal drive train assemblies.

When the clinician desires to detach the end effector 1000 from the proximal shaft portion 201 of the surgical tool 100, the clinician returns the third and fourth drive systems 430, 450 into their neutral positions. The clinician may then slide the locking collar 260 proximally on the proximal outer tube segment 202 into the starting position shown in FIG. 22. When in that position, the spring arm portions of the proximal articulation links 222, 226 cause the toothed portions thereof to disengage the toothed portions of the distal articulation links 242, 246. The clinician may then apply an unlocking motion UL to the proximal end 517 of the unlocking tube 514 to move the unlocking tube 514 and the unlocking collar 516 attached thereto in the distal direction "DD". As the unlocking collar 516 moves distally, it biases the cleated fingers 544 out of engagement with their respective holes 383 in the distal end portion 381 of the proximal drive shaft segment 380 and contacts the tapered mounting portion 512 to force the distal magnet 510 out of magnetic engagement with the proximal magnet 504.

Figure 22A:
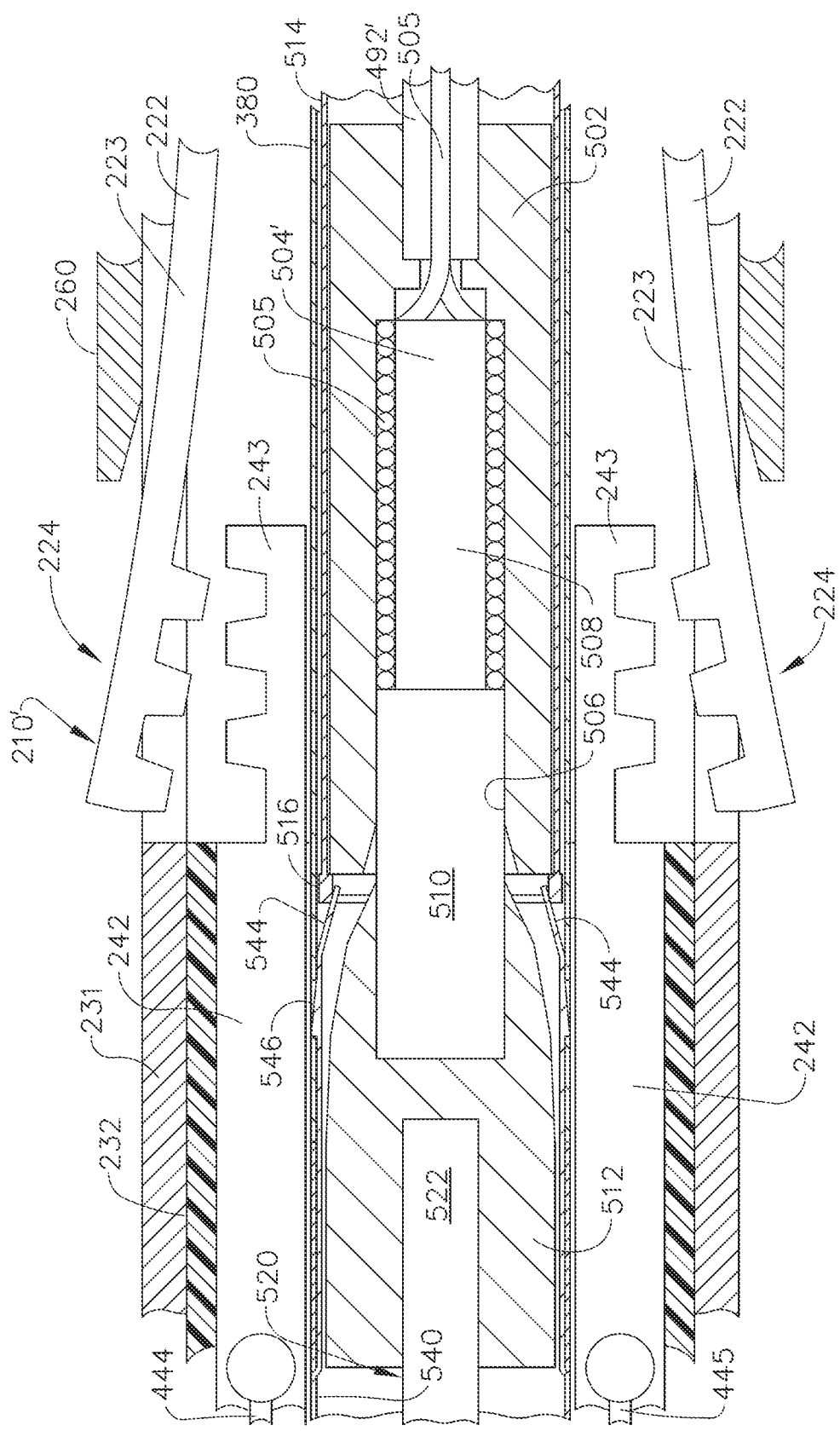
FIG. 22A is a cross-sectional view of a quick disconnect joint embodiment wherein the distal shaft portion has been initially engaged with the proximal shaft portion.
Figure 23A:
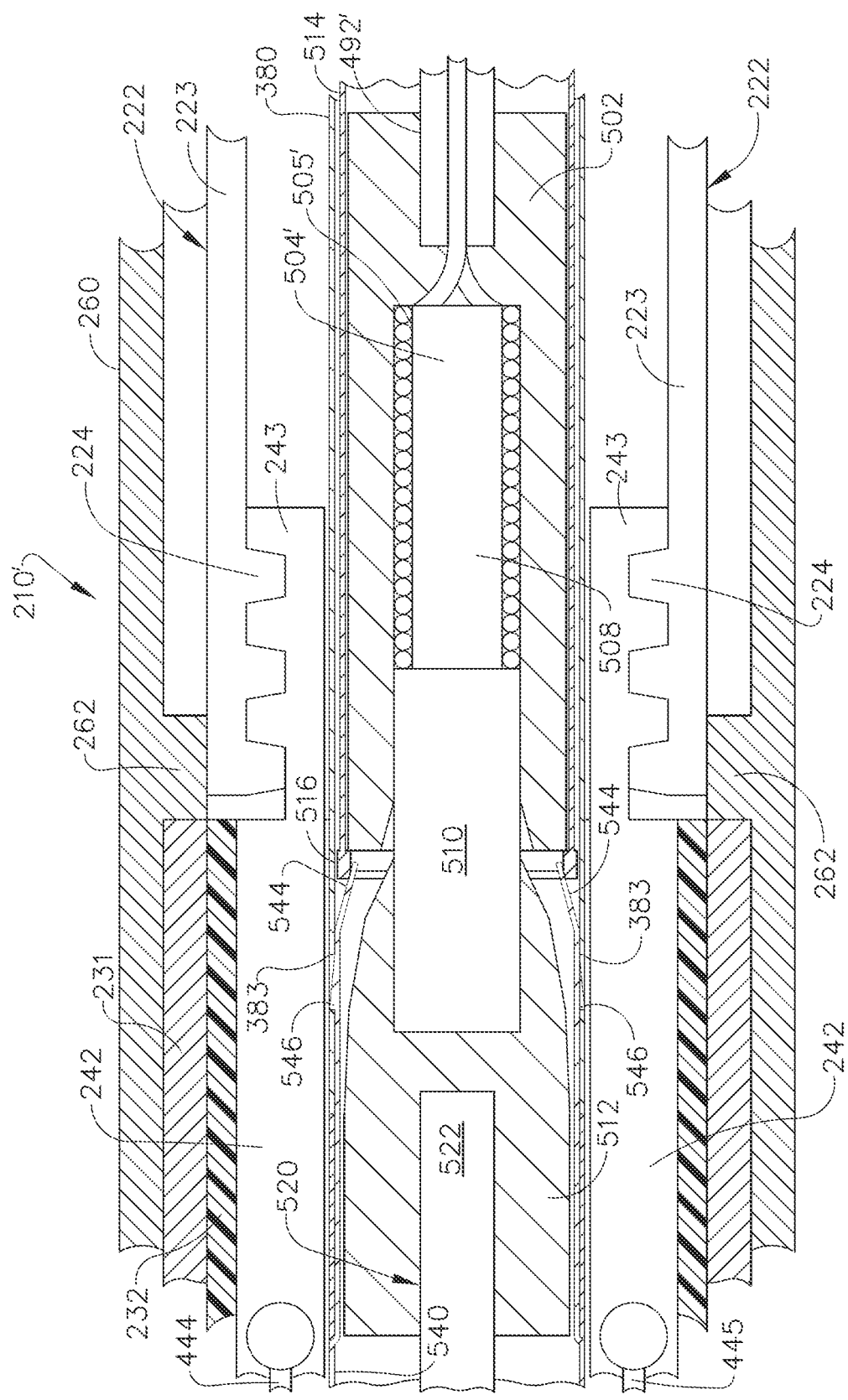
FIG. 23A is another cross-sectional view of the quick disconnect joint embodiment of FIG. 22A wherein the distal shaft portion has been attached to the proximal shaft portion.
Figure 23B:
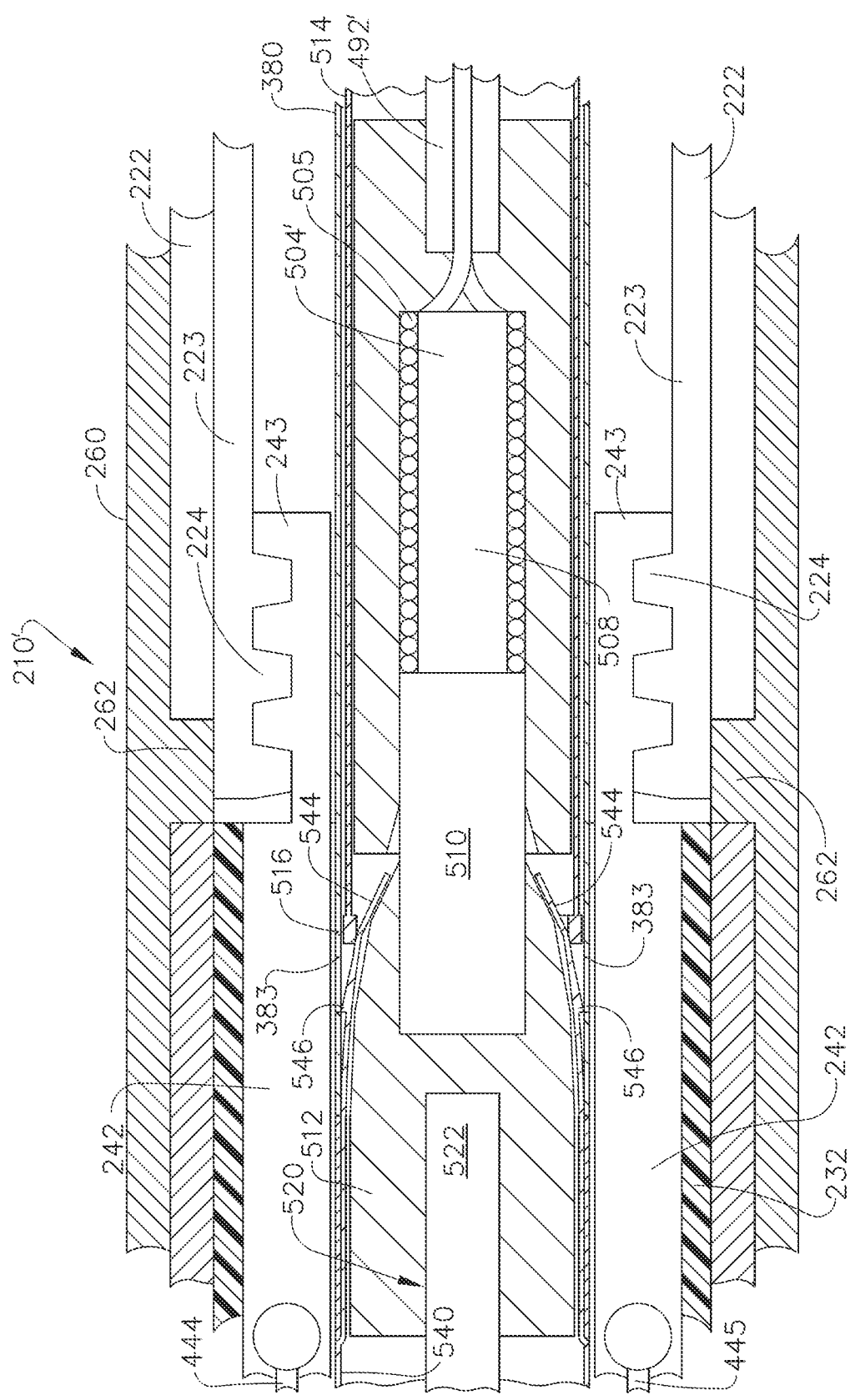
FIG. 23B is another cross-sectional view of the quick disconnect joint embodiment of FIG. 22A wherein the distal shaft portion has been disengaged from the proximal shaft portion.
Figure 24:
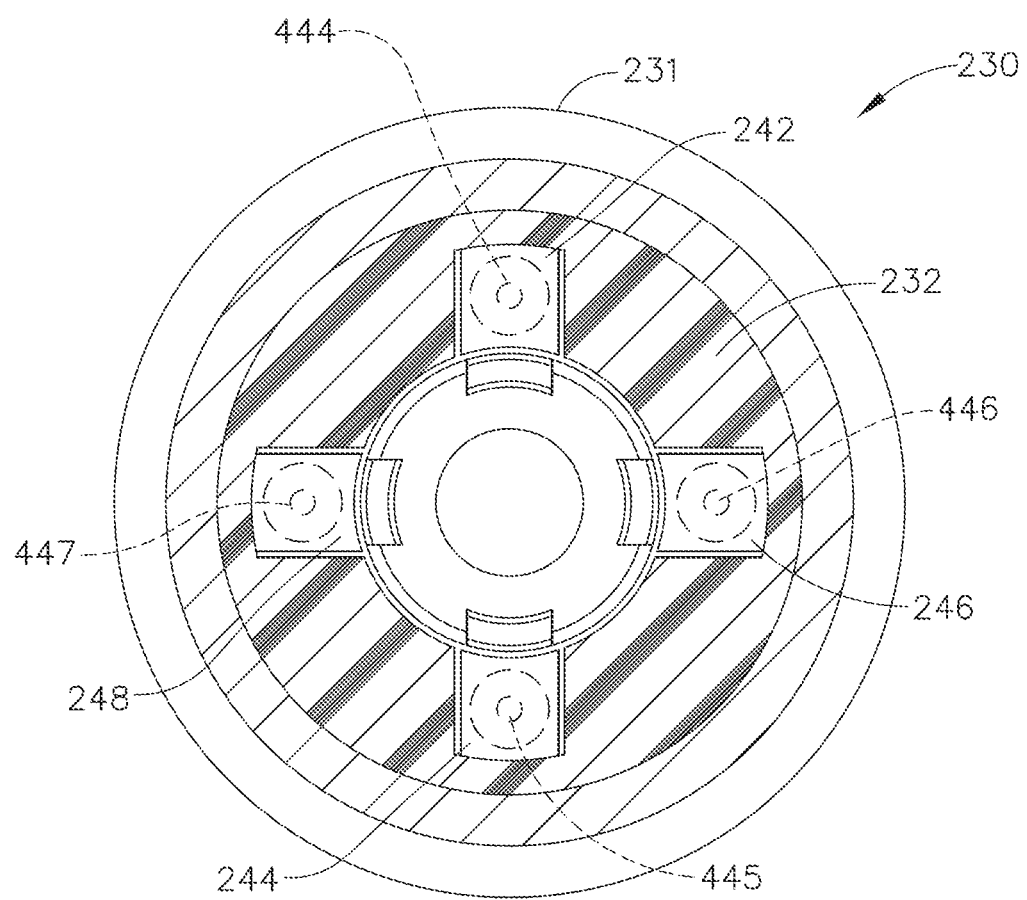
FIG. 24 is a cross-sectional view of the distal shaft portion of FIGS. 19-23 taken along line 24-24 in FIG. 21.

FIGS. 22A, 23A and 23B depict an alternative coupling arrangement or quick disconnect joint assembly 210" that is similar to the quick disconnect joint 210 described above except that an electromagnet 504' is employed to couple the distal drive rod segment 520 to the proximal drive rod segment 492'. As can be seen in these Figures, the proximal drive rod segment 492' is hollow to accommodate conductors 505 that extend from a source of electrical power in the robotic system 10. The conductors 505 are wound around a piece of iron 508. When the clinician brings the distal shaft portion 230 into engagement with the proximal shaft portion 201 as shown in FIG. 22A, electrical current may be passed through the conductors 505 in a first direction to cause the magnet 504' to attract the magnet 510 into coupling engagement as shown in FIG. 23A. When the clinician desires to detach the end effector 1000 from the proximal shaft portion 201 of the surgical tool 100, the clinician returns the third and fourth drive systems 430, 450 into their neutral positions. The clinician may then slide the locking collar 260 proximally on the proximal outer tube segment 202 into the starting position shown in FIG. 22A. When in that position, the spring arm portions of the proximal articulation links 222, 226 cause the toothed portions thereof to disengage the toothed portions of the distal articulation links 242, 246. The clinician may then apply an unlocking motion UL to the proximal end 517 of the unlocking tube 514 to move the unlocking tube 514 and the unlocking collar 516 attached thereto in the distal direction "DD". In addition, the electrical current may be passed through the conductors 505 in an opposite direction to cause the electromagnet 504' to repel magnet 510 to assist in separating the shaft segments. As the clinician moves the unlocking tube distally, the unlocking collar 516 biases the cleated fingers 544 out of engagement with their respective holes 383 in the distal end portion 381 of the proximal drive shaft segment 380 and contacts the tapered mounting portion 512 to further separate the shaft segments.

The coupling arrangements or quick detach joint assemblies described above may offer many advantages. For example, such arrangements may employ a single release/engagement motions that cannot be left semi-engaged. Such engagement motions can be employed to simultaneously operably couple several drive train assemblies wherein at least some drive train assemblies provide control motions that differ from the control motions provided by other drive train assemblies. For example, some drive trains may provide rotary control motions and be longitudinally shiftable to provide axial control motions and some may just provide rotary or axial control motions. Other drive train assemblies may provide push/pull motions for operating various end effector systems/components. The unique and novel locking collar arrangement ensures that either the distal drive train assemblies are locked to their respective proximal drive train assemblies or they are unlocked and may be detached therefrom. When locked together, all of the drive train assemblies are radially supported by the locking collar which prevents any uncoupling.

Figure 25:
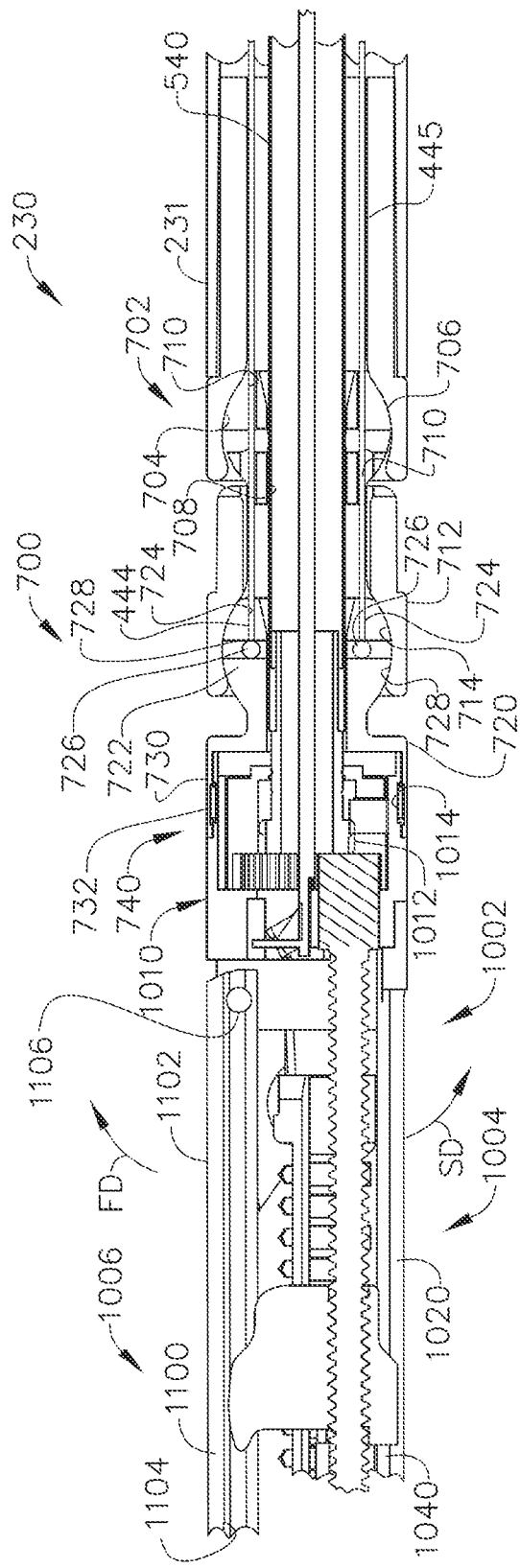
FIG. 25 is a cross-sectional view of a portion of an articulation joint and end effector embodiment.

The surgical tool 100 depicted in FIGS. 5 and 11-16 includes an articulation joint 700 that cooperates with the third and fourth drive systems 430, 450, respectively for articulating the end effector 1000 about the longitudinal tool axis "LT". The articulation joint 700 includes a proximal socket tube 702 that is attached to the distal end 233 of the distal outer tube portion 231 and defines a proximal ball socket 704 therein. See FIG. 25. A proximal ball member 706 is movably seated within the proximal ball socket 704. As can be seen in FIG. 25, the proximal ball member 706 has a central drive passage 708 that enables the distal drive shaft segment 540 to extend therethrough. In addition, the proximal ball member 706 has four articulation passages 710 therein which facilitate the passage of distal cable segments 444, 445, 446, 447 therethrough. As can be further seen in FIG. 25, the articulation joint 700 further includes an intermediate articulation tube segment 712 that has an intermediate ball socket 714 formed therein. The intermediate ball socket 714 is configured to movably support therein an end effector ball 722 formed on an end effector connector tube 720. The distal cable segments 444, 445, 446, 447 extend through cable passages 724 formed in the end effector ball 722 and are attached thereto by lugs 726 received within corresponding passages 728 in the end effector ball 722. Other attachment arrangements may be employed for attaching distal cable segments 444, 445, 446, 447 to the end effector ball 722.

A unique and novel rotary support joint assembly, generally designated as 740, is depicted in FIGS. 26 and 27. The illustrated rotary support joint assembly 740 includes a connector portion 1012 of the end effector drive housing 1010 that is substantially cylindrical in shape. A first annular race 1014 is formed in the perimeter of the cylindrically-shaped connector portion 1012. The rotary support joint assembly 740 further comprises a distal socket portion 730 that is formed in the end effector connector tube 720 as shown in FIGS. 26 and 27. The distal socket portion 730 is sized relative to the cylindrical connector portion 1012 such that the connector portion 1012 can freely rotate within the socket portion 730. A second annular race 732 is formed in an inner wall 731 of the distal socket portion 730. A window 733 is provided through the distal socket 730 that communicates with the second annular race 732 therein. As can also be seen in FIGS. 26 and 27, the rotary support joint assembly 740 further includes a ring-like bearing 734. In various exemplary embodiments, the ring-like bearing 734 comprises a plastic deformable substantially-circular ring that has a cut 735 therein. The cut forms free ends 736, 737 in the ring-like bearing 734. As can be seen in FIG. 26, the ring-like bearing 734 has a substantially annular shape in its natural unbiased state.

To couple a surgical end effector 1000 (e.g., a first portion of a surgical instrument) to the articulation joint 700 (e.g., a second portion of a surgical instrument), the cylindrically shaped connector position 1012 is inserted into the distal socket portion 730 to bring the second annular race 732 into substantial registry with the first annular race 1014. One of the free ends 736, 737 of the ring-like bearing is then inserted into the registered annular races 1014, 732 through the window 733 in the distal socket portion 730 of the end effector connector tube 720. To facilitate easy insertion, the window or opening 733 has a tapered surface 738 formed thereon. See FIG. 26. The ring-like bearing 734 is essentially rotated into place and, because it tends to form a circle or ring, it does not tend to back out through the window 733 once installed. Once the ring-like bearing 734 has been inserted into the registered annular races 1014, 732, the end effector connector tube 720 will be rotatably affixed to the connector portion 1012 of the end effector drive housing 1010. Such arrangement enables the end effector drive housing 1010 to rotate about the longitudinal tool axis LT-LT relative to the end effector connector tube 720. The ring-like bearing 734 becomes the bearing surface that the end effector drive housing 1010 then rotates on. Any side loading tries to deform the ring-like bearing 734 which is supported and contained by the two interlocking races 1014, 732 preventing damage to the ring-like bearing 734. It will be understood that such simple and effective joint assembly employing the ring-like bearing 734 forms a highly lubricious interface between the rotatable portions 1010, 730. If during assembly, one of the free ends 736, 737 is permitted to protrude out through the window 733 (see e.g., FIG. 27), the rotary support joint assembly 740 may be disassembled by withdrawing the ring-like bearing member 732 out through the window 733. The rotary support joint assembly 740 allows for easy assembly and manufacturing while also providing for good end effector support while facilitating rotary manipulation thereof.

The articulation joint 700 facilitates articulation of the end effector 1000 about the longitudinal tool axis LT. For example, when it is desirable to articulate the end effector 1000 in a first direction "FD" as shown in FIG. 5, the robotic system 10 may power the third drive system 430 such that the third drive spindle assembly 436 (FIGS. 11-13) is rotated in a first direction thereby drawing the proximal cable end portion 434A and ultimately distal cable segment 444 in the proximal direction "PD" and releasing the proximal cable end portion 434B and distal cable segment 445 to thereby cause the end effector ball 722 to rotate within the socket 714. Likewise, to articulate the end effector 1000 in a second direction "SD" opposite to the first direction FD, the robotic system 10 may power the third drive system 430 such that the third drive spindle assembly 436 is rotated in a second direction thereby drawing the proximal cable end portion 434B and ultimately distal cable segment 445 in the proximal direction "PD" and releasing the proximal cable end portion 434A and distal cable segment 444 to thereby cause the end effector ball 722 to rotate within the socket 714. When it is desirable to articulate the end effector 1000 in a third direction "TD" as shown in FIG. 5, the robotic system 10 may power the fourth drive system 450 such that the fourth drive spindle assembly 456 is rotated in a third direction thereby drawing the proximal cable end portion 454A and ultimately distal cable segment 446 in the proximal direction "PD" and releasing the proximal cable end portion 454B and distal cable segment 447 to thereby cause the end effector ball 722 to rotate within the socket 714. Likewise, to articulate the end effector 1000 in a fourth direction "FTH" opposite to the third direction TD, the robotic system 10 may power the fourth drive system 450 such that the fourth drive spindle assembly 456 is rotated in a fourth direction thereby drawing the proximal cable end portion 454B and ultimately distal cable segment 447 in the proximal direction "PD" and releasing the proximal cable end portion 454A and distal cable segment 446 to thereby cause the end effector ball 722 to rotate within the socket 714.

The end effector embodiment depicted in FIGS. 5 and 11-16 employs rotary and longitudinal motions that are transmitted from the tool mounting portion 300 through the elongate shaft assembly for actuation. The drive shaft assembly employed to transmit such rotary and longitudinal motions (e.g., torsion, tension and compression motions) to the end effector is relatively flexible to facilitate articulation of the end effector about the articulation joint. FIGS. 28 and 29 illustrate an alternative drive shaft assembly 600 that may be employed in connection with the embodiment illustrated in FIGS. 5 and 11-16 or in other embodiments. In the embodiment depicted in FIG. 5 which employs the quick disconnect joint 210, the proximal drive shaft segment 380 comprises a segment of drive shaft assembly 600 and the distal drive shaft segment 540 similarly comprises another segment of drive shaft assembly 600. The drive shaft assembly 600 includes a drive tube 602 that has a series of annular joint segments 604 cut therein. In that illustrated embodiment, the drive tube 602 comprises a distal portion of the proximal drive shaft segment 380.

The drive tube 602 comprises a hollow metal tube (stainless steel, titanium, etc.) that has a series of annular joint segments 604 formed therein. The annular joint segments 604 comprise a plurality of loosely interlocking dovetail shapes 606 that are, for example, cut into the drive tube 602 by a laser and serve to facilitate flexible movement between the adjoining joint segments 604. See FIG. 29. Such laser cutting of a tube stock creates a flexible hollow drive tube that can be used in compression, tension and torsion. Such arrangement employs a full diametric cut that is interlocked with the adjacent part via a "puzzle piece" configuration. These cuts are then duplicated along the length of the hollow drive tube in an array and are sometimes "clocked" or rotated to change the tension or torsion performance.

Figure 30:
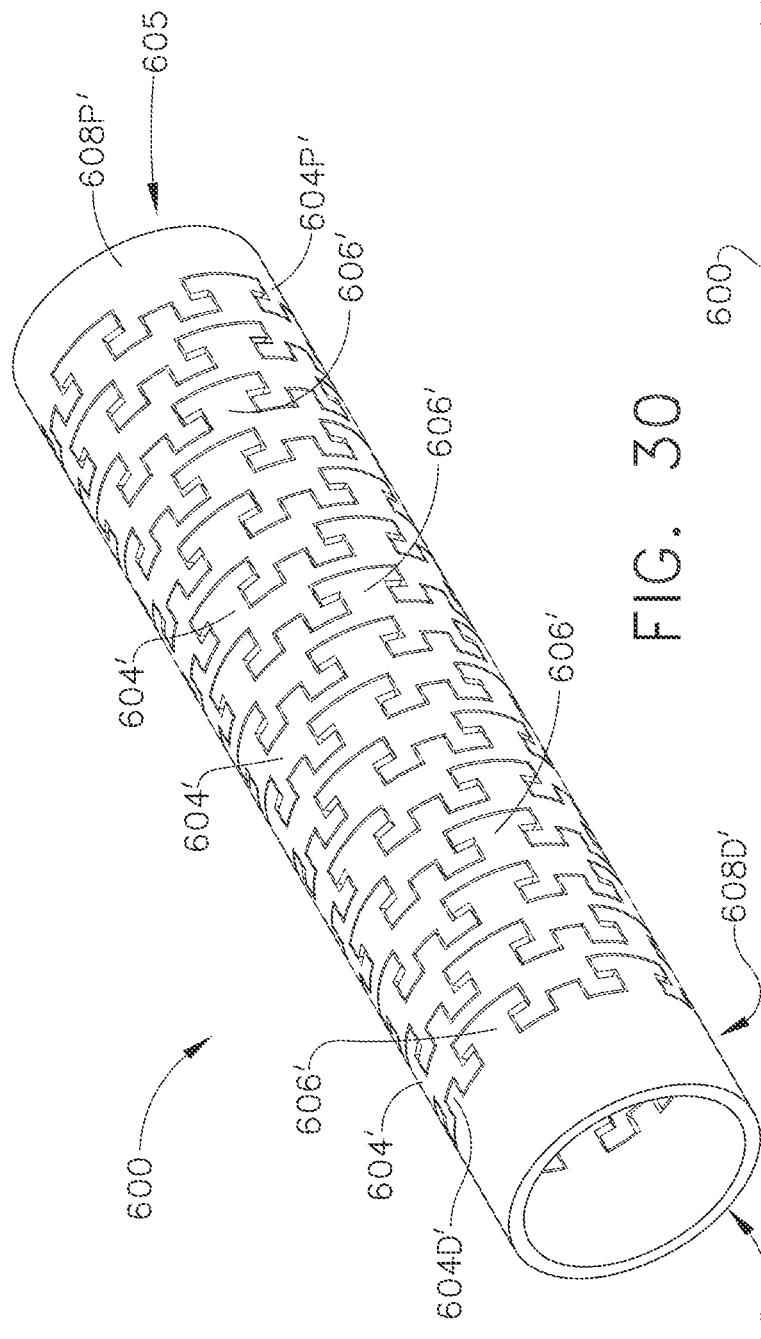
FIG. 30 is a perspective view of a drive shaft assembly embodiment.
Figure 31:
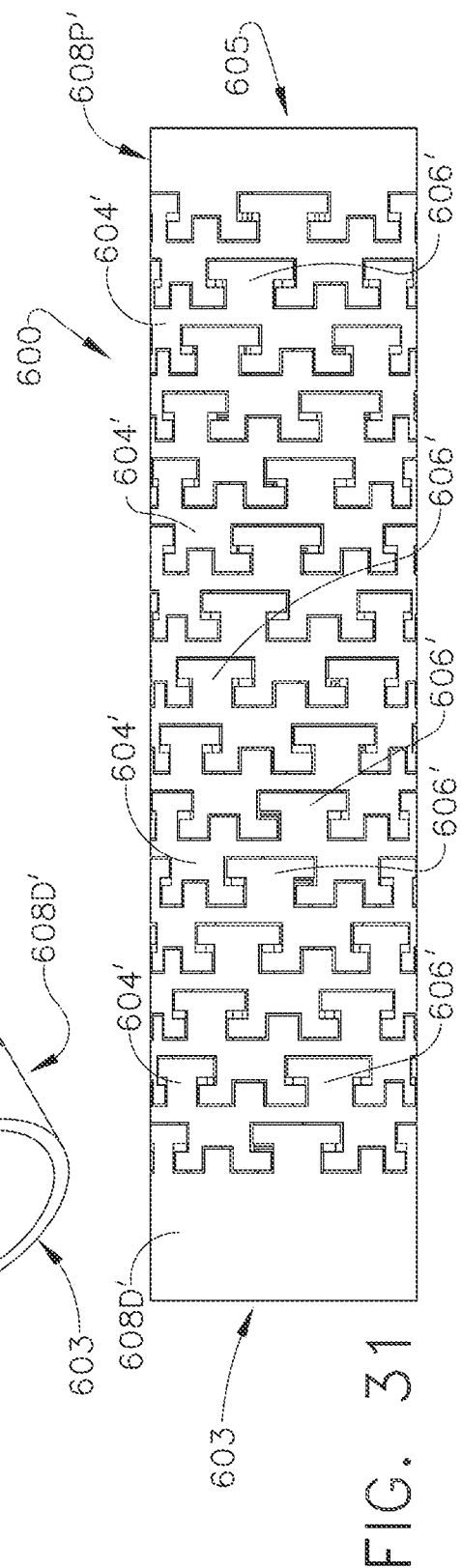
FIG. 31 is a side view of the drive shaft assembly of FIG. 31.

FIGS. 30-34 illustrate alternative exemplary micro-annular joint segments 604' that comprise plurality of laser cut shapes 606' that roughly resemble loosely interlocking, opposed "T" shapes and T-shapes with a notched portion therein. The annular joint segments 604, 604' essentially comprise multiple micro-articulating torsion joints. That is, each joint segment 604, 604' can transmit torque while facilitating relative articulation between each annular joint segment. As shown in FIGS. 30 and 31, the joint segment 604D' on the distal end 603 of the drive tube 602 has a distal mounting collar portion 608D that facilitates attachment to other drive components for actuating the end effector or portions of the quick disconnect joint, etc. and the joint segment 604P' on the proximal end 605 of the drive tube 602 has a proximal mounting collar portion 608P' that facilitates attachment to other proximal drive components or portions of the quick disconnect joint.

Figure 34:
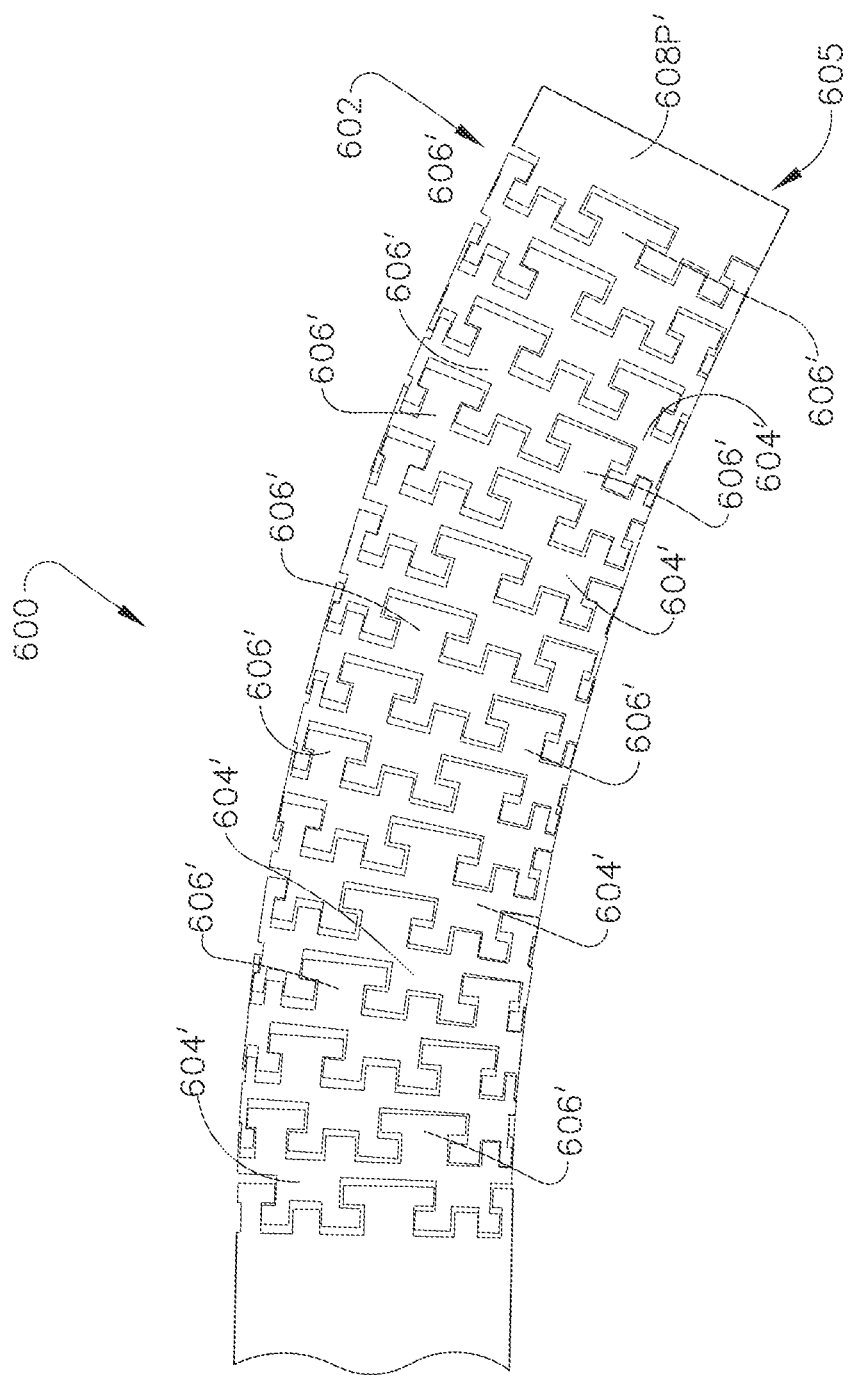
FIG. 34 is another view of the drive shaft assembly of FIGS. 30 and 31 assuming an arcuate or "flexed" configuration.
Figure 34A:
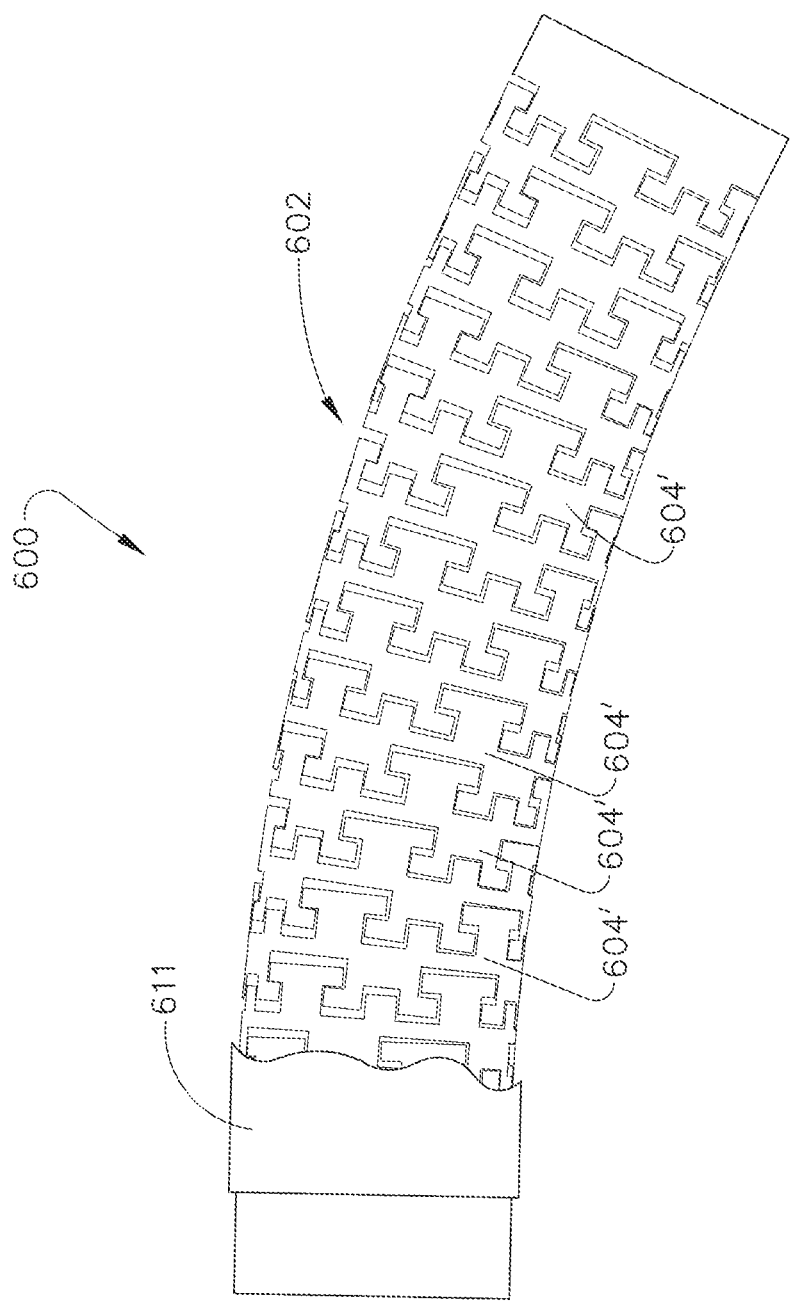
FIG. 34A is a side view of a drive shaft assembly embodiment assuming an arcuate or "flexed" configuration.
Figure 34B:
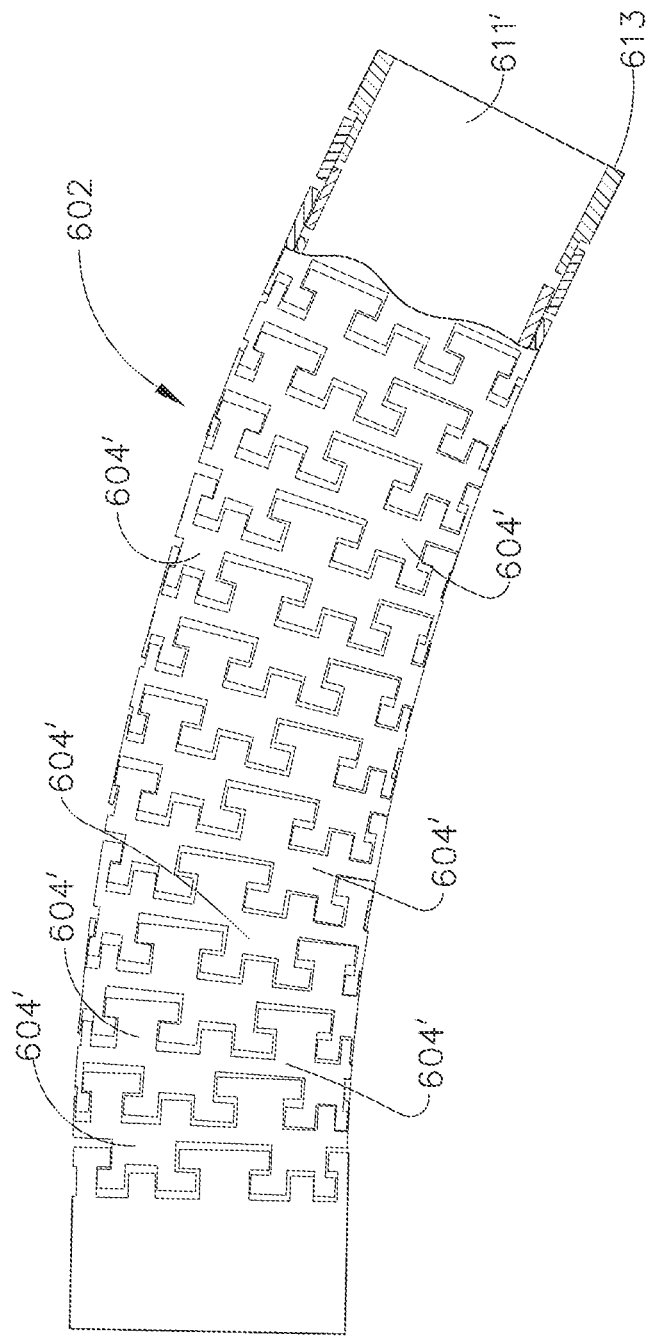
FIG. 34B is a side view of another drive shaft assembly embodiment assuming an arcuate or "flexed" configuration.

The joint-to-joint range of motion for each particular drive shaft assembly 600 can be increased by increasing the spacing in the laser cuts. For example, to ensure that the joint segments 604' remain coupled together without significantly diminishing the drive tube's ability to articulate through desired ranges of motion, a secondary constraining member 610 is employed. In the embodiment depicted in FIGS. 32 and 33, the secondary constraining member 610 comprises a spring 612 or other helically-wound member. In various exemplary embodiments, the distal end 614 of the spring 612 corresponds to the distal mounting collar portion 608D and is wound tighter than the central portion 616 of the spring 612. Similarly, the proximal end 618 of the spring 612 is wound tighter than the central portion 616 of the spring 612. In other embodiments, the constraining member 610 is installed on the drive tube 602 with a desired pitch such that the constraining member also functions, for example, as a flexible drive thread for threadably engaging other threaded control components on the end effector and/or the control system. It will also be appreciated that the constraining member may be installed in such a manner as to have a variable pitch to accomplish the transmission of the desired rotary control motions as the drive shaft assembly is rotated. For example, the variable pitch arrangement of the constraining member may be used to enhance open/close and firing motions which would benefit from differing linear strokes from the same rotation motion. In other embodiments, for example, the drive shaft assembly comprises a variable pitch thread on a hollow flexible drive shaft that can be pushed and pulled around a ninety degree bend. In still other embodiments, the secondary constraining member comprises an elastomeric tube or coating 611 applied around the exterior or perimeter of the drive tube 602 as illustrated in FIG. 34A. In still another embodiment, for example, the elastomeric tube or coating 611' is installed in the hollow passageway 613 formed within the drive tube 602 as shown in FIG. 34B.

Such drive shaft arrangements comprise a composite torsional drive axle which allows superior load transmission while facilitating a desirable axial range of articulation. See, e.g., FIGS. 34 and 34A-B. That is, these composite drive shaft assemblies allow a large range of motion while maintaining the ability to transmit torsion in both directions as well as facilitating the transmission of tension and compression control motions therethrough. In addition, the hollow nature of such drive shaft arrangements facilitate passage of other control components therethrough while affording improved tension loading. For example, some other embodiments include a flexible internal cable that extends through the drive shaft assembly which can assist in the alignment of the joint segments while facilitating the ability to apply tension motions through the drive shaft assembly. Moreover, such drive shaft arrangements are relatively easily to manufacture and assemble.

FIGS. 35-38 depict a segment 620 of a drive shaft assembly 600'. This embodiment includes joint segments 622, 624 that are laser cut out of tube stock material (e.g., stainless steel, titanium, polymer, etc.). The joint segments 622, 624 remain loosely attached together because the cuts 626 are radial and are somewhat tapered. For example, each of the lug portions 628 has a tapered outer perimeter portion 629 that is received within a socket 630 that has a tapered inner wall portion. See, e.g., FIGS. 36 and 38. Thus, there is no assembly required to attach the joint segments 622, 624 together. As can be seen in the Figures, joint segment 622 has opposing pivot lug portions 628 cut on each end thereof that are pivotally received in corresponding sockets 630 formed in adjacent joint segments 624.

FIGS. 35-38 illustrate a small segment of the drive shaft assembly 600'. Those of ordinary skill in the art will appreciate that the lugs/sockets may be cut throughout the entire length of the drive shaft assembly. That is, the joint segments 624 may have opposing sockets 630 cut therein to facilitate linkage with adjoining joint segments 622 to complete the length of the drive shaft assembly 600'. In addition, the joint segments 624 have an angled end portion 632 cut therein to facilitate articulation of the joint segments 624 relative to the joint segments 622 as illustrated in FIGS. 37 and 38. In the illustrated embodiment, each lug 628 has an articulation stop portion 634 that is adapted to contact a corresponding articulation stop 636 formed in the joint segment 622. See FIGS. 37 and 38. Other embodiments, which may otherwise be identical to the segment 620, are not provided with the articulation stop portions 634 and stops 636.

As indicated above, the joint-to-joint range of motion for each particular drive shaft assembly can be increased by increasing the spacing in the laser cuts. In such embodiments, to ensure that the joint segments 622, 624 remain coupled together without significantly diminishing the drive tube's ability to articulate through desired ranges of motion, a secondary constraining member in the form of an elastomeric sleeve or coating 640 is employed. Other embodiments employ other forms of constraining members disclosed herein and their equivalent structures. As can be seen in FIG. 35, the joint segments 622, 624 are capable of pivoting about pivot axes "PA-PA" defined by the pivot lugs 628 and corresponding sockets 630. To obtain an expanded range of articulation, the drive shaft assembly 600' may be rotated about the tool axis TL-TL while pivoting about the pivot axes PA-PA.

FIGS. 39-44 depict a segment 640 of another drive shaft assembly 600". The drive shaft assembly 600" comprises a multi-segment drive system that includes a plurality of interconnected joint segments 642 that form a flexible hollow drive tube 602". A joint segment 642 includes a ball connector portion 644 and a socket portion 648. Each joint segment 642 may be fabricated by, for example, metal injection molding "MIM" and be fabricated from 17-4, 17-7, 420 stainless steel. Other embodiments may be machined from 300 or 400 series stainless steel, 6065 Or 7071 aluminum or titanium. Still other embodiments could be molded out of plastic infilled or unfilled Nylon, Ultem, ABS, Polycarbonate or Polyethylene, for example. As can be seen in the Figures, the ball connector 644 is hexagonal in shape. That is, the ball connector 644 has six arcuate surfaces 646 formed thereon and is adapted to be rotatably received in like-shaped sockets 650. Each socket 650 has a hexagonally-shaped outer portion 652 formed from six flat surfaces 654 and a radially-shaped inner portion 656. See FIG. 42. Each joint segment 642 is identical in construction, except that the socket portions of the last joint segments forming the distal and proximal ends of the drive shaft assembly 600 may be configured to operably mate with corresponding control components. Each ball connector 644 has a hollow passage 645 therein that cooperate to form a hollow passageway 603 through the hollow flexible drive tube 602".

Figure 46:
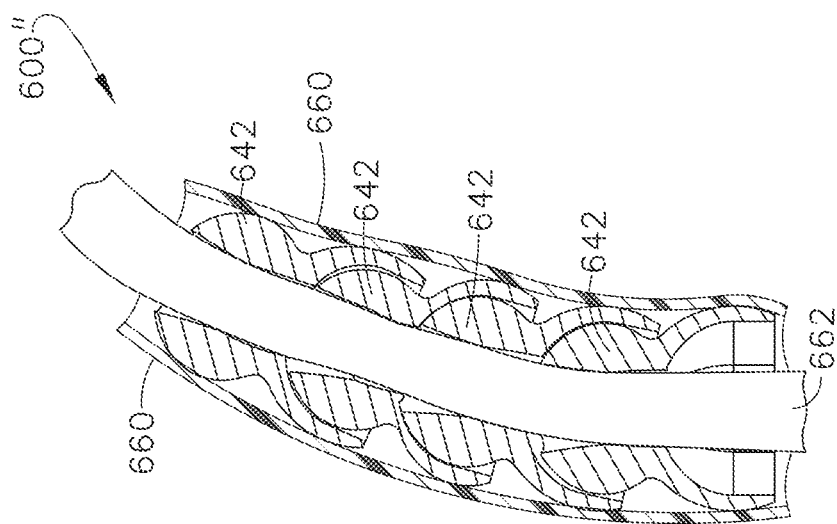
FIG. 46 is another cross-sectional view of the drive shaft assembly of FIG. 45.
Figure 45:
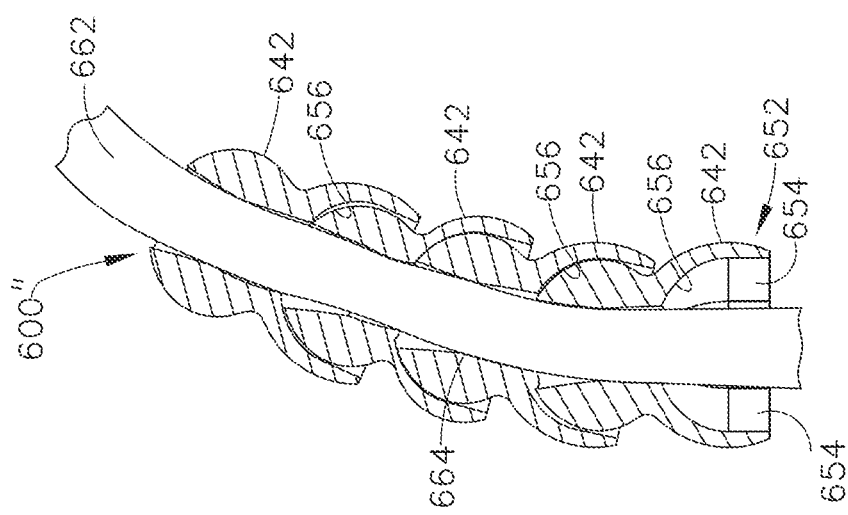
FIG. 45 is another cross-sectional view of a portion of another drive shaft assembly embodiment.

As can be seen in FIGS. 43 and 44, the interconnected joint segments 642 are contained within a constraining member 660 which comprises a tube or sleeve fabricated from a flexible polymer material, for example. FIG. 45 illustrates a flexible inner core member 662 extending through the interconnected joint segments 642. The inner core member 662 comprises a solid member fabricated from a polymer material or a hollow tube or sleeve fabricated from a flexible polymer material. FIG. 46 illustrates another embodiment wherein a constraining member 660 and an inner core member 662 are both employed.

Drive shaft assembly 600" facilitates transmission of rotational and translational motion through a variable radius articulation joint. The hollow nature of the drive shaft assembly 600" provides room for additional control components or a tensile element (e.g., a flexible cable) to facilitate tensile and compressive load transmission. In other embodiments, however, the joint segments 624 do not afford a hollow passage through the drive shaft assembly. In such embodiments, for example, the ball connector portion is solid. Rotary motion is translated via the edges of the hexagonal surfaces. Tighter tolerances may allow greater load capacity. Using a cable or other tensile element through the centerline of the drive shaft assembly 600", the entire drive shaft assembly 600" can be rotated bent, pushed and pulled without limiting range of motion. For example, the drive shaft assembly 600" may form an arcuate drive path, a straight drive path, a serpentine drive path, etc.

FIGS. 5 and 47-54 illustrate one surgical end effector 1000 that may be effectively employed with the robotic system 10. The end effector 1000 comprises an endocutter 1002 that has a first jaw 1004 and a second jaw 1006 that is selectively movable relative to the first jaw 1004. In the embodiment illustrated in FIGS. 5 and 47-54, the first jaw 1004 comprises a support member 1019 in the form of an elongate channel 1020 that is configured to operably support a staple cartridge 1030 therein. The second jaw 1006 comprises an anvil assembly 1100. As can be seen in FIGS. 47, 49, 53 and 55, the anvil assembly 1100 comprises an anvil body 1102 that has a staple forming surface 1104 thereon. The anvil body 1102 has a passage 1106 that is adapted to register with mounting holes 1022 in the elongate channel 1020. A pivot or trunnion pin (not shown) is inserted through the holes 1022 and passage 1104 to pivotally couple the anvil 1100 to the elongate channel 1020. Such arrangement permits the anvil assembly 1100 to be selectively pivoted about a closure axis "CA-CA" that is substantially transverse to the longitudinal tool axis "LT-LT" (FIG. 48) between an open position wherein the staple forming surface 1104 is spaced away from the cartridge deck 1044 of the staple cartridge 1040 (FIGS. 47-50) and closed positions (FIGS. 51-54) wherein the staple forming surface 1104 on the anvil body 1102 is in confronting relationship relative to the cartridge deck 1042.

The embodiment of FIGS. 5 and 47-54 employs a closure assembly 1110 that is configured to receive opening and closing motions from the fifth drive system 470. The fifth drive system 470 serves to axially advance and retract a drive rod assembly 490. As described above, the drive rod assembly 490 includes a proximal drive rod segment 492 that operably interfaces with the drive solenoid 474 to receive axial control motions therefrom. The proximal drive rod segment 492 is coupled to a distal drive rod segment 520 through the drive rod coupler 502. The distal drive rod segment 520 is somewhat flexible to facilitate articulation of the end effector 1000 about articulation joint 700 yet facilitate the axial transmission of closing and opening motions therethrough. For example, the distal drive rod segment 520 may comprise a cable or laminate structure of titanium, stainless spring steel or Nitinol.

Figure 51:
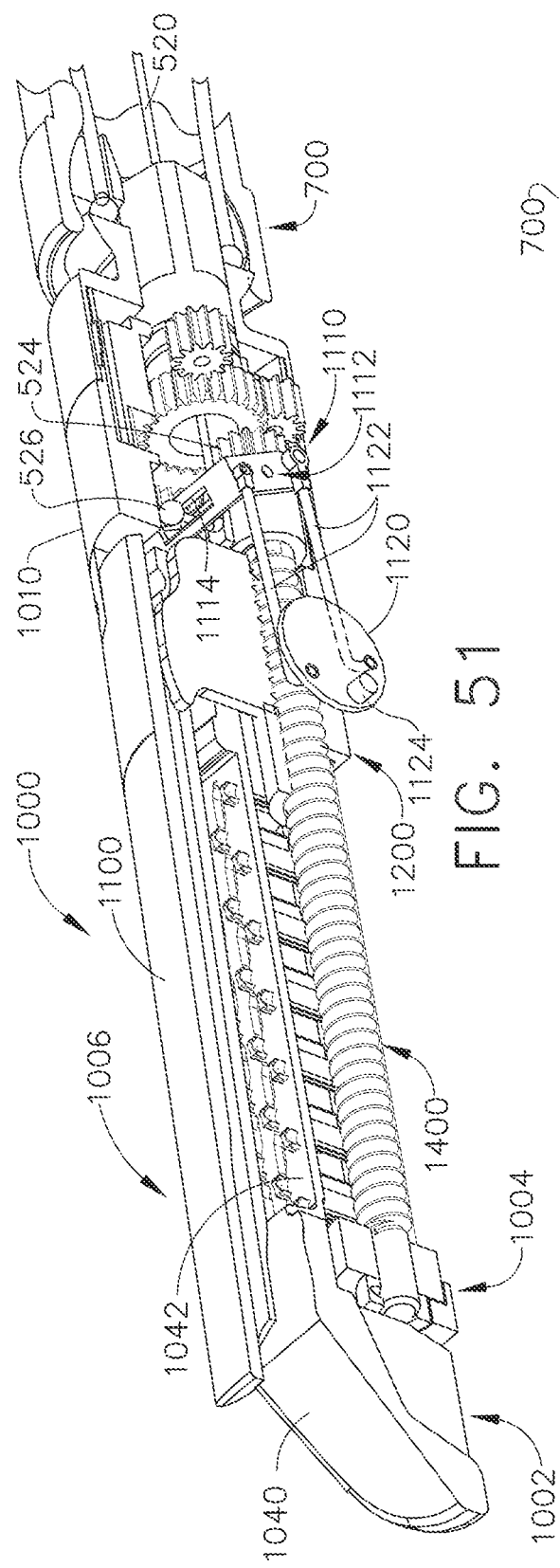
FIG. 51 is a partial cross-sectional perspective view of the end effector embodiment of FIGS. 47-50 with the anvil thereof in a closed position.
Figure 52:
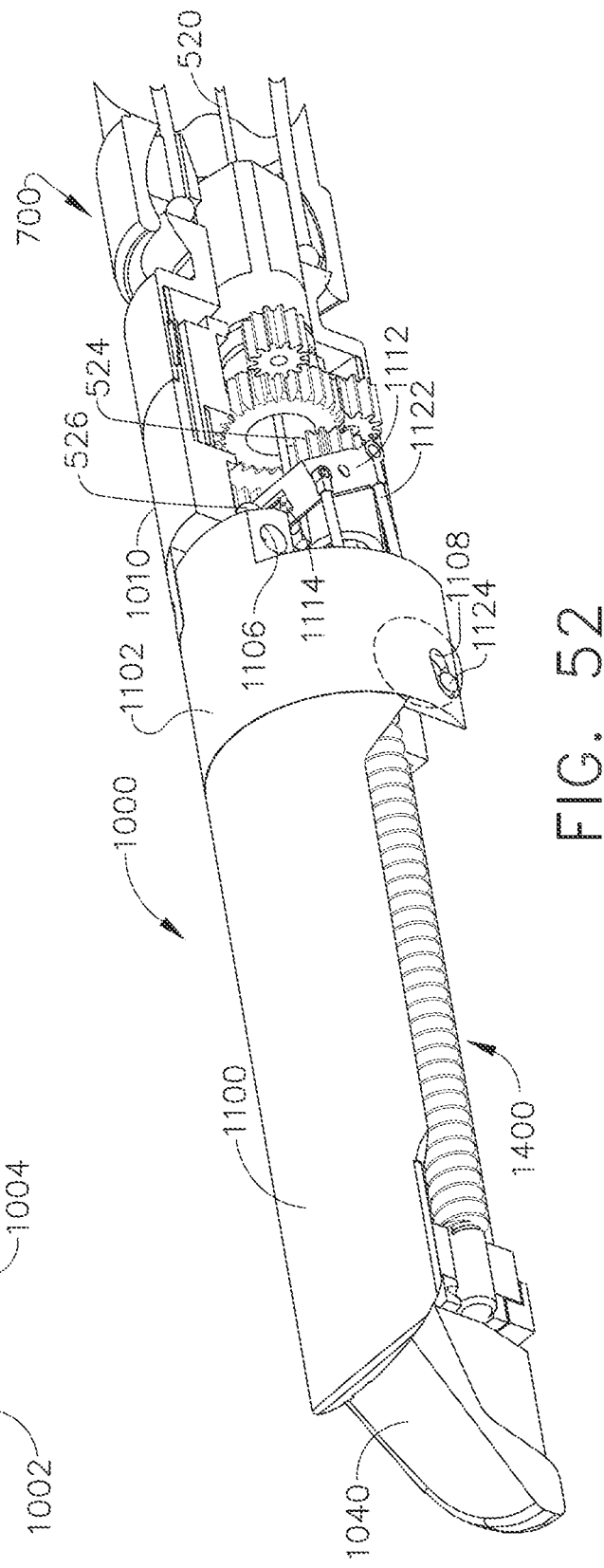
FIG. 52 is another partial cross-sectional perspective view of the end effector embodiment of FIG. 51.
Figure 53:
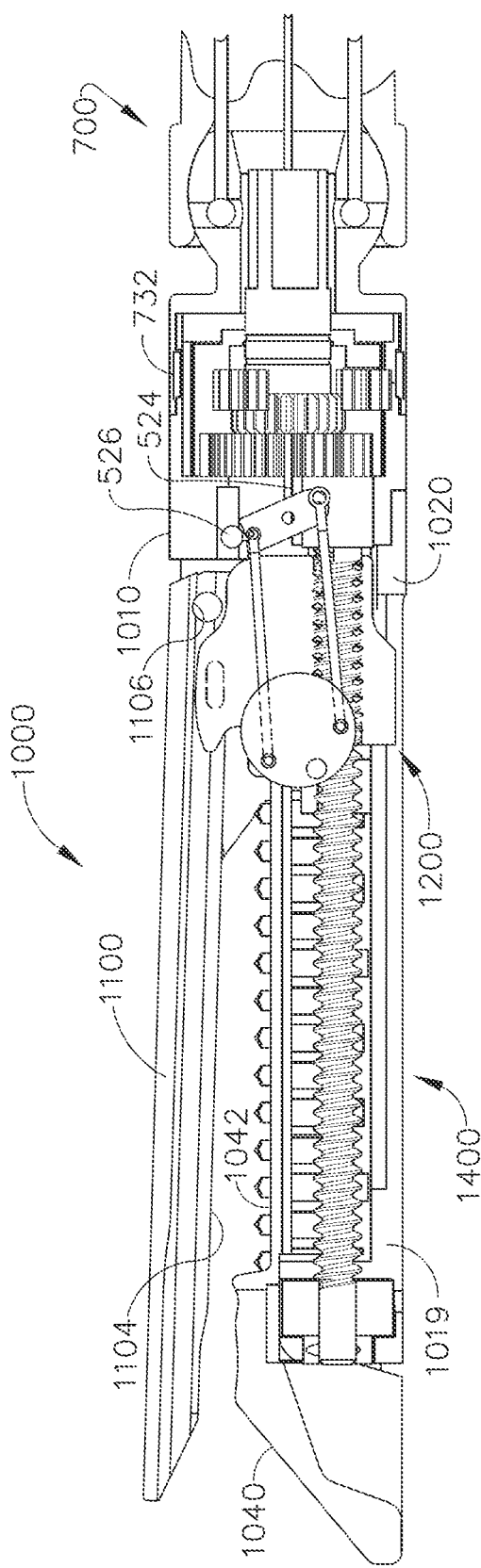
FIG. 53 is a side cross-sectional view of the end effector embodiment of FIGS. 51 and 52 with the anvil thereof in a partially closed position.
Figure 54:
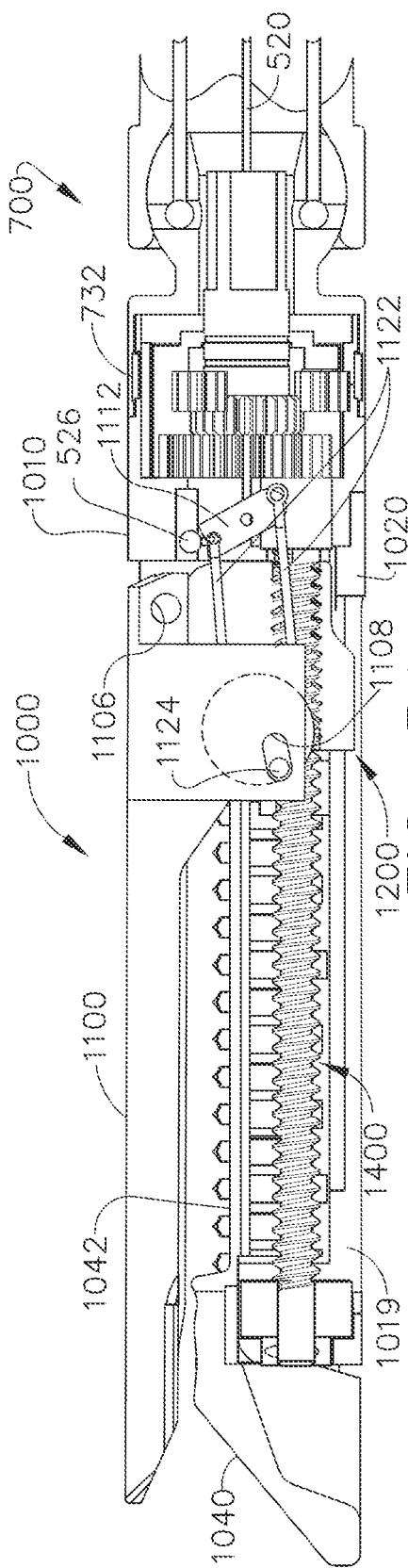
FIG. 54 is another side cross-sectional view of the end effector embodiment of FIGS. 51-53 with the anvil in a closed position.
Figure 55:
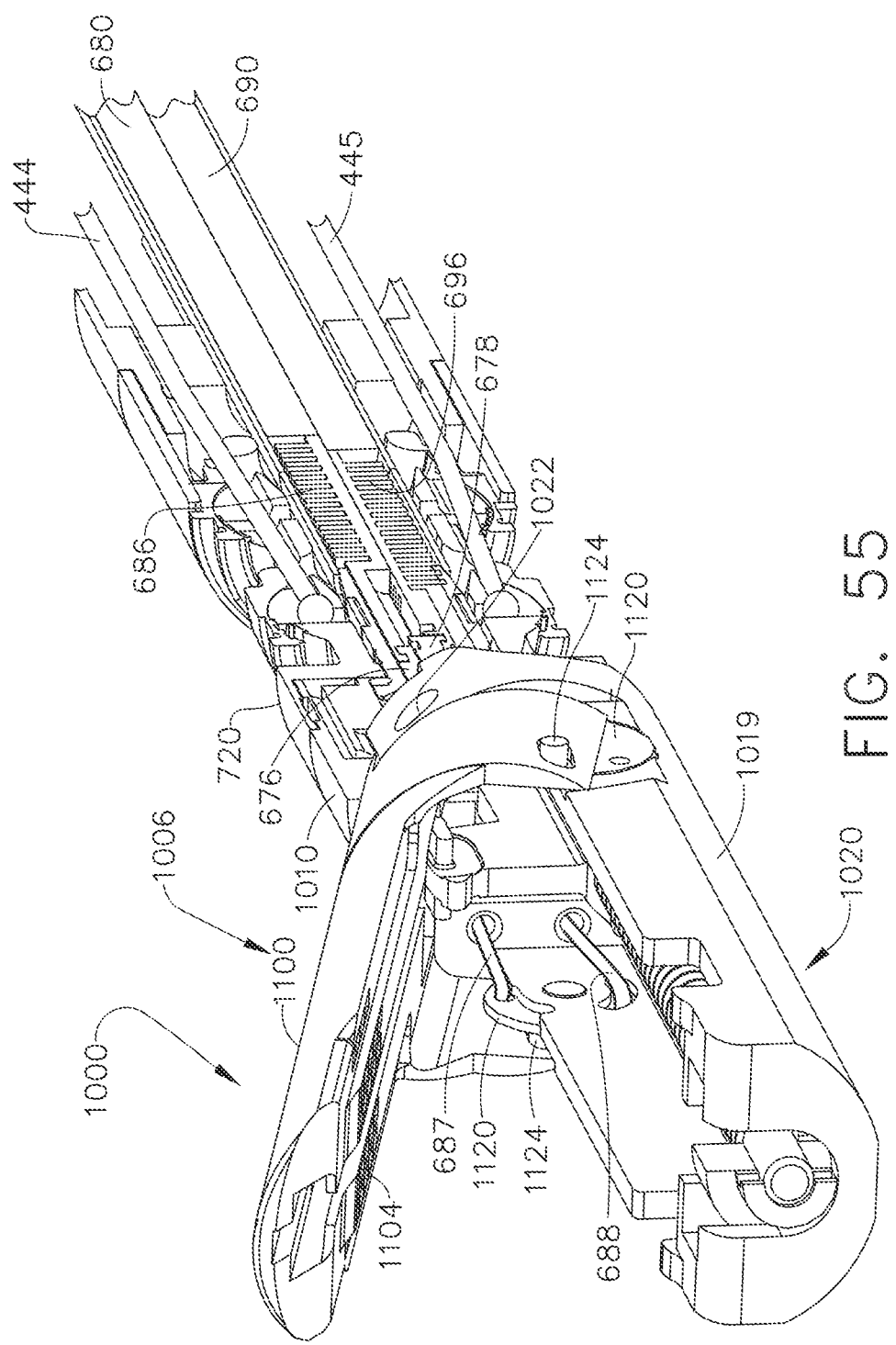
FIG. 55 is a cross-sectional perspective view of another end effector embodiment and portion of another elongate shaft assembly embodiment.

The closure assembly 1110 includes a closure linkage 1112 that is pivotally attached to the elongate channel 1020. As can be seen in FIGS. 48, 51 and 52, the closure linkage 1112 has an opening 1114 therein through which the distal end 524 of the distal drive rod segment 520 extends. A ball 526 or other formation is attached to the distal drive rod segment 520 to thereby attach the distal end 524 of the distal drive rod segment 520 to the closure linkage 1112. The closure assembly 1110 further includes a pair of cam discs 1120 that are rotatably mounted on the lateral sides of the elongate channel 1020. One cam disc 1120 is rotatably supported on one lateral side of the elongate channel 1020 and the other cam disc 1120 is rotatably supported to the other lateral side of the elongate channel 1020. See FIG. 60. A pair of pivot links 1122 are attached between each cam disc 1120 and the closure linkage 1112. Thus, pivotal travel of the closure linkage 1112 by the drive rod assembly 490 will result in the rotation of the cam discs 1120. Each cam disc 1120 further has an actuator pin 1124 protruding therefrom that is slidably received in a corresponding cam slot 1108 in the anvil body 1102.

Actuation of the second jaw 1006 or anvil assembly 1100 will now be described. FIGS. 47-50 illustrate the anvil assembly 1100 in the open position. After the end effector 1000 has been positioned relative to the tissue to be cut and stapled, the robotic controller 12 may activate the drive solenoid 474 in the first or distal direction "DD" which ultimately results in the distal movement of the drive yoke 472 which causes the drive rod assembly 490 to move in the distal direction "DD". Such movement of the drive rod assembly 490 results in the distal movement of the distal drive rod segment 520 which causes the closure linkage 1112 to pivot from the open position to the closed position (FIGS. 51-54). Such movement of the closure linkage 1112 causes the cam discs 1120 to rotate in the "CCW" direction. As the cam discs rotate in the "CCW" direction, interaction between the actuator pins 1124 and their respective cam slot 1108 causes the anvil assembly 1100 to pivot closed onto the target tissue. To release the target tissue, the drive solenoid 474 is activated to pull the drive rod assembly 490 in the proximal direction "PD" which results in the reverse pivotal travel of the closure linkage 1112 to the open position which ultimately causes the anvil assembly 1100 to pivot back to the open position.

Figure 56:
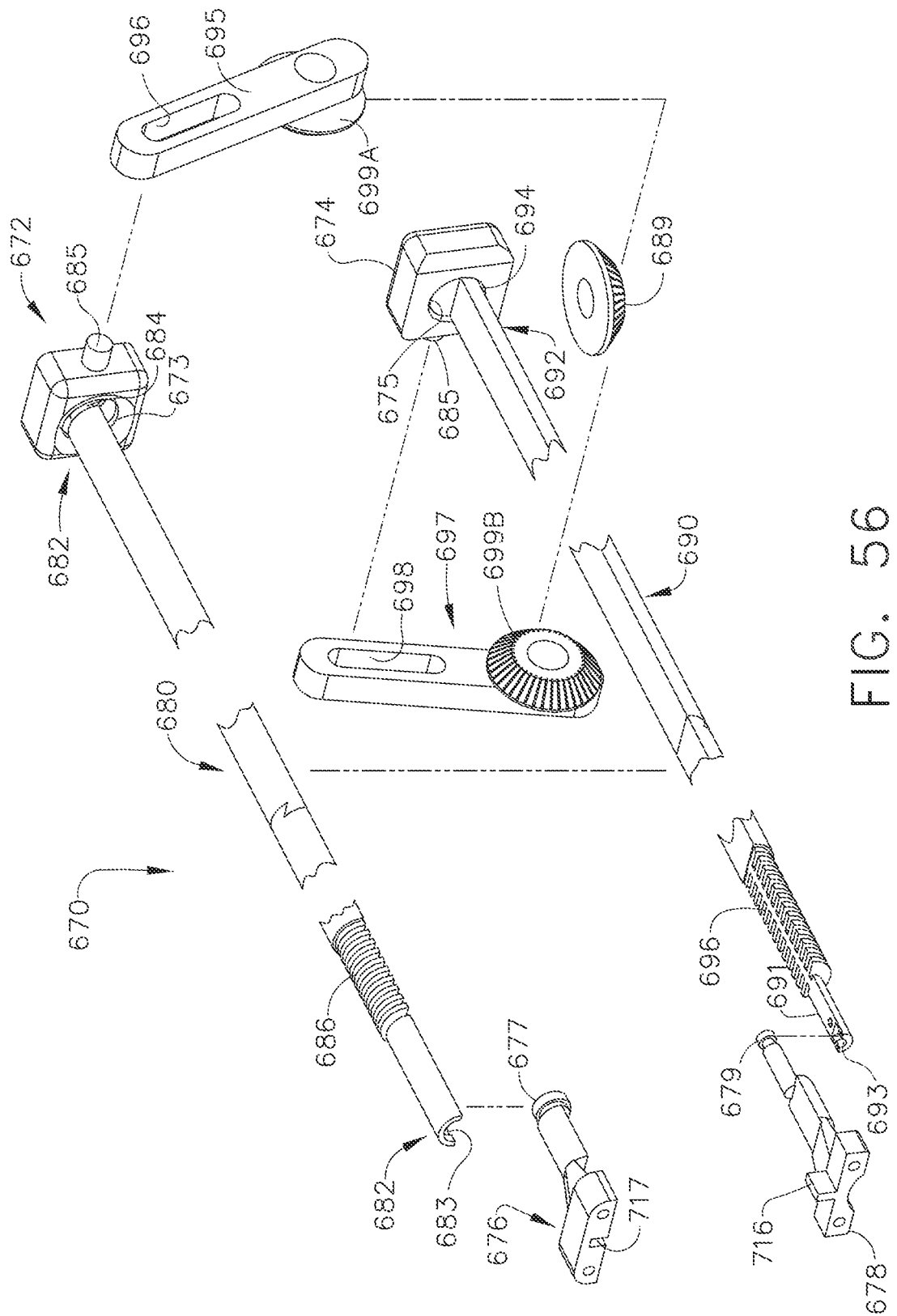
FIG. 56 is an exploded perspective view of a closure system embodiment.
Figure 57:
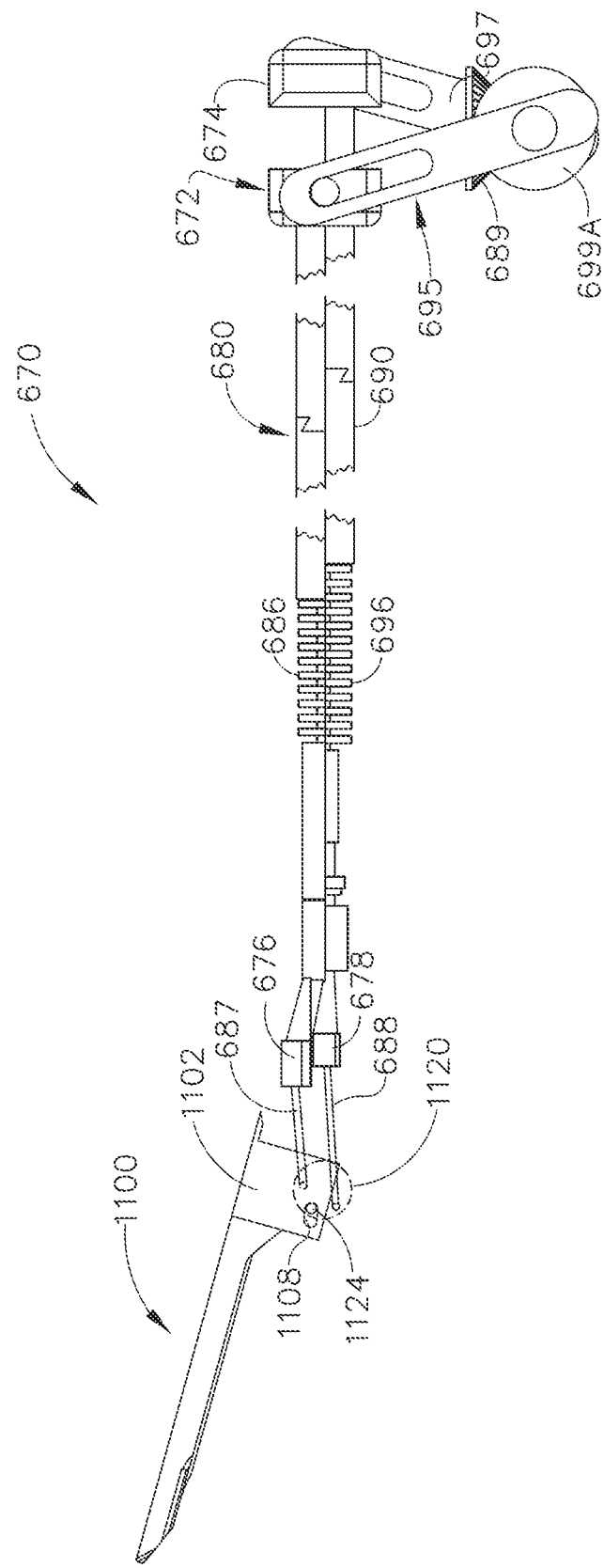
FIG. 57 is a side view of the closure system embodiment of FIG. 56 with the anvil in an open position.
Figure 59A:
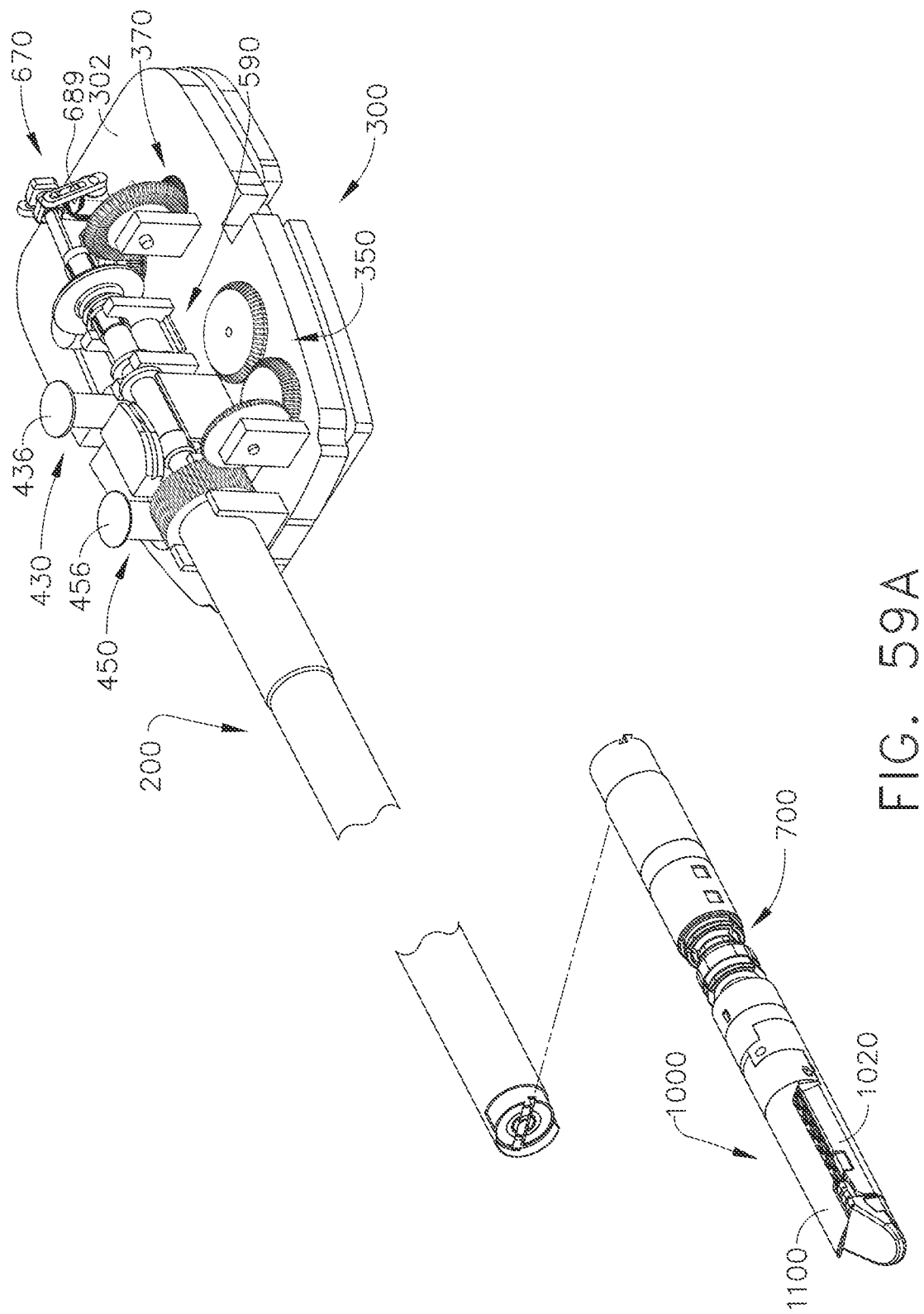
FIG. 59A is a front perspective view of a portion of another surgical tool embodiment that employs the closure system embodiment of FIGS. 56-59 with the actuation solenoid omitted for clarity.

FIGS. 55-59 illustrate another closure system 670 for applying opening and closing motions to the anvil 1100. As can be seen in FIG. 56, for example, the closure system 670 includes a first mounting block or member 672 that rotatably supports a first closure rod segment 680. The first closure rod segment 680 has a substantially semi-circular, cross-sectional shape. A proximal end 682 of the first closure rod segment 680 has a first ball connector 684 thereon that is rotatably supported within a first mounting socket 673 formed in the mounting block 672. To facilitate articulation of the end effector 1000 by the articulation joint 700, the first closure rod segment 680 also has a first serrated portion 686 that coincides with the articulation joint 700 as illustrated in FIGS. 58 and 59. The closure system 670 further includes a second mounting block or member 674 that rotatably supports a second closure rod segment 690. The second closure rod segment 690 has a substantially semi-circular, cross-sectional shape. A proximal end 692 of the second closure rod segment 690 has a second ball connector 694 thereon that is rotatably supported within a second mounting socket 675 formed in the second mounting block 674. To facilitate articulation of the end effector 1000 by the articulation joint 700, the second closure rod segment 690 also has a second serrated portion 696 that coincides with the articulation joint 700 as illustrated in FIGS. 58 and 59.

As can also be seen in FIG. 56, the closure system 670 further has a first pivot link 676 that is attached to a distal end 682 of the first closure rod segment 680. The first pivot link 676 has a first pivot lug 677 formed thereon that is configured to be rotatably supported within a first socket 683 formed in the distal end 682 of the first closure rod segment 680. Such arrangement permits the first pivot link 676 to rotate relative to the first closure rod segment 680. Likewise, a second pivot link 678 is attached to a distal end 691 of the second closure rod segment 690 such that it can rotate relative thereto. The second pivot link 678 has a second pivot lug 1679 formed thereon that is configured to extend through an opening in the first pivot lug 677 to be rotatably supported within a second socket 692 in a distal end 1691 of the second closure rod segment 690. In addition, as can be seen in FIG. 56, the first and second pivot links 676, 678 are movably keyed to each other by a key 716 on the second pivot link 678 that is slidably received within a slot 717 in the first pivot link 676. In at least one embodiment, the first pivot link 676 is attached to each of the cam discs 1120 by first linkage arms 687 and the second pivot link 678 is attached to each of the cam discs 1120 by second linkage arms 688.

In the illustrated embodiment, the closure system 670 is actuated by the drive solenoid 474. The drive solenoid 474 is configured to operably interface with one of the first and second mounting blocks 672, 674 to apply axial closing and opening motions thereto. As can be seen in FIGS. 56-59, such drive arrangement may further comprise a first pivot link and gear assembly 695 that is movably attached to the first mounting block 672 by a pin 685 that extends into a slot 696 in the first pivot link and gear assembly 695. Similarly, a second pivot link and gear assembly 697 is movably attached to the second mounting block 674 by a pin 685 that extends into a slot 698 in the second pivot link and gear assembly 697. The first pivot link and gear assembly 695 has a first bevel gear 699A rotatably mounted thereto and the second pivot link and gear assembly 697 has a second bevel gear 699B rotatably attached thereto. Both first and second bevel gears 699A, 699B are mounted in meshing engagement with an idler gear 689 rotatably mounted on the tool mounting plate 304. See FIG. 59A. Thus, when the first mounting block 672 is advanced in the distal direction "DD" which also results in the movement of the first closure rod segment 680 and first pivot link 676 in the distal direction DD, the bevel gears 689, 699A, 699B will result in the movement of the second closure rod 690 and second pivot link 678 in the proximal direction "PD". Likewise, when the first mounting block 672 is advanced in the proximal direction "PD" which also results in the movement of the first closure rod segment 680 and first pivot link 676 in the proximal direction PD, the bevel gears 689, 699A, 699B will result in the movement of the second closure rod 690 and second pivot link 678 in the distal direction "DD".

FIG. 58 illustrates the anvil 1100 in the open position. As can be seen in that Figure, the first closure rod 680 is slightly proximal to the second closure rod 690. To close the anvil, the drive solenoid 474 is powered to axially advance the first closure rod 680 in the distal direction "DD". Such action causes the first pivot link 676 and first linkage arms 687 to rotate the cam discs 1120 in the counter-clockwise "CCW" direction as shown in FIG. 59. Such motion also results in the movement of the second closure rod 690 is the proximal direction causing the second pivot link 678 and second linkage arms 688 to also pull the cam discs 1120 in the counter-clockwise "CCW" direction. To open the anvil, the drive solenoid 474 applies an axial control motion to the first mounting block 672 to return the first and second control rod segments 680, 690 to the positions shown in FIG. 58.

Figure 60:
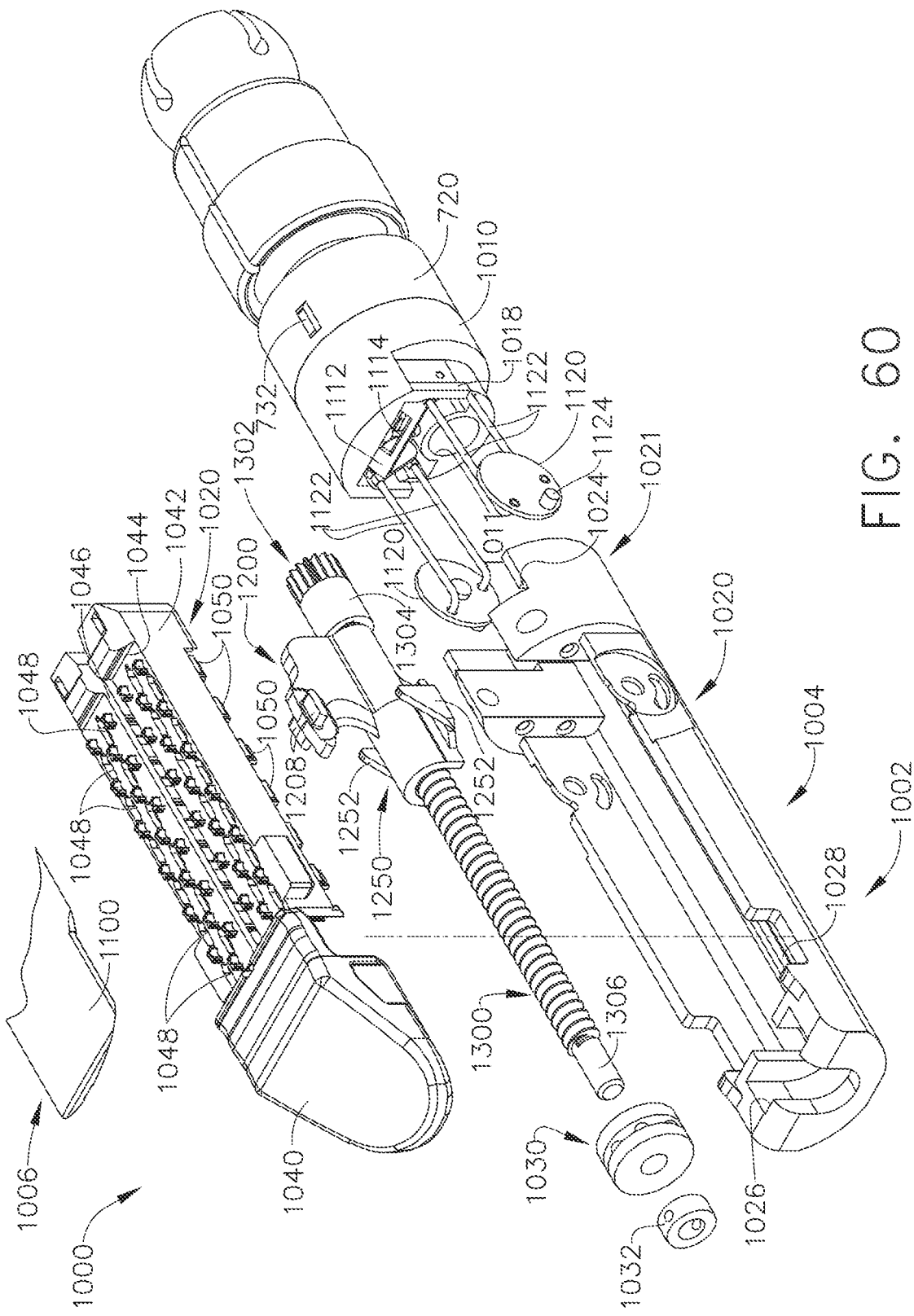
FIG. 60 is an exploded assembly view of another end effector embodiment.
Figure 61:
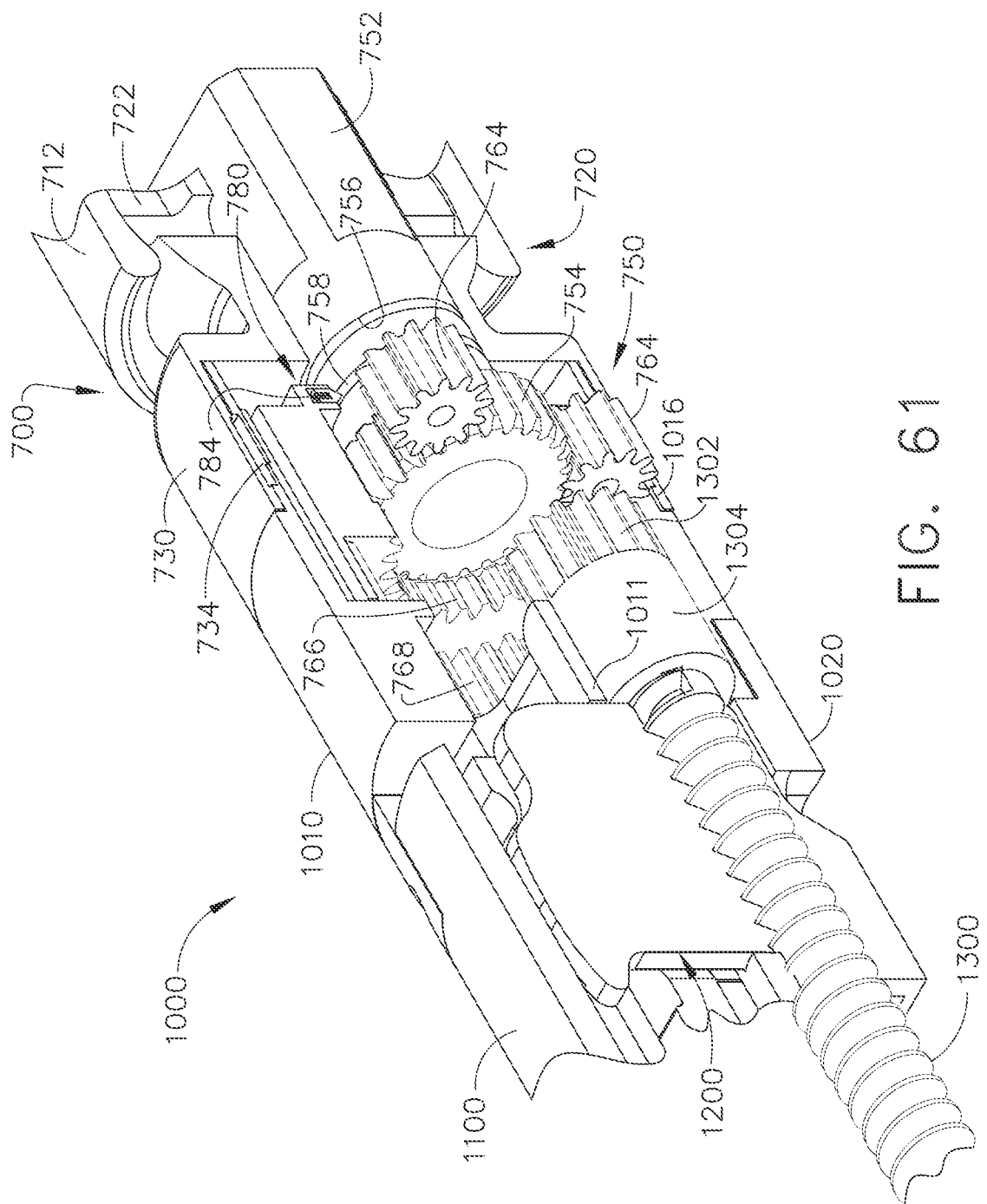
FIG. 61 is a partial perspective view of a drive system embodiment.
Figure 62:
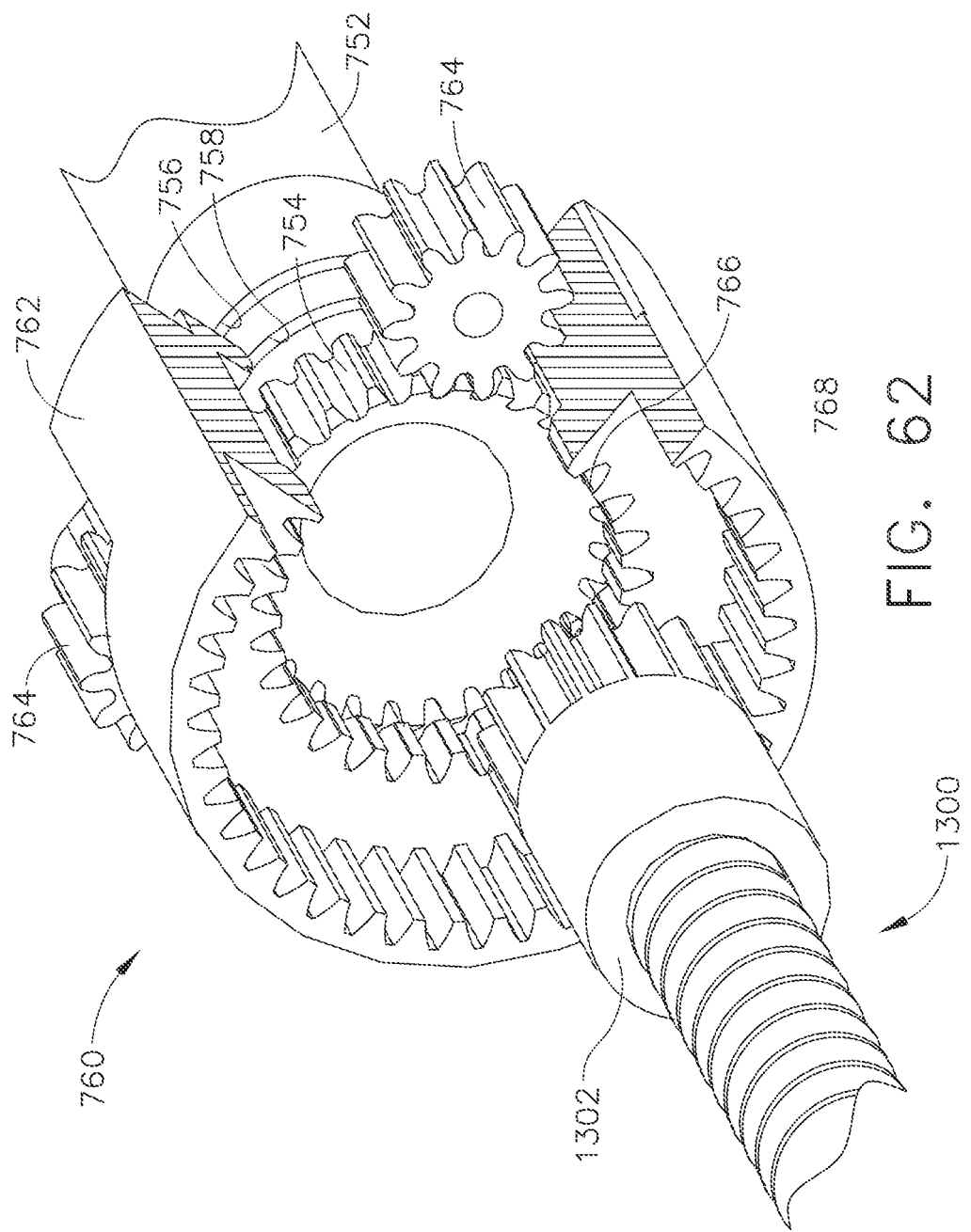
FIG. 62 is a partial front perspective view of a portion of the drive system embodiment of FIG. 61.
Figure 64:
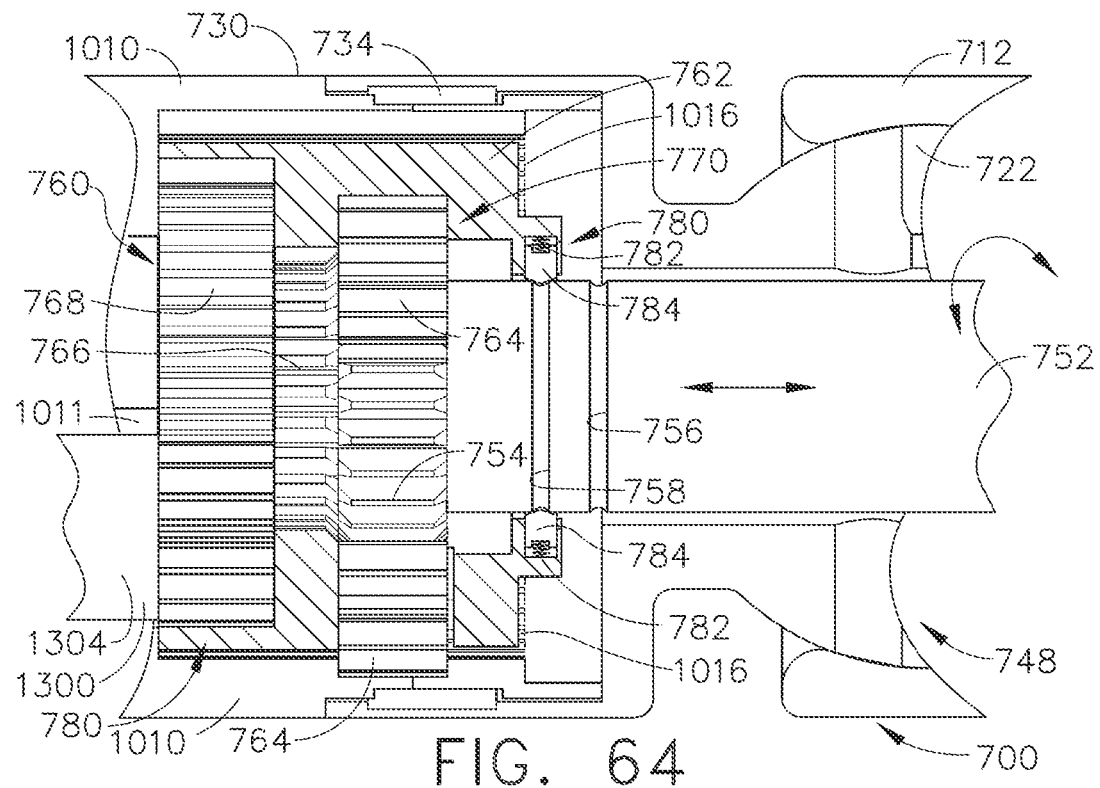
FIG. 64 is a partial cross-sectional side view of the drive system embodiment of FIGS. 61-63 in a first axial drive position.
Figure 65:
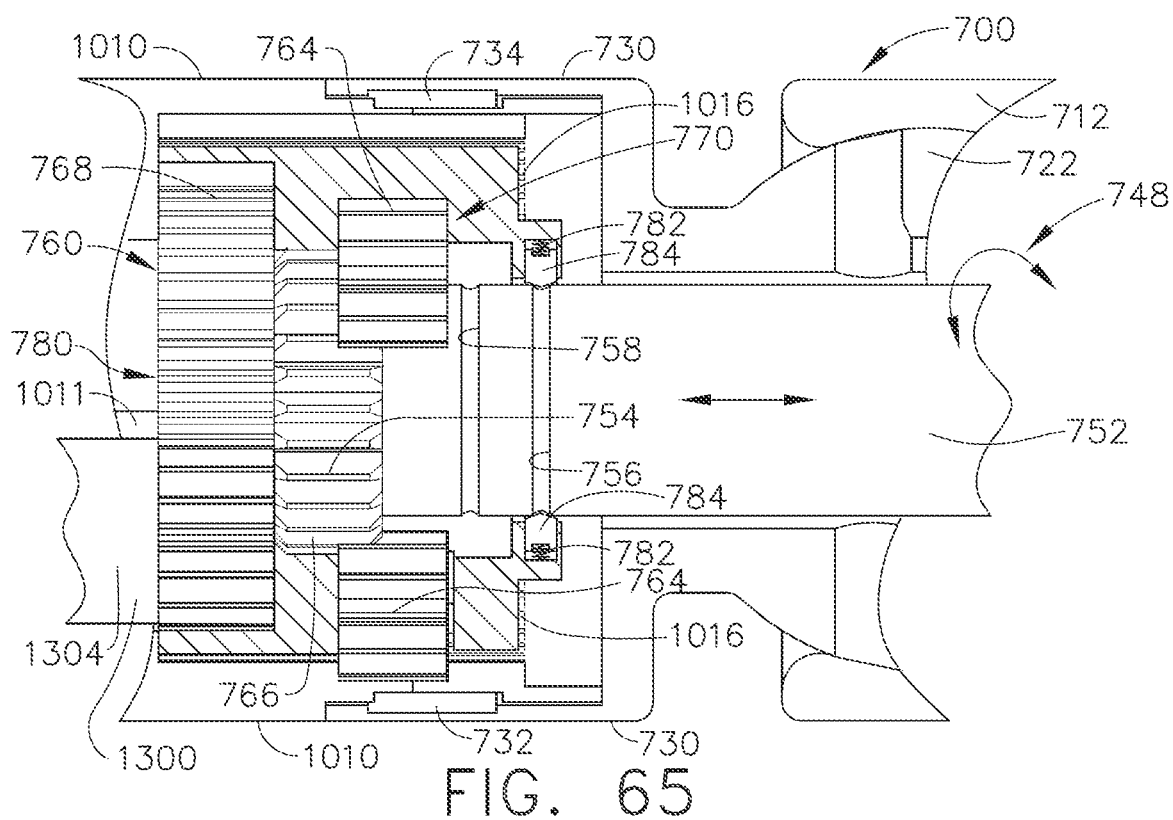
FIG. 65 is another partial cross-sectional side view of the drive system embodiment of FIGS. 61-64 in a second axial drive position.
Figure 66:
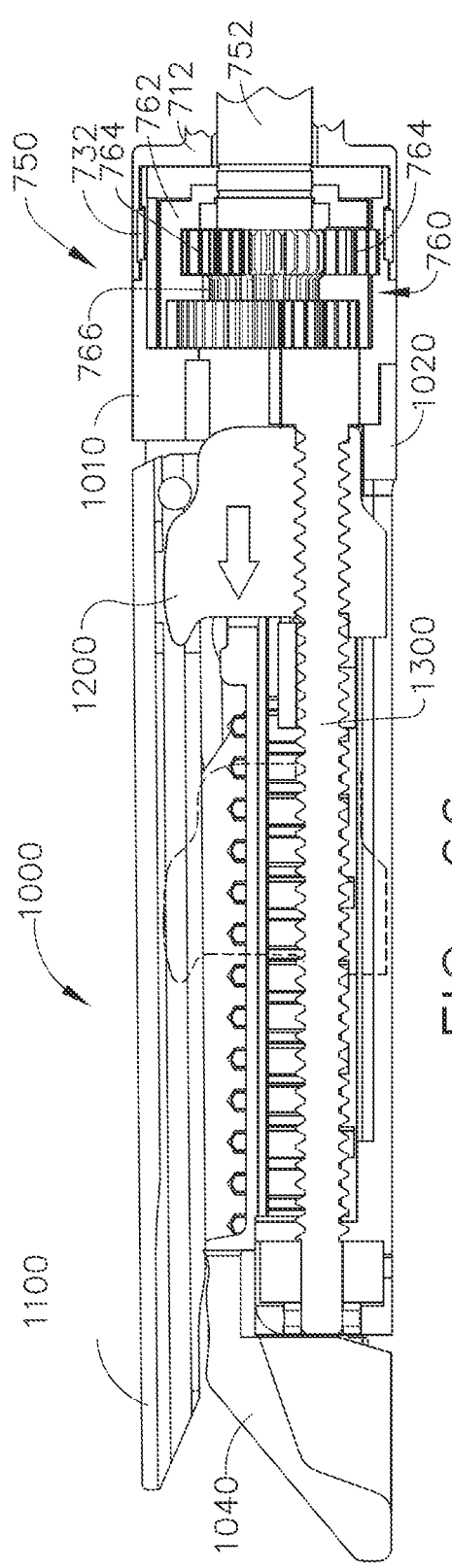
FIG. 66 is a cross-sectional view of an end effector and drive system embodiment wherein the drive system is configured to fire the firing member.

The end effector embodiment 1000 illustrated in FIG. 60 includes a drive arrangement generally designated as 748 that facilitates the selective application of rotary control motions to the end effector 1000. The end effector 1000 includes a firing member 1200 that is threadably journaled on an implement drive shaft 1300. As can be seen in FIG. 61, the implement drive shaft 1300 has a bearing segment 1304 formed thereon that is rotatably supported in a bearing sleeve 1011. The implement drive shaft 1300 has an implement drive gear 1302 that operably meshes with a rotary transmission generally designated as 750 that operably interfaces with the elongate channel 1020 and is operably supported by a portion of the elongate shaft assembly 200. In one exemplary form, the rotary transmission 750 includes a differential interlock assembly 760. As can be seen in FIGS. 64 and 65, the differential interlock assembly 760 includes a differential housing 762 that is configured to selectively rotate relative to the end effector drive housing 1010 and to rotate with the end effector housing 1010.

The distal drive shaft segment 540 is attached to a sun gear shaft 752 that has a sun gear 754 attached thereto. Thus, sun gear 754 will rotate when the distal drive shaft segment 540 is rotated. Sun gear 754 will also move axially with the distal drive shaft segment 540. The differential interlock assembly 760 further includes a plurality of planet gears 764 that are rotatably attached to the differential housing 762. In at least one embodiment, for example, three planet gears 764 are employed. Each planet gear 764 is in meshing engagement with a first end effector ring gear 1016 formed within the end effector drive housing 1010. In the illustrated exemplary embodiment shown in FIG. 60, the end effector drive housing 1010 is non-rotatably attached to the elongate channel 1020 by a pair of opposing attachment lugs 1018 (only one attachment lug 1018 can be seen in FIG. 60) into corresponding attachment slots 1024 (only one attachment slot 1024 can be seen in FIG. 60) formed in the proximal end 1021 of the elongate channel 1020. Other methods of non-movably attaching the end effector drive housing 1010 to the elongate channel 1020 may be employed or the end effector drive housing 1010 may be integrally formed with the elongate channel 1020. Thus, rotation of the end effector drive housing 1010 will result in the rotation of the elongate channel 1020 of the end effector 1000.

In the embodiment depicted in FIGS. 61-65, the differential interlock assembly 760 further includes a second ring gear 766 that is formed within the differential housing 762 for meshing engagement with the sun gear 754. The differential interlock assembly 760 also includes a third ring gear 768 formed in the differential housing 762 that is in meshing engagement with the implement drive gear 1302. Rotation of the differential housing 762 within the end effector drive housing 1010 will ultimately result in the rotation of the implement drive gear 1302 and the implement drive shaft 1300 attached thereto.

Figure 67:
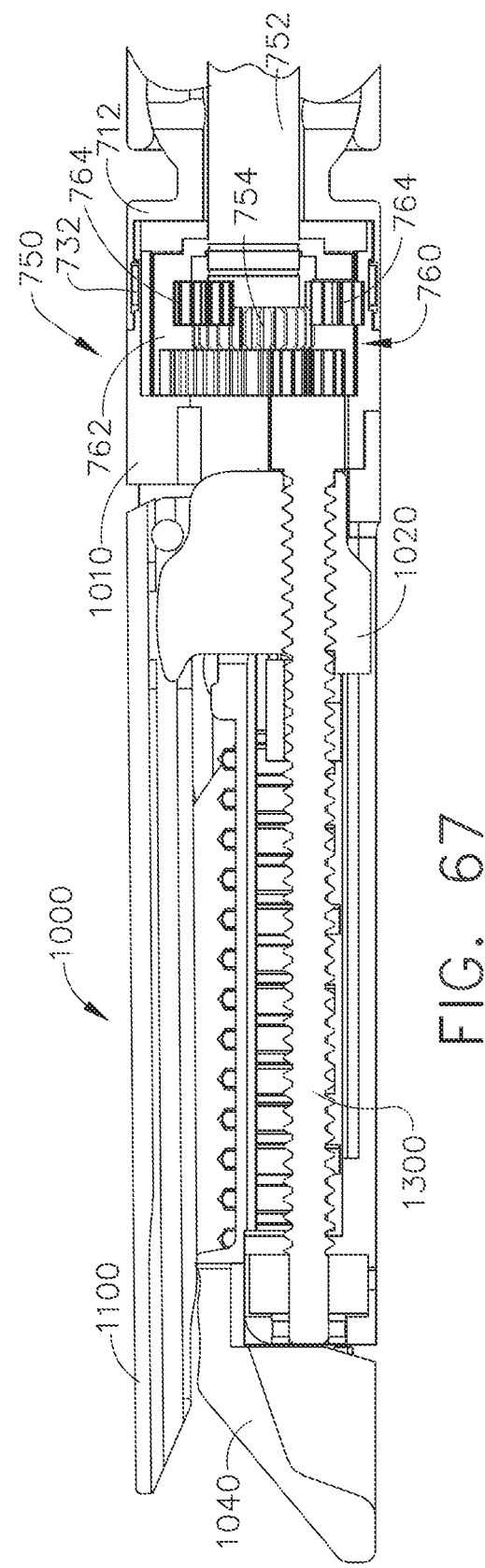
FIG. 67 is another cross-sectional view of the end effector and drive system embodiment wherein the drive system is configured to rotate the entire end effector.
Figure 70:
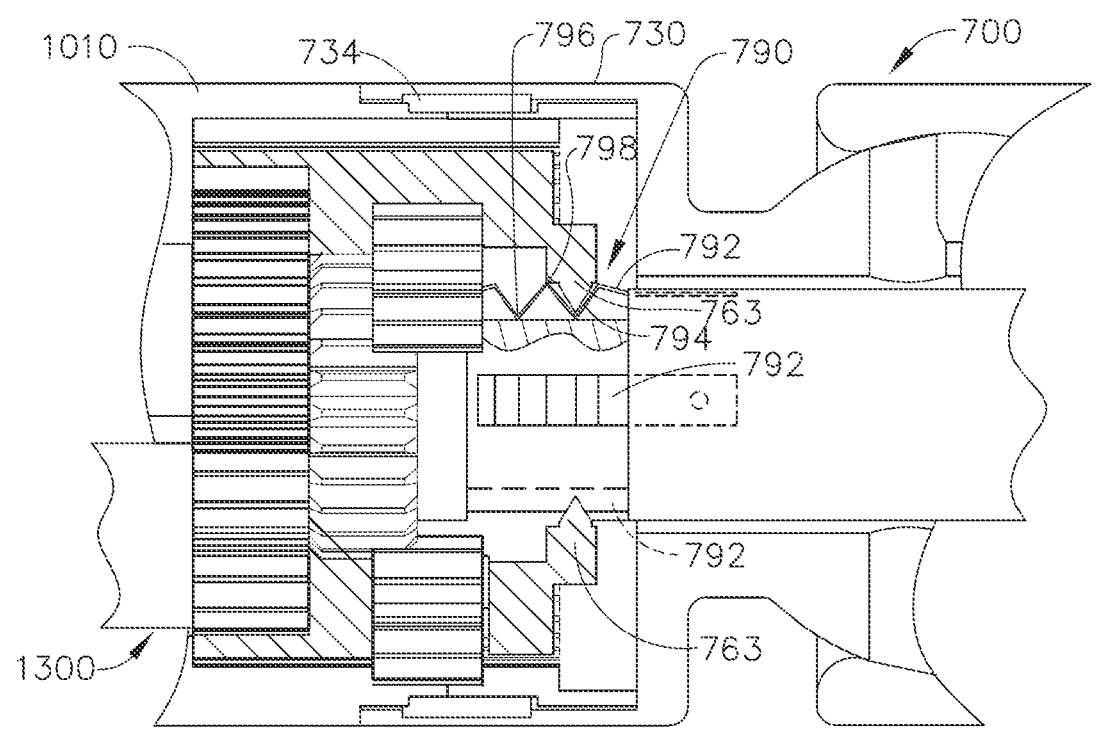
FIG. 70 is a cross-sectional view of another end effector and drive system embodiment wherein the drive system is configured to rotate the entire end effector.

When the clinician desires to rotate the end effector 1000 about the longitudinal tool axis LT-LT distal to the articulation joint 700 to position the end effector in a desired orientation relative to the target tissue, the robotic controller 12 may activate the shifter solenoid 394 to axially move the proximal drive shaft segment 380 such that the sun gear 754 is moved to a "first axial" position shown in FIGS. 65, 67 and 70. As described in detail above, the distal drive shaft segment 540 is operably coupled to the proximal drive shaft segment 380 by the quick disconnect joint 210. Thus, axial movement of the proximal drive shaft segment 380 may result in the axial movement of the distal drive shaft segment 540 and the sun gear shaft 752 and sun gear 754. As was further described above, the shifting system 390 controls the axial movement of the proximal drive shaft segment 380. When in the first axial position, the sun gear 754 is in meshing engagement with the planetary gears 764 and the second ring gear 766 to thereby cause the planetary gears 764 and the differential housing 762 to rotate as a unit as the sun gear 754 is rotated.

Rotation of the proximal drive shaft segment 380 is controlled by the second drive system 370. Rotation of the proximal drive shaft segment 380 results in rotation of the distal drive shaft segment 540, the sun gear shaft 752 and sun gear 754. Such rotation of the differential housing 762 and planetary gears 764 as a unit applies a rotary motion to the end effector drive housing 1010 of sufficient magnitude to overcome a first amount of friction F1 between the end effector drive housing 1010 and the distal socket portion 730 of the intermediate articulation tube 712 to thereby cause the end effector drive housing 1010 and end effector 1000 attached thereto to rotate about the longitudinal tool axis "LT-LT" relative to the distal socket tube 730. Thus, when in such position, the end effector drive housing 1010, the differential housing 762 and the planetary gears 764 all rotate together as a unit. Because the implement shaft 1300 is supported by the bearing sleeve 1011 in the end effector drive housing, the implement shaft 1300 also rotates with the end effector drive housing 1010. See FIG. 61. Thus, rotation of the end effector drive housing 1010 and the end effector 1000 does not result in relative rotation of the implement drive shaft 1300 which would result in displacement of the firing member 1200. In the illustrated exemplary embodiment, such rotation of the end effector 1000 distal of the articulation joint 700 does not result in rotation of the entire elongate shaft assembly 200.

When it is desired to apply a rotary drive motion to the implement drive shaft 1300 for driving the firing member 1200 within the end effector 1000, the sun gear 754 is axially positioned in a "second axial" position to disengage the second ring gear 766 while meshingly engaging the planetary gears 764 as shown in FIGS. 61, 62, 64 and 66. Thus, when it is desired to rotate the implement drive shaft 1300, the robotic controller 12 activates the shifter solenoid 394 to axially position the sun gear 754 into meshing engagement with the planetary gears 764. When in that second axial or "firing position", the sun gear 754 only meshingly engages the planetary gears 764.

Rotation of the proximal drive shaft segment 380 may be controlled by the second drive system 370. Rotation of the proximal drive shaft segment 380 results in rotation of the distal drive shaft segment 540, the sun gear shaft 752 and sun gear 754. As the sun gear 754 is rotated in a first firing direction, the planetary gears 764 are also rotated. As the planetary gears 764 rotate, they also cause the differential housing 762 to rotate. Rotation of the differential housing 762 causes the implement shaft 1300 to rotate due to the meshing engagement of the implement drive gear 1302 with the third ring gear 768. Because of the amount of friction F1 existing between the end effector drive housing 1010 and the distal socket portion 730 of the intermediate articulation tube 712, rotation of the planetary gears 764 does not result in the rotation of the end effector housing 1010 relative to the intermediate articulation tube 712. Thus, rotation of the drive shaft assembly results in rotation of the implement drive shaft 1300 without rotating the entire end effector 1000.

Such unique and novel rotary transmission 750 comprises a single drive system that can selectively rotate the end effector 1000 or fire the firing member 1200 depending upon the axial position of the rotary drive shaft. One advantage that may be afforded by such arrangement is that it simplifies the drives that must transverse the articulation joint 700. It also translates the central drive to the base of the elongate channel 1020 so that the implement drive shaft 1300 can exist under the staple cartridge 1040 to the drive the firing member 1200. The ability for an end effector to be rotatable distal to the articulation joint may vastly improve the ability to position the end effector relative to the target tissue.

As indicated above, when the drive shaft assembly is positioned in a first axial position, rotation of the drive shaft assembly may result in rotation of the entire end effector 1000 distal of the articulation joint 700. When the drive shaft assembly is positioned in a second axial position (in one example—proximal to the first axial position), rotation of the drive shaft assembly may result in the rotation of the implement drive shaft 1300.

Figure 63:
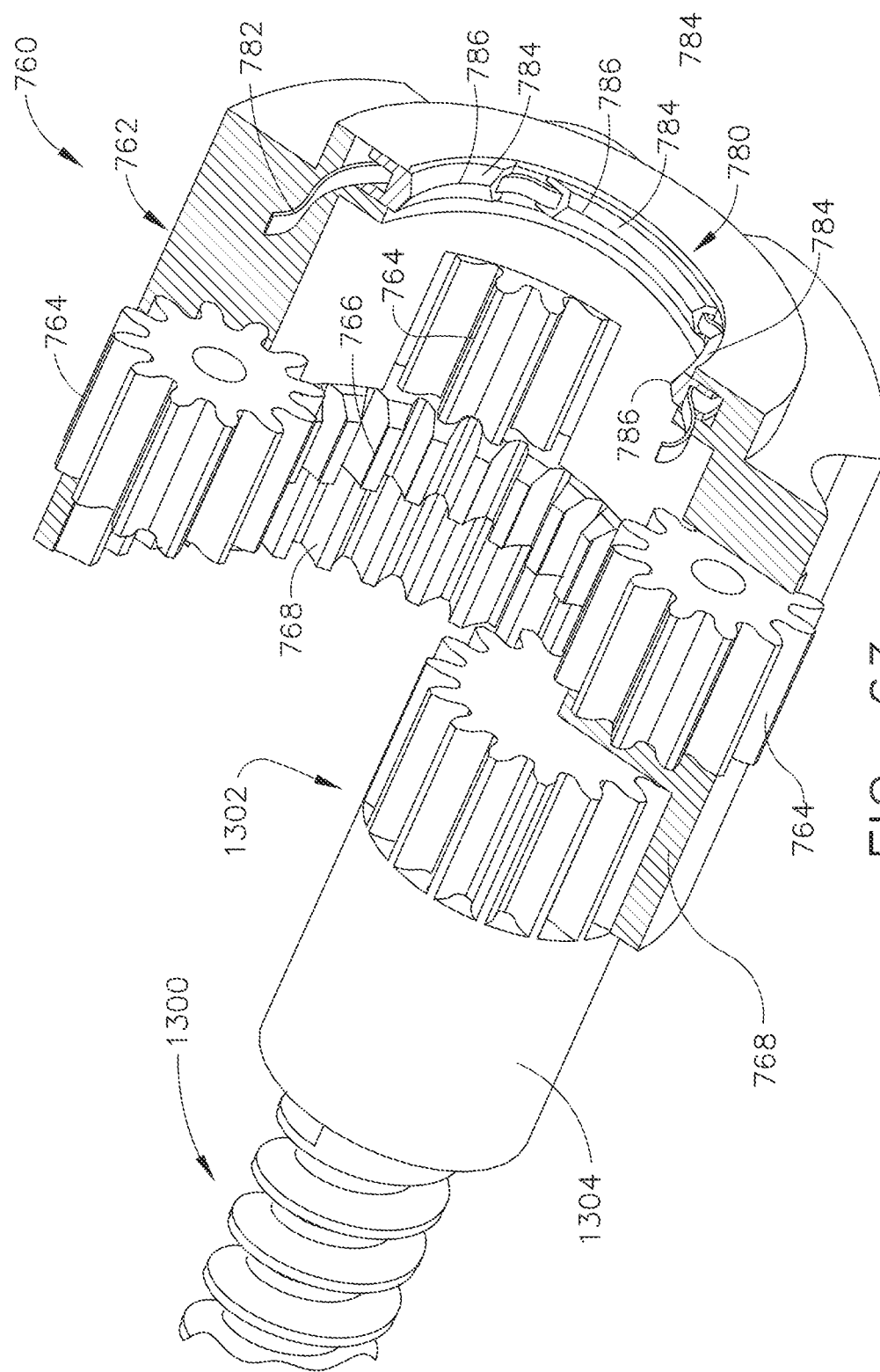
FIG. 63 is a partial rear perspective view of a portion of the drive system embodiment of FIGS. 61 and 62.

The rotary transmission embodiment depicted in FIGS. 64 and 65 includes a differential locking system 780 which is configured to retain the drive shaft assembly in the first and second axial positions. As can be seen in FIGS. 64 and 65, the differential locking system 780 comprises a first retention formation 756 in the sun gear shaft 752 that corresponds to the first axial position of the drive shaft assembly and a second retention formation 758 in the sun gear shaft 752 that correspond to the second axial position of the drive shaft assembly. In the illustrated exemplary embodiment, the first retention formation comprises a first radial locking groove 757 in the sun gear shaft 752 and the second retention formation 758 comprises a second radial locking groove 759 formed in the sun gear shaft 752. The first and second locking grooves 757, 759 cooperate with at least one spring-biased locking member 784 that is adapted to retainingly engage the locking grooves 757, 759 when the drive shaft assembly is in the first and second axial positions, respectively. The locking members 784 have a tapered tip 786 and are movably supported within the differential housing 762. A radial wave spring 782 may be employed to apply a biasing force to the locking members 784 as shown in FIG. 63. When the drive shaft assembly is axially moved into the first position, the locking members 784 snap into engagement with the first radial locking groove 7576. See FIG. 65. When the drive shaft assembly is axially moved into the second axial position, the locking members 784 snap into engagement with the second radial locking groove 759. See FIG. 64. In alternative embodiments, the first and second retention formations may comprise, for example, dimples that correspond to each of the locking members 784. Also in alternative embodiments wherein the drive shaft assembly is axially positionable in more than two axial positions, addition retention formations may be employed which correspond to each of those axial positions.

Figure 71:
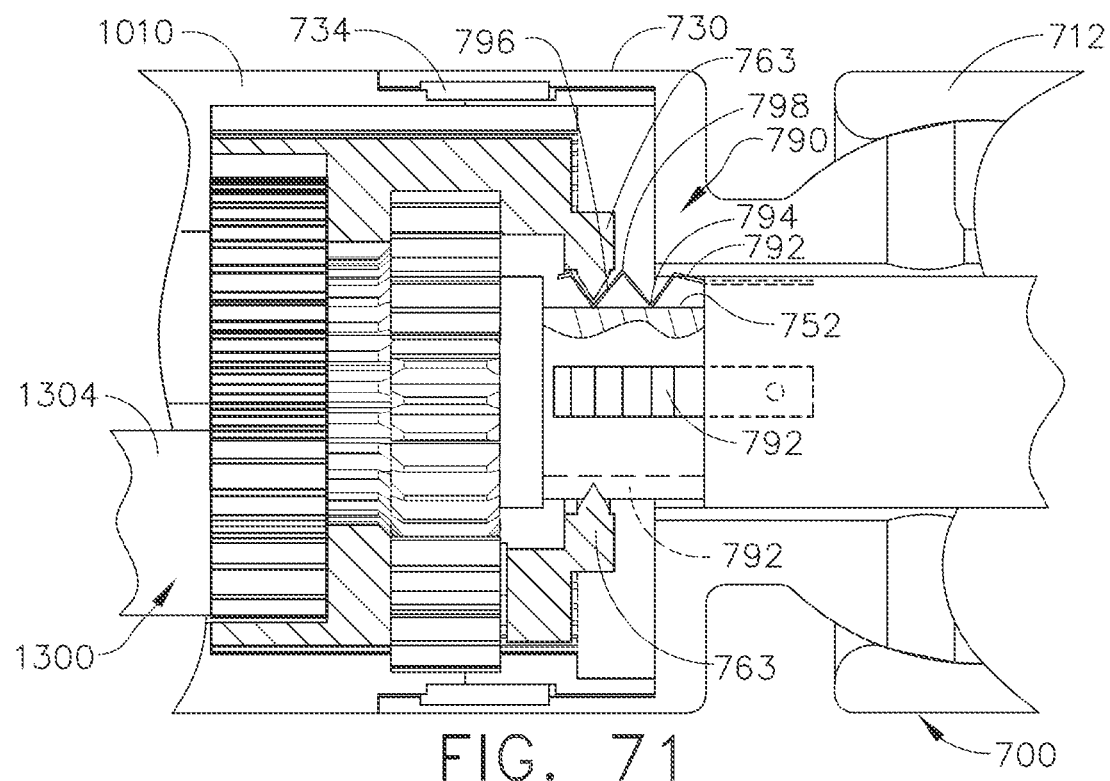
FIG. 71 is another cross-sectional view of the end effector and drive system embodiment of FIG. 70 wherein the drive system is configured to fire the firing member of the end effector.

FIGS. 70 and 71 illustrate an alternative differential locking system 790 that is configured to ensure that the drive shaft assembly is locked into one of a plurality of predetermined axial positions. The differential locking system 790 is configured to ensure that the drive shaft assembly is positionable in one of the first and second axial positions and is not inadvertently positioned in another axial position wherein the drive system is not properly operable. In the embodiment depicted in FIGS. 70 and 71, the differential locking system 790 includes a plurality of locking springs 792 that are attached to the drive shaft assembly. Each locking spring 792 is formed with first and second locking valleys 794, 796 that are separated by a pointed peak portion 798. The locking springs 792 are located to cooperate with a pointed locking members 763 formed on the differential housing 762. Thus, when the pointed locking members 763 are seated in the first locking valley 794, the drive shaft assembly is retained in the first axial position and when the pointed locking members 763 are seated in the second locking valleys 796, the drive shaft assembly is retained in the second axial position. The pointed peak portion 798 between the first and second locking valleys 794, 796 ensure that the drive shaft assembly is in one of the first and second axial positions and does not get stopped in an axial position between those two axial positions. If additional axial positions are desired, the locking springs may be provided with additional locking valleys that correspond to the desired axial positions.

Figure 72:
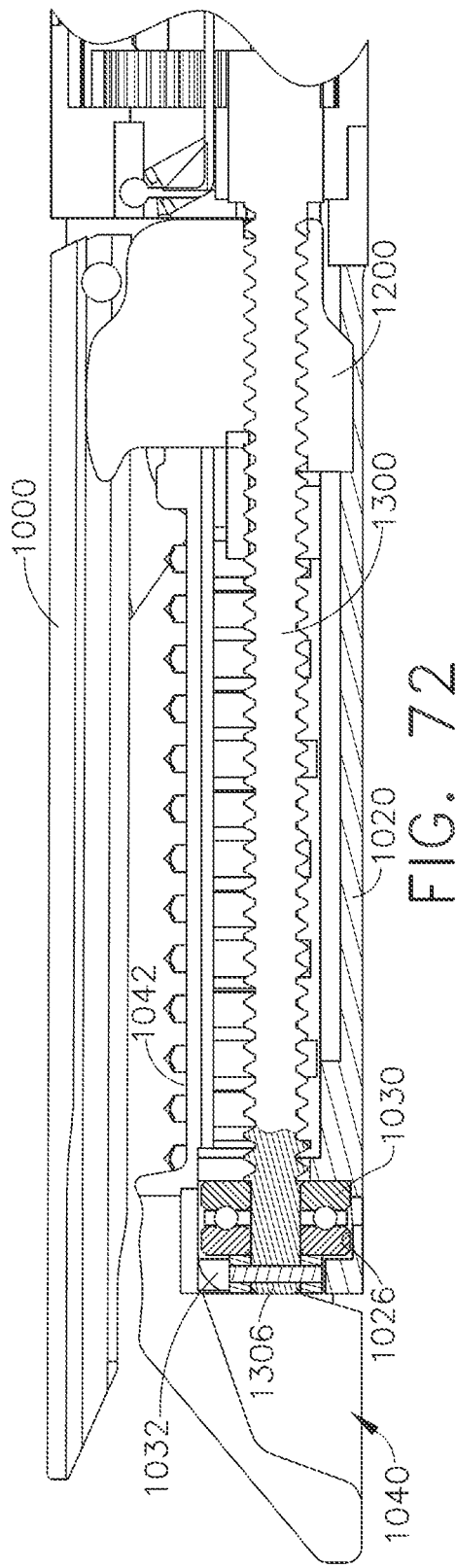
FIG. 72 is a cross-sectional side view of an end effector embodiment.
Figure 73:
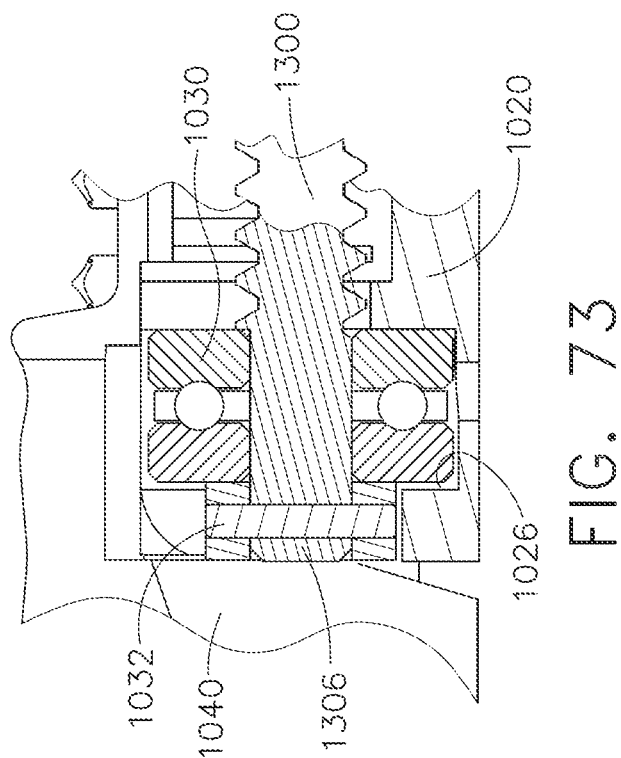
FIG. 73 is an enlarged cross-sectional view of a portion of the end effector embodiment of FIG. 72.

Referring to FIGS. 60, 72 and 73, a thrust bearing 1030 is supported within a cradle 1026 in the elongate channel 1020. The distal end portion 1306 of the implement drive shaft 1300 is rotatably received within the thrust bearing 1030 and protrudes therethrough. A retaining collar 1032 is pinned or otherwise affixed to the distal end 1030 as shown in FIG. 73 to complete the installation. Use of the thrust bearing 1030 in this manner may enable the firing member 1200 to be "pulled" as it is fired from a starting position to an ending position within the elongate channel 1020. Such arrangement may minimize the risk of buckling of the implement drive shaft 1300 under high load conditions. The unique and novel mounting arrangement and location of the thrust bearing 1030 may result in a seating load that increases with the anvil load which further increases the end effector stability. Such mounting arrangement may essentially serve to place the implement drive shaft 1300 in tension during the high load firing cycle. This may avoid the need for the drive system gears to both rotate the implement drive shaft 1300 and resist the buckling of the shaft 1300. Use of the retaining collar 1032 may also make the arrangement easy to manufacture and assemble. The firing member 1200 is configured to engage the anvil and retain the anvil at a desired distance from the cartridge deck as the firing member 1200 is driven from the starting to ending position. In this arrangement for example, as the firing member 1200 assembly moves distally down the elongate channel 1020, the length of the portion of the anvil that resembles a cantilever beam becomes shorter and stiffer thereby increasing the magnitude of downward loading occurring at the distal end of the elongate channel 1020 further increasing the bearing seating load.

One of the advantages of utilizing rotary drive members for firing, closing, rotating, etc. may include the ability to use the high mechanical advantage of the drive shaft to accommodate the high loads needed to accomplish those instrument tasks. However, when employing such rotary drive systems, it may be desirable to track the number of rotations that the drive shaft is driven to avoid catastrophic failure or damage to the drive screw and other instrument components in the event that the drive shaft or movable end effector component is driven too far in the distal direction. Thus, some systems that include rotary drive shafts have, in the past, employed encoders to track the motor rotations or sensors to monitor the axial position of the movable component. The use of encoders and/or sensors require the need for additional wiring, electronics and processing power to accommodate such a system which can lead to increased instrument costs. Also, the system's reliability may be somewhat difficult to predict and its reliability depends upon software and processors.

Figure 76:
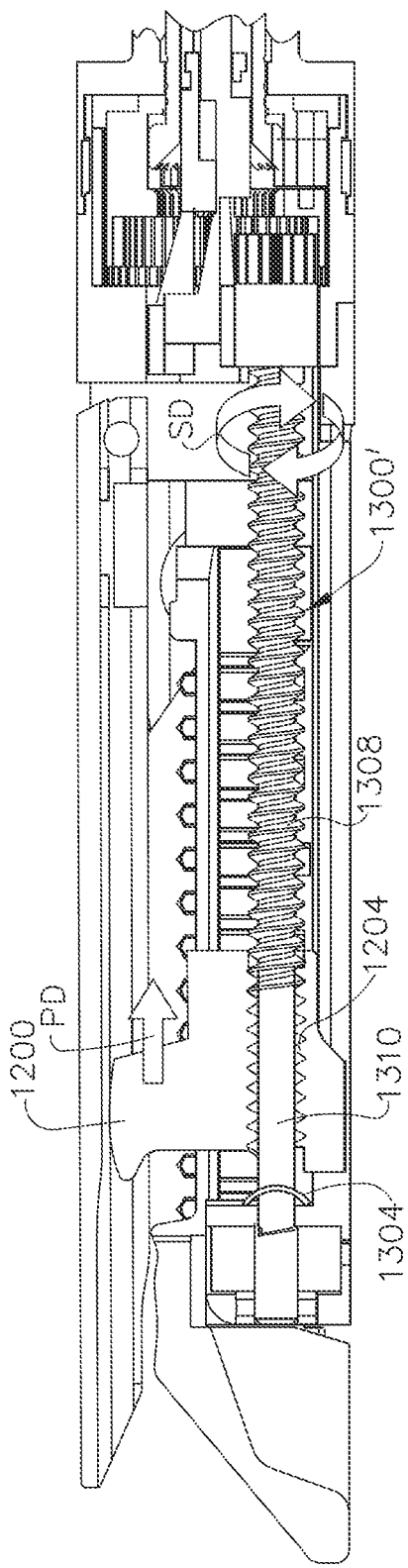
FIG. 76 is another cross-sectional side view of the end effector embodiment of FIGS. 74 and 75 wherein the firing member thereof is being retracted.

FIGS. 74-76 depict a mechanical stroke limiting system 1310 for limiting the linear stroke of the firing member 1200 as the firing member 1200 is driven from a starting to an ending position. The stroke limiting system 1310 employs an implement drive shaft 1300' wherein the screw threads 1308 on the implement drive shaft 1300' do not extend to the distal end 1306 of the drive shaft 1300'. For example, as can be seen in FIGS. 74-76, the implement drive shaft 1300' includes an un-threaded section 1309. The firing member 1200 has a body portion 1202 that has a series of internal threads 1204 that are adapted to threadably interface with the screw threads 1308 on the implement drive shaft 1300' such that, as the implement drive shaft 1300' is rotated in a first firing direction, the firing member 1200 is driven in the distal direction "DD" until it contacts the unthreaded section 1309 at which point the firing member 1200 stops its distal advancement. That is, the firing member 1200 will advance distally until the internal threads 1204 in the firing member 1200 disengage the threads 1308 in the implement drive shaft 1300'. Any further rotation of the implement drive shaft 1300' in the first direction will not result in further distal advancement of the firing member 1200. See, e.g., FIG. 75.

The illustrated exemplary mechanical stroke limiting system 1310 further includes a distal biasing member 1312 that is configured to be contacted by the firing member 1200 when the firing member 1200 has been advanced to the end of its distal stroke (i.e., the firing member will no longer advance distally with the rotation of the implement drive shaft in the first rotary direction). In the embodiment depicted in FIGS. 74-76, for example, the biasing member 1312 comprises a leaf spring 1314 that is positioned within the elongate channel 1020 as shown. FIG. 74 illustrates the leaf spring 1314 prior to contact by the firing member 1200 and FIG. 75 illustrates the leaf spring 1314 in a compressed state after it has been contacted by the firing member 1200. When in that position, the leaf spring 1314 serves to bias the firing member 1200 in the proximal direction "PD" to enable the internal threads 1204 in the firing member 1200 to re-engage the implement drive shaft 1300' when the implement drive shaft 1300' is rotated in a second retraction direction. As the implement drive shaft 1300' is rotated in the second retraction direction, the firing member 1200 is retracted in the proximal direction. See FIG. 76.

Figure 77:
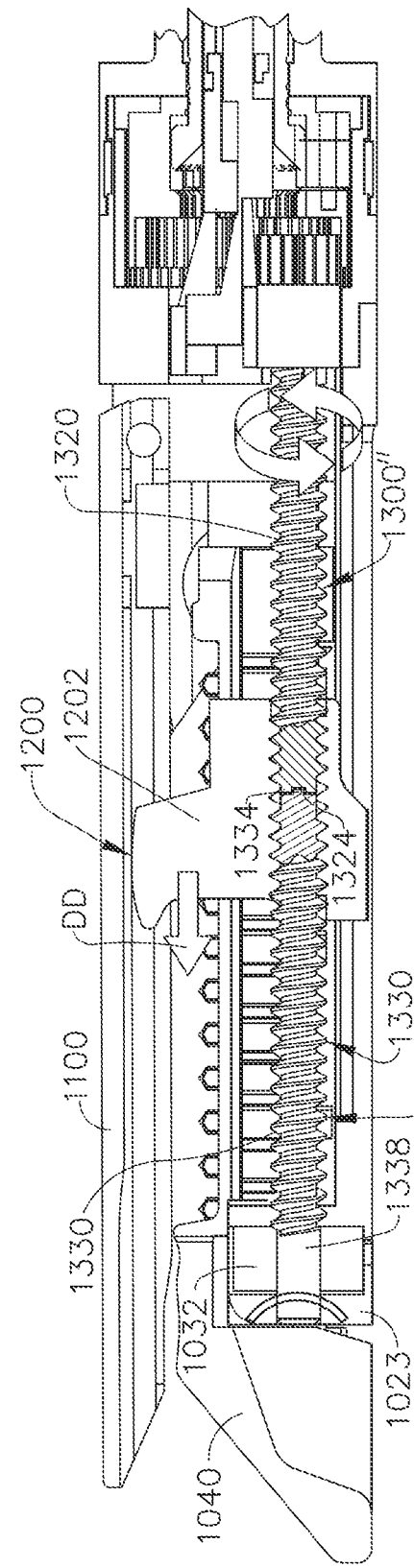
FIG. 77 is a cross-sectional side view of another end effector embodiment wherein the firing member thereof has been partially driven through its firing stroke.
Figure 78:
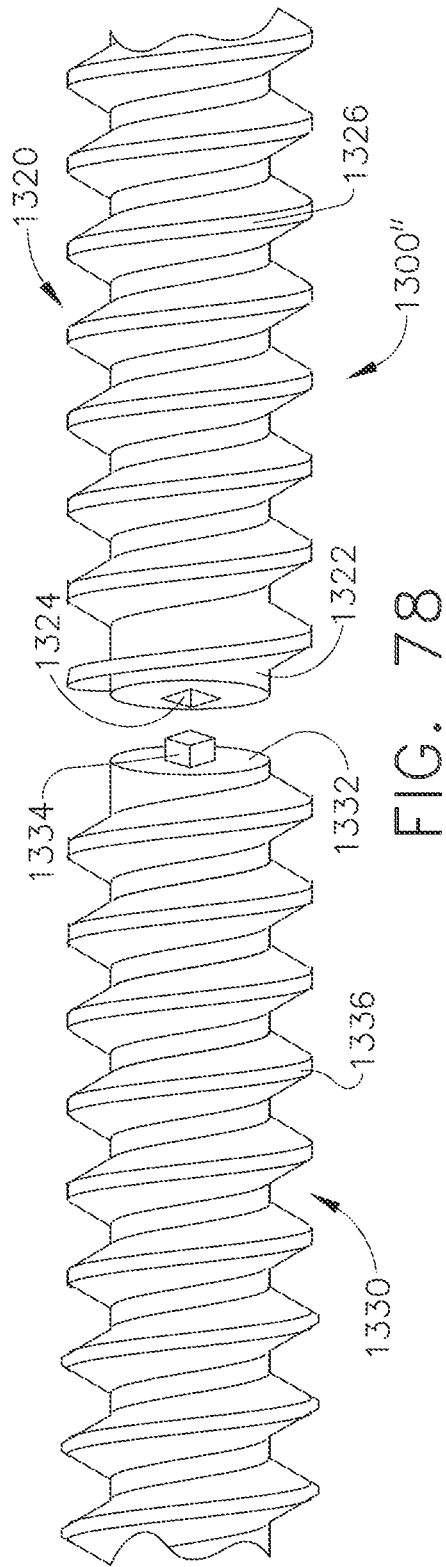
FIG. 78 is an exploded assembly view of a portion of an implement drive shaft embodiment.
Figure 79:
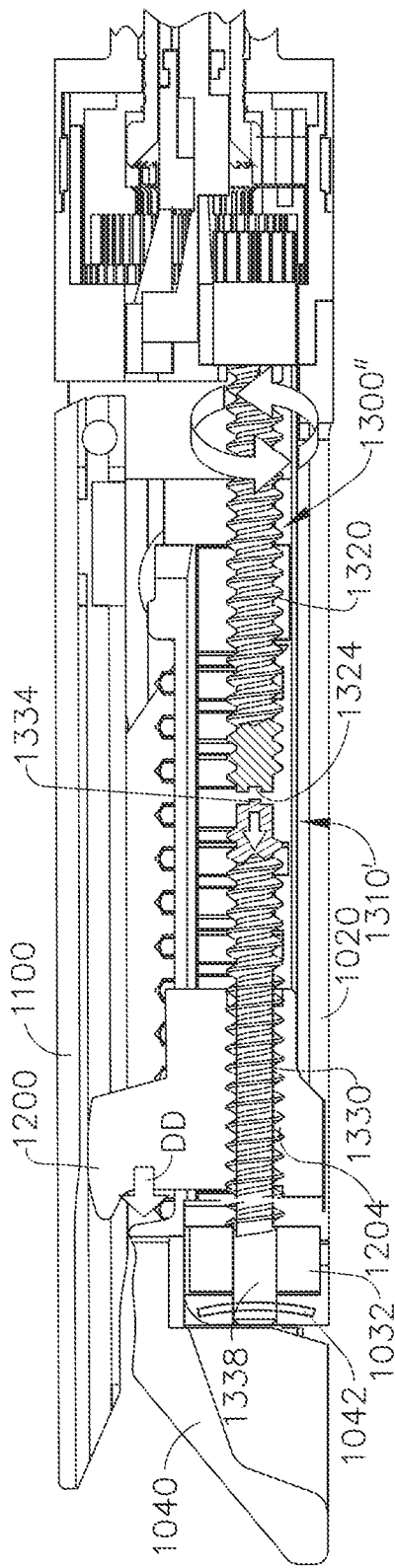
FIG. 79 is another cross-sectional side view of the end effector of FIG. 77 with the firing member thereof at the end of its firing stroke.
Figure 80:
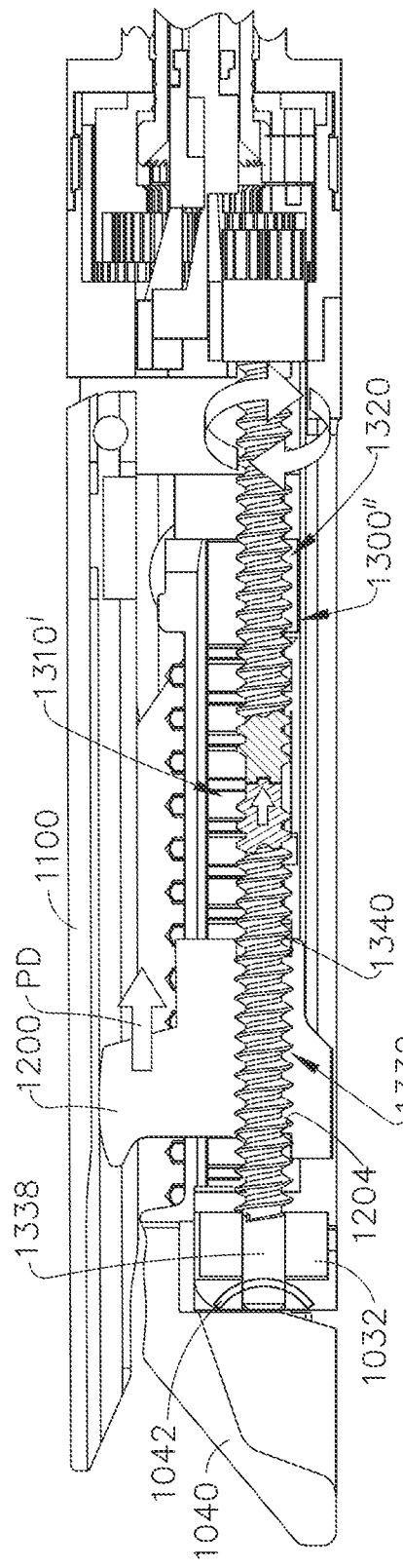
FIG. 80 is another cross-sectional side view of the end effector of FIGS. 77 and 78 wherein the firing member is being retracted.

FIGS. 77-80 illustrate another stroke limiting system 1310'. The stroke limiting system 1310' employs a two-part implement drive shaft 1300". In at least one form, for example, the implement drive shaft 1300" includes a proximal implement drive shaft segment 1320 that has a socket 1324 in a distal end 1322 thereof and a distal drive shaft segment 1330 that has a lug 1334 protruding from a proximal end 1332 thereof. The lug 1334 is sized and shaped to be received within the socket 1324 such that threads 1326 on the proximal drive shaft segment 1320 cooperate with threads 1336 on the distal drive shaft segment 1330 to form one continuous drive thread 1340. As can be seen in FIGS. 77, 79 and 80, a distal end 1338 of the distal drive shaft segment 1330 extends through a thrust bearing 1032 that is movably supported in the distal end 1023 of the elongate channel 1020. That is, the thrust bearing 1032 is axially movable within the elongate channel 1020. A distal biasing member 1342 is supported within the elongate channel 1020 for contact with the thrust bearing 1032. FIG. 78 illustrates the firing member 1200 being driven in the distal direction "DD" as the implement drive shaft 1300" is driven in a first rotary direction. FIG. 79 illustrates the firing member 1200 at the distal end of its stroke. Further rotation of the implement drive shaft 1300" in the first rotary direction causes the thrust bearing 1032 to compress the biasing member 1342 and also allows the distal shaft segment 1330 to slip if the proximal segment 1320 continues to turn. Such slippage between the proximal and distal implement drive shaft segments 1320, 1330 prevent the firing member 1200 from being further advanced distally which could ultimately damage the instrument. However, after the first rotary motion has been discontinued, the biasing member 1342 serves to bias the distal shaft segment 1320 in the proximal direction such that the lug 1334 is seated in the socket 1324. Thereafter, rotation of the implement shaft 1300" in a second rotary direction results in the movement of the firing member 1200 in the proximal direction "PD" as shown in FIG. 80.

Figure 81:
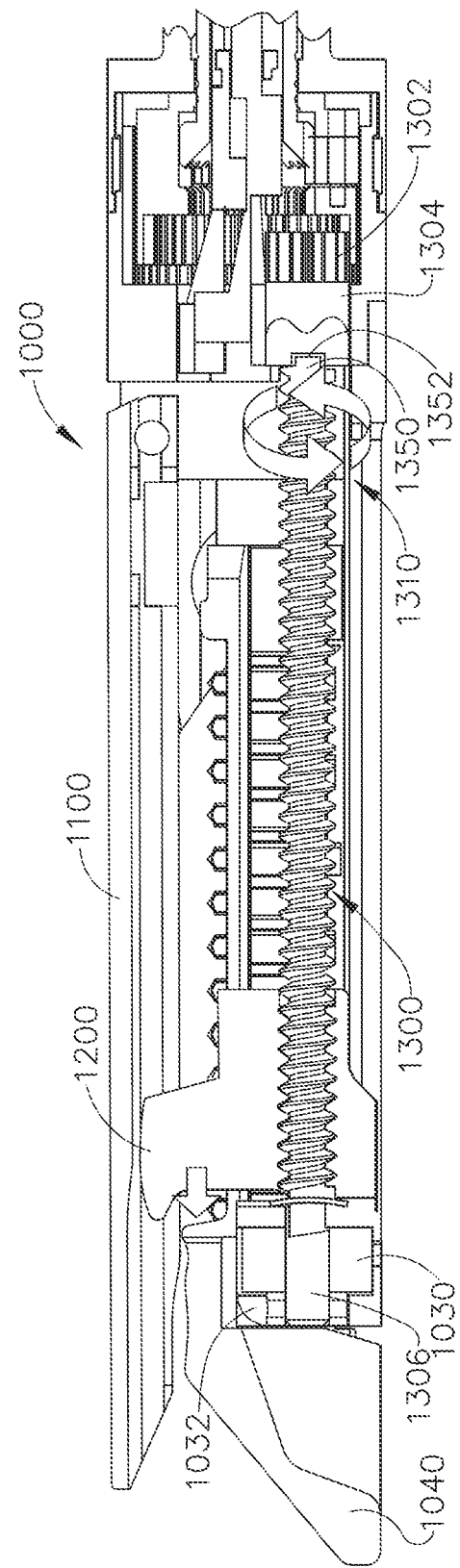
FIG. 81 is a cross-sectional side view of another end effector embodiment wherein the firing member is at the end of its firing stroke.

FIG. 81 illustrates another stroke limiting system 1310". In this embodiment, the implement drive shaft 1300 has a lug 1350 formed thereon that is sized and shaped to be received within a socket 1352 in the bearing segment 1304 that has the implement drive gear 1302 formed thereon or otherwise attached thereto. FIGS. 81A and 81B illustrate different lugs 1350' (FIG. 81A) and 1350" (FIG. 81B) that are configured to releasably engage corresponding sockets 1352' and 1352", respectively. The leaf spring 1314 is positioned to be contacted by the firing member 1200 when the firing member 1200 has reached the end of its stroke. Further rotation of the implement drive shaft 1300 will result in the lug 1350, 1350', 1350" slipping out of the socket 1352, 1352', 1352", respectively to thereby prevent further rotation of the implement shaft 1300. Once the application of rotational motion to the implement drive shaft 1300 is discontinued, the leaf spring 1314 will apply a biasing motion to the firing member 1200 to ultimately bias the implement drive shaft 1300 in the proximal direction "PD" to seat the lug 1350 in the socket 1352. Rotation of the implement drive shaft 1300 in the second rotary direction will result in the retraction of the firing member 1200 in the proximal direction "PD" to the starting position. Once the firing member 1200 has returned to the starting position, the anvil 1100 may then be opened.

In the illustrated exemplary embodiment, the firing member 1200 is configured to engage the anvil 1100 as the firing member 1200 is driven distally through the end effector to affirmatively space the anvil from the staple cartridge to assure properly formed closed staples, especially when an amount of tissue is clamped that is inadequate to do so. Other forms of firing members that are configured to engage and space the anvil from the staple cartridge or elongate channel and which may be employed in this embodiment and others are disclosed in U.S. Pat. No. 6,978,921, entitled SURGICAL STAPLING INSTRUMENT INCORPORATING AN E-BEAM FIRING MECHANISM, the disclosure of which is herein incorporated by reference in its entirety. As can be seen in FIGS. 82 and 83, the body portion 1202 of the firing member 1200 includes a foot portion 1206 that upwardly engages a channel slot 1028 in the elongate channel 1020. See FIG. 60. Similarly, the knife body includes a pair of laterally-protruding upper fins 1208. When fired with the anvil 1100 closed, the upper fins 1208 advance distally within a longitudinal anvil slot 1103 extending distally through anvil 1100. Any minor upward deflection in the anvil 1100 is overcome by a downward force imparted by the upper fins 1208.

In general, the loads necessary to close and advance the firing member i.e., "fire" the firing member could conceivably exceed 200 lbs. Such force requirements, however, may require the internal threads 1204 in the firing member to comprise relative fine threads of a power-type thread configuration such as Acme threads. Further, to provide sufficient support to the upper fins 1208 to avoid the firing member 1200 from binding as it is driven distally through the end effector, it may be desirable for at least 5-15 threads in the firing member to be engaged with the threads on the implement drive shaft at any given time. However, conventional manufacturing methods may be unsuitable for forming sufficient threads in the firing member body 1202 within an 0.08 inch-0.150 inch diameter opening and which have sufficient thread depth.

FIGS. 82-84 illustrate a firing member 1200' that may address at least some of the aforementioned challenges. As can be seen in those Figures, the body portion 1202' of the firing member has a hollow shaft socket 1210 extending therethrough that is sized to receive the implement shaft therethrough. The internal threads in this embodiment are formed by a series of rods 1214 that extend transversely through holes 1212 in the shaft socket 1210 as shown. As can be seen in FIG. 84, the pins 1214 rest on the minor diameter of the pitch of the threads 1308 on the implement drive shaft 1300.

Figure 85:
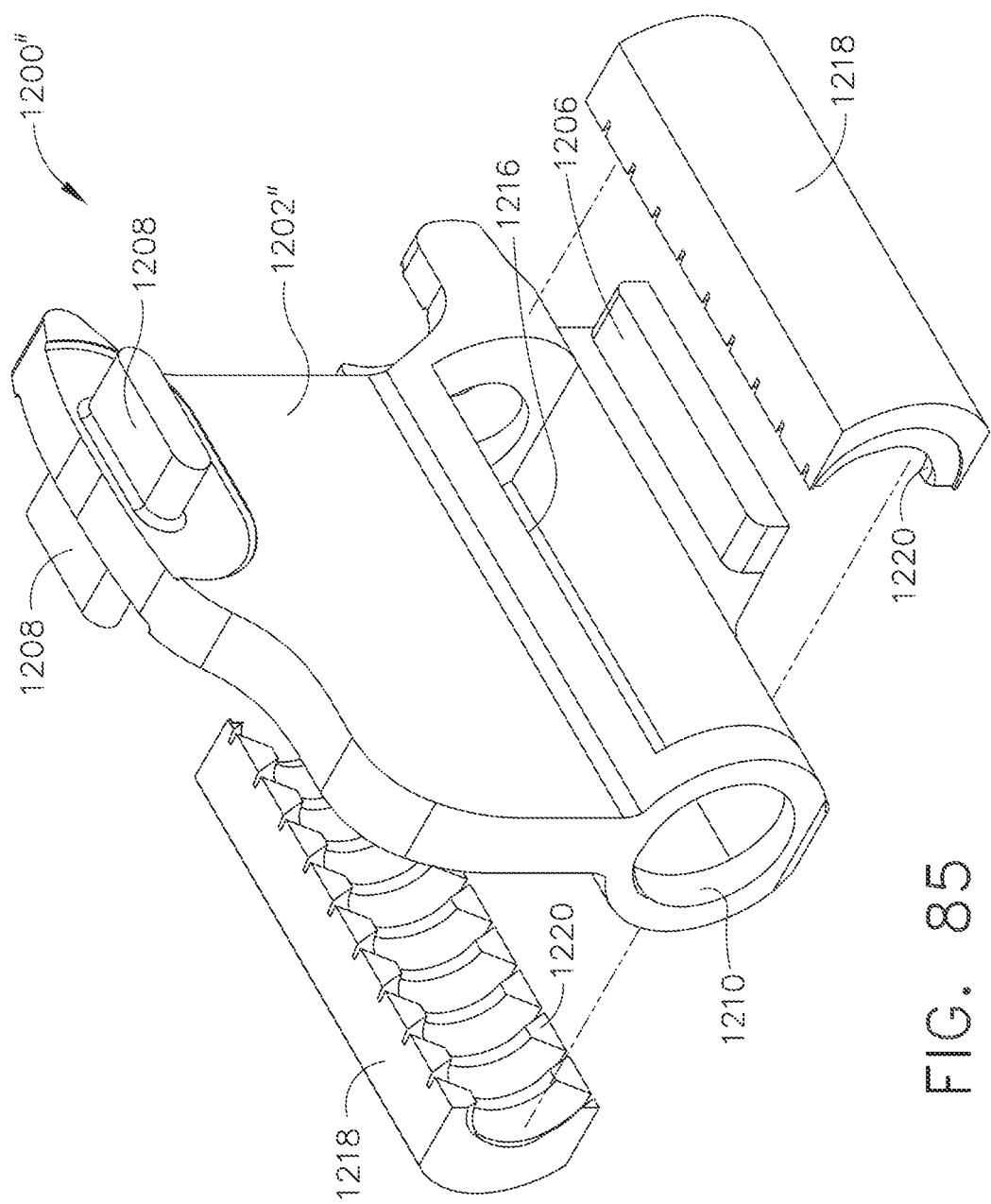
FIG. 85 is an exploded assembly view of another firing member embodiment.

FIG. 85 illustrates another firing member 1200" that may also address at least some of the above-discussed manufacturing challenges. As can be seen in that Figure, the body portion 1202" of the firing member 100" has a hollow shaft socket 1210 extending therethrough that is sized to receive the implement shaft therethrough. A pair of windows 1216 are formed in the body portion 1202" as shown. The internal threads 1220 in this embodiment are formed on plugs 1218 that are inserted into the windows 1216 and are attached therein by welding, adhesive, etc. FIGS. 86 and 87 illustrate another firing member 1200" wherein access into the socket 1210 is gained through access windows 1230A, 1230B formed in the body portion 1202". For example, a pair of access windows 1230A are provided through one side of the socket portion 1210 to enable internal thread segments 1232 to be formed within the opposite wall of the socket 1210. Another access window 1230B is provided through the opposite side of the socket portion 1210 so that a central internal thread segment 1234 can be formed in the opposite wall between the internal thread segments 1232. The thread segments 1232, 1234 cooperate to threadably engage the threads 1308 on the implement drive shaft 1300.

End effector 1000 is configured to removably support a staple cartridge 1040 therein. See FIG. 60. The staple cartridge 1040 includes a cartridge body 1042 that is configured to be operably seated with the elongate channel 1020. The cartridge body 1042 has an elongate slot 1046 therein for accommodating the firing member 1200. The cartridge body 1042 further defines an upper surface referred to herein as the cartridge deck 1044. In addition, two lines of staggered staple apertures 1048 are provided on each side of the elongate slot 1046. The staple apertures 1048 operably support corresponding staple drivers 1050 that support one or two surgical staples (not shown) thereon. A variety of such staple driver arrangements are known and may be employed without departing from the spirit and scope of the various exemplary embodiments of the invention.

The firing member embodiments also employ a wedge sled assembly 1250 for driving contact with the staple drivers operably supported within the staple cartridge 1040. As can be seen in FIG. 60, the wedge sled assembly 1250 includes at least two wedges 1252 that are oriented for driving contact with the lines of staple drivers operably supported within the staple cartridge 1040. As the firing member 1200 is driven distally, the wedge sled assembly 1250 travels with the firing member 1220 and the wedges 1252 thereon force the drivers 1050 upward towards the closed anvil 1100. As the drivers 1050 are driven upwardly, the surgical staples supported thereon are driven out of their respective apertures 1048 into forming contact with the staple forming surface 1104 of the closed anvil 1100.

Various exemplary end effector embodiments disclosed herein may also employ a unique and novel firing lockout arrangement that will prevent the clinician from inadvertently advancing or "firing" the firing member when a cartridge is not present, a cartridge has not been properly seated within the end effector and/or when a spent cartridge remains installed in the end effector. For example, as will be discussed in further detail below, the firing lockout arrangement may interact with the implement drive shaft 1300 and/or the firing member 1200 to prevent inadvertent advancement of the firing member 1200 when one of the aforementioned conditions exist.

Figure 90:
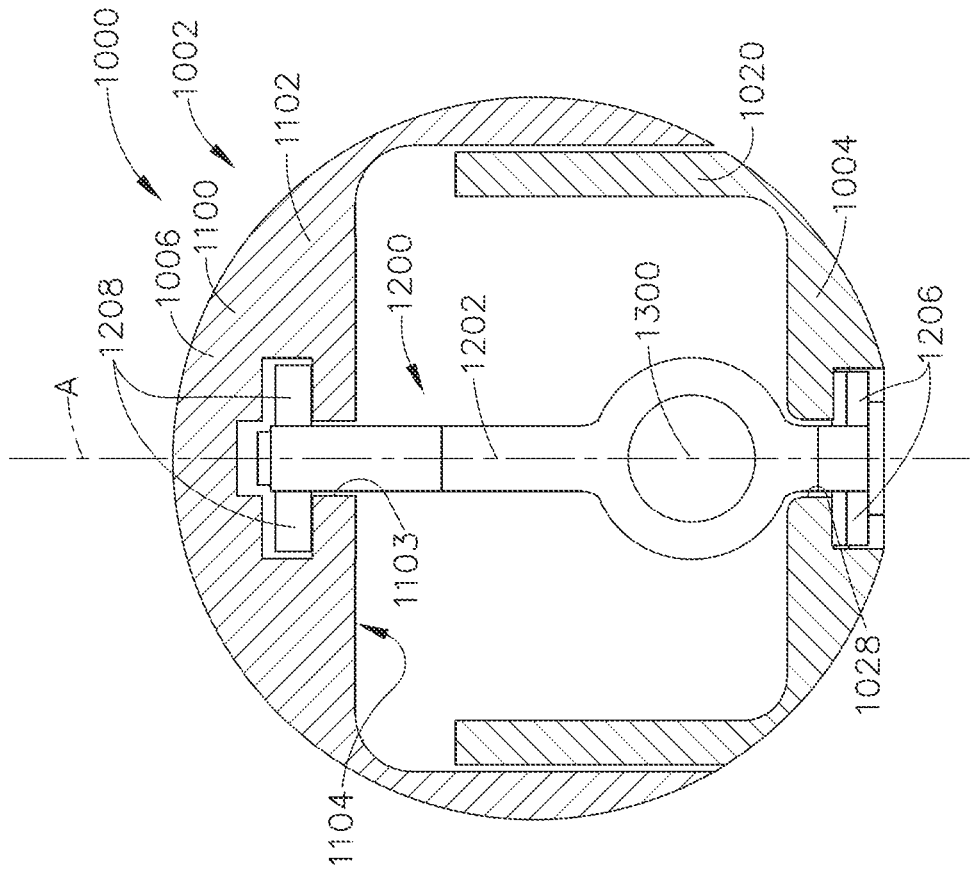
FIG. 90 is a cross-sectional elevational view of the surgical end effector of FIG. 60 in a closed configuration without a staple cartridge installed therein.

In the illustrated exemplary embodiment, rotation of the implement drive shaft 1300 in a first rotary or "firing" direction will cause the firing member 1200 to be driven distally through the staple cartridge 1040 if the firing member 1200 is properly aligned with the elongate slot 1046 in the cartridge body 1042 (FIG. 60), the channel slot 1028 in the elongate channel 1020 and the anvil slot 1103 in the anvil 1100, for example. Referring primarily to FIG. 90, the elongate slot 1046, the channel slot 1028 and/or the anvil slot 1103 can guide the firing member 1200 as it moves along the path through the surgical end effector 1000, for example, during a firing stroke. When the firing member 1200 is in the operable configuration, the channel slot 1028 is configured to receive the foot portion 1206 of the firing member 1200 and the anvil slot 1103 is configured to receive the upper fins 1208 of the firing member 1200, for example. When a portion of the firing member 1200 is positioned in the channel slot 1028 and/or the anvil slot 1103, the firing member 1200 can be aligned or substantially aligned with the axis A. The channel slot 1028 and/or the anvil slot 1103 can guide the firing member 1200 and maintain the alignment of the firing member 1200 with the axis A as the firing member 1200 moves from the initial position to the secondary position relative to the cartridge body 1042, for example.

Figure 89:
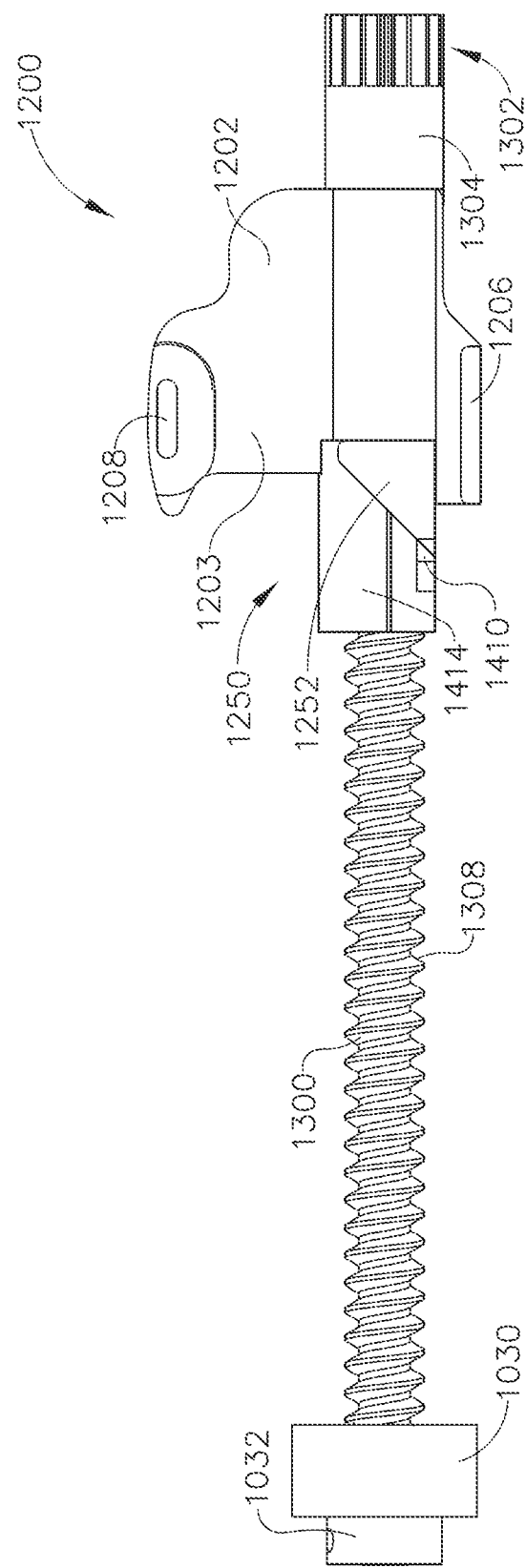
FIG. 89 is a side elevational view of the firing member, implement drive shaft, wedge sled assembly and alignment portion of FIG. 88.

As was briefly discussed above, in various surgical staple cartridge examples, the surgical staples are supported on movable staple drivers supported in the cartridge body. Various exemplary end effector embodiments employ a wedge sled assembly 1250 that is configured to contact the staple drivers as the wedge sled assembly is driven distally through the staple cartridge to drive the staples out of their respective cavities in the cartridge body and into forming contact with the closed anvil. In at least one exemplary embodiment, the wedge sled 1250 is positioned within the staple cartridge 1040. Thus, each new staple cartridge 1040 has its own wedge sled operably supported therein. When the clinician properly seats a new staple cartridge 1040 into the elongate channel, the wedge sled 1250 is configured to straddle the implement drive shaft 1300 and engage the firing member 1200 in the manner illustrated in FIGS. 60, 88 and 89, for example. As can be seen in those Figures, the exemplary wedge sled assembly 1250 can comprise a sled body 1414, a flange 1410, and wedges 1252. The sled body 1414 can be positioned around a portion of the implement drive shaft 1300 when the wedge sled assembly 1250 is positioned in the elongate channel 1020. The sled body 1414 can be structured such that the sled body 1414 avoids contact with the implement drive shaft 1300 when the sled body 1414 is positioned around the implement drive shaft 1300. The sled body 1414 can comprise a contour 1412, for example, that curves over and/or around the implement drive shaft 1300. In such embodiment, for example, a flange 1410 extends between the sled body 1414 and each of the wedges 1252. In addition, the sled body 1414 has a notch 1415 therein that is configured to receive therein a portion of the firing member body 1203. Referring primarily to FIG. 89, the flange 1410 can extend substantially parallel to the foot portion 1206 of the firing member 1200 when the firing member 1200 engages the wedge sled assembly 1250.

When a new staple cartridge 1040 has been properly installed in the elongate channel 1020, initial actuation of the firing member 1200 (e.g., by rotating the implement drive shaft 1300) causes a portion of the firing member body 1203 to enter the notch 1415 in the wedge sled 1250 which thereby results in the alignment of the firing member 1200 with the elongate slot 1046 in the cartridge body 1042 (FIG. 60), the channel slot 1028 in the elongate channel 1020 and the anvil slot 1103 in the anvil 1100 to enable the firing member 1250 to be distally advanced through the staple cartridge 1040. Hence, the wedge sled may also be referred to herein as an "alignment member". If the staple cartridge 1040 has been improperly installed in the elongate channel, activation of the firing member 1200 will not result in the aligning engagement with the notch 1415 in the wedge sled 1250 and the firing member 1200 will remain out of alignment with the channel slot 1028 in the elongate channel 1020 and the anvil slot 1103 in the anvil 1100 to thereby prevent the firing member 1250 from being fired.

After a new staple cartridge 1040 has been properly installed in the elongate channel 1020, the clinician fires the firing member by applying a first rotary motion to the implement drive shaft 1300. Once the firing member 1250 has been distally driven through the staple cartridge 1250 to its distal-most position, a reverse rotary motion is applied to the implement drive shaft 1300 to return the firing member 1250 to its starting position external to the surgical staple cartridge 1040 to enable the spent cartridge to be removed from the elongate channel 1020 and a new staple cartridge to be installed therein. As the firing member 1250 is returned to its starting position, the wedge sled 1250 remains in the distal end of the staple cartridge and does not return with the firing member 1200. Thus, as the firing member 1200 moves proximally out of the staple cartridge 1040 and the anvil slot 1103 in the anvil, the rotary motion of the implement drive shaft 1300 causes the firing member 1200 to pivot slightly into an inoperable position. That is, when the firing member 1200 is in the inoperable position (outside of the cartridge), should the clinician remove the spent cartridge 1040 and fail to replace it with a fresh cartridge containing a new wedge sled 1250 and then close the anvil 1110 and attempt to fire the firing member 1200, because there is no wedge sled present to align the firing member 1200, the firing member 1200 will be unable to advance distally through the elongate channel 1020. Thus, such arrangement prevents the clinician from inadvertently firing the firing member 1200 when no cartridge is present.

In such exemplary embodiment, the firing member 1200 can be substantially aligned with an axis A when the firing member 1200 is oriented in an operable configuration such that the firing member 1200 can move along a path established through the end effector 1000. The axis A can be substantially perpendicular to the staple forming surface 1104 of the anvil 1100 and/or the cartridge deck 1044 of the staple cartridge 1040 (FIG. 60). In other exemplary embodiments, the axis A can be angularly oriented relative to the staple forming surface 1104 of the anvil 1100 and/or the cartridge deck 1044 of the staple cartridge 1040. Further, in at least one exemplary embodiment, the axis A can extend through the center of the surgical end effector 1000 and, in other exemplary embodiments, the axis A can be positioned on either side of the center of the surgical end effector 1000.

Figure 91:
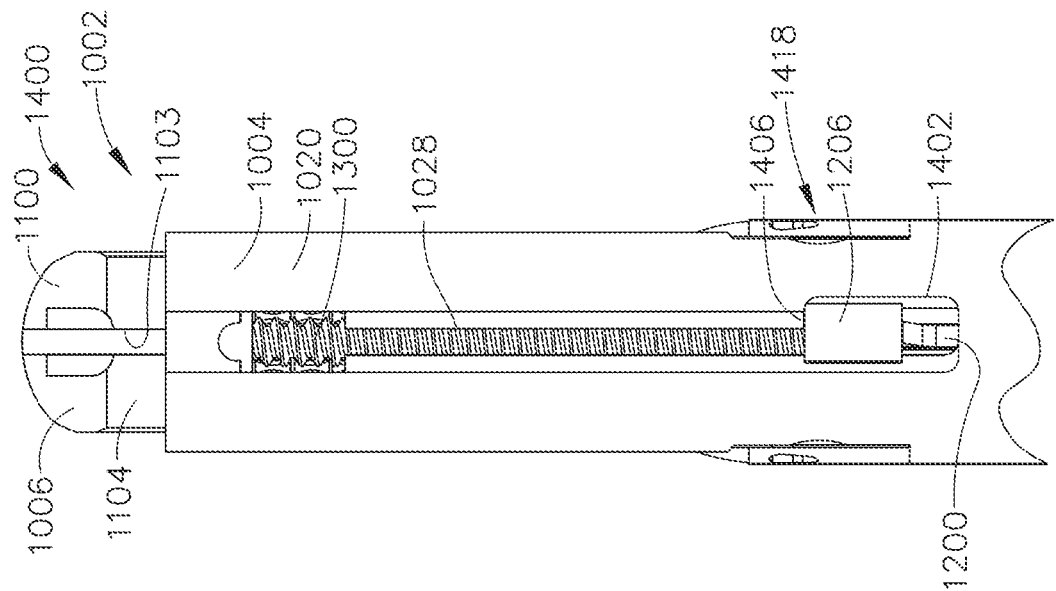
FIG. 91 is a bottom view of a surgical end effector having a firing lockout according to various exemplary embodiments of the present disclosure.

FIGS. 91-97 illustrate one exemplary form of a surgical end effector 1400 that employs a unique and novel firing lockout arrangement. As can be seen in FIGS. 91-95, when the firing member 1200 is in the initial position, the firing member 1200 is in an inoperable configuration which prevents its distal advancement through the end effector due to the misalignment of the firing member 1200 with the channel slot 1028 and the anvil slot 1103. The firing member 1200 may be retained in the inoperable configuration by a firing lockout generally designated as 1418. Referring primarily to FIGS. 91-93, in at least one form, for example, the firing lockout 1418 includes a first lockout groove or notch 1402 that is formed in the elongate channel 1020. In other exemplary embodiments, however, the first lockout notch 1402 can form an opening in the first jaw 1004, the second jaw 1006, the elongate channel 1020 and/or the anvil 1100, for example. In various exemplary embodiments, the first lockout notch 1402 is located in the surgical end effector 1400 such that the first lockout notch 1402 retainingly engages a portion of the firing member 1200 when the firing member 1200 is in the inoperable configuration. The first lockout notch 1402 can be near, adjacent to, and/or connected to the channel slot 1028 in the elongate channel 1020, for example. Referring primarily to FIG. 91, the channel slot 1028 can have a slot width along the length thereof. In at least one exemplary embodiment, the first lockout notch 1402 can extend from the channel slot 1028 such that the combined width of the channel slot 1028 and the first lockout notch 1402 exceeds the slot width of the channel slot 1028. As can be seen in FIG. 91, when the firing member 1200 is in the inoperable configuration, the foot portion 1206 of the firing member 1200 extends into the first lockout notch 1402 to thereby prevent its inadvertent distal advancement through the elongate channel 1020.

When a new staple cartridge 1040 has been properly installed in the elongate channel 1020, initiation of the firing stroke causes the firing member to engage the wedge sled 1250 positioned within the staple cartridge 1040 which moves the firing member 1200 into driving alignment with the elongate slot 1046 in the cartridge body 1042, the channel slot 1028 in the elongate channel 1020 and the anvil slot 1103 in the anvil 1100 to enable the firing member 1250 to be distally advanced therethrough. As the firing member 1200 moves from the initial position to the secondary position relative to the staple cartridge 1040, the firing member 1200 can move past the first lockout notch 1402, for example. The first lockout notch 1402 can have a length of approximately 0.25 inches, for example. In some other exemplary embodiments, the first lockout notch 1402 can have a length of approximately 0.15 inches to approximately 0.25 inches, for example, or of approximately 0.25 inches to approximately 1.0 inch, for example.

Figure 94:
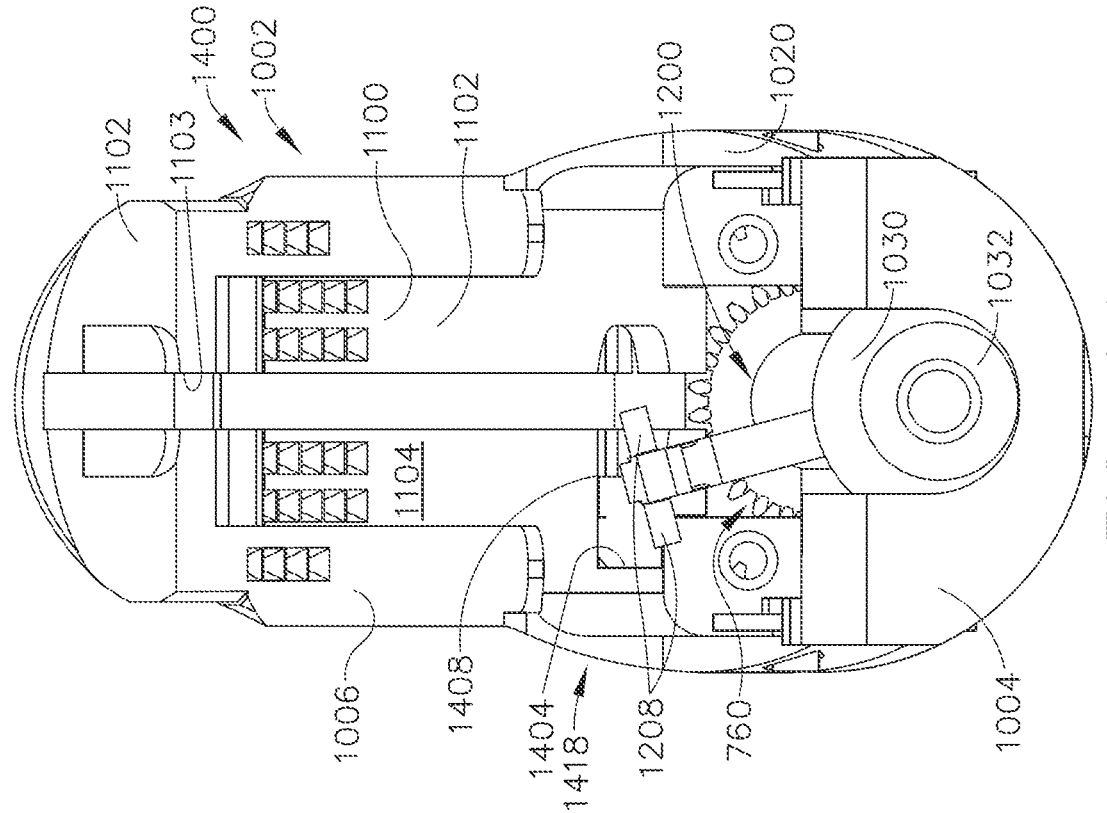
FIG. 94 is an end elevational view of the surgical end effector of FIG. 91 in an open and inoperable configuration.
Figure 96:
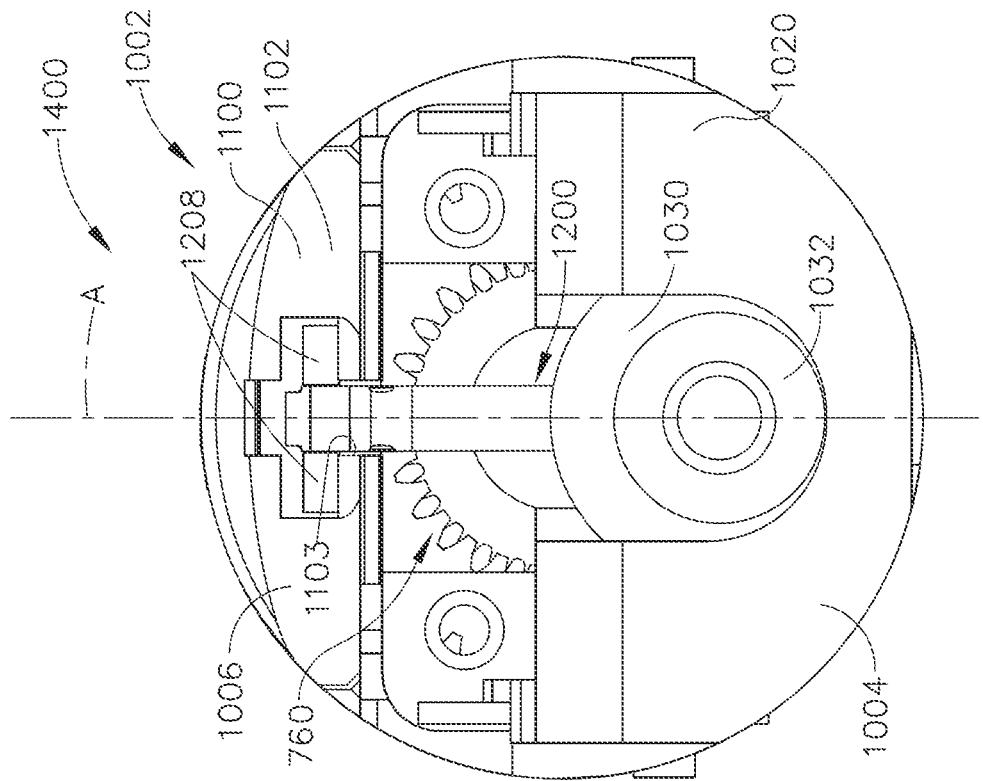
FIG. 96 is an elevational, cross-sectional view of the surgical end effector of FIG. 91 in a closed and operable configuration having a wedge sled assembly and an alignment portion in a first set of positions therein.
Figure 97:
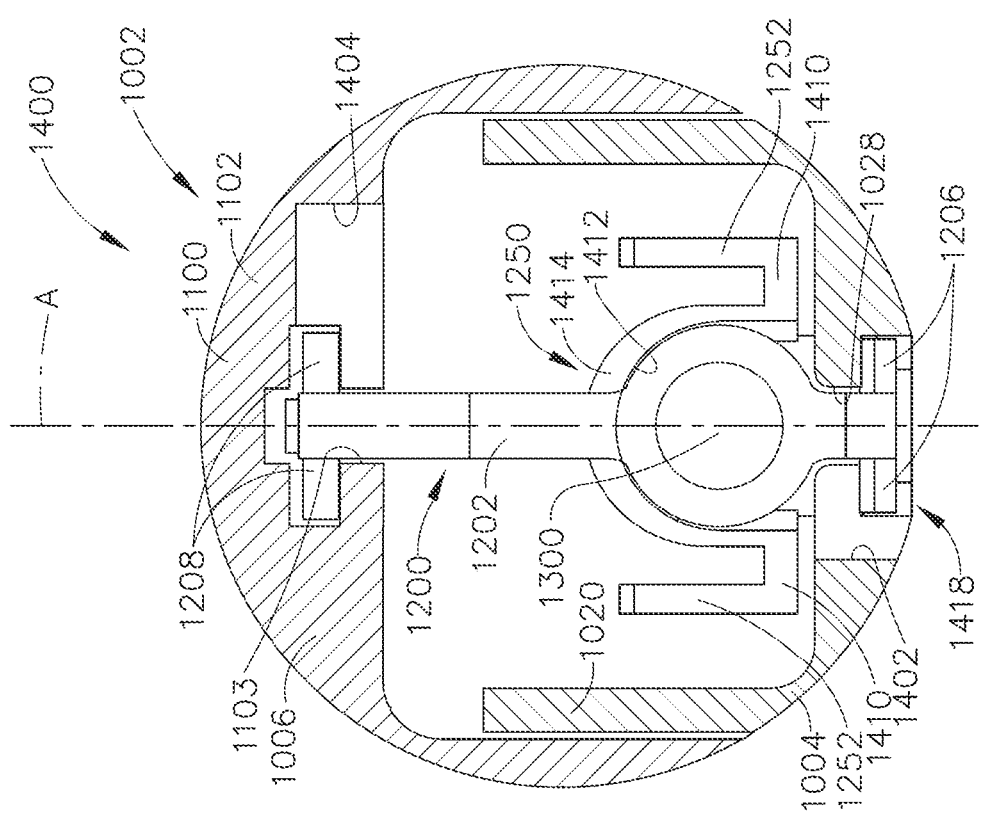
FIG. 97 is another end elevational view of the surgical end effector of FIG. 91 in a closed and operable configuration.
Figure 98:
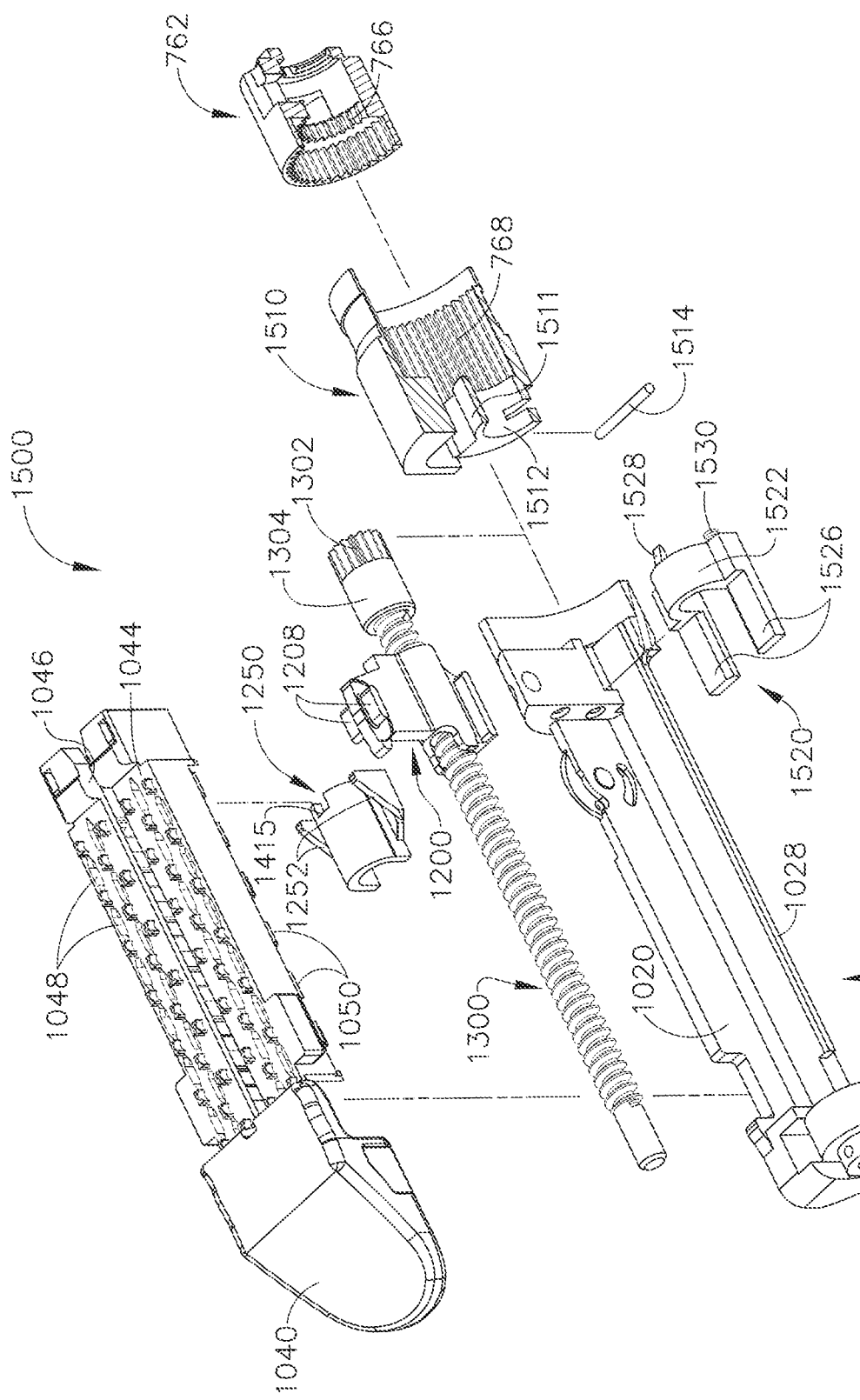
FIG. 98 is an exploded perspective view of a surgical end effector with some components thereof shown in cross section and other components thereof omitted for clarity.
Figure 100:
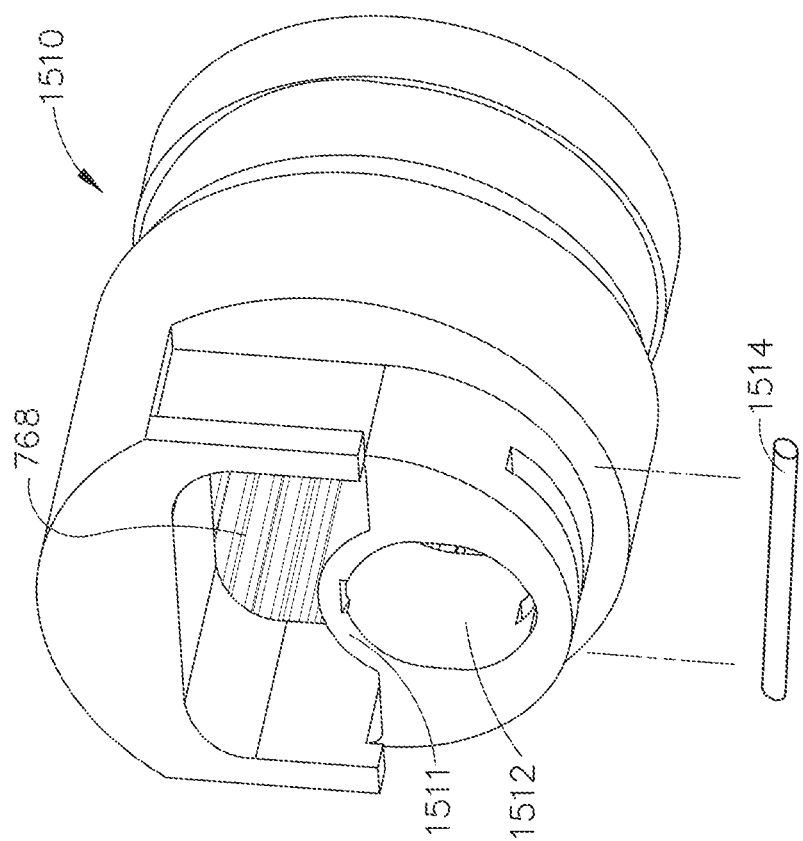
FIG. 100 is a perspective view of the end effector drive housing depicted in FIG. 98.

Referring primarily to FIGS. 93 and 94, the surgical end effector 1400 can be structured to accommodate the upper fins 1208 of the firing member 1200 when the firing member 1200 is in the inoperable configuration. For example, the firing lockout 1418 can include a second lockout groove or notch 1404 in the anvil 1100. In the illustrated exemplary embodiment, for example, the second lockout notch 1404 can be near, adjacent to, and/or connected to the anvil slot 1103 in the anvil 1100, for example. The anvil slot 1103 can have a slot width along the length thereof. In at least one exemplary embodiment, the second lockout notch 1404 can extend from the anvil slot 1103 such that the combined width of the anvil slot 1103 and the second lockout notch 1404 exceeds the slot width of the anvil slot 1103. The second lockout notch 1404 can extend a length or distance in the surgical end effector 1400. The firing member 1200 can be structured to engage the second lockout notch 1404 along the length thereof when the firing member 1200 is in the inoperable configuration. As the firing member 1200 moves from the initial position to the secondary position relative to the staple cartridge 1040, the firing member 1200 can move past the second lockout notch 1404, for example. The second lockout notch 1404 can have a length of approximately 0.25 inches, for example. In some other exemplary embodiments, the second lockout notch 1404 can have a length of approximately 0.15 inches to approximately 0.25 inches, for example, or of approximately 0.25 inches to approximately 1.0 inch, for example. Referring primarily to FIG. 93, the first lockout notch 1402 can extend from the channel slot 1028 in a first direction X and the second lockout notch 1404 can extend from the anvil slot 1103 in a second direction Y. In at least one exemplary embodiment, the first direction X can be substantially laterally opposite to the second direction Y. In such exemplary embodiments, the foot portion 1206 of the firing member 1200 can pivot into the first lockout notch 1402 and the upper fins 1208 of the firing member 1200 can pivot into the second lockout notch 1404 when the firing member 1200 moves to the inoperable configuration.

Referring primarily to FIGS. 92-94, when the firing member 1200 is oriented in the inoperable configuration, corresponding portions of the firing member 1200 engage the first and second lockout notches 1402, 1404. The firing member 1200 can be positioned at least partially within the first and second lockout notches 1402, 1404 when the firing member 1200 is in the inoperable configuration. The firing member 1200 can shift into the first and second lockout notches 1402, 1404 when the firing member 1200 moves to the inoperable configuration. Further, when the firing member 1200 is oriented in the operable configuration, the firing member 1200 can disengage the first and second lockout notches 1402, 1404.

Figure 95:
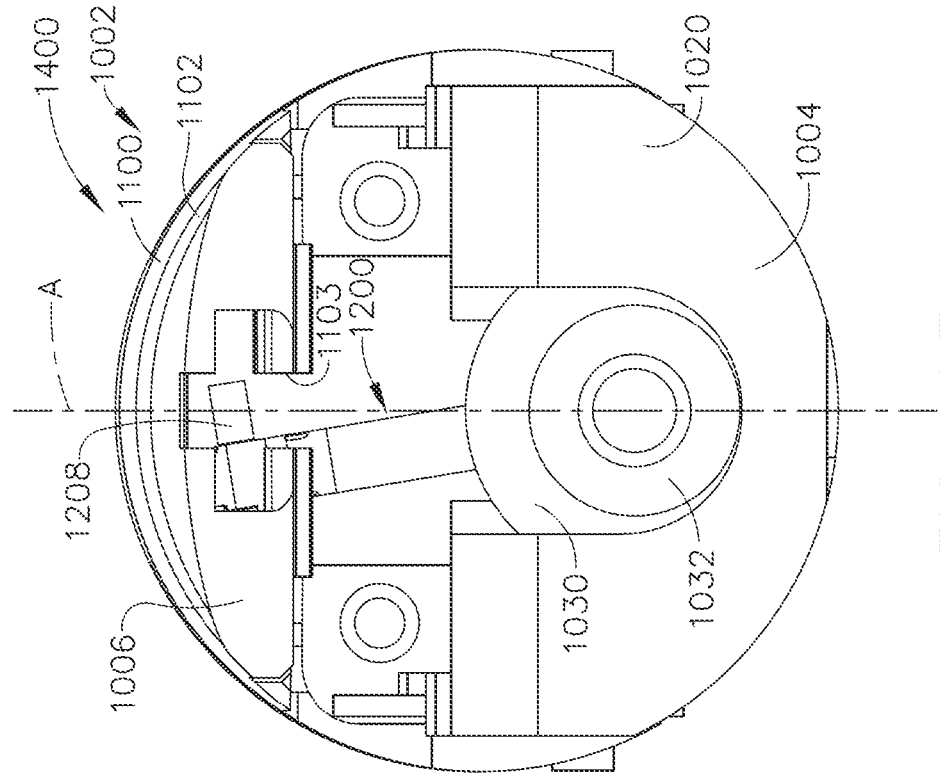
FIG. 95 is an end elevational view of the surgical end effector of FIG. 91 in a closed and inoperable configuration.

A portion or portions of the surgical end effector 1400 can block the firing member 1200 and limit or prevent movement of the firing member 1200 through the surgical end effector 1400 when the firing member 1200 is oriented in the inoperable configuration (see, e.g., FIG. 95). For example, the first jaw 1004, the second jaw 1006, the elongate channel 1020 and/or the anvil 1100 can be configured to block the firing member 1200 when it is in the operable configuration. In some exemplary embodiments, the first lockout notch 1402 has a first blocking surface or edge 1406 (FIGS. 91 and 92) formed thereon and the second lockout notch 1404 has a second blocking surface or edge 1408 formed thereon (FIG. 94). Attempts to fire the firing member 1200 while the firing member 1200 is in the inoperable configuration will result in corresponding portions of the firing member 1200 contacting one or both of the first and second blocking surfaces 1406, 1408 to prevent the firing member 1200 from moving from the initial position towards the secondary positions. In at least one exemplary embodiment, the surgical end effector 1400 need not have both the first blocking edge 1406 and the second blocking edge 1408.

FIGS. 97-104 illustrate another exemplary surgical end effector embodiment 1500 that employs another exemplary firing lockout arrangement. For example, as can be seen in those Figures, a surgical end effector 1500 can comprise the elongate channel 1020, the implement drive shaft 1300, and the firing member 1200. The surgical end effector 1500 can also comprise an end effector drive housing 1510 (see, e.g. FIG. 100). Similar to the end effector drive housing 1010 described herein, the end effector drive housing 1510 can comprise a bearing sleeve 1511 and the third ring gear or housing drive member 768. The bearing sleeve 1511 can be structured such that the bearing segment 1304 of the implement drive shaft 1300 can be moveably positioned in the bearing sleeve 1511. The bearing segment 1304 can move in the bearing sleeve 1511 as the implement drive shaft 1300 moves between an inoperable position and an operable position, as described herein. The bearing sleeve 1511 can comprise a bore 1512 having an elongated cross-section such as, for example, a cross-sectional shape comprising an oval, an ellipse and/or semicircles having longitudinal and/or parallel sides therebetween. In such exemplary embodiments, the bearing segment 1304 can be positioned against or near a first side of the bore 1512 such as, for example, a first semicircle, when the implement drive shaft 1300 is in the inoperable position. Further, the bearing segment 1304 can be positioned against or near a second side of the bore 1512 such as, for example, a second semicircle, when the implement drive shaft 1300 is in the operable position.

The implement drive shaft 1300 can be moveable between the inoperable position and the operable position. As described herein, a biasing member 1520 and/or a portion of the staple cartridge 1040 can move the implement drive shaft 1300 between the inoperable position and the operable position, for example. In the illustrated embodiment and others, the implement drive gear 1302 of the implement drive shaft 1300 can be engaged with the third ring gear 768 of the end effector drive housing 1510 when the implement drive shaft 1300 is in the operable position. The implement drive gear 1302 can be an external gear, for example, and the third ring gear 768 can be an internal gear, for example. The implement drive gear 1302 can move into engagement with the third ring gear 768 when the implement drive shaft 1300 moves from the inoperable position to the operable position. Further, the implement drive gear 1302 can be disengaged from the third ring gear 768 when the implement drive shaft 1300 is in the inoperable position. In at least one exemplary embodiment, the implement drive gear 1302 can move out of engagement with the third ring gear 768 when the implement drive shaft 1300 moves from the operable position to the inoperable position. Similar to other exemplary embodiments described herein, when the implement drive shaft 1300 is engaged with the third ring gear 768 in the end effector drive housing 1510, the drive system 750 (FIG. 61) can drive the firing member 1200 through the elongate channel 1020 of the surgical end effector 1500, for example, during a firing stroke.

Referring primarily to FIGS. 101 and 102, the bearing segment 1304 can be positioned against the first side of the bore 1512 of the bearing sleeve 1511 when the implement drive shaft 1300 is in the inoperable position. A retaining pin 1514 (FIGS. 98, 100, 101 and 103) can be structured to bias the bearing segment 1304 against the first side of the bore 1512 such that the implement drive shaft 1300 is held in the inoperable position, for example, and the implement drive gear 1302 is held out of engagement with the third ring gear 768, for example. In some exemplary embodiments, the retaining pin 1514 can be spring-loaded such that retaining pin 1514 exerts a force on the bearing segment 1304 to move the implement drive shaft 1300 towards the inoperable position. The implement drive shaft 1300 can remain in the inoperable position until another force overcomes the force exerted by the retaining pin 1514 to move the implement drive shaft 1300 towards the operable position, for example, and the implement drive gear 1302 into engagement with the third ring gear 768, for example.

Referring primarily to FIGS. 103 and 104, the bearing segment 1304 can be positioned against the second side of the bore 1512 of the bearing sleeve 1511 when the implement drive shaft 1300 is in the operable position. In various exemplary embodiments, the force exerted by the retaining pin 1514 (FIGS. 98, 100, 101 and 103) can be overcome to move the bearing segment 1304 against the second side of the bore 1512 such that the implement drive shaft 1300 is in the operable position, for example, and the implement drive gear 1302 is engaged with the third ring gear 768, for example. As described herein, the biasing element 1520 can exert a force on the bearing segment 1304 that overcomes the force exerted by the retaining pin 1515, for example.

The surgical end effector 1500 can comprise the biasing element 1520, which can be moveable between a first set of positions (see, e.g., FIG. 103) and a second set of positions (see, e.g., FIG. 101). The second set of positions can be distal to the first set of positions relative to the end effector drive housing 1510. When the biasing element 1520 is in the first set of positions, the biasing element 1520 can be structured to move the implement drive shaft 1300 to the operable position, for example. When the biasing element 1520 is in the second set of positions, the biasing element 1520 can release the implement drive shaft 1300 such that the implement drive shaft can return to the inoperable position, for example.

The biasing element 1520 can be an independent element positionable in the surgical end effector 1500. The biasing element 1520 can be moveably retained in the surgical end effector 1500, for example, and can be operably engageable with the staple cartridge 1040, for example. The staple cartridge 1040 can comprise the biasing element 1520. In some exemplary embodiments, the biasing element 1520 can be integrally formed with the wedge sled assembly 1250 of the staple cartridge 1040, for example, and the biasing element 1520 can be moveably retained in the staple cartridge 1040, for example. In such exemplary embodiments, the biasing element 1520 can move through the elongate channel 1020 as the wedge sled assembly 1250 and/or the firing member 1200 moves through the elongate channel 1020, for example, during a firing stroke.

Figure 99:
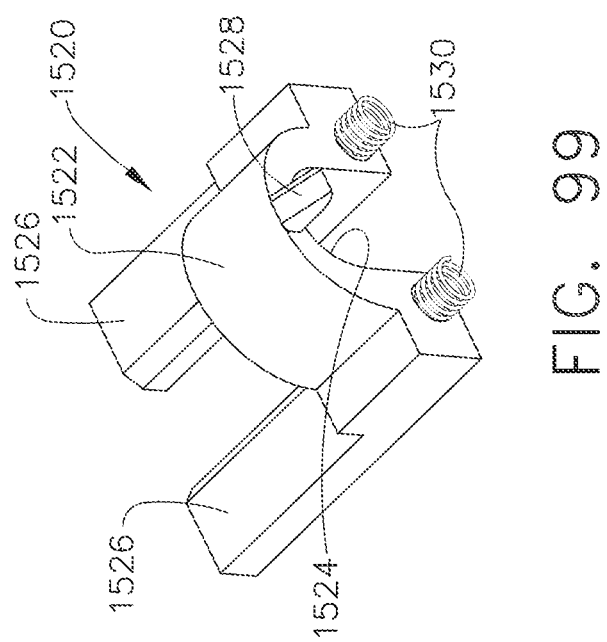
FIG. 99 is a perspective view of the biasing element depicted in FIG. 98.

Referring primarily to FIG. 99, the biasing element 1520 can comprise a biasing body 1522 and legs 1526 extending from the biasing body 1522. The biasing body 1522 can be positioned around a portion of the implement drive shaft 1300 in the surgical end effector 1500. In some exemplary embodiments, the biasing body 1522 can be structured such that the biasing body 1522 avoids contact with the implement drive shaft 1300 when the biasing body 1522 is positioned around the implement drive shaft 1300. The biasing body 1522 can comprise a contour 1524, for example, that curves over and/or around the implement drive shaft 1300. The legs 1526 can extend along a portion of the elongate channel 1020 and/or on either side of the implement drive shaft 1300. The biasing element 1520 can also comprise at least one extension or wedge 1528. As described herein, the wedge 1528 can moveably engage the bearing sleeve 1511 and/or the bearing segment 1304 to move the implement drive shaft into the operable position. The biasing element 1520 can also comprise at least one spring 1530. The spring 1530 can be deformable between an initial configuration (FIG. 101) and deformed configurations (FIG. 103), for example. The spring 1530 can hold the biasing element 1520 in the first set of positions relative to the end effector drive housing 1510 until a force deforms the spring 1530 from the initial configuration to a deformed configuration. When the spring 1530 moves from the initial configuration to the deformed configuration, the biasing element 1520 can move from the second set of positions to the first set of positions relative to the end effector drive housing 1510.

Referring primarily to FIG. 101, before the insertion of the staple cartridge 1040 (FIG. 103) into the elongate channel 1020, the spring 1530 can be in the initial configuration, for example, and the biasing element 1520 can be in the second set of positions, for example. The retaining pin 1514 can hold the bearing segment 1304 against the first side of the bore 1512, for example. In such exemplary embodiments, the implement drive shaft 1300 can be held in the inoperable position by the retaining pin 1514.

Referring now to FIG. 103, installation of the staple cartridge 1040 in the elongate channel 1020 moves the biasing element 1520 proximally against the force of springs 1530 into a first set of positions wherein the wedge 1528 moveably engages the bearing sleeve 1511 and the bearing segment 1304 to bias the bearing segment 1304 and the implement drive gear 1302 of the implement drive shaft 1300 into meshing engagement with the third ring gear 768. Thereafter, actuation of the firing drive system as described herein will result in the firing of the firing member 1200. In some exemplary embodiments, a portion of the staple cartridge 1040 is configured to directly contact the biasing element 1520 to move the biasing element 1520 to the first set of positions. In other exemplary embodiments, a portion of the staple cartridge 1040 is configured to contact another element in the surgical end effector 1500 such as, for example, the firing member 1200, to operable move the biasing element 1520 to the first set of positions. In still other exemplary embodiments, the staple cartridge 1040 has the biasing element 1520 integrally formed therewith.

In various exemplary embodiments, the biasing element 1520 can move through the elongate channel 1020 of the surgical end effector 1500 as the firing member 1200 and/or the wedge sled assembly 1250 are driven through the elongate channel 1020 by the implement drive shaft 1300, for example, during a firing stroke, as described herein. The biasing element 1520 can be integrally formed with and/or fixed to the wedge sled assembly 1250 of the staple cartridge 1040. In such exemplary embodiments, when the staple cartridge 1040 is initially seated in the elongate channel 1020, the wedge sled assembly 1250 and the biasing element 1520 can be positioned in an initial position relative to the staple cartridge 1040 and/or the elongate channel 1020. The initial position of the biasing element 1520 can correspond to the first set of positions such that the biasing element 1520 moveably engages the bearing sleeve 1511 of the end effector drive housing 1510 to move the implement drive shaft 1300 into the operable position, as described herein. During the firing stroke, the wedge sled assembly 1250 and the biasing element 1520 can be moved away from the initial or first set of positions, for example. The biasing element 1520 can move to the second set of positions, for example. When the biasing element 1520 moves past the first set of positions and into the second set of positions, the biasing element 1520 may no longer engage the bearing sleeve 1511 of the end effector drive housing 1510 to hold the implement drive shaft 1300 in the operable configuration. Though the biasing element 1520 may not bias the implement drive gear 1302 of the implement drive shaft 1300 into engagement with the third ring gear 768 when the biasing element 1520 moves into the second set of positions, the channel slot 1028, the anvil slot 1103, and/or the elongate slot 1046 in the staple cartridge 1040 serve to guide the firing member 1200 in a firing orientation that retains the implement drive gear 1302 of the implement drive shaft 1300 in meshing engagement with the third ring gear 768 and thereby prevents the implement drive shaft 1300 from returning to the inoperable position during the firing stroke.

In at least one exemplary embodiment, the firing member 1200 and/or the implement drive shaft 1300 can drive the wedge sled assembly 1250 and/or the biasing element 1520 to the second set of positions during the firing stroke. In various exemplary embodiments, upon completion of the firing stroke, the firing member 1200 can return to the initial position, however, the wedge sled assembly 1250, including the biasing element 1520, can remain in the second set of positions, for example. The firing member 1200 can return to a proximal position in the surgical end effector 1500, for example, and the biasing element 1520 can remain in a distal position in the surgical end effector 1500, for example. When the firing member 1200 is in the initial position and the biasing element 1520 is in the second set of positions, the bearing segment 1304 of the implement drive shaft 1300 can shift in the bearing sleeve 1511 such that the implement drive shaft 1300 moves into the inoperable position, for example, and the implement drive gear 1302 moves out of engagement with the third ring gear 768, for example. In various exemplary embodiments, the implement drive shaft 1300 can remain in the inoperable position until the biasing element 1520 is drawn back into the first set of positions and/or until a replacement biasing element 1520 is positioned in the first set of positions, for example. For example, the spent staple cartridge 1040 is removed from the elongate channel 1020 and replaced with a replacement staple cartridge 1040, which can comprise a biasing element 1520 located in its first positions. When the replacement staple cartridge 1040 is positioned in the elongate channel 1020, the biasing element 1520 thereof shifts the implement drive gear 1302 into engagement with the third ring gear 768, for example, and into the operable position, for example. In such exemplary embodiments, the surgical end effector 1500 can be prevented from being re-fired when no cartridge 1040 or a spent cartridge 1040 is seated in the elongate channel 1020. In addition, if the staple cartridge has not been properly seated in the elongate channel 1020 such that the biasing element 1520 has not moved the implement drive shaft 1300 into meshing engagement with the third ring gear 768, the firing member 1200 cannot be fired.

As described above, a surgical instrument system can include a surgical housing, replaceable end effector assemblies that can be connected to the surgical housing for use during a surgical technique and then disconnected from the housing after they have been used, and a motor and/or an actuator configured to fire the end effectors. In various circumstances, a surgeon can choose from several different replaceable end effectors for use during a surgical procedure. For example, a surgeon may first select a first replaceable end effector configured to staple and/or incise a patient's tissue that includes a staple cartridge length of approximately 15 millimeters ("mm"), for example, to make a first cut in the patient tissue. In such an embodiment, a cutting blade and/or a staple-driving sled can be advanced along the approximately 15 mm length of the staple cartridge by a drive screw in order to cut and staple approximately 15 mm of patient tissue. The surgeon may then select a second replaceable end effector, also configured to staple and/or incise patient tissue, which can include a staple cartridge length of approximately 30 mm to make a second cut in the patient's tissue. In such an embodiment, a cutting blade and/or a staple-driving sled can be advanced along the approximately 30 mm length of the staple cartridge by a drive screw to cut and staple approximately 30 mm of the patient's tissue. The surgeon may also select a replaceable end effector configured to staple and/or incise patient tissue that includes a staple cartridge length of approximately 45 mm to make a cut in the patient's tissue, for example. In such an embodiment, a cutting blade and/or a staple driving sled can be advanced along the approximately 45 mm length of the staple cartridge by a drive screw to cut and staple approximately 45 mm of the patient's tissue. The surgeon may also select a replaceable end effector, which can also be configured to staple and/or incise patient tissue, which includes a staple cartridge length of approximately 60 mm to make a cut in the patient's tissue, for example. In such an embodiment, a cutting blade and/or a staple driving sled can be advanced along the approximately 60 mm length of the staple cartridge by a drive screw to cut and staple approximately 60 mm of the patient's tissue. The 15 mm, 30 mm, 45 mm, and/or 60 mm lengths of the end effectors discussed above are exemplary. Other lengths can be used. In certain embodiments, a first end effector can include a staple cartridge having a length of x, a second end effector can include a staple cartridge having a length of approximately 2*x, a third end effector can include a staple cartridge having a length of approximately 3*x, and a fourth end effector can include a staple cartridge having a length of approximately 4*x, for example.

In some surgical instrument systems utilizing replaceable end effectors having different lengths, the drive screws in each of the different replaceable end effectors may be identical except that the length of each drive screw may be different in order to accommodate the different length of the associated replaceable end effector. For example, a replaceable end effector comprising a 30 mm staple cartridge may require a drive screw which is longer than the drive screw of a replaceable end effector comprising a 15 mm staple cartridge. In each instance of such surgical instrument systems, however, each drive screw which utilizes the same thread pitch and/or thread lead, described in greater detail below, may require the motor to rotate the drive shaft a different number or revolutions depending on the length of the end effector being used in order for each end effector to be fully fired. For instance, a drive screw providing a 30 mm firing stroke may require twice as many revolutions in order to be fully actuated as compared to a drive screw providing a 15 mm firing stroke. In such surgical instrument systems, electronic communication between the surgical housing and the replaceable end effector can be utilized to ensure that the electric motor in the surgical housing turns a correct number of revolutions for the length of the attached replaceable end effector. For example, a replaceable end effector may include an electronic circuit that can be identified by the surgical instrument system so that surgical instrument system can turn the motor a correct number of revolutions for the attached end effector. In addition to or in lieu of the above, the replaceable end effector may include a sensor that senses when an end effector has been completely actuated. In such an embodiment, the sensor can be in signal communication with a controller in the housing configured to stop the motor when the appropriate signal is received. While suitable for their intended purposes, such electronic communication between the surgical housing and the replaceable end effector may increase the complexity and/or cost of such surgical instrument systems.

As outlined above, end effectors having different lengths can be used on the same surgical instrument system. In the surgical instrument systems described above, replaceable end effectors having different firing lengths include drive screws that revolve a different number of times to accommodate the different firing lengths. In order to accommodate the different number of revolutions required for different drive screws, the motor driving the drive screw is operated for a longer duration or a shorter duration, and/or a larger number of revolutions or a smaller number of revolutions, depending on whether a longer firing length or a shorter firing length is needed. Embodiments of replaceable end effectors described below enable a surgical instrument system comprising a motor configured to turn a fixed or set number of revolutions to actuate end effectors having different firing lengths. By operating the motor a fixed number of revolutions, the need for the surgical instrument system to identify the length of the end effector may not be necessary. Each end effector in the embodiments described below includes a drive screw with a thread pitch and/or thread lead that enables an actuating portion of an end effector, such as a cutting blade, for example, to travel the full length of a particular end effector in the fixed number of revolutions of the motor.

Figure 105:
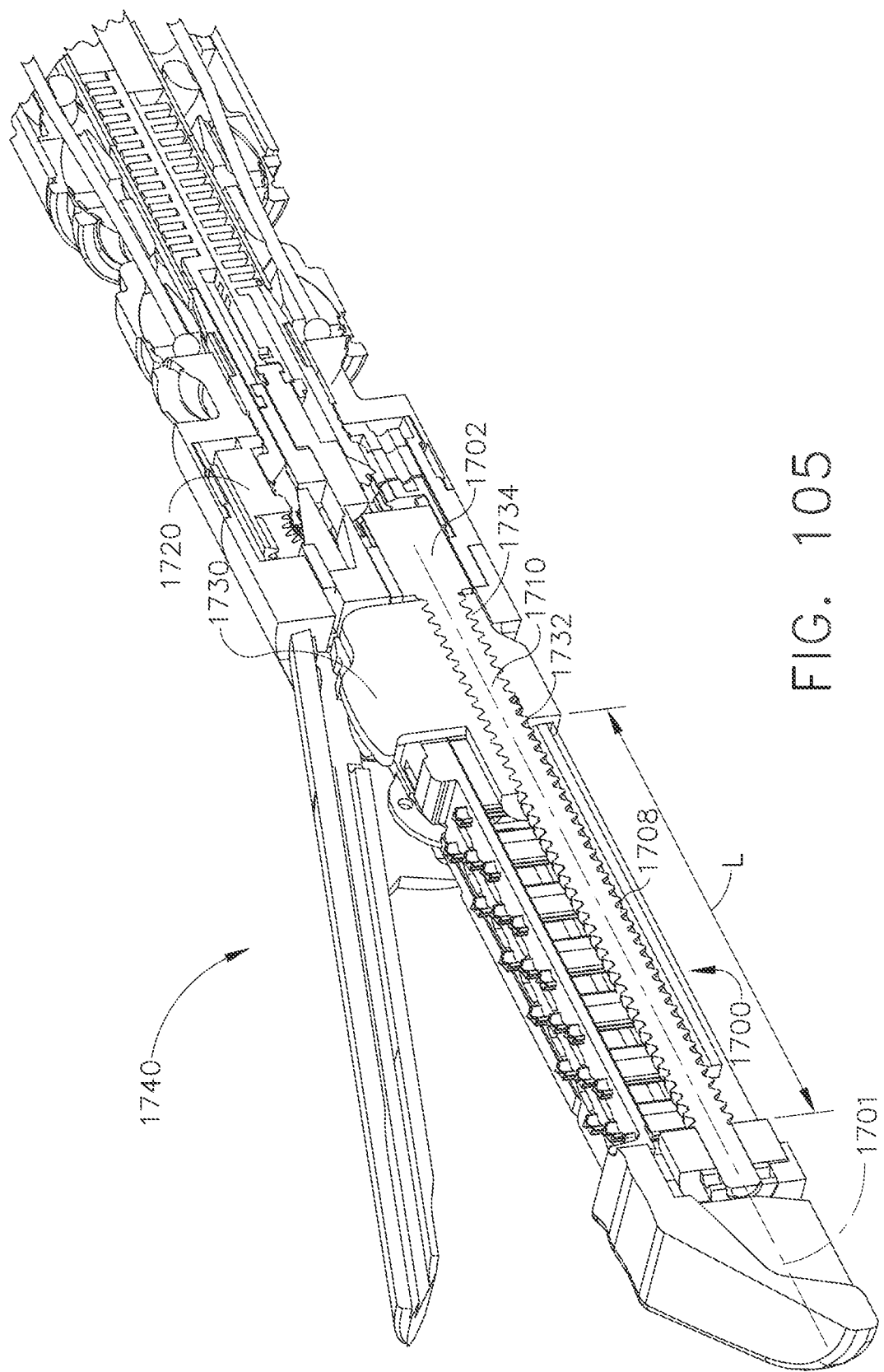
FIG. 105 is a cross-sectional perspective view of an end effector for a surgical instrument comprising a drive screw configured to drive a firing member of the end effector.

Referring to FIG. 105, a drive screw 1700 can be rotated in a first direction to move a cutting blade 1730 of an end effector 1740 in a distal direction indicated by arrow E. In use, the drive screw 1700 can be rotated a fixed or set number of times to advance the cutting blade 1730 a full firing length, indicated by length L in FIG. 105. For each revolution of the drive screw 1700, in certain embodiments, the cutting blade 1730 can be moved in the direction of arrow E by an amount equal to the thread pitch, thread lead, and/or distance between adjacent windings of thread 1708 on the drive screw 1700, described below in greater detail. In various embodiments, a first drive screw can include a first set of characteristics that defines a first firing length while a second drive screw can include a second set of characteristics that defines a second firing length wherein the first set of characteristics can be different than the second set of characteristics.

Now referring to FIGS. 106A, 107, 108A, and 109A, further to the above, the distance between thread windings on a drive screw can be proportional to the angle of threads on the drive screw. Put differently, the angle at which threads are arranged on a drive screw can be a characteristic of a drive screw that defines the thread pitch and/or thread lead of the drive screw. A longer drive screw for use in a longer end effector can utilize a larger thread pitch and/or thread lead than a shorter drive screw for use in a shorter end effector in embodiments where the drive screws, and a motor driving the drive screws, turn a fixed number of revolutions. The drive screw 1700 in FIG. 106A includes a single thread A arranged at an angle α relative to the longitudinal axis 1701 on the drive screw 1700 wherein the thread A defines a thread pitch and/or thread lead having a length X. FIG. 106B shows a cross-sectional view of the drive screw 1700 and the single thread A. In certain embodiments, the drive screw 1700 may include more than one thread, as described in greater detail below.

FIG. 107A shows a drive screw 1700' which can include a first thread A' and a second thread B'. FIG. 107B shows a cross-sectional view of the drive screw 1700' wherein the first thread A' and the second thread B' are positioned approximately 180° out of phase with each other on the drive screw 1700'. In various embodiments, a drive screw with a first thread A' and a second thread B' can increase the number of threads per unit length compared to a drive screw using a single thread A' or B'. Where a drive screw includes more than one thread, the distance from a winding of a first thread to an adjacent winding of a second thread is referred to as "thread pitch." The distance from one winding of a thread to the next winding of the same thread is referred to as "thread lead." For a drive screw with a single thread, the thread pitch and the thread lead are the same. For example, and with reference to FIG. 107A, the distance from a winding of thread A' to an adjacent winding of thread B' defines the thread pitch of the drive screw 1700'. The distance from a winding of thread A' to the next winding of thread A' defines the thread lead of the drive screw 1700'. Thus, the thread lead of the drive screw 1700' in FIG. 107A is equal to X' and the thread pitch is equal to X'/2. The drive screw 1700 shown in FIGS. 106A and 106B has a single thread and therefore the thread pitch and thread lead are both equal to X. The thread lead of a drive screw determines the length that a firing member, such as a cutting blade 1730 and/or a staple driver, for example, will travel for a single revolution of the drive screw.

Returning to FIG. 107A, the first thread A' and the second thread B' each are arranged at an angle β relative to the longitudinal axis 1701 of the drive screw 1700'. Angle β is less than angle α and the thread lead X' of the drive screw 1700' in FIG. 107A is greater than the thread lead X of the drive screw 1700 shown in FIG. 106A. For a single rotation of the drive screw 1700', a cutting blade will move a length X' along the drive screw 1700'. For example, the thread lead X' can be double the thread pitch or thread lead X of the drive screw 1700 shown in FIG. 106A wherein, as a result, a cutting blade engaged with the drive screw 1700' of FIG. 107A will move twice the distance for a single revolution of drive screw 1700' as would a cutting blade engaged with the drive screw 1700 of FIG. 106A.

FIG. 108A shows a drive screw 1700" which can include a first thread A", a second thread B", and a third thread C" each extending at an angle γ relative to the longitudinal axis 1701 of the drive screw 1700". FIG. 108B is a cross-sectional view of the drive screw 1700" and shows the threads A", B", and C" arranged approximately 120° out of phase. The angle γ is smaller than the angle β in FIG. 107A and the thread lead X" of the drive screw 1700" in FIG. 108A is greater than the thread lead X' of the drive screw 1700' shown in FIG. 107A. Similarly, FIG. 109A shows a drive screw 1700'" which can include a first thread A'", a second thread B'", a third thread C'", and a fourth thread D'", each of which extends at an angle δ relative to the longitudinal axis Z of the drive screw 1700'". FIG. 109B is a cross-sectional view of the drive screw 1700'" and shows the threads arranged approximately 90° out of phase. The angle δ is smaller than angle γ and the thread lead X'" of the drive screw 1700'" is larger than that of drive screw 1700" in FIG. 108A.

An exemplary surgical instrument system may include a housing and a motor in the housing configured to turn a fixed number of revolutions that results in a drive screw of a connected replaceable end effector turning 30 revolutions, for example. The surgical instrument system can further include a plurality of replaceable surgical stapler end effectors, wherein each of the end effectors can include a cutting blade and/or staple driver driven by the drive screw, for example. In at least one such embodiment, a first replaceable end effector can include a staple cartridge having a length of 15 mm, for example. The drive screw 1700 shown in FIGS.

2A and 2B can be used in the first replaceable end effector. The thread lead X can be set to 0.5 mm, for example, so that the cutting blade and/or staple driver can travel the 15 mm length of the staple cartridge in the 30 revolutions of the drive screw 1700. A second replaceable end effector can include a staple cartridge having a length of 30 mm, for example, and a drive screw, such as drive screw 1700" illustrated in FIGS. 107A and 107B, for example. The thread lead X' of the drive screw 1700' can be set to 1.0 mm, for example, so that the cutting blade and/or staple drive can travel the 30 mm length of the staple cartridge in the 30 revolutions of the drive screw 1700'. Similarly, a third replaceable end effector with a staple cartridge having a length of 45 mm, for example, can include a drive screw, such as drive screw 1700" in FIGS. 108A and 108B, having a thread lead X" of 1.5 mm, for example, so that the cutting blade and/or staple drive travels the 45 mm length of the staple deck in the 30 revolutions of the drive screw 1700". A fourth replaceable end effector with a staple cartridge having a length of 60 mm, for example can include a drive screw, such as drive screw 1700''' in FIGS. 109A and 109B, having a thread lead X''' of 2.0 mm, for example, so that the cutting blade and/or staple drive travels the 60 mm length of the staple deck in the 30 revolutions of the drive screw 1700'''.

Figure 110:
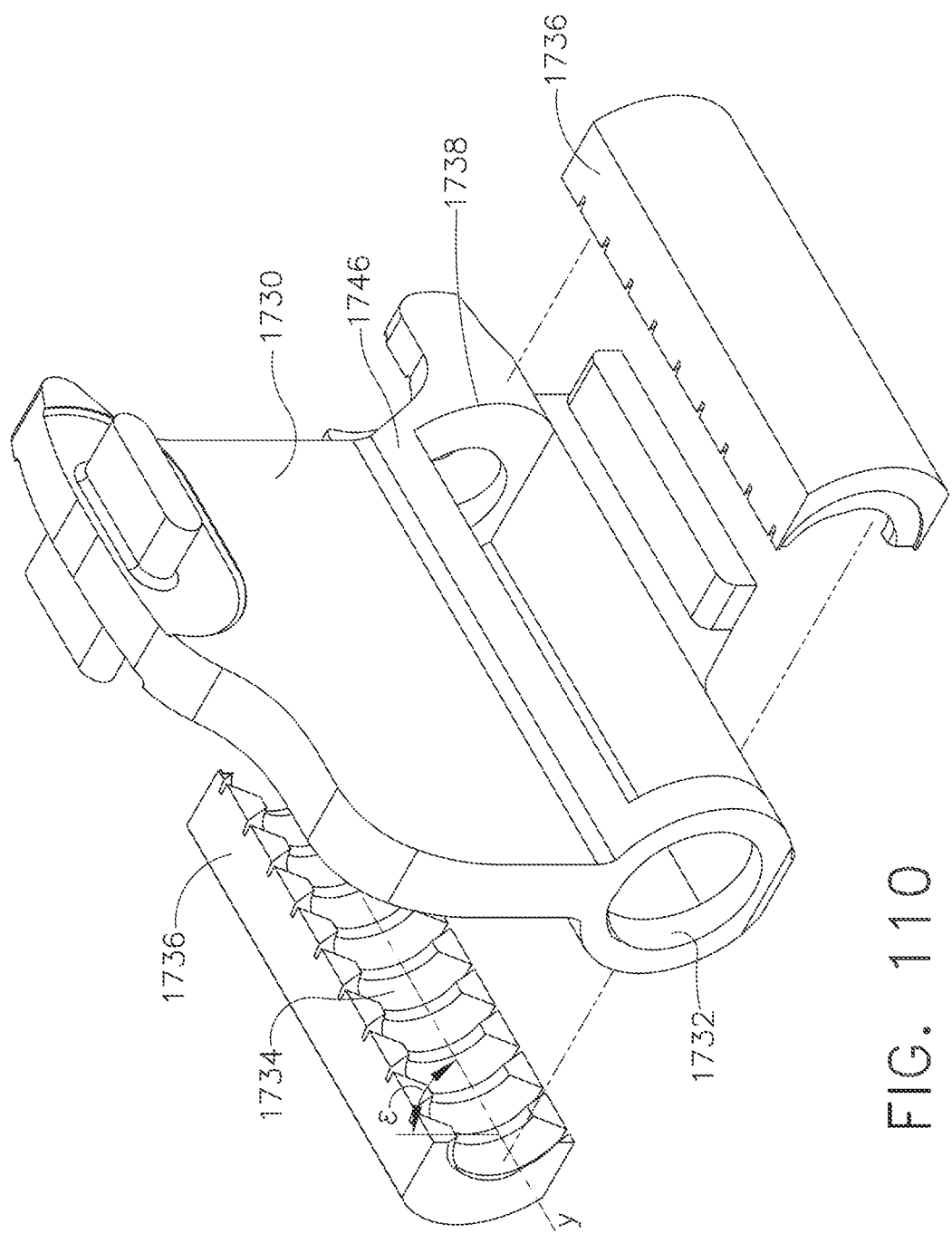

FIG. 110 shows the cutting blade 1730 of FIG. 105 removed from the remainder of the end effector 1740. The cutting blade 1730 includes a passage 1732 though which the drive screw 1700 passes. Side portions 1736 form interior walls of the passage 1732 and can include recesses, such a grooves 1734, for example, which are configured to receive threads 1708 on the drive screw 1700. The grooves 1734 are oriented at an angle ε that corresponds to the angle of the threads 1708 on the drive screw 1700. For example, if the threads 1708 are set to the angle α, shown in FIG. 106A, then the angle ε of the grooves 1734 can also be set to the angle α. Correspondingly, the angle ε of the grooves 1734 can be set to the angles β, δ and/or γ, for example, of the corresponding drive screw used therewith.

In various embodiments, as illustrated in the exploded view of FIG. 110, the side portions 1736 can be assembled into windows 1738 defined in a shaft portion 1746 of the cutting blade 1730. In certain embodiments, a cutting blade 1730 can comprise integral side portions. In at least one embodiment, the side portions can comprise an appropriate groove angle ε matching an angle of the threads 1708 on a drive screw 1700 which can be formed in the passage 1732 defined therein. Providing a cutting blade 1730 with an appropriate groove angle ε for a particular drive screw can be accomplished in numerous ways. In certain embodiments, a generic cutting blade 1730 can be provided that does not include side portions 1736 assembled into the windows 1738 of the shaft portion 1746 thereof wherein various sets of side portions 1736 can be provided such that a desired set of side portions 1736 can be selected from the various sets of side portions 1736 and then assembled to the generic cutting blade 1730 so that such an assembly can be used with a specific drive screw. For instance, a first set of side portions 1736, when assembled to the cutting blade 1730, can configure the cutting blade 1730 to be used with a first drive screw and a second set of side portions 1736, when assembled to the cutting blade 1730, can configure the cutting blade 1730 to be used with a second drive screw, and so forth. In certain other embodiments, a cutting blade 1730 can be provided with side portions formed integrally therewith. In at least one such embodiment, the grooves 1734 can be formed, e.g., with a tap, at the angle ε that matches the angle of threads 1708 of a particular drive screw 1700.

Figure 111:
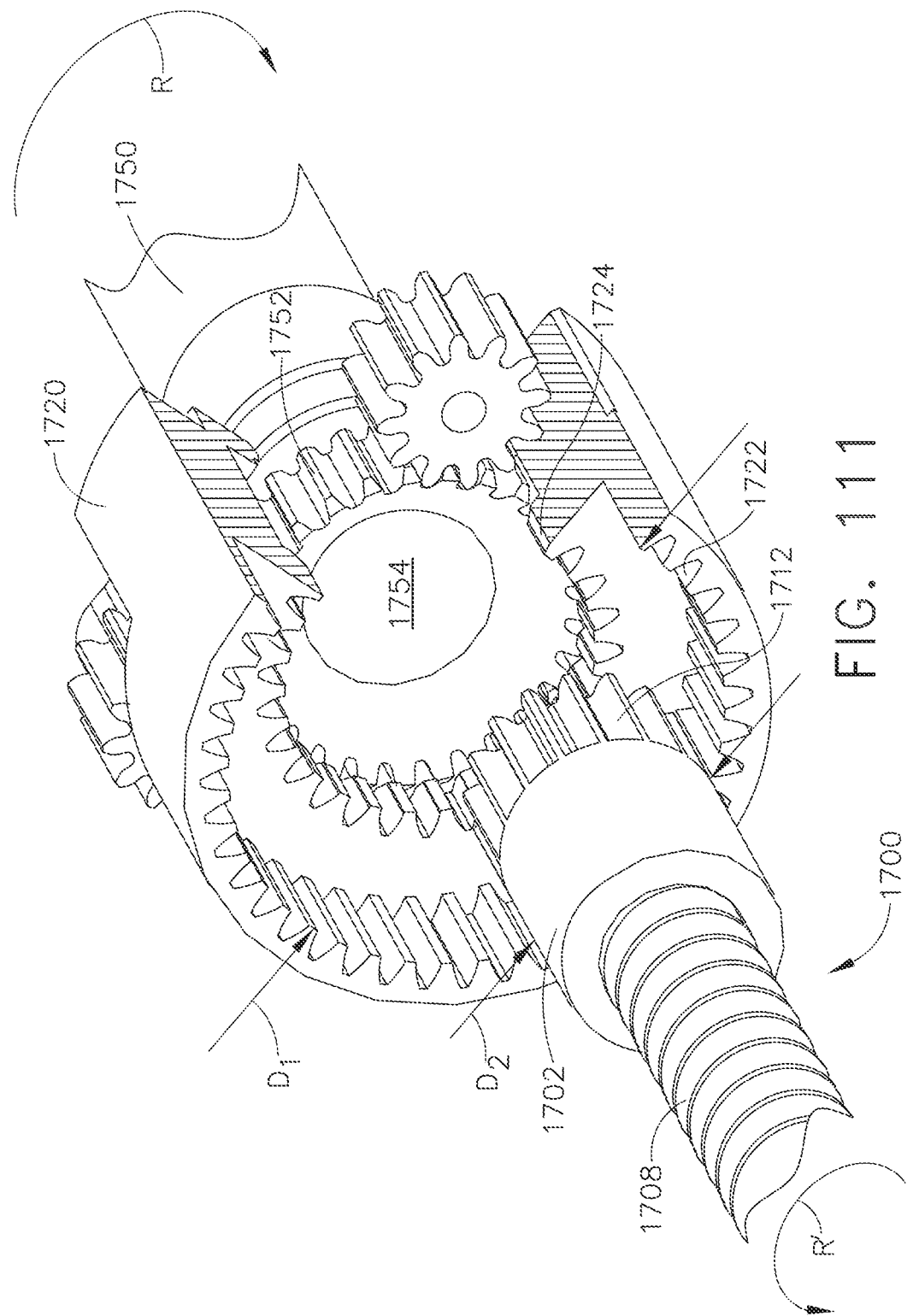
Figure 112:
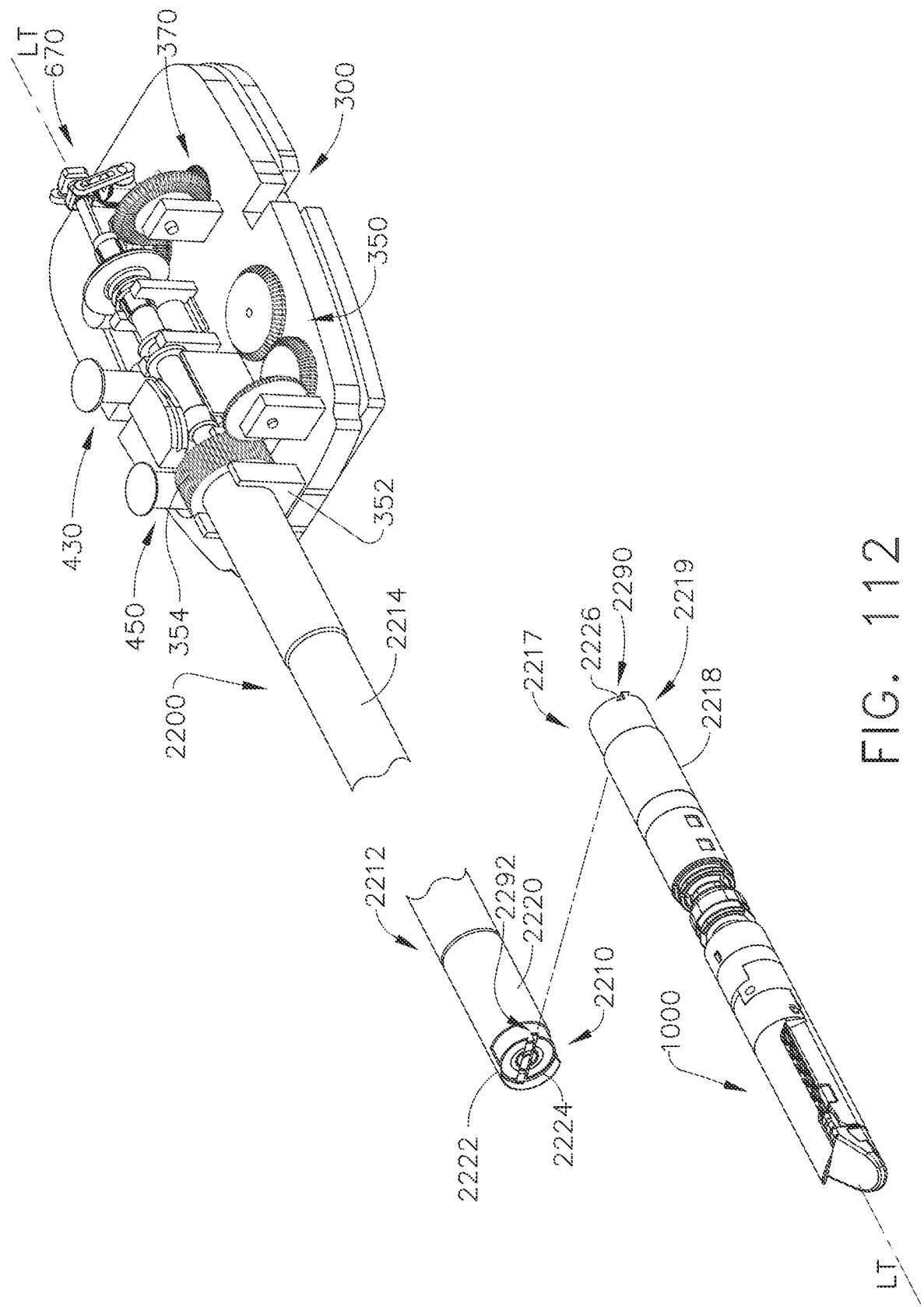
Figure 112A:
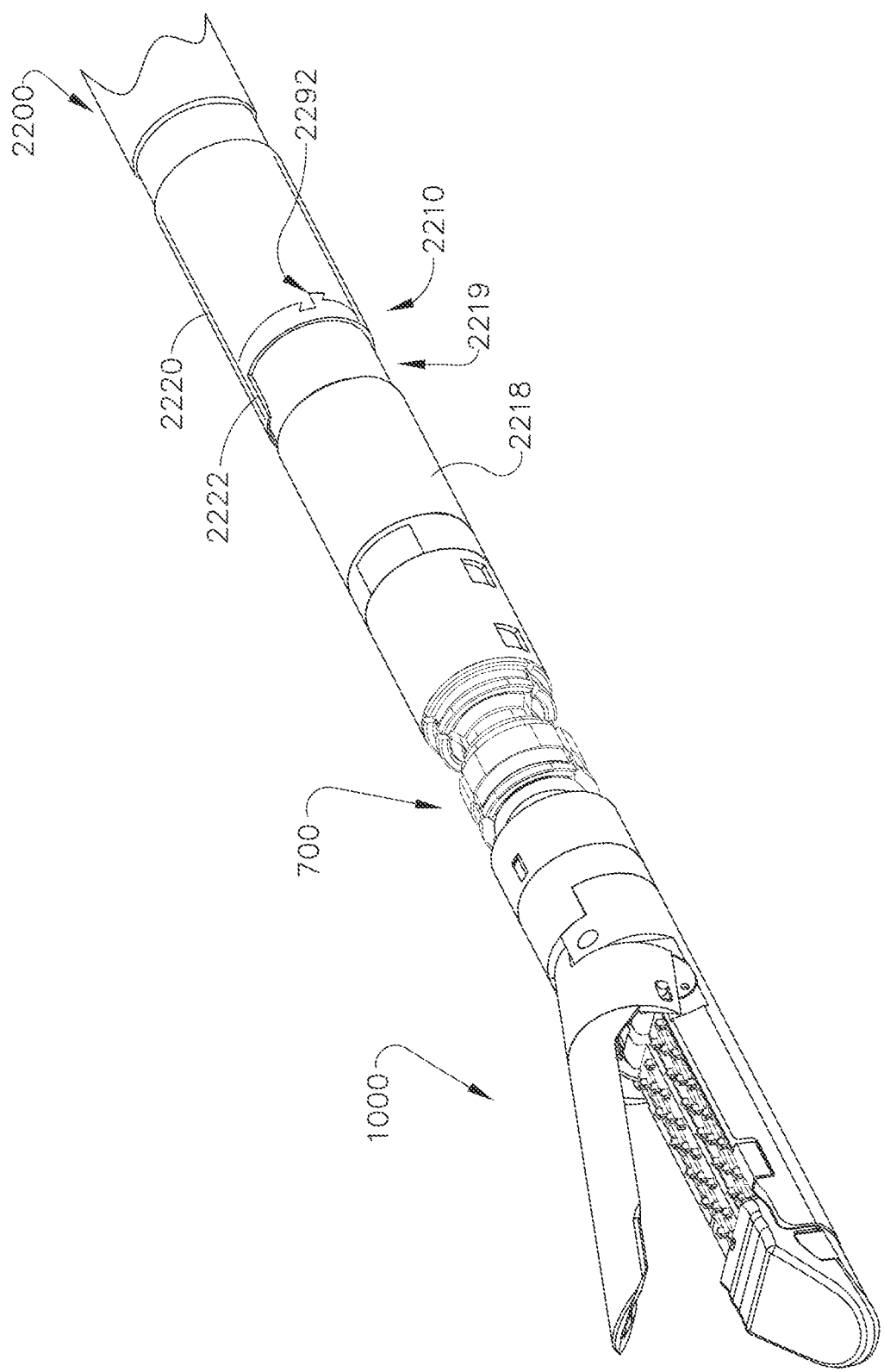

FIG. 111 illustrates the drive screw 1700 coupled to a drive shaft 1750 via an intermediate gear 1720 disposed therebetween. The drive shaft 1750 is turned by a motor. As described above, the motor can complete a fixed or set number of revolutions and, as a result, the drive shaft 1750 can turn a fixed number of revolutions R. In certain embodiments, the number of revolutions R turned by the drive shaft 1750 may be equal to the fixed number of revolutions turned by the motor. In alternative embodiments, the number of revolutions R turned by the drive shaft 1750 may be greater than or less than the fixed number revolutions turned by the motor. In various embodiments, one or more gears arranged between the motor and the drive shaft 1750 can cause the drive shaft 1750 to complete more revolutions or fewer revolutions than the motor. In certain embodiments, the drive shaft 1750 can include an external spline gear 1752 surrounding and/or attached to the distal end 1754 of the drive shaft 1750. The external spline gear 1752 can engage an internal spline gear 1724 defined in the intermediate gear 1720 in order to transmit rotation of the drive shaft 1750 to the intermediate gear 1720. As a result, in at least one embodiment, the intermediate gear 1720 can complete the same revolutions R as the drive shaft 1750.

The intermediate gear 1720 can include a second gear 1722 that is engaged to a gear 1712 surrounding and/or attached to a proximal end 1702 of the drive screw 1700. The second gear 1722 of the intermediate gear 1720 defines a first diameter D1 and the gear 1712 on the proximal end 1702 of the drive screw 1700 defines a second diameter D2. The second diameter D2 can be different than the first diameter D1. When the first diameter D1 and the second diameter D2 are different, they can define a gear ratio that is different than 1:1. As shown in FIG. 111, in certain embodiments, diameter D1 can be larger than diameter D2 such that the drive screw 1700 will complete more revolutions R' than the revolutions R turned by the drive shaft 1750 and the intermediate gear 1720. In alternative embodiments, diameter D1 can be smaller than diameter D2 such that the drive screw 1700 will turn fewer revolutions R' than the revolutions R turned by the drive shaft 1750 and the intermediate gear 1720.

The gear ratio between the second gear 1722 of the intermediate gear 1720 and the gear 1712 of the drive screw 1700 can be set so that the drive screw 1700 completes a certain number of revolutions when the drive shaft 1750 completes its fixed number of revolutions. If the intermediate gear 1722 is part of the replaceable end effector assembly, then the gear ratio between the intermediate gear 1722 and the drive screw 1700 in each replaceable end effector assembly can be set so that the motor in the surgical housing can turn a fixed number of revolutions. For example, referring to FIG. 111, assuming that the drive shaft 1750 turns a fixed 30 revolutions and that the replaceable surgical stapler includes a 15 mm staple cartridge and if the end effector includes a drive screw with a thread lead of 0.25 mm, then the drive screw will complete 60 revolutions to advance a cutting blade and/or a staple driver the 15 mm length of the staple cartridge. In at least one embodiment, the intermediate gear 1720 can be sized so that the second interior gear 1722 has a diameter D1 that is double the diameter D2 of the external gear 1712 of the drive screw 1700. As a result, the drive screw 1700 will complete 60 revolutions when the drive shaft 1750 completes 30 revolutions. If a second replaceable surgical stapler includes a 30 mm staple cartridge, then a drive screw with a thread lead of 0.25 mm will complete 120 revolutions to advance a cutting blade and/or staple driver the 30 mm length. The intermediate gear 1720 of the replaceable surgical stapler can be sized so that the second interior gear 1722 has a diameter D1 that is four times the diameter D2 of the external gear 1712 of the drive screw 1700. As a result, the drive screw 1700 will complete 120 revolutions when the drive shaft 1750 completes 30 revolutions.

Returning to FIG. 105, in certain embodiments, a firing path of the firing member, e.g., cutting blade 1730, can be linear. In certain embodiments, the firing patch can be curved and/or curvilinear. In certain embodiments, the drive screw 1708 can be flexible to enable the drive screw 1708 to follow lateral motions of the firing member along a curved and/or curvilinear path, for example. In certain embodiments, the firing member can be flexible or can include at least one flexible portion to enable portions of the firing member to displace laterally relative to the drive screw 1708, for example, along a curved and/or curvilinear path while remaining portions of the firing member are not laterally displaced relative to the drive screw 1708. In certain embodiments, the firing length may be defined by the distance moved by the firing member along the firing path regardless of the overall net displacement. In various other embodiments, the firing length may be defined by the overall net displacement of the firing member regardless of the firing path.

In various embodiments, a kit for use with a surgical instrument system may be provided that includes various replaceable end effectors having different lengths. In certain embodiments, the kit may include a selection of replaceable end effectors having different lengths from which a surgeon may choose for use in a surgical operation on a patient. The kit can also include several replaceable end effectors of each length. In certain embodiments, the kit may include a sequence of replaceable end effectors of different lengths wherein the sequence is predetermined for a particular surgical procedure. For example, a certain surgical procedure first may call for a 15 mm incision, then a second 15 mm incision, and finally a 30 mm incision. A surgical kit for this surgical procedure can include three replaceable end effectors configured to incise and staple a patient's tissue. The first two replaceable end effectors can include an approximately 15 mm length and the third replaceable end effector can include an approximately 30 mm length.

FIGS. 112-117 illustrate another exemplary elongate shaft assembly 2200 that has another exemplary quick disconnect coupler arrangement 2210 therein. In at least one form, for example, the quick disconnect coupler arrangement 2210 includes a proximal coupler member 2212 in the form of a proximal outer tube segment 2214 that has tube gear segment 354 thereon that is configured to interface with the first drive system 350 in the above-described manner. As discussed above, the first drive system 350 serves to rotate the elongate shaft assembly 2200 and the end effector 1000 operably coupled thereto about the longitudinal tool axis "LT-LT". The proximal outer tube segment 2214 has a "necked-down" distal end portion 2216 that is configured to receive a locking tube segment 2220 thereon. The quick disconnect arrangement 2210 further includes a distal coupler member 2217 in the form of a distal outer tube portion 2218 that is substantially similar to the distal outer tube portion 231 described above except that the distal outer tube portion 2218 includes a necked down proximal end portion 2219. A distal outer formation or dovetail joint 2226 is formed on the end of the proximal end portion 2219 of the distal outer tube segment 2218 that is configured to drivingly engage a proximal outer formation or dovetail joint 2228 that is formed on the distal end portion 2216 of the proximal outer tube segment 2214.

Figure 113:
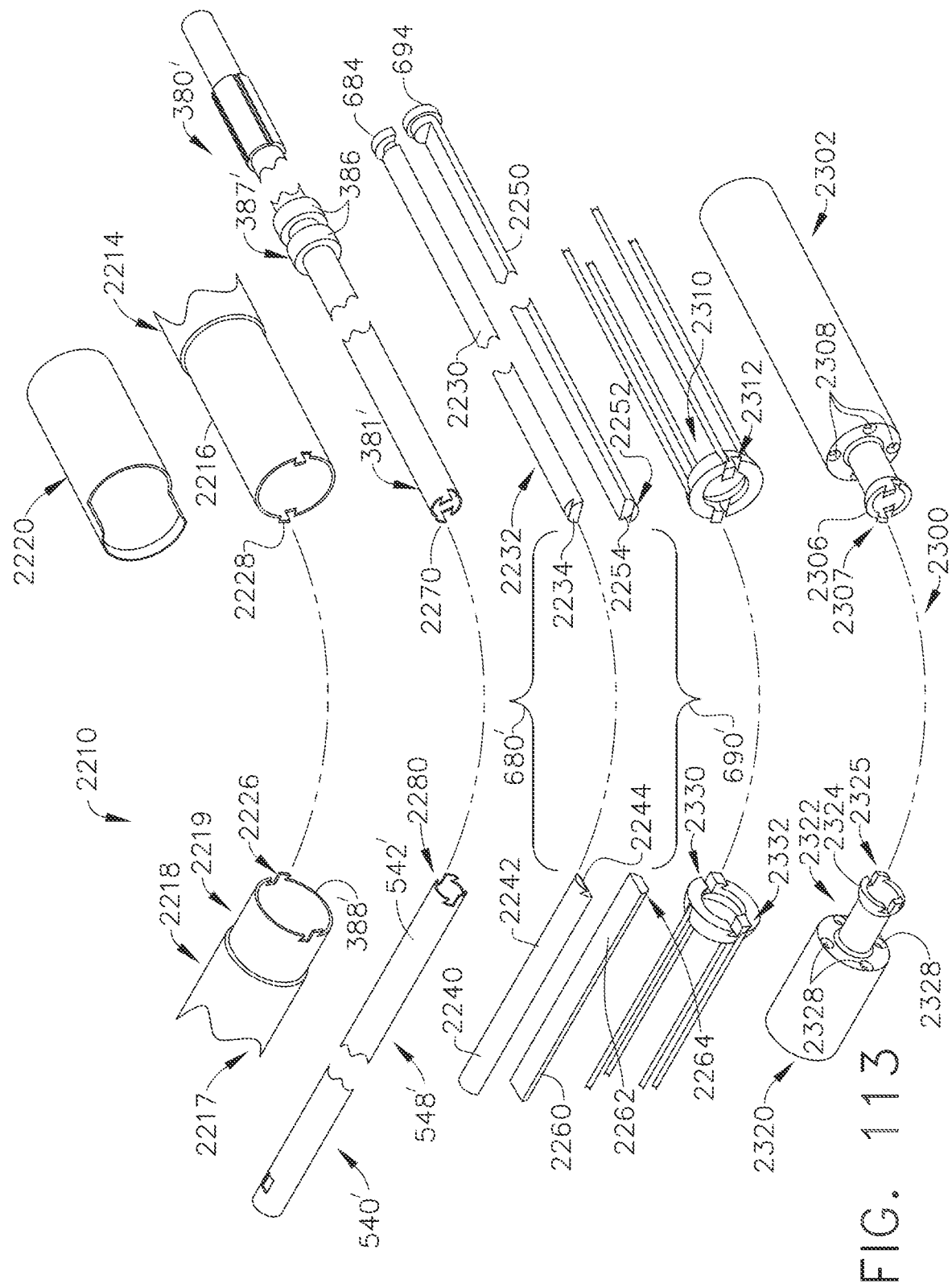
Figure 114:
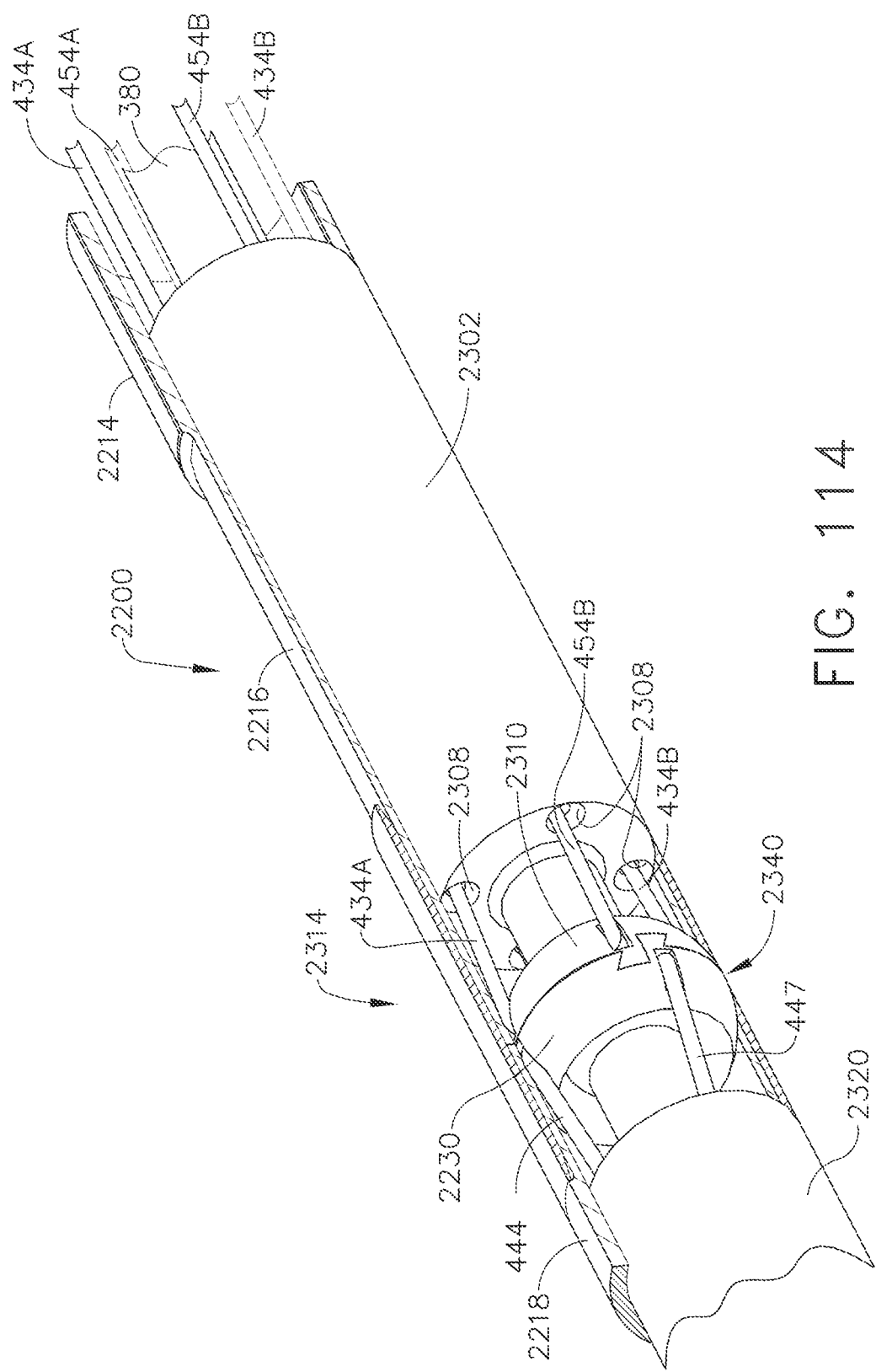

The exemplary embodiment depicted in FIGS. 112-117 employs an exemplary embodiment of the closure system 670 described above. The quick disconnect coupler arrangement 2210 is configured to facilitate operable coupling of proximal closure drive train assemblies to corresponding distal drive train assemblies. For example, as can be seen in FIG. 113, the elongate shaft assembly 2200 may include a first proximal closure drive train assembly in the form of a first proximal closure rod segment 2230 and a first distal closure drive train assembly in the form of a first distal closure rod segment 2240 that are configured to be linked together through the quick disconnect coupler arrangement 2210. That is, in at least one exemplary form, the first proximal closure rod segment 2230 has a first closure joint formation or dovetail joint segment 2234 formed on a distal end 2232 thereof. Likewise, the first distal closure rod segment 2240 has a second closure joint formation or a dovetail joint segment 2244 formed on a proximal end 2242 thereof that is adapted to laterally slidably engage the first dovetail joint segment 2234. Still referring to FIG. 113, the elongate shaft assembly 2200 may include a second proximal closure drive train assembly in the form of a second proximal closure rod segment 2250 and a second distal closure drive train assembly in the form of a second distal closure rod segment 2260 that are configured to be linked together through the quick disconnect coupler arrangement 2210. That is, in at least one exemplary form, the second proximal closure rod segment 2250 has a third closure joint formation or dovetail closure joint segment 2254 formed on a distal end 2252 thereof. Likewise, the distal second distal closure rod segment 2260 may have a fourth closure joint formation or dovetail closure joint segment 2264 formed on a proximal end 2262 of the distal second closure rod segment 2260 that is adapted to laterally engage the third dovetail joint segment 2254.

In the illustrated embodiment and others, the first proximal closure rod segment 2230 and the second proximal closure rod segment 2250 extend through the proximal drive shaft segment 380'. The proximal drive shaft segment 380' comprises a proximal rotary drive train assembly 387' and the distal drive shaft segment 540' comprises a distal rotary drive train assembly 548'. When the proximal rotary drive train assembly 387' is operably coupled to the distal rotary drive train assembly 548', the drive shaft assembly 388' is formed to transmit rotary control motions to the end effector 1000. In at least one exemplary embodiment, the proximal drive shaft segment 380' is substantially similar to the proximal drive shaft segment 380 described above, except that the distal end 381' of the proximal drive shaft segment 380' has a distal formation or dovetail drive joint 2270 formed thereon. Similarly, the distal drive shaft segment 540' may be substantially similar to the distal drive shaft segment 540 described above, except that a proximal formation dovetail drive joint 2280 is formed on the proximal end 542' thereof that is adapted to drivingly engage the distal dovetail drive joint 2270 through the quick disconnect coupler arrangement 2210. The first distal closure rod segment 2240 and the distal second closure rod segment 2260 may also extend through the distal drive shaft segment 540'.

This exemplary embodiment may also include an articulation coupling joint 2300 that interfaces with the third and fourth drive cables 434, 454. As can be seen in FIG. 113, the articulation coupling joint 2300 comprises a proximal articulation tube 2302 that has a proximal ball joint segment 2306 formed on a distal end 2304 thereof. The proximal articulation tube 2302 includes passages 2308 for receiving the cable end portions 434A', 434B', 454A', 454B' therethrough. A proximal ball joint segment 2310 is movably supported on the proximal ball segment 2306. Proximal cable segments 434A', 434B', 454A', 454B' extend through passages 2308 to be attached to the proximal ball joint segment 2310. The proximal articulation tube 2302, the proximal ball joint segment 2310 and the proximal cable segments 434A', 434B', 454A', 454B' may be collectively referred to as a proximal articulation drive train portion 2314.

The exemplary articulation coupling joint 2300 may also comprise a distal articulation tube 2320 that has a distal ball joint segment 2324 formed on a proximal end 2322 thereof. The distal ball joint segment 2324 has a first distal formation or dovetail joint 2325 formed thereon that is adapted to drivingly engage a first proximal formation or dovetail joint 2307 formed on the proximal ball joint segment 2306 such that when the first distal dovetail joint 2325 drivingly engages the first proximal dovetail joint 2307, the distal ball joint segment 2324 and the proximal ball joint segment 2306 form an internal articulation ball assembly. In addition, the articulation coupling joint 2300 further comprises a distal ball segment 2330 that is supported on the distal ball joint segment 2324 and has a second distal formation or dovetail joint 2332 formed thereon that is adapted to drivingly engage a second proximal formation or dovetail joint 2312 on the proximal ball joint segment 2310. The distal cable segments 444, 445, 446, 447 are attached to the distal ball segment 2340 and extend through passages 2328 in the distal articulation tube 2320. When joined together, the proximal ball joint segment 2310 and the distal ball joint segment 2324 form an articulation ball 2340 that is movably journaled on the internal articulation ball. The distal articulation tube 2320, the distal ball segment 2340 and the distal cable segments 444, 445, 446, 4447 may be collectively referred to as a proximal articulation drive train assembly 2316.

Figure 115:
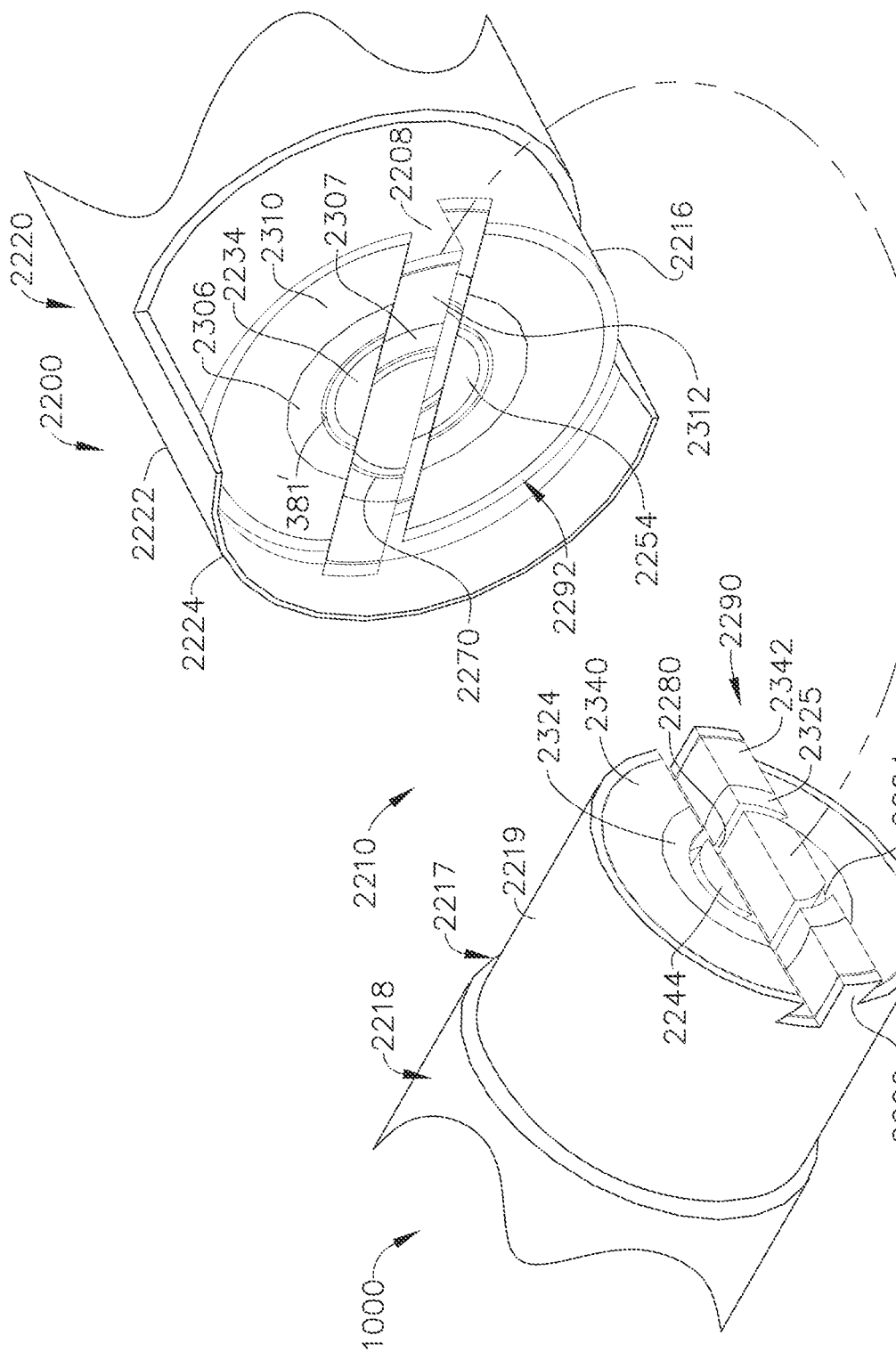

As can be seen in FIG. 115, the distal portions of the elongate shaft assembly 2200 may be assembled such that the following joint segments are retained in registration with each other by the distal coupler 2217 or distal outer tube portion 2218 to form a distal dovetail joint assembly generally referred to as 2290: 2226, 2332, 2325, 2280, 2244 and 2264. Likewise, the elongate shaft assembly 2200 may be assembled such that the proximal coupler member 2212 or proximal outer tube segment 2214 retains the following joint segments in registration with each other to form a proximal dovetail joint assembly generally designated as 2292: 2228, 2312, 2307, 2270, 2234 and 2254.

The end effector 1000 may be operably coupled to the elongate shaft assembly 2200 as follows. To commence the attachment, the clinician moves the locking tube segment 2220 to a first unlocked position shown in FIGS. 115 and 116. As can be seen in those Figures, the locking tube segment has an abutment segment 2224 formed on its distal end 2222. When in the unlocked position, the abutment segment 2224 protrudes distally beyond the proximal dovetail joint assembly 2292 to form an abutment surface for laterally joining the distal dovetail joint assembly 2290 with the proximal dovetail joint assembly 2292. That is, the clinician may laterally align the distal dovetail joint assembly 2290 with the proximal dovetail joint assembly 2292 and then slide the distal dovetail joint assembly 2290 into lateral engagement with the proximal dovetail joint assembly 2292 until the distal dovetail joint assembly 2290 contacts the abutment segment 2224 at which point all of the corresponding proximal and distal joint segments are simultaneously interconnected. Thereafter, the clinician may move the locking tube segment 2220 distally to a second locked position as shown in FIG. 117. When in that position, the locking tube segment 2220 covers the quick disconnect joint 2210 and prevents any relative lateral movement between the distal dovetail assembly 2290 and the proximal dovetail assembly 2292.

While the various exemplary embodiments described above are configured to operably interface with and be at least partially actuated by a robotic system, the end effector and elongate shaft components may be effectively employed in connection with handheld instruments. For example, FIGS. 118-120 depict a handheld surgical instrument 2400 that may employ various components and systems described above to operably actuate an end effector 1000 coupled thereto. In the exemplary embodiment depicted in FIGS. 118-120, a quick disconnect joint 2210 is employed to couple the end effector 1000 to the elongate shaft assembly 2402. To facilitate articulation of the end effector 1000 about the articulation joint 700, the proximal portion of the elongate shaft assembly 2402 includes an exemplary manually actuatable articulation drive 2410.

Referring now to FIGS. 121-123, in at least one exemplary form, the articulation drive 2410 includes four axially movable articulation slides that are movably journaled on the proximal drive shaft segment 380' between the proximal outer tube segment 2214 and the proximal drive shaft segment 380'. For example, the articulation cable segment 434A' is attached to a first articulation slide 2420 that has a first articulation actuator rod 2422 protruding therefrom. Articulation cable segment 434B' is attached to a second articulation slide 2430 that is diametrically opposite from the first articulation slide 2420. The second articulation slide 2430 has a second articulation actuator rod 2432 protruding therefrom. Articulation cable segment 454A' is attached to a third articulation slide 2440 that has a third articulation actuator rod 2442 protruding therefrom. Articulation cable segment 454B' is attached to a fourth articulation slide 2450 that is diametrically opposite to the third articulation slide 2440. A fourth articulation actuator rod 2452 protrudes from the fourth articulation slide 2450. Articulation actuator rods 2422, 2432, 2442, 2452 facilitate the application of articulation control motions to the articulation slides 2420, 2430, 2440, 2450, respectively by an articulation ring assembly 2460.

As can be seen in FIG. 121, the articulation actuator rods 2422, 2432, 2442, 2452 movably pass through a mounting ball 2470 that is journaled on a proximal outer tube segment 2404. In at least one embodiment, the mounting ball 2470 may be manufactured in segments that are attached together by appropriate fastener arrangements (e.g., welding, adhesive, screws, etc.). As shown in FIG. 109, the articulation actuator rods 2422 and 2432 extend through slots 2472 in the proximal outer tube segment 2404 and slots 2474 in the mounting ball 2470 to enable the articulation slides 2420, 2430 to axially move relative thereto. Although not shown, the articulation actuator rods 2442, 2452 extend through similar slots 2472, 2474 in the proximal outer tube segment 2404 and the mounting ball 2470. Each of the articulation actuator rods 2422, 2432, 2442, 2452 protrude out of the corresponding slots 2474 in the mounting ball 2470 to be operably received within corresponding mounting sockets 2466 in the articulation ring assembly 2460. See FIG. 122.

In at least one exemplary form, the articulation ring assembly 2460 is fabricated from a pair of ring segments 2480, 2490 that are joined together by, for example, welding, adhesive, snap features, screws, etc. to form the articulation ring assembly 2460. The ring segments 2480, 2490 cooperate to form the mounting sockets 2466. Each of the articulation actuator rods has a mounting ball 2468 formed thereon that are each adapted to be movably received within a corresponding mounting socket 2466 in the articulation ring assembly 2460.

Various exemplary embodiments of the articulation drive 2410 may further include an exemplary locking system 2486 configured to retain the articulation ring assembly 2460 in an actuated position. In at least one exemplary form, the locking system 2486 comprises a plurality of locking flaps formed on the articulation ring assembly 2460. For example, the ring segments 2480, 2490 may be fabricated from a somewhat flexible polymer or rubber material. Ring segment 2480 has a series of flexible proximal locking flaps 2488 formed therein and ring segment 2490 has a series of flexible distal locking flaps 2498 formed therein. Each locking flap 2388 has at least one locking detent 2389 formed thereon and each locking flap 2398 has at least one locking detent 2399 thereon. Locking detents 2389, 2399 may serve to establish a desired amount of locking friction with the articulation ball so as to retain the articulation ball in position. In other exemplary embodiments, the locking detents 2389, 2390 are configured to matingly engage various locking dimples formed in the outer perimeter of the mounting ball 2470.

Operation of the articulation drive 2410 can be understood from reference to FIGS. 122 and 123. FIG. 122 illustrates the articulation drive 2410 in an unarticulated position. In FIG. 123, the clinician has manually tilted the articulation ring assembly 2460 to cause the articulation slide 2420 to move axially in the distal direction "DD" thereby advancing the articulation cable segment 434A' distally. Such movement of the articulation ring assembly 2460 also results in the axial movement of the articulation slide 2430 in the proximal direction which ultimately pulls the articulation cable 434B in the proximal direction. Such pushing and pulling of the articulation cable segments 434A', 434B' will result in articulation of the end effector 1000 relative to the longitudinal tool axis "LT-LT" in the manner described above. To reverse the direction of articulation, the clinician simply reverses the orientation of the articulation ring assembly 2460 to thereby cause the articulation slide 2430 to move in the distal direction "DD" and the articulation slide 2420 to move in the proximal direction "PD". The articulation ring assembly 2460 may be similarly actuated to apply desired pushing and pulling motions to the articulation cable segments 454A', 454B'. The friction created between the locking detents 2389, 2399 and the outer perimeter of the mounting ball serves to retain the articulation drive 2410 in position after the end effector 1000 has been articulated to the desired position. In alternative exemplary embodiments, when the locking detents 2389, 2399 are positioned so as to be received in corresponding locking dimples in the mounting ball, the mounting ball will be retained in position.

In the illustrated exemplary embodiments and others, the elongate shaft assembly 2402 operably interfaces with a handle assembly 2500. An exemplary embodiment of handle assembly 2500 comprises a pair of handle housing segments 2502, 2504 that are coupled together to form a housing for various drive components and systems as will be discussed in further detail below. See, e.g., FIGS. 118 and 119. The handle housing segments 2502, 2504 may be coupled together by screws, snap features, adhesive, etc. When coupled together, the handle segments 2502, 2504 may form a handle assembly 2500 that includes a pistol grip portion 2506.

To facilitate selective rotation of the end effector 1000 about the longitudinal tool axis "LT=LT", the elongate shaft assembly 2402 may interface with a first drive system, generally designated as 2510. The drive system 2510 includes a manually-actuatable rotation nozzle 2512 that is rotatably supported on the handle assembly 2500 such that it can be rotated relative thereto as well as be axially moved between a locked position and an unlocked position.

The surgical instrument 2400 may include a closure system 670 as was described above for applying opening and closing motions to the anvil 1100 of the end effector 1000. In this exemplary embodiment, however, the closure system 670 is actuated by a closure trigger 2530 that is pivotally mounted to the handle frame assembly 2520 that is supported within the handle housing segments 2502, 2504. The closure trigger 2530 includes an actuation portion 2532 that is pivotally mounted on a pivot pin 2531 that is supported within the handle frame assembly 2520. See FIG. 124. Such exemplary arrangement facilitates pivotal travel toward and away from the pistol grip portion 2506 of the handle assembly 2500. As can be seen in FIG. 124, the closure trigger 2530 includes a closure link 2534 that is linked to the first pivot link and gear assembly 695 by a closure wire 2535. Thus, by pivoting the closure trigger 2530 toward the pistol grip portion 2506 of the handle assembly 2500 into an actuated position, the closure link 2534 and closure wire 2535 causes the first pivot link and gear assembly 695 to move the first closure rod segment 680 in the distal direction "DD" to close the anvil.

The surgical instrument 2400 may further include a closure trigger locking system 2536 to retain the closure trigger in the actuated position. In at least one exemplary form, the closure trigger locking system 2536 includes a closure lock member 2538 that is pivotally coupled to the handle frame assembly 2520. As can be seen in FIGS. 125 and 126, the closure lock member 2538 has a lock arm 2539 formed thereon that is configured to ride upon an arcuate portion 2537 of the closure link 2532 as the closure trigger 2530 is actuated toward the pistol grip portion 2506. When the closure trigger 2530 has been pivoted to the fully actuated position, the lock arm 2539 drops behind the end of the closure link 2532 and prevents the closure trigger 2530 from returning to its unactuated position. Thus, the anvil 1100 will be locked in its closed position. To enable the closure trigger 2530 to return to its unactuated position and thereby result in the movement of the anvil from the closed position to the open position, the clinician simply pivots the closure lock member 2538 until the lock arm 2539 thereof disengages the end of the closure link 2532 to thereby permit the closure link 2532 to move to the unactuated position.

The closure trigger 2532 is returned to the unactuated position by a closure return system 2540. For example, as can be seen in FIG. 124, one exemplary form of the closure trigger return system 2540 includes a closure trigger slide member 2542 that is linked to the closure link 2534 by a closure trigger yoke 2544. The closure trigger slide member 2542 is slidably supported within a slide cavity 2522 in the handle frame assembly 2520. A closure trigger return spring 2546 is positioned within the slide cavity 2520 to apply a biasing force to the closure trigger slide member 2542. Thus, when the clinician actuates the closure trigger 2530, the closure trigger yoke 2544 moves the closure trigger slide member 2542 in the distal direction "DD" compressing the closure trigger return spring 2546. When the closure trigger locking system 2536 is disengaged and the closure trigger is released 2530, the closure trigger return spring 2546 moves the closure trigger slide member 2542 in the proximal direction "PD" to thereby pivot the closure trigger 2530 into the starting unactuated position.

The surgical instrument 2400 can also employ any of the various exemplary drive shaft assemblies described above. In at least one exemplary form, the surgical instrument 2400 employs a second drive system 2550 for applying rotary control motions to a proximal drive shaft assembly 380'. See FIG. 128. The second drive system 2550 may include a motor assembly 2552 that is operably supported in the pistol grip portion 2506. The motor assembly 2552 may be powered by a battery pack 2554 that is removably attached to the handle assembly 2500 or it may be powered by a source of alternating current. A second drive gear 2556 is operably coupled to the drive shaft 2555 of the motor assembly 2552. The second drive gear 2556 is supported for meshing engagement with a second rotary driven gear 2558 that is attached to the proximal drive shaft segment 380' of the drive shaft assembly. In at least one form, for example, the second drive gear 2556 is also axially movable on the motor drive shaft 2555 relative to the motor assembly 2552 in the directions represented by arrow "U" in FIG. 128. A biasing member, e.g., a coil spring 2560 or similar member, is positioned between the second drive gear 2556 and the motor housing 2553 and serves to bias the second drive gear 2556 on the motor drive shaft 2555 into meshing engagement with a first gear segment 2559 on the second driven gear 2558.

The second drive system 2550 may further include a firing trigger assembly 2570 that is movably, e.g., pivotally attached to the handle frame assembly 2520. In at least one exemplary form, for example, the firing trigger assembly 2570 includes a first rotary drive trigger 2572 that cooperates with a corresponding switch/contact (not shown) that electrically communicates with the motor assembly 2552 and which, upon activation, causes the motor assembly 2552 to apply a first rotary drive motion to the second driven gear 2558. In addition, the firing trigger assembly 2570 further includes a retraction drive trigger 2574 that is pivotal relative to the first rotary drive trigger. The retraction drive trigger 2574 operably interfaces with a switch/contact (not shown) that is in electrical communication with the motor assembly 2552 and which, upon activation, causes the motor assembly 2552 to apply a second rotary drive motion to the second driven gear 2558. The first rotary drive motion results in the rotation of the drive shaft assembly and the implement drive shaft in the end effector to cause the firing member to move distally in the end effector 1000. Conversely, the second rotary drive motion is opposite to the first rotary drive motion and will ultimately result in rotation of the drive shaft assembly and the implement drive shaft in a rotary direction which results in the proximal movement or retraction of the firing member in the end effector 1000.

The illustrated embodiment also includes a manually actuatable safety member 2580 that is pivotally attached to the closure trigger actuation portion 2532 and is selectively pivotable between a first "safe" position wherein the safety member 2580 physically prevents pivotal travel of the firing trigger assembly 2570 and a second "off" position, wherein the clinician can freely pivot the firing trigger assembly 2570. As can be seen in FIG. 124, a first dimple 2582 is provided in the closure trigger actuation portion 2532 that corresponds to the first position of the safety member 2580. When the safety member 2580 is in the first position, a detent (not shown) on the safety member 2580 is received within the first dimple 2582. A second dimple 2584 is also provided in the closure trigger actuation portion 2532 that corresponds to the second position of the safety member 2580. When the safety member 2580 is in the second position, the detent on the safety member 2580 is received within the second dimple 2582.

In at least some exemplary forms, the surgical instrument 2400 may include a mechanically actuatable reversing system, generally designated as 2590, for mechanically applying a reverse rotary motion to the proximal drive shaft segment 380' in the event that the motor assembly 2552 fails or battery power is lost or interrupted. Such mechanical reversing system 2590 may also be particularly useful, for example, when the drive shaft system components operably coupled to the proximal drive shaft segment 380' become jammed or otherwise bound in such a way that would prevent reverse rotation of the drive shaft components under the motor power alone. In at least one exemplary form, the mechanically actuatable reversing system 2590 includes a reversing gear 2592 that is rotatably mounted on a shaft 2524A formed on the handle frame assembly 2520 in meshing engagement with a second gear segment 2562 on the second driven gear 2558. See FIG. 126. Thus, the reversing gear 2592 freely rotates on shaft 2524A when the second driven gear 2558 rotates the proximal drive shaft segment 380' of the drive shaft assembly.

In various exemplary forms, the mechanical reversing system 2590 further includes a manually actuatable driver 2594 in the form of a lever arm 2596. As can be seen in FIGS. 129 and 130, the lever arm 2596 includes a yoke portion 2597 that has elongate slots 2598 therethrough. The shaft 2524A extends through slot 2598A and a second opposing shaft 2598B formed on the handle housing assembly 2520 extends through the other elongate slot to movably affix the lever arm 2596 thereto. In addition, the lever arm 2596 has an actuator fin 2597 formed thereon that can meshingly engage the reversing gear 2592. There is a detent or interference that keeps the lever arm 2596 in the unactuated state until the clinician exerts a substantial force to actuate it. This keeps it from accidentally initiating if inverted. Other embodiments may employ a spring to bias the lever arm into the unactuated state. Various exemplary embodiments of the mechanical reversing system 2590 further includes a knife retractor button 2600 that is movably journaled in the handle frame assembly 2520. As can be seen in FIGS. 129 and 130, the knife retractor button 2600 includes a disengagement flap 2602 that is configured to engage the top of the second drive gear 2556. The knife retractor button 2600 is biased to a disengaged position by a knife retractor spring 2604. When in the disengaged position, the disengagement flap 2602 is biased out of engagement with the second drive gear 2556. Thus, until the clinician desires to activate the mechanical reversing system 2590 by depressing the knife retractor button 2600, the second drive gear 2556 is in meshing engagement with the first gear segment 2559 of the second driven gear 2558.

When the clinician desires to apply a reverse rotary drive motion to the proximal drive shaft segment 380', the clinician depresses the knife retractor button 2600 to disengage the first gear segment 2559 on the second driven gear 2558 from the second drive gear 2556. Thereafter, the clinician begins to apply a pivotal ratcheting motion to the manually actuatable driver 2594 which causes the gear fin 2597 thereon to drive the reversing gear 2592. The reversing gear 2592 is in meshing engagement with the second gear segment 2562 on the second driven gear 2558. Continued ratcheting of the manually actuatable driver 2594 results in the application of a reverse rotary drive motion to the second gear segment 2562 and ultimately to the proximal drive shaft segment 380'. The clinician may continue to ratchet the driver 2594 for as many times as are necessary to fully release or reverse the associated end effector component(s). Once a desired amount of reverse rotary motion has been applied to the proximal drive shaft segment 380', the clinician releases the knife retractor button 2600 and the driver 2594 to their respective starting or unactuated positions wherein the fin 2597 is out of engagement with the reversing gear 2592 and the second drive gear 2556 is once again in meshing engagement with the first gear segment 2559 on the second driven gear 2558.

The surgical instrument 2400 can also be employed with an end effector 1000 that includes a rotary transmission 750 as was described in detail above. As discussed above, when the drive shaft assembly is in a first axial position, rotary motion applied thereto results in the rotation of the entire end effector 1000 about the longitudinal tool axis "LT-LT" distal to the articulation joint 700. When the drive shaft assembly is in the second position, rotary motion applied thereto results in the rotation of the implement drive shaft which ultimately causes the actuation of the firing member within the end effector 1000.

The surgical instrument 2400 may employ a shifting system 2610 for selectively axially shifting the proximal drive shaft segment 380' which moves the shaft gear 376 into and out of meshing engagement with the first rotary driven gear 374. For example, the proximal drive shaft segment 380' is movably supported within the handle frame assembly 2520 such that the proximal drive shaft segment 380' may move axially and rotate therein. In at least one exemplary form, the shifting system 2610 further includes a shifter yoke 2612 that is slidably supported by the handle frame assembly 2520. See FIGS. 124 and 127. The proximal drive shaft segment 380' has a pair of collars 386 (shown in FIGS. 124 and 128) thereon such that shifting of the shifter yoke 2612 on the handle frame assembly 2520 results in the axial movement of the proximal drive shaft segment 380'. In at least one form, the shifting system 2610 further includes a shifter button assembly 2614 operably interfaces with the shifter yoke 2612 and extends through a slot 2505 in the handle housing segment 2504 of the handle assembly 2500. See FIGS. 135 and 136. A shifter spring 2616 is mounted with the handle frame assembly 2520 such that it engages the proximal drive shaft segment 380'. See FIGS. 127 and 134. The spring 2616 serves to provide the clinician with an audible click and tactile feedback as the shifter button assembly 2614 is slidably positioned between the first axial position depicted in FIG. 135 wherein rotation of the drive shaft assembly results in rotation of the end effector 1000 about the longitudinal tool axis "LT-LT" relative to the articulation joint 700 (illustrated in FIG. 67) and the second axial position depicted in FIG. 136 wherein rotation of the drive shaft assembly results in the axial movement of the firing member in the end effector (illustrated in FIG. 66). Thus, such arrangement enables the clinician to easily slidably position the shifter button assembly 2614 while holding the handle assembly 2500.

FIGS. 137-147 illustrate a lockable articulation joint 2700 that, in one exemplary embodiment, is substantially identical to the articulation joint 700 described above except for the differences discussed below. In one exemplary embodiment, the articulation joint 2700 is locked and unlocked by an articulation lock system 2710. The articulation joint 2700 includes a proximal socket tube 702 that is attached to the distal end 233 of the distal outer tube portion 231 and defines a proximal ball socket 704 therein. See FIG. 137. A proximal ball member 706 that is attached to an intermediate articulation tube segment 712 is movably seated within the proximal ball socket 704 within the proximal socket tube 702. As can be seen in FIG. 137, the proximal ball member 706 has a central drive passage 708 that enables the distal drive shaft segment 540 to extend therethrough. In addition, the proximal ball member 706 has four articulation passages 710 therein which facilitate the passage of distal cable segments 444, 445, 446, 447 therethrough. As can be further seen in FIG. 137, the intermediate articulation tube segment 712 has an intermediate ball socket 714 formed therein. The intermediate ball socket 714 is configured to movably support therein an end effector ball 722 formed on an end effector connector tube 720. The distal cable segments 444, 445, 446, 447 extend through cable passages 724 formed in the end effector ball 722 and are attached thereto by lugs 726 received within corresponding passages 728 in the end effector ball 722. Other attachment arrangements may be employed for attaching distal cable segments 444, 445, 446, 447 to the end effector ball 722.

As can be seen in FIG. 137, one exemplary form of the articulation lock system 2710 includes a lock wire or member 2712 that extends through the distal outer tube portion 231 of elongate shaft assembly and the proximal socket tube 702. The lock wire 2712 has a proximal end 2720 that is attached to a transfer disc 2722 that is operably supported in the handle portion 2500 (generally represented in broken lines in FIG. 137). For example, the transfer disc 2722 is mounted on a spindle shaft 2724 that is coupled to a boss 2726 formed in the handle 2500. An actuator cable or wire 2730 is attached to the transfer disc 2722 and may be manually actuated (i.e., pushed or pulled) by the clinician. In other embodiments wherein the surgical instrument is attached to the robotic system, the actuator cable 2730 may be configured to receive control motions from the robotic system to actuate the transfer disc 2722.

As can be seen in FIGS. 143-146, the lock wire 2712 has a pair of unlocking wedges 2714, 2716 formed on its distal end 2715. The first unlocking wedge 2714 is configured to operably interface with the ends 2742, 2744 of a distal locking ring 2740 that is journaled on the intermediate articulation tube 712. In its normal "locked" state as shown in FIG. 143, the distal locking ring 2740 applies a circumferentially-extending locking or squeezing force to the intermediate articulation tube 712 to squeeze the intermediate articulation tube 712 onto the end effector ball 722 to prevent its movement within the socket 714. As can be seen in FIGS. 143-146, the ends 2742, 2744 of the distal locking ring 2740 are tapered to define a conical or V-shaped opening 2746 therebetween configured to receive the first unlocking wedge 2714 therebetween.

As can be further seen in FIGS. 143-146, the second locking wedge 2716 is configured to interface with the ends 2752, 2754 of a proximal locking ring 2750 that is journaled on the proximal socket tube 702. In its normal "locked" state as shown in FIG. 143, the proximal locking ring 27450 applies a circumferentially-extending locking or squeezing force to the proximal socket tube 702 to squeeze the proximal socket tube 702 onto the proximal ball member 706 to prevent its movement within the proximal ball socket 704. As can be seen in FIGS. 143-146, the ends 2752, 2754 of the proximal locking ring 2750 are tapered to define a conical or V-shaped opening 2756 therebetween configured to receive the second unlocking wedge 2716 therebetween.

When the articulation joint 2700 is unlocked by actuation the articulation lock system 2710, the end effector 1000 may be selectively articulated in the various manners described above by actuating the distal cable segments 444, 445, 446, 447. Actuation of the articulation lock system 2710 may be understood from reference to FIGS. 138, 139 and 143-146. FIG. 143 depicts the positions of the first and second unlocking wedges 2714, 2716 with respect to the distal and proximal locking rings 2740, 2750. When in that state, locking ring 2740 prevents movement of the end effector ball 722 within the socket 714 and the locking ring 2750 prevents the proximal ball member 706 from moving within socket 704. To unlock the articulation joint 2700, the actuation cable 2726 is pulled in the proximal direction "PD" which ultimately results in the locking wire 2712 being pushed in the distal direction "DD" to the position shown in FIG. 144. As can be seen in FIG. 144, the first unlocking wedge 2714 has moved distally between the ends 2742, 2744 of the distal locking ring 2740 to spread the ring 2740 to relieve the squeezing force applied to the intermediate articulation tube 712 to permit the end effector ball 722 to move within the socket 714. Likewise, the second unlocking wedge 2716 has moved distally between the ends 2752, 2754 of the proximal locking ring 2750 to spread the ring 2750 to relieve the squeezing force on the proximal socket tube 702 to permit the proximal ball member 706 to move within the socket 704. When in that unlocked position, the articulation system may be actuated to apply actuation motions to the distal cable segments 444, 445, 446, 447 in the above described manners to articulate the end effector 1000 as illustrated in FIGS. 138 and 139. For example, FIGS. 143 and 144 illustrate the position of the first and second locking wedges 2714, 2716 when the end effector 1000 has been articulated into the position illustrated in FIG. 138. Likewise, FIGS. 145, 146 illustrate the position of the first and second locking wedges 2714, 2716 when the end effector 1000 has been articulated into the position illustrated in FIG. 139. Once the clinician has articulated the end effector to the desired position, the clinician (or robotic system) applies a pushing motion to the actuation cable to rotate the transfer disc 2722 and move the locking wire 2712 to the position shown in FIGS. 143, 145 to thereby permit the locking rings 2740, 2750 to spring to their clamped or locked positions to retain the end effector 1000 in that locked position.

FIGS. 148-156 illustrate another end effector embodiment 2800 that, in one exemplary form, is substantially identical to the end effector 1000 except for the differences discussed below. The end effector 2800 includes an anvil assembly 2810 that is opened and closed by applying a rotary closure motion thereto. The anvil assembly 2810 is pivotally supported on an elongate channel 2830 for selective movement between an open position (FIGS. 148 and 149) and a closed position (FIGS. 150-153). The elongate channel 2830 may be substantially identical to elongate channel 1020 described above, except for the differences discussed below. For example, in the illustrated embodiment, the elongate channel 2830 has an end effector connector housing 2832 formed thereon that may be coupled to an end effector connector tube 720 by the ring-like bearing 734 as described above. As can be seen in FIG. 148, the end effector connector housing 2832 operably supports a rotary transmission assembly 2860 therein.

As can be seen in FIGS. 148 and 149, the anvil assembly 2810 includes a pair of anvil trunnions 2812 (only one trunnion can be seen in FIG. 148) that are movably received within corresponding trunnion slots 2814 formed in the elongate channel 2830. The underside of the anvil assembly 2810 further has an anvil open ramp 2816 formed thereon for pivotal engagement with an anvil pivot pin 1201' on the firing member 1200'. Firing member 1200' may be substantially identical to firing member 1200 described above except for the noted differences. In addition, the anvil assembly 2810 further includes a closure pin 2818 that is configured for operable engagement with a rotary closure shaft 2910 that receives rotary closure motions from the rotary transmission assembly 2860 as will be discussed in further detail below. The firing member 1200' is rotatably journaled on an implement drive shaft 1300 that is rotatably supported within an elongate channel 2830 that is configured to support a surgical staple cartridge therein (not shown). The implement drive shaft 1300 has a bearing segment 1304 formed thereon that is rotatably supported in a bearing sleeve 2834 formed in the end effector connector housing 2832.

In the exemplary illustrated embodiment, the rotary transmission assembly 2860 includes a rotary drive shaft 2870 that extends longitudinally through the elongate shaft assembly to operably interface with the tool mounting portion (if the end effector 2800 is powered by a robotic system) or with the firing trigger of a handle assembly (if the end effector 2800 is to be manually operated). For those embodiments employing an articulation joint, the portion of the rotary drive shaft 2870 that extends through the articulation joint 700 may comprise any of the flexible drive shaft assemblies disclosed herein. If no articulation joint is employed, the rotary drive shaft may be rigid. As can be most particularly seen in FIGS. 148 and 149 the rotary drive shaft 2870 has a rotary drive head 2872 formed thereon or attached thereto that has a first ring gear 2874 formed thereon. In addition, the rotary drive head 2872 further has a second ring gear 2876 formed thereon for selective meshing engagement with a shifter gear 2882 attached to a rotary shifter shaft 2880.

The shifter shaft 2880 may comprise any one of the rotary drive shaft assemblies described above and extends through the elongate shaft assembly to operably interface with a tool mounting portion 300 (if the end effector 2800 is driven by a robotic system) or the handle assembly (if the end effector is to be manually operated). In either case, the shifter shaft 2800 is configured to receive longitudinally shifting motions to longitudinally shift the shifter gear 2882 within the rotary drive head 2872 and rotary drive motions to rotate the shifter gear 2882 as will be discussed in further detail below.

As can be further seen in FIGS. 148 and 149, the rotary transmission assembly 2860 further includes a transfer gear assembly 2890 that has a body 2892, a portion of which is rotatably supported within a cavity 2873 in the rotary drive head 2872. The body 2892 has a spindle 2894 that rotatably extends through a spindle mounting hole 2838 formed in a bulkhead 2836 in the end effector connector housing 2832. The body 2892 further has a shifter ring gear 2896 formed therein for selective meshing engagement with the shifter gear 2882 on the rotary shifter shaft 2880. A transfer gear 2900 is mounted to a transfer gear spindle 2902 that protrudes from the body 2892 and is slidably received within the arcuate slot 2840 in the bulkhead 2836. See FIGS. 155 and 156. The transfer gear 2900 is in meshing engagement with the first ring gear 2874 formed in the rotary drive head 2872. As can be seen in FIGS. 153-156, the arcuate slot 2840 that has a centrally disposed flexible detent 2842 protruding therein. The detent 2842 is formed on a web 2844 formed by a detent relief slot 2846 formed adjacent to the arcuate slot 2840 as shown in FIG. 155.

The rotary closure shaft 2910 has a bearing portion 2912 that is rotatably supported through a corresponding opening in the bulkhead 2836. The rotary closure shaft 2910 further has a closure drive gear 2914 that is configured for selective meshing engagement with the transfer gear 2900. The implement drive shaft 1300 also has an implement drive gear 1302 that is configured for selective meshing engagement with the transfer gear 2900.

Operation of the end effector 2800 will now be explained with reference to FIGS. 148-155. FIGS. 148 and 149 illustrate the end effector 2800 with the anvil assembly 2810 in the open position. To move the anvil assembly 2810 to the closed position shown in FIG. 150, the shifter shaft 2880 is located such that the shifter gear 2882 is in meshing engagement with the shifter ring gear 2896 in the body 2892. The shifter shaft 2880 may be rotated to cause the body 2892 to rotate to bring the transfer gear 2900 into meshing engagement with the closure drive gear 2914 on the closure shaft 2910. See FIG. 153. When in that position, the locking detent 2842 retains the transfer gear spindle 2902 in that position. Thereafter, the rotary drive shaft 2870 is rotated to apply rotary motion to the transfer gear 2900 which ultimately rotates the closure shaft 2910. As the closure shaft 2910 is rotated, a rotary spindle portion 2916 which is in engagement with the closure pin 2818 on the anvil assembly 2810 results in the anvil assembly 2810 moving proximally causing the anvil assembly 2810 to pivot on the anvil pivot pin 1201' on the firing member 1200'. Such action causes the anvil assembly 2810 to pivot to the closed position shown in FIG. 150. When the clinician desires to drive the firing member 1200' distally down the elongate channel 2830, the shifter shaft 2880 is once again rotated to pivot the transfer gear spindle 2902 to the position shown in FIG. 154. Again, the locking detent 2842 retains the transfer gear spindle 2902 in that position. Thereafter, the rotary drive shaft 2870 is rotated to apply rotary motion to the drive gear 1302 on the implement drive shaft 1300. Rotation of the implement drive shaft 1300 in one direction causes the firing member 1200' to be driven in the distal direction "DD". Rotation of the implement drive shaft 1300 in an opposite direction will cause the firing member 1200' to be retracted in the proximal direction "PD". Thus, in those applications wherein the firing member 1200' is configured to cut and fire staples within a staple cartridge mounted in the elongate channel 2830, after the firing member 1200' has been driven to its distal-most position within the elongate channel 2830, the rotary drive motion applied to the implement drive shaft 1300 by the rotary drive shaft assembly 2870 is reversed to retract the firing member 1200' back to its starting position shown in FIG. 150. To release the target tissue from the end effector 2800, the clinician again rotates the shifter shaft 2800 to once again bring the transfer gear 2900 into meshing engagement with the drive gear 2914 on the closure drive shaft 2910. Thereafter, a reverse rotary motion is applied to the transfer gear 2900 by the rotary drive shaft 2870 to cause the closure drive shaft 2910 to rotate the drive spindle 2916 and thereby cause the anvil assembly 2810 to move distally and pivot to the open position shown in FIGS. 148 and 149. When the clinician desires to rotate the entire end effector 2800 about the longitudinal tool axis "LT-LT", the shifter shaft is longitudinally shifted to bring the shifter gear 2882 into simultaneously meshing engagement with the second ring gear 2876 on the rotary drive head 2872 and the shifter ring gear 2896 on the transfer gear body 2892 as shown in FIG. 152. Thereafter, rotating the rotary drive shaft 2880 causes the entire end effector 2800 to rotate about the longitudinal tool axis "LT-LT" relative to the end effector connector tube 720.

FIGS. 157-170 illustrate another end effector embodiment 3000 that employs a pull-type motions to open and close the anvil assembly 3010. The anvil assembly 3010 is movably supported on an elongate channel 3030 for selective movement between an open position (FIGS. 168 and 169) and a closed position (FIGS. 157, 160 and 170). The elongate channel 3030 may be substantially identical to elongate channel 1020 described above, except for the differences discussed below. The elongate channel 3030 may be coupled to an end effector drive housing 1010 in the manner described above. The end effector drive housing 1010 may also be coupled to an end effector connector tube 720 by the ring-like bearing 734 as described above. As can be seen in FIG. 157, the end effector drive housing 1010 may support a drive arrangement 748 and rotary transmission 750 as described above.

As can be seen in FIG. 160, the anvil assembly 3010 includes a pair of anvil trunnions 3012 (only one trunnion can be seen in FIG. 160) that are movably received within corresponding trunnion slots 3032 formed in the elongate channel 3030. The underside of the anvil assembly 2810 further has an anvil open notches 3016 formed thereon for pivotal engagement with the upper fins 1208 on the firing member 3100. See FIG. 168. Firing member 3100 may be substantially identical to firing member 1200 described above except for the noted differences. In the illustrated embodiment, the end effector 3000 further includes an anvil spring 3050 that is configured to apply a biasing force on the anvil trunnions 3012. One form of anvil spring 3050 is illustrated in FIG. 159. As can be seen in that Figure, the anvil spring 3050 may be fabricated from a metal wire and have two opposing spring arms 3052 that are configured to bear upon the anvil trunnions 3012 when the anvil trunnions are received within their respective trunnion slots 3032. in addition, as can be further seen in FIG. 159, the anvil spring 3050 has two mounting loops 3054 formed therein that are adapted to be movably supported on corresponding spring pins 3034 formed on the elongate channel 3030. See FIG. 158. As will be discussed in further detail below, the anvil spring 3050 is configured to pivot on the spring pins 3034 within the elongate channel 3030. As can be most particularly seen in FIG. 158, a portion 3035 of each side wall of the elongate channel is recessed to provide clearance for the movement of the anvil spring 3050.

As can be seen in FIGS. 157 and 160-170, the end effector 3000 further includes a closure tube 3060 that is movably supported on the elongate channel 3030 for selective longitudinal movement thereon. To facilitate longitudinal movement of the closure tube 3060, the embodiment depicted in FIGS. 157 and 160-170 includes a closure solenoid 3070 that is linked to the closure tube 3060 by a linkage arm 3072 that is pivotally pinned or otherwise attached to the closure tube 3030. When the solenoid is actuated, the linkage arm 3072 is driven in the distal direction which drives the closure tube 3060 distally on the end of the elongate channel 3030. As the closure tube 3060 moves distally, it causes the anvil assembly 3010 to pivot to a closed position. In an alternative embodiment, the solenoid may comprise an annular solenoid mounted on the distal end of the end effector drive housing 1010. The closure tube would be fabricated from a metal material that could be magnetically attracted and repelled by the annular solenoid to result in the longitudinal movement of the closure tube.

In at least one form, the end effector 3060 further includes a unique anvil locking system 3080 to retain the anvil assembly 3010 locked in position when it is closed onto the target tissue. In one form, as can be seen in FIG. 157, the anvil locking system 3080 includes an anvil lock bar 3082 that extends transversely across the elongate channel 3030 such that the ends thereof are received within corresponding lock bar windows 3036 formed in the elongate channel 3030. See FIG. 158. Referring to FIG. 161, when the closure tube 3060 is in its distal-most "closed" position, the ends of the lock bar 3082 protrude laterally out through the lock bar windows 3036 and extend beyond the proximal end of the closure tube 3060 to prevent it from moving proximally out of position. The lock bar 3082 is configured to engage a solenoid contact 3076 supported in the end effector drive housing 1010. The solenoid contact 3076 is wired to a control system for controlling the solenoid 3070. The control system includes a source of electrical power either supplied by a battery or other source of electrical power in the robotic system or handle assembly, whichever the case may be.

The firing member 3100 is rotatably journaled on an implement drive shaft 1300 that is rotatably supported within an elongate channel 2830 that is configured to support a surgical staple cartridge therein (not shown). The implement drive shaft 1300 has a bearing segment 1304 formed thereon that is rotatably supported in a bearing sleeve 2834 formed in the end effector connector housing 2832 and operably interfaces with the rotary transmission 750 in the manner described above. Rotation of the implement drive shaft 1300 in one direction causes the firing member 3100 to be driven distally through the elongate channel 3030 and rotation of the implement drive shaft 1300 in an opposite rotary direction will cause the firing member 1200" to be retracted in the proximal direction "PD". As can be seen in FIGS. 157 and 160-170, the firing member 3100 has an actuation bar 3102 configured to engage the lock bar 3082 as will be discussed in further detail below.

The anvil locking system 3080 further includes an anvil pulling assembly 3090 for selectively pulling the anvil into wedging locking engagement with the closure tube 3060 when the closure tube 3060 has been moved into its distal-most position wherein the distal end of the closure tube 3060 is in contact with an anvil ledge 3013 formed on the anvil assembly 3010. In one form, the anvil pulling assembly 3090 includes a pair of anvil pull cables 3092 that are attached to the proximal end of the anvil assembly 3010 and protrude proximally through the elongate shaft assembly to the tool mounting portion or handle assembly, whichever the case may be. The pull cables 3092 may be attached to an actuator mechanism on the handle assembly or be coupled to one of the drive systems on the tool mounting portion that is configured to apply tension to the cables 3092.

Operation of the end effector 3000 will now be described. FIGS. 168 and 169 illustrate the anvil assembly 3010 in an open position. FIG. 168 illustrates the firing member 3100 in proximal-most position wherein a new staple cartridge (not shown) may be mounted in the elongate channel 3030. The closure tube 3060 is also in its proximal-most unactuated position. Also, as can be seen in FIG. 167, when the firing member 3100 is in its proximal-most position, the actuation bar 3102 has biased the lock bar into engagement with the solenoid contact 3076 which enables the solenoid to be activated for the next closure sequence. Thus, to commence the closure process, the rotary drive shaft 752 is actuated to move the firing member 3100 to its starting position illustrated in FIG. 169. When in that position, the actuation bar 3102 has moved in the proximal direction sufficiently to enable the lock bar 3082 to move out of engagement with the solenoid contact 3076 such that when power is supplied to the solenoid control circuit, the solenoid link 3072 is extended. Control power is then applied—either automatically or through a switch or other control mechanism in the handle assembly to the solenoid 3070 which moves the closure tube 3060 distally until the distal end of the closure tube 3060 contacts the ledge 3013 on the anvil assembly 3010 to cause the anvil assembly to pivot closed on the firing member 1200" as shown in FIG. 162. As can be seen in that Figure, the lock bar 3082 is positioned to prevent movement of the closure tube 3060 in the proximal direction. When in that position, the clinician then applies tension to the pull cables 3092 to pull the proximal end of the anvil assembly 3010 into wedging engagement with the closure tube 3060 to lock the anvil assembly 3010 in the closed position. Thereafter, the firing member 1200" may be driven in the distal direction through the tissue clamped in the end effector 3000. Once the firing process has been completed. The implement drive shaft is rotated in an opposite direction to return the firing member 3100 to its starting position wherein the actuation bar 3102 has once again contacted the lock bar 3082 to flex it into contact with the solenoid contact 3076 and to pull the ends of the lock bar 3082 into the windows 3036 in the elongate channel 3030. When in that position, when power is supplied to the solenoid control system, the solenoid 3070 retracts the closure tube 3060 in the proximal direction to its starting or open position shown in FIGS. 167 and 168. As the closure tube 3060 moves proximally out of engagement with the anvil assembly 3010, the anvil spring 3050 applies a biasing force to the anvil trunnions 3012 to bias the anvil assembly to the open position shown in FIG. 168.

FIGS. 171-178 illustrate another exemplary elongate shaft assembly 3200 that has another exemplary quick disconnect coupler arrangement 3210 therein. In at least one form, for example, the quick disconnect coupler arrangement 3210 includes a proximal coupler member 3212 in the form of a proximal outer tube segment 3214 that, in one arrangement, may have a tube gear segment 354 thereon that is configured to interface with the first drive system 350 in the above-described manner when the device is to be robotically controlled. In another embodiment, however, the proximal outer tube segment 3214 may interface with a manually-actuatable rotation nozzle 2512 mounted to a handle assembly in the above-described manner. As discussed above, the first drive system 350 in a robotically-controlled application or the rotation nozzle 2512 in a handheld arrangement serve to rotate the elongate shaft assembly 3200 and the end effector operably coupled thereto about the longitudinal tool axis "LT-LT". See FIG. 171. The proximal outer tube segment 3214 has a "necked-down" distal end portion 3216 that is configured to receive a locking collar thereon.

In the exemplary embodiment depicted in FIGS. 171-178, the elongate shaft assembly 3200 includes a proximal drive shaft segment 380" that may be substantially identical to the proximal drive shaft segment 380 described above except for the differences discussed below and be configured to receive rotary and axial control motions from the robotic system or handle assembly in the various manners disclosed herein. The illustrated embodiment may be used with an articulation joint 700 as described above and include articulation cables 434 and 454 that may be coupled to the articulation control drives in the various manners described herein. A proximal filler material 3220 is provided within the proximal outer tube segment 3214 to provide axial support for the articulation cable end portions 434A, 434B, 454A, 454B. Each articulation cable end portion 434A, 434B, 454A, 454B extends through a corresponding proximal articulation passage 3222 provided through the proximal filler material 3220. Each articulation cable end portion 434A, 434B, 454A, 454B further has a proximal articulation clip 3224 attached thereto that is configured to slide within the corresponding articulation passage 3222. The proximal articulation clips 3224 may be fabricated from metal or polymer material and each have a pair of flexible clip arms 3226 that each have a fastener cleat 3228 formed thereon. Likewise, the proximal drive shaft segment 380" is movable received in a shaft passage 3230 in the proximal filler material 3220. A drive shaft connection clip 3240 thereon. In one exemplary form, the drive shaft connection clip 3240 is formed with a central tubular connector portion 3242 and two flexible clip arms 3244 thereon that each have a fastener cleat 3248 thereon.

As can be further seen in FIGS. 171, 172 and 176-178, the quick disconnect arrangement 3210 further includes a distal coupler member 3250 in the form of a distal outer tube segment 3252 that is substantially similar to the distal outer tube portion 231 described above except that the distal outer tube segment 3252 includes a necked down proximal end portion 3254. The distal outer tube segment 3252 is operably coupled to an end effector 1000 of the various types disclosed herein and includes a distal drive shaft segment 540" that may be substantially similar to distal drive shaft segment 540 described above except for the differences noted below. A distal filler material 3260 is provided within the distal outer tube segment 3252 to provide axial support for the distal articulation cable segments 444, 445, 446, 447. Each distal articulation cable segment 444, 445, 446, 447 extends through a corresponding distal articulation passage 3262 provided through the distal filler material 3260. Each distal articulation cable segment 444, 445, 446, 447 further has a distal articulation bayonet post 3270 attached thereto that is configured to slide between the clip arms 3226 of the corresponding proximal articulation clip 3224. Each distal articulation bayonet post 3270 is configured to be retainingly engaged by the fastener cleats 3228 on the corresponding clip arms 3226. Likewise, the distal drive shaft segment 540" is movably received in a distal shaft passage 3264 in the distal filler material 3260. A distal drive shaft bayonet post 3280 is attached to the proximal end of the distal drive shaft segment 540" such that it may protrude proximally beyond the distal articulation bayonet posts 3270. FIG. 172 illustrates the position of the distal drive shaft bayonet post 3280 (in broken lines) relative to the distal articulation bayonet posts 3270. The distal drive shaft bayonet post 3280 is configured to be retainingly engaged by the fastener cleats 3248 on the corresponding clip arms 3244 on the drive shaft connection clip 3240.

As can be seen in FIGS. 171-178, the exemplary quick disconnect coupler arrangement 3210 further includes an axially movable lock collar 3290 that is movably journaled on the necked down proximal end portion 3254 of the distal outer tube segment 3252. As can be most particularly seen in FIG. 174, one form of the lock collar 3290 includes an outer lock sleeve 3292 that is sized to be slidably received on the necked down portions 3216, 3254 of the proximal outer tube segment 3214 and distal outer tube segment 3254, respectively. The outer lock sleeve 3292 is coupled to central lock body 3294 by a bridge 3295. The bridge 3295 is configured to slide through a distal slot 3255 in the necked down portion 3254 of the distal outer tube segment 3254 as well as a proximal slot 3217 in the necked down portion 3216 of the proximal outer tube segment 3214 that is slidably received within the necked down proximal end portion 3254 of the distal outer tube segment 3252 and may also slidably extend into the necked down portion 3216 of the proximal outer tube segment 3214. As can be further seen in FIG. 174, the central lock body 3294 has a plurality of passages 3296 for receiving the articulation posts and clips therethrough. Likewise, the central lock body 3294 has a central drive shaft passage 3298 for movably receiving the distal drive shaft segment 540" therein.

Use of the exemplary quick disconnect coupler arrangement 3210 will now be described. Referring first to FIGS. 171 and 172, the distal coupler member 3250 is axially aligned with the proximal coupler member 3212 such that the bridge 3295 is aligned with the slot 3217 in the necked down portion 3216 of the proximal outer tube segment 3214 and the distal drive shaft bayonet post 3280 is aligned with the central tubular connector portion 3242 on the proximal drive shaft connector clip 3240. Thereafter, the distal coupler member 3250 is brought into abutting engagement with the proximal coupler member 3212 to cause the distal drive shaft bayonet post 3280 to slide into the central tubular segment 3214 an ultimately into retaining engagement with the fastener cleats 3248 on the proximal drive shaft connector clip 3240. Such action also causes each distal articulation bayonet connector post 3270 to be retainingly engaged by the fastener cleats 3228 on the proximal articulation connector clips 3224 as shown in FIG. 176. It will be appreciated that as the distal drive shaft bayonet post 3280 is inserted between the clip arms 3244, the clip arms 3244 flex outward until the fastener cleats 3248 engage a shoulder 3281 on the post 3280. Likewise, as each of the distal articulation bayonet posts 3270 are inserted between their corresponding connector arms 3226, the connector arms 3226 flex outward until the fastener cleats 3228 engage a shoulder 3271 on the post 3270. Once the distal drive shaft segment 540" has been connected to the proximal drive shaft segment 380" and the distal articulation cable segments 444, 445, 446, 447 have been connected to the articulation cable end portions 434A, 434B, 454A, 454B, respectively, the user may then slide the outer lock sleeve 3292 proximally to the position shown in FIGS. 177 and 178. When in that position, the central lock body 3294 prevents the clip arms 3244, 3226 from flexing outward to thereby lock the distal coupler member 3250 to the proximal coupler member 3212. To disconnect the distal coupler member 3250 from the proximal coupler member 3212, the user moves the outer lock sleeve 392 to the position shown in FIGS. 175 and 176 and thereafter pulls the coupler members 3250, 3212 apart. As opposing axial separation motions are applied to the coupler members 3250, 3212, the clip arms 3244 and 3226 are permitted to flex out of engagement with the distal drive shaft bayonet post and the distal articulation bayonet posts, respectively.

Non-Limiting Examples

One exemplary form comprises a surgical tool for use with a robotic system that includes a tool drive assembly that is operatively coupled to a control unit of the robotic system that is operable by inputs from an operator and is configured to robotically-generate output motions. In at least one exemplary form, the surgical tool includes a drive system that is configured to interface with a corresponding portion of the tool drive assembly of the robotic system for receiving the robotically-generated output motions therefrom. A drive shaft assembly operably interfaces with the drive system and is configured to receive the robotically-generated output motions from the drive system and apply control motions to a surgical end effector that operably interfaces with the drive shaft assembly. A manually-actuatable control system operably interfaces with the drive shaft assembly to selectively apply manually-generated control motions to the drive shaft assembly.

In connection with another general exemplary form, there is provided a surgical tool for use with a robotic system that includes a tool drive assembly that is operatively coupled to a control unit of the robotic system that is operable by inputs from an operator and is configured to provide at least one rotary output motion to at least one rotatable body portion supported on the tool drive assembly. In at least one exemplary form, the surgical tool includes a surgical end effector that comprises at least one component portion that is selectively movable between first and second positions relative to at least one other component portion thereof in response to control motions applied thereto. An elongate shaft assembly is operably coupled to the surgical end effector and comprises at least one gear-driven portion that is in operable communication with the at least one selectively movable component portion. A tool mounting portion is operably coupled to the elongate shaft assembly and is configured to operably interface with the tool drive assembly when coupled thereto. At least one exemplary form further comprises a tool mounting portion that comprises a driven element that is rotatably supported on the tool mounting portion and is configured for driving engagement with a corresponding one of the at least one rotatable body portions of the tool drive assembly to receive corresponding rotary output motions therefrom. A drive system is in operable engagement with the driven element to apply robotically-generated actuation motions thereto to cause the corresponding one of the at least one gear driven portions to apply at least one control motion to the selectively movable component. A manually-actuatable reversing system operably interfaces with the elongate shaft assembly to selectively apply manually-generated control motions thereto.

In accordance with another exemplary general form, there is provided a surgical tool for use with a robotic system that includes a tool drive assembly that is operatively coupled to a control unit of the robotic system that is operable by inputs from an operator and is configured to robotically-generate rotary output motions. In at least one exemplary form, the surgical tool comprises a rotary drive system that is configured to interface with a corresponding portion of the tool drive assembly of the robotic system for receiving the robotically-generated rotary output motions therefrom. A rotary drive shaft assembly operably interfaces with the rotary drive system and is configured to receive the robotically-generated rotary output motions from the rotary drive system and apply rotary drive motions to a surgical end effector operably that interfaces with the rotary drive shaft assembly. A manually-actuatable reversing system operably interfaces with the rotary drive shaft assembly to selectively apply manually-generated rotary drive motions to the rotary drive shaft assembly.

Another exemplary form comprises a surgical stapling device that includes an elongate shaft assembly that has a distal end and defines a longitudinal tool axis. The device further includes an end effector that comprises an elongate channel assembly that includes a portion that is configured to operably support a surgical staple cartridge therein. An anvil is movably supported relative to the elongate channel assembly. The surgical stapling device further comprises a rotary joint that couples the elongate channel assembly to the distal end of the elongate shaft assembly to facilitate selective rotation of the elongate channel assembly about the longitudinal tool axis relative to the distal end of the elongate shaft assembly.

Another exemplary form comprises a rotary support joint assembly for coupling a first portion of a surgical instrument to a second portion of a surgical instrument. In at least one exemplary form, the rotary support joint assembly comprises a first annular race in the first portion and a second annular race in the second portion and which is configured for substantial registration with the first annular race when the second portion is joined with the first portion. A ring-like bearing is supported within the registered first and second annular races.

In connection with another exemplary general form, there is provided a rotary support joint assembly for coupling a surgical end effector to an elongate shaft assembly of a surgical instrument. In at least one exemplary form, the rotary support joint assembly comprises a cylindrically-shaped connector portion on the surgical end effector. A first annular race is provided in the perimeter of the connector portion. A socket is provided on the elongate shaft and is sized to receive the cylindrically-shaped connector portion therein such that the cylindrically-shaped connector portion may freely rotate relative to the socket. A second annular race is provided in an inner wall of the socket and is configured for substantial registration with the first annular race when the cylindrically-shaped connector portion is received within the socket. A window is provided in the socket in communication with the second annular race. A ring-like bearing member that has a free end is insertable through the window into the first and second registered annular races.

In connection with another exemplary general form, there is provided a method for rotatably coupling a first portion of a surgical instrument to a second portion of a surgical instrument. In various exemplary forms, the method comprises forming a first annular race in the first portion and forming a second annular race in the second portion. The method further includes inserting the first portion into the second portion such that the first and second annular races are in substantial registration and inserting a ring-like bearing within the registered first and second annular races.

Another exemplary form comprises a drive shaft assembly for a surgical instrument that includes a plurality of movably interlocking joint segments that are interconnected to form a flexible hollow tube. A flexible secondary constraining member is installed in flexible constraining engagement with the plurality of movably interlocking joint segments to retain the interlocking joint segments in movable interlocking engagement while facilitating flexing of the drive shaft assembly.

In accordance with another general exemplary form, there is provided a composite drive shaft assembly for a surgical instrument that includes a plurality of movably interlocking joint segments that are cut into a hollow tube by a laser and which has a distal end and a proximal end. A flexible secondary constraining member is in flexible constraining engagement with the plurality of movably interlocking joint segments to retain the interlocking joint segments in movable interlocking engagement while facilitating flexing of the drive shaft assembly.

In accordance with yet another exemplary general form, there is provided a drive shaft assembly for a surgical instrument that includes a plurality of movably interconnected joint segments wherein at least some joint segments comprise a ball connector portion that is formed from six substantially arcuate surfaces. A socket portion is sized to movably receive the ball connector portion of an adjoining joint segment therein. A hollow passage extends through each ball connector portion to form a passageway through the drive shaft assembly. The drive shaft assembly may further include a flexible secondary constraining member installed in flexible constraining engagement with the plurality of movably interconnected joint segments to retain the joint segments in movable interconnected engagement while facilitating flexing of the drive shaft assembly.

Another exemplary form comprises a method of forming a flexible drive shaft assembly for a surgical instrument. In various exemplary embodiments, the method comprises providing a hollow shaft and cutting a plurality of movably interconnected joint segments into the hollow shaft with a laser. The method further comprises installing a secondary constraining member on the hollow shaft to retain the movably interconnected joint segments in movable interconnected engagement while facilitating flexing of the drive shaft assembly.

In connection with another exemplary form, there is provided a method of forming a flexible drive shaft assembly for a surgical instrument. In at least one exemplary embodiment, the method comprises providing a hollow shaft and cutting a plurality of movably interconnected joint segments into the hollow shaft with a laser. Each joint segment comprises a pair of opposing lugs wherein each lug has a tapered outer perimeter portion that is received within a corresponding socket that has a tapered inner wall portion which cooperates with the tapered outer perimeter portion of the corresponding lug to movably retain the corresponding lug therein.

Another exemplary general form comprises a rotary drive arrangement for a surgical instrument that has a surgical end effector operably coupled thereto. In one exemplary form, the rotary drive arrangement includes a rotary drive system that is configured to generate rotary drive motions. A drive shaft assembly operably interfaces with the rotary drive system and is selectively axially movable between a first position and a second position. A rotary transmission operably interfaces with the drive shaft assembly and the surgical end effector such that when the drive shaft assembly is in the first axial position, application of one of the rotary drive motions to the drive shaft assembly by the rotary drive system causes the rotary transmission to apply a first rotary control motion to the surgical end effector and when the drive shaft assembly is in the second axial position, application of the rotary drive motion to the drive shaft assembly by the rotary drive system causes the rotary transmission to apply a second rotary control motion to the surgical end effector.

In connection with another exemplary general form, there is provided a surgical tool for use with a robotic system that includes a tool drive assembly that is operatively coupled to a control unit of the robotic system that is operable by inputs from an operator and is configured to generate output motions. In at least one exemplary form the surgical tool comprises a tool mounting portion that is configured operably interface with a portion of the robotic system. A rotary drive system is operably supported by the tool mounting portion and interfaces with the tool drive assembly to receive corresponding output motions therefrom. An elongate shaft assembly operably extends from the tool mounting portion and includes a drive shaft assembly that operably interfaces with the rotary drive system. The drive shaft assembly is selectively axially movable between a first position and a second position. The surgical tool further comprises a surgical end effector that is rotatably coupled to the elongate shaft assembly for selective rotation relative thereto. A rotary transmission operably interfaces with the drive shaft assembly and the surgical end effector such that when the drive shaft assembly is in the first axial position, application of one of the rotary drive motions to the drive shaft assembly by the rotary drive system causes the rotary transmission to apply a first rotary control motion to the surgical end effector and when the drive shaft assembly is in the second axial position, application of the rotary drive motion to the drive shaft assembly by the rotary drive system causes the rotary transmission to apply a second rotary control motion to the surgical end effector.

In connection with yet another exemplary general form, there is provided a surgical instrument that comprises a handle assembly and a drive motor that is operably supported by the handle assembly. An elongate shaft assembly operably extends from the handle assembly and includes a drive shaft assembly that operably interfaces with the drive motor and is selectively axially movable between a first position and a second position. A surgical end effector is rotatably coupled to the elongate shaft assembly for selective rotation relative thereto. A rotary transmission operably interfaces with the drive shaft assembly and the surgical end effector such that when the drive shaft assembly is in the first axial position, application of a rotary drive motion to the drive shaft assembly by the drive motor causes the rotary transmission to apply a first rotary control motion to the surgical end effector and when the drive shaft assembly is in the second axial position, application of the rotary drive motion to the drive shaft assembly by the drive motor causes the rotary transmission to apply a second rotary control motion to the surgical end effector.

Various exemplary embodiments also comprise a differential locking system for a surgical instrument that includes a surgical end effector that is powered by a rotary drive shaft assembly that is movable between a plurality of discrete axial positions. In at least one form, the differential locking system comprises at least one retention formation on the rotary drive shaft assembly that corresponds to each one of the discrete axial positions. At least one lock member is operably supported relative to rotary drive shaft assembly for retaining engagement with the at least one retention formation when the rotary drive shaft assembly is moved to the discrete axial positions associated therewith.

In connection with another exemplary general form, there is provided a differential locking system for a surgical instrument that includes a surgical end effector powered by a rotary drive shaft assembly that is movable between a first axial position and a second axial position. In at least one exemplary form, the differential locking system comprises a differential housing that operably interfaces with the rotary drive shaft assembly and the surgical end effector. At least one spring-biased lock member operably supported by the differential housing for retaining engagement with a first portion of the rotary drive shaft assembly when the rotary drive shaft assembly is in the first axial position and the at least one spring-biased lock member further configured to retainingly engage a second portion of the rotary drive shaft assembly when the rotary drive shaft assembly is in the second axial position.

In connection with yet another exemplary general form, there is provided a differential locking system for a surgical instrument that includes a surgical end effector that is powered by a rotary drive shaft assembly that is movable between a first axial position and a second axial position. In at least one exemplary form, the differential locking system comprises a differential housing that operably interfaces with the rotary drive shaft assembly and the surgical end effector. At least one spring member is provided on a portion of the rotary drive shaft assembly wherein each spring member defines a first retaining position that corresponds to the first axial position of the rotary drive shaft assembly and a second retaining position that corresponds to the second axial position of the rotary drive shaft assembly. A lock member is operably supported by the differential housing and corresponds to each of the at least one spring members for retaining engagement therewith such that the lock member retainingly engages the corresponding spring member in the first retaining position when the rotary drive shaft assembly is in the first axial position and the lock member retainingly engages the corresponding spring member in the second retaining position when the rotary drive shaft assembly is in the second axial position.

Various other exemplary embodiments comprise a surgical instrument that includes an end effector and a proximal rotary drive train assembly that is operably coupled to a source of rotary and axial control motions. The proximal rotary drive train assembly is longitudinally shiftable in response to applications of the axial control motions thereto. The surgical instrument further includes a distal rotary drive train assembly that is operably coupled to the end effector to apply the rotary control motions thereto. A proximal axial drive train assembly is operably coupled to another source of axial control motions. A distal axial drive train assembly is operably coupled to the end effector to apply the axial control motions thereto. The instrument further comprises a coupling arrangement for simultaneously attaching and detaching the proximal rotary drive train assembly to the distal rotary drive train assembly and the proximal axial drive train assembly to the distal axial drive train assembly.

In connection with another general aspect, there is provided a coupling arrangement for attaching an end effector including a plurality of distal drive train assemblies that are configured to apply a plurality of control motions to the end effector to corresponding proximal drive train assemblies communicating with a source of drive motions. In one exemplary form, the coupling arrangement comprises a proximal attachment formation on a distal end of each proximal drive train assembly and a proximal coupler member that is configured to operably support each proximal drive train assembly therein such that the proximal attachment formations thereon are retained in substantial coupling alignment. A distal attachment formation is provided on a proximal end of each distal drive train assembly. Each distal attachment formation is configured to operably engage a proximal attachment formation on the distal end of a corresponding proximal drive train when brought into coupling engagement therewith. A distal coupler member is operably coupled to the end effector and is configured to operably support each distal drive train therein to retain the distal attachment formations thereon in substantial coupling alignment. A locking collar is movable from an unlocked position wherein the distal drive train assemblies may be decoupled from the corresponding proximal drive train assemblies and a locked position wherein the distal drive train assemblies are retained in coupled engagement with their corresponding proximal drive train assemblies.

In connection with another general aspect, there is provided a surgical instrument that includes an end effector that is configured to perform surgical activities in response to drive motions applied thereto. An exemplary form of the instrument further includes a source of drive motions and a first proximal drive train assembly that operably interfaces with the source of drive motions for receiving corresponding first drive motions therefrom. A second proximal drive train assembly operably interfaces with the source of drive motions for receiving corresponding second drive motions therefrom. A first distal drive train assembly operably interfaces with the end effector and is configured to receive the corresponding first drive motions from the first proximal drive train assembly when it is operably coupled thereto. A second distal drive train assembly operably interfaces with the end effector and is configured to receive the corresponding second drive motions from the second proximal drive train assembly when it is operably coupled thereto. The instrument further comprises a coupling arrangement that includes a first coupling member that operably supports the first and second proximal drive train assemblies therein. The coupling arrangement further includes a second coupling member that operably supports the first and second distal drive train assemblies therein and is configured for axial alignment with the first coupling member such that when the second coupling member is axially aligned with the first coupling member, the first distal drive train assembly is in axial alignment with the first proximal drive train assembly for operable engagement therewith and the second distal drive train assembly is in axial alignment with the second proximal drive train assembly for operable engagement therewith. A locking collar is movably journaled on one of the first and second coupling members and is configured to move between an unlocked position wherein the first and second distal drive train assemblies are detachable from the first and second proximal drive train assemblies, respectively and a locked position wherein the first and second distal drive train assemblies are retained in operable engagement with the first and second proximal drive train assemblies, respectively.

In accordance with another general aspect, there is provided a surgical cartridge that includes a cartridge body that defines a path therethrough for operably receiving a firing member of a surgical instrument. The surgical cartridge further includes an alignment member that is operably supported in the cartridge body and is configured to move the firing member from an inoperable configuration wherein firing member is misaligned with the path to an operable configuration wherein the firing member is in alignment with the path when the firing member is driven into contact therewith.

In accordance with yet another general aspect, there is provided an end effector for a surgical instrument. In at least one form, the end effector comprises a support member that has a slot and a lockout notch that is adjacent to the slot. The end effector further comprises a firing member that is movable between an inoperable configuration and an operable configuration, wherein the firing member is aligned with the slot and is structured to translate in the slot when it is in the operable configuration and wherein the firing member is engaged with the lockout notch and misaligned with the slot when it is in the inoperable configuration.

Another exemplary embodiment comprises a surgical instrument that includes an elongate channel that is configured to removably support a cartridge therein. In at least one form, the cartridge comprises a cartridge body and an alignment member that is movably supported within the cartridge body for movement from a first position to a second position therein. The surgical instrument also comprises a firing member that is operably supported relative to the elongate channel for movement between a starting position and an ending position upon application of actuation motions thereto. The firing member is incapable from moving from the starting position to the ending position unless the firing member is in operable engagement with the alignment member in the cartridge body.

Another exemplary embodiment comprises an end effector for a surgical instrument. In at least one form, the end effector comprises an elongate channel that is configured to removably support a cartridge therein. A firing member is operably supported relative to the elongate channel for movement between a starting and ending position. An implement drive shaft is in operable engagement with the firing member for moving the firing member between the starting and ending positions upon applications of actuation motions thereto from a drive arrangement. The implement drive shaft is moveable from an inoperable position wherein the implement drive shaft is out of operable engagement with the drive arrangement to an operable position wherein the implement drive shaft is in operable engagement with the drive arrangement. The end effector further comprises an alignment member that is movably supported for contact with the implement drive shaft to move the implement drive shaft from the inoperable position to the operable position upon installation of a cartridge in the elongate channel.

Another exemplary embodiment includes a surgical instrument that comprises an elongate channel and a cartridge that is removably supported in the elongate channel. A firing member is operably supported relative to the elongate channel for movement between a starting and ending position. An implement drive shaft is in operable engagement with the firing member for moving the firing member between the starting and ending positions upon applications of actuation motions thereto from a drive arrangement. The implement drive shaft is moveable from an inoperable position wherein the implement drive shaft is out of operable engagement with the drive arrangement to an operable position wherein the implement drive shaft is in operable engagement with the drive arrangement. The surgical instrument further comprises an alignment member movably supported for contact with the implement drive shaft to move the implement drive shaft from the inoperable position to the operable position upon installation of a cartridge in the elongate channel.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed exemplary embodiments, many modifications and variations to those exemplary embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical stapler, comprising:
   an elongate shaft;
   an articulation joint; and
   an end effector articulatable relative to said elongate shaft about said articulation joint, wherein said end effector comprises:
      a first jaw;
      a second jaw movable relative to said first jaw; and
      a staple cartridge comprising a plurality of staples removably stored therein, wherein said staple cartridge comprises a proximal end and a distal end, and wherein said staples are deployable progressively from said proximal end to said distal end; and
   a motor-driven firing drive, comprising:
      a rotatable input drive comprising a threaded transmission portion, wherein said rotatable input drive is rotatable in a first direction and a second direction;
      a flexible output shaft configured to be actuated by said rotatable input drive, wherein said flexible output shaft comprises:
         a hollow body portion comprising an intermediate section and a plurality of slits defined in said intermediate section, wherein said intermediate section extends through said articulation joint; and
         a longitudinal axis, wherein said hollow body portion is constrained from revolving about said longitudinal axis, wherein said rotatable input drive is configured to translate said flexible output shaft distally when said rotatable input drive is rotated in said first direction, wherein said rotatable input drive is configured to translate said flexible output shaft proximally when said rotatable input drive is rotated in said second direction, wherein said flexible output shaft is movable through said first jaw and said second jaw during a staple firing stroke when said flexible output shaft is actuated by said rotatable input drive.

2. The surgical stapler of claim 1, wherein said flexible output shaft comprises a plurality of annular joints.

3. The surgical stapler of claim 1, wherein said flexible output shaft comprises an array of articulation joints comprising interlocking projections and recesses.

4. The surgical stapler of claim 1, wherein said flexible output shaft comprises a joint lattice comprising operably engaged projections and recesses.

5. The surgical stapler of claim 1, wherein said flexible output shaft comprises a plurality of interlocking dovetail members.

6. A surgical stapling assembly, comprising:
   an elongate shaft;
   an end effector, comprising:
      a first jaw;
      a second jaw movable relative to said first jaw; and a staple cartridge comprising a plurality of staples removably stored therein;
an articulation joint, wherein said end effector is articulatable relative to said elongate shaft about said articulation joint; and
a motor-driven firing drive, comprising:
  a rotatable input drive system comprising a threaded transmission portion, wherein said rotatable input drive system is rotatable in a first direction and a second direction; and
  a flexible output shaft configured to be actuated by said rotatable input drive system, wherein said flexible output shaft comprises:
    a hollow body portion comprising an intermediate section and a plurality of intrinsic articulation joints defined in said intermediate section, wherein said plurality of intrinsic articulation joints comprises a plurality of cuts, and wherein said intermediate section extends through said articulation joint; and
    a longitudinal axis, wherein said flexible output shaft is constrained from revolving about said longitudinal axis, wherein said rotatable input drive system is configured to translate said flexible output shaft toward said end effector when said rotatable input drive system is rotated in said first direction, wherein said rotatable input drive system is configured to translate said flexible output shaft away from said end effector when said rotatable input drive system is rotated in said second direction, and wherein said flexible output shaft is movable through said first jaw and said second jaw during a staple firing stroke when said flexible output shaft is actuated by said rotatable input drive system.

7. The surgical stapling assembly of claim 6, wherein said plurality of intrinsic articulation joints comprises a plurality of annular joints.

8. The surgical stapling assembly of claim 6, wherein said plurality of intrinsic articulation joints comprises interlocking projections and recesses.

9. The surgical stapling assembly of claim 6, wherein said plurality of intrinsic articulation joints comprises a joint lattice comprising operably engaged projections and recesses.

10. The surgical stapling assembly of claim 6, wherein said plurality of intrinsic articulation joints comprises a plurality of interlocking dovetail members.

11. A surgical stapling assembly, comprising:
an elongate shaft;
an articulation joint; and
an end effector attached to said elongate shaft by way of said articulation joint, wherein said end effector comprises:
  a first jaw;
  a second jaw movable relative to said first jaw; and
  a staple cartridge comprising a plurality of staples removably stored therein, wherein said staples are deployable during a staple firing stroke; and
a motor-driven firing drive, comprising:
  a rotatable input drive comprising a threaded transmission portion, wherein said rotatable input drive is rotatable in a first direction and a second direction; and
  a flexible output drive member configured to be actuated by said rotatable input drive, wherein said flexible output drive member comprises:
    a hollow body portion comprising an intermediate section and a plurality of slots defined in said intermediate section, wherein said intermediate section extends through said articulation joint; and
    a longitudinal axis, wherein said hollow body portion is constrained from revolving about said longitudinal axis, wherein said rotatable input drive is configured to translate said flexible output drive member distally when said rotatable input drive is rotated in said first direction, wherein said rotatable input drive is configured to translate said flexible output drive member proximally when said rotatable input drive is rotated in said second direction, wherein said flexible output drive member is movable through said first jaw and said second jaw during a staple firing stroke when said flexible output drive member is actuated by said rotatable input drive.

12. The surgical stapling assembly of claim 11, wherein said flexible output drive member comprises a plurality of annular joints.

13. The surgical stapling assembly of claim 11, wherein said flexible output drive member comprises an array of articulation joints comprising interlocking projections and recesses.

14. The surgical stapling assembly of claim 11, wherein said flexible output drive member comprises a joint lattice comprising operably engaged projections and recesses.

15. The surgical stapling assembly of claim 11, wherein said flexible output drive member comprises a plurality of interlocking dovetail members.

* * * * *